United States Patent
Cha et al.

(10) Patent No.: US 12,391,678 B2
(45) Date of Patent: Aug. 19, 2025

(54) COMPOUND AND ORGANIC LIGHT EMITTING DEVICE COMPRISING SAME

(71) Applicant: LG CHEM, LTD., Seoul (KR)

(72) Inventors: Yongbum Cha, Daejeon (KR); Sung Kil Hong, Daejeon (KR); Dong Uk Heo, Daejeon (KR); Woo Jin Cho, Daejeon (KR); Jaegoo Lee, Daejeon (KR)

(73) Assignee: LG CHEM, LTD., Seoul (KR)

( * ) Notice: Subject to any disclaimer, the term of this patent is extended or adjusted under 35 U.S.C. 154(b) by 828 days.

(21) Appl. No.: 17/760,585

(22) PCT Filed: Jun. 1, 2021

(86) PCT No.: PCT/KR2021/006773
§ 371 (c)(1),
(2) Date: Mar. 15, 2022

(87) PCT Pub. No.: WO2022/014857
PCT Pub. Date: Jan. 20, 2022

(65) Prior Publication Data
US 2022/0367819 A1    Nov. 17, 2022

(30) Foreign Application Priority Data
Jul. 13, 2020 (KR) .................. 10-2020-0086347

(51) Int. Cl.
| | | |
|---|---|---|
| *C07D 405/04* | (2006.01) | |
| *C07D 405/10* | (2006.01) | |
| *C07D 405/14* | (2006.01) | |
| *C07D 409/14* | (2006.01) | |
| *C09K 11/06* | (2006.01) | |
| *H10K 85/60* | (2023.01) | |
| *H10K 50/16* | (2023.01) | |
| *H10K 50/18* | (2023.01) | |

(52) U.S. Cl.
CPC ......... *C07D 405/04* (2013.01); *C07D 405/10* (2013.01); *C07D 405/14* (2013.01); *C07D 409/14* (2013.01); *C09K 11/06* (2013.01); *H10K 85/615* (2023.02); *H10K 85/622* (2023.02); *H10K 85/654* (2023.02); *H10K 85/6574* (2023.02); *H10K 85/6576* (2023.02); *C09K 2211/1018* (2013.01); *H10K 50/16* (2023.02); *H10K 50/18* (2023.02)

(58) Field of Classification Search
None
See application file for complete search history.

(56) References Cited

U.S. PATENT DOCUMENTS

| | | |
|---|---|---|
| 2004/0251816 A1 | 12/2004 | Leo et al. |
| 2016/0118599 A1 | 4/2016 | Jeong et al. |
| 2017/0005275 A1 | 1/2017 | Jeon et al. |
| 2018/0159050 A1* | 6/2018 | Kim ............... C07D 409/14 |
| 2019/0189929 A1 | 6/2019 | Heo et al. |
| 2019/0378990 A1 | 12/2019 | Cha et al. |
| 2020/0048230 A1* | 2/2020 | Heo ............... H10K 85/654 |
| 2020/0207778 A1* | 7/2020 | Bae ............... H10K 85/654 |
| 2021/0053934 A1 | 2/2021 | Cha et al. |
| 2021/0143344 A1 | 5/2021 | Han et al. |

FOREIGN PATENT DOCUMENTS

| | | |
|---|---|---|
| CN | 107778219 A | 3/2018 |
| CN | 109563065 A | 4/2019 |
| CN | 110446702 A | 11/2019 |
| KR | 10-2000-0051826 A | 8/2000 |
| KR | 10-2014-0143590 A | 12/2014 |
| KR | 10-2016-0047670 A | 5/2016 |
| KR | 10-2017-0004793 A | 1/2017 |
| KR | 10-2019-0139782 A | 12/2019 |
| KR | 10-2020-0020582 A | 2/2020 |
| KR | 10-2020-0024725 A | 3/2020 |
| KR | 10-2020-0032020 A | 3/2020 |
| KR | 10-2020-0034618 A | 3/2020 |
| KR | 10-2021-0154570 A | 12/2021 |
| WO | 2003-012890 A2 | 2/2003 |

OTHER PUBLICATIONS

Liu et al., "A Novel Linking Strategy of Using 9,10-Dihydroacridine to Construct Efficient Host Materials for Red Phosphorescent Organic Light-Emitting Diodes", Chem. Eur. J. (2018) vol. 24, No. 45, pp. 11755-11762.

* cited by examiner

*Primary Examiner* — Robert S Loewe
(74) *Attorney, Agent, or Firm* — Bryan Cave Leighton Paisner LLP

(57) ABSTRACT

A compound represented by Chemical Formula 1 and an organic light emitting device including the same.

[Chemical Formula 1]

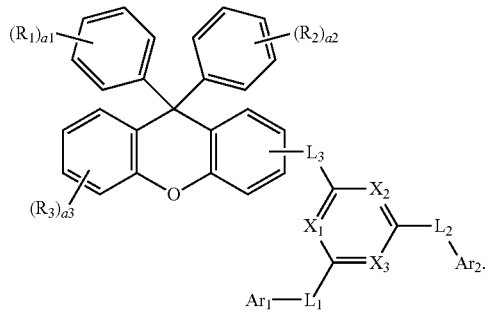

10 Claims, 1 Drawing Sheet

[FIG. 1]
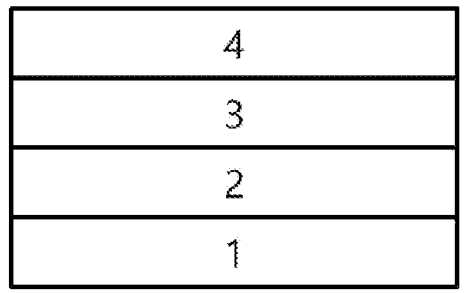
[FIG. 2]
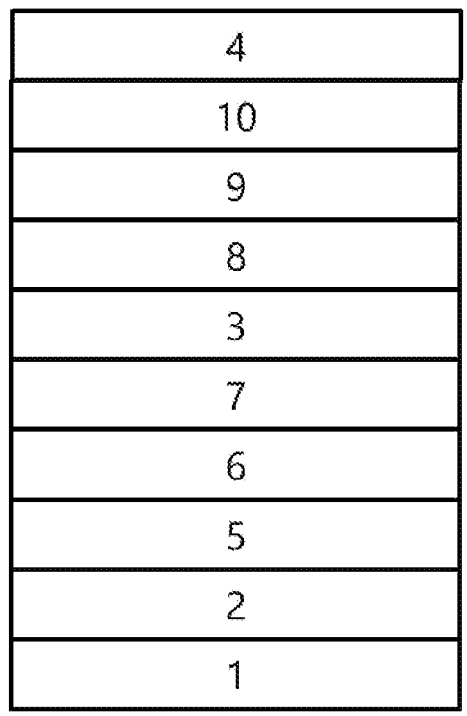

COMPOUND AND ORGANIC LIGHT EMITTING DEVICE COMPRISING SAME

CROSS-REFERENCE TO RELATED APPLICATION(S)

This application is a National Stage Application of International Application No. PCT/KR2021/006773 filed on Jun. 1, 2021, which claims priority to Korean Patent Application No. 10-2020-0086347 filed on Jul. 13, 2020, the disclosure of which is incorporated herein by reference in its entirety.

FIELD OF DISCLOSURE

The present disclosure relates to a novel compound and an organic light emitting device comprising the same.

BACKGROUND

In general, an organic light emitting phenomenon refers to a phenomenon where electric energy is converted into light energy by using an organic material. The organic light emitting device using the organic light emitting phenomenon has characteristics such as a wide viewing angle, an excellent contrast, a fast response time, an excellent luminance, driving voltage and response speed, and thus many studies have proceeded.

The organic light emitting device generally has a structure which comprises an anode, a cathode, and an organic material layer interposed between the anode and the cathode. The organic material layer frequently has a multilayered structure that comprises different materials in order to enhance efficiency and stability of the organic light emitting device, and for example, the organic material layer may be formed of a hole injection layer, a hole transport layer, a light emitting layer, an electron transport layer, an electron injection layer and the like. In the structure of the organic light emitting device, if a voltage is applied between two electrodes, the holes are injected from an anode into the organic material layer and the electrons are injected from the cathode into the organic material layer, and when the injected holes and electrons meet each other, an exciton is formed, and light is emitted when the exciton falls to a ground state again.

There is a continuing need for the development of new materials for the organic materials used in the organic light emitting devices as described above.

RELATED ARTS

Korean Unexamined Patent Application Publication No. 10-2000-0051826

SUMMARY

The present disclosure relates to a novel compound and an organic light emitting device comprising the same.

Provided herein is a compound represented by the following Chemical Formula 1:

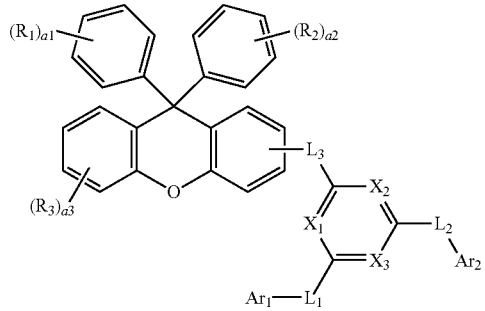

[Chemical Formula 1]

wherein in Chemical Formula 1,
$X_1$ to $X_3$ are each independently N or CH, and at least one of $X_1$ to $X_3$ is N,
$Ar_1$ and $Ar_2$ are each independently a substituted or unsubstituted $C_{6-60}$ aryl; or a substituted or unsubstituted $C_{2-60}$ heteroaryl containing any one or more selected from the group consisting of N, O and S, wherein $Ar_1$ is substituted with one, two or three cyano groups,
$L_1$ to $L_3$ are each independently a single bond; or a substituted or unsubstituted $C_{6-60}$ arylene;
$R_1$ to $R_3$ are each independently hydrogen; deuterium; halogen; cyano; nitro; amino; a substituted or unsubstituted $C_{1-60}$ alkyl; a substituted or unsubstituted $C_{3-60}$ cycloalkyl; a substituted or unsubstituted $C_{2-60}$ alkenyl; a substituted or unsubstituted $C_{6-60}$ aryl; or a substituted or unsubstituted $C_{2-60}$ heteroaryl containing any one or more selected from the group consisting of N, O and S, or two adjacent groups of $R_1$s, two adjacent groups of $R_2$s, or two adjacent groups of $R_3$s are linked with each other respectively to form a $C_{6-60}$ aromatic ring or a $C_{2-60}$ heteroaromatic ring containing one or more selected from the group consisting of N, O and S,
a1 and a2 are each independently an integer of 0 to 5, and
a3 is an integer of 0 to 4.

Also provided herein is an organic light emitting device comprising: a first electrode; a second electrode that is provided to face the first electrode; and an organic material layer including one or more layers that are provided between the first electrode and the second electrode, wherein one or more layers of the organic material layer include the compound represented by Chemical Formula 1.

The above-mentioned compound represented by Chemical Formula 1 can be used as a material of an organic material layer of an organic light emitting device, and can improve the efficiency, achieve low driving voltage and/or improve lifetime characteristics in the organic light emitting device. In particular, the compound represented by the Chemical Formula 1 may be used as a hole injection material, hole transport material, hole injection and transport material, light emitting material, electron transport material, or electron injection material.

BRIEF DESCRIPTION OF THE DRAWINGS

FIG. 1 shows an example of an organic light emitting device comprising a substrate 1, an anode 2, a light emitting layer 3, and a cathode 4.

FIG. 2 shows an example of an organic light emitting device comprising a substrate 1, an anode 2, a hole injection layer 5, a hole transport layer 6, an electron blocking layer 7, a light emitting layer 3, a hole blocking layer 8, an electron transport layer 9, an electron injection layer 10, and a cathode 4.

DETAILED DESCRIPTION

Hereinafter, embodiments of the present disclosure will be described in more detail to facilitate understanding of the invention.

The present disclosure provides the compound represented by Chemical Formula 1.

As used herein, the notation

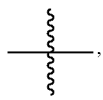

or ⫶ means a bond linked to another substituent group.

As used herein, the term "substituted or unsubstituted" means being unsubstituted or substituted with one or more substituents selected from the group consisting of deuterium; a halogen group; a cyano group; a nitro group; a hydroxy group; a carbonyl group; an ester group; an imide group; an amino group; a phosphine oxide group; an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamine group; an aralkylamine group; a heteroarylamine group; an arylamine group; an arylphosphine group; and a heterocyclic group containing at least one of N, O and S atoms, or being unsubstituted or substituted with a substituent to which two or more substituents of the above-exemplified substituents are connected. For example, "a substituent in which two or more substituents are connected" may be a biphenyl group. Namely, a biphenyl group may be an aryl group, or it may also be interpreted as a substituent in which two phenyl groups are connected.

In the present disclosure, the carbon number of a carbonyl group is not particularly limited, but is preferably 1 to 40. Specifically, the carbonyl group may be a compound having the following structural formulas, but is not limited thereto.

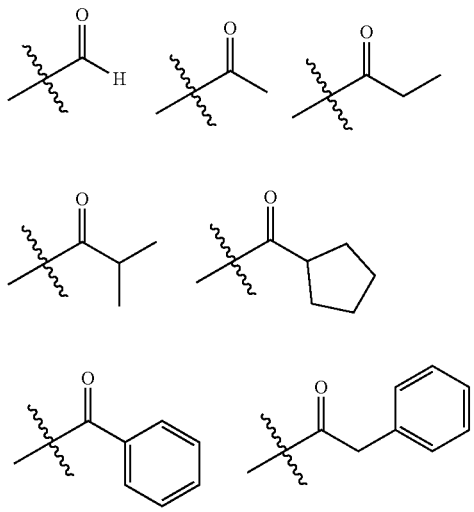

In the present disclosure, an ester group may have a structure in which oxygen of the ester group may be substituted by a straight-chain, branched-chain, or cyclic alkyl group having 1 to 25 carbon atoms, or an aryl group having 6 to 25 carbon atoms. Specifically, the ester group may be a compound having the following structural formulas but is not limited thereto

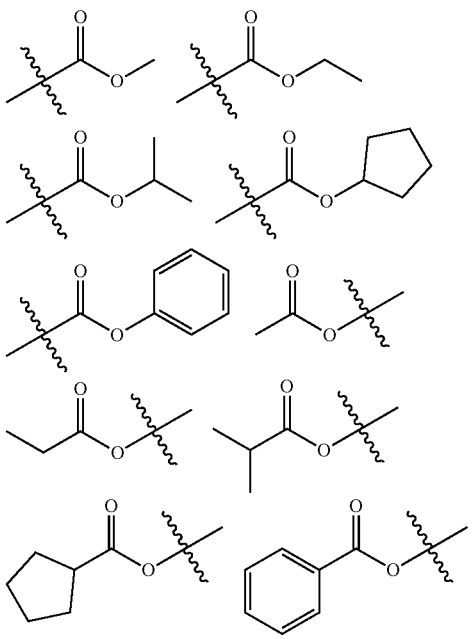

In the present disclosure, the carbon number of an imide group is not particularly limited, but is preferably 1 to 25. Specifically, the imide group may be a compound having the following structural formulas, but is not limited thereto.

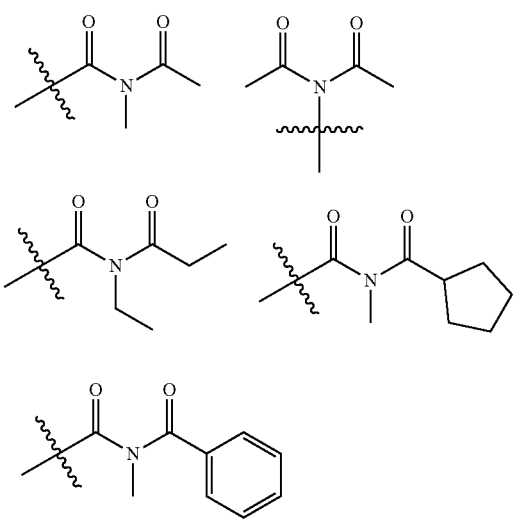

In the present disclosure, a silyl group specifically includes a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but is not limited thereto.

In the present disclosure, a boron group specifically includes a trimethylboron group, a triethylboron group, a t-butyldimethylboron group, a triphenylboron group, and a phenylboron group, but is not limited thereto.

In the present disclosure, examples of a halogen group include fluorine, chlorine, bromine, or iodine.

In the present disclosure, the alkyl group may be straight-chain or branched-chain, and the carbon number thereof is not particularly limited, but is preferably 1 to 40. According to one embodiment, the carbon number of the alkyl group is 1 to 20. According to another embodiment, the carbon number of the alkyl group is 1 to 10. According to another embodiment, the carbon number of the alkyl group is 1 to 6. Specific examples of the alkyl group include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methyl-hexyl, and the like, but are not limited thereto.

In the present disclosure, the alkenyl group may be straight-chain or branched-chain, and the carbon number thereof is not particularly limited, but is preferably 2 to 40. According to one embodiment, the carbon number of the alkenyl group is 2 to 20. According to another embodiment, the carbon number of the alkenyl group is 2 to 10. According to still another embodiment, the carbon number of the alkenyl group is 2 to 6. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present disclosure, a cycloalkyl group is not particularly limited, but the carbon number thereof is preferably 3 to 60. According to one embodiment, the carbon number of cycloalkyl group is 3 to 30. According to another embodiment, the carbon number of the cycloalkyl group is 3 to 20. According to still another embodiment, the carbon number of the cycloalkyl group is 3 to 6.

Specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present disclosure, an aryl group is not particularly limited, but the carbon number thereof is preferably 6 to 60, and it may be a monocyclic aryl group or a polycyclic aryl group. According to one embodiment, the carbon number of the aryl group is 6 to 30. According to one embodiment, the carbon number of the aryl group is 6 to 20. According to one embodiment, the carbon number of the aryl group is 6 to 14. The aryl group may be a phenyl group, a biphenyl group, a terphenyl group or the like as the monocyclic aryl group, but is not limited thereto. The polycyclic aryl group includes a naphthyl group, an anthracenyl group, a phenanthryl group, a pyrenyl group, a perylenyl group, a chrysenyl group, or the like, but is not limited thereto.

In the present disclosure, the fluorenyl group may be substituted, and two substituents may be linked with each other to form a spiro structure. In the case where the fluorenyl group is substituted,

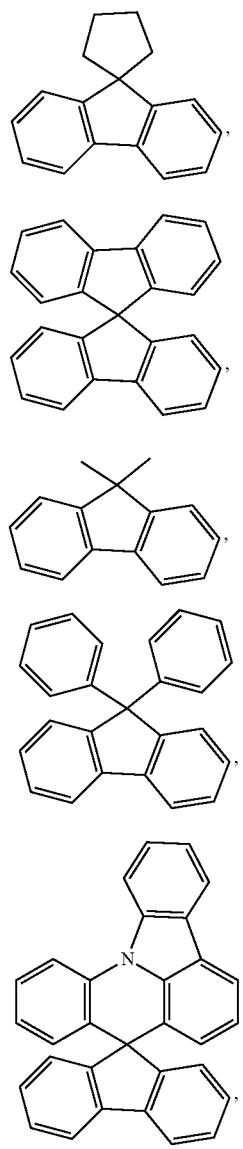

and the like can be formed. However, the structure is not limited thereto.

In the present disclosure, a heterocyclic group is a heterocyclic group containing one or more of O, N, P, Si and S as a heteroatom, and the carbon number thereof is not particularly limited, but is preferably 2 to 60. Examples of the heterocyclic group include a thiophene group, a furan group, a pyrrole group, an imidazole group, a thiazole group, an oxazol group, an oxadiazol group, a triazol group, a pyridyl group, a bipyridyl group, a pyrimidyl group, a triazine group, an acridyl group, a pyridazine group, a pyrazinyl group, a quinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzoimidazole group, a benzothiazol group, a benzocarbazole group, a benzothiophene group, a dibenzothiophene group, a benzofuranyl group, a phenanthroline group, an isoxazolyl group, a thiadiazolyl group, a phenothiazinyl group, a dibenzofuranyl group, and the like, but are not limited thereto.

In the present disclosure, the aryl group in the aralkyl group, the aralkenyl group, the alkylaryl group and the arylamine group is the same as the above-mentioned examples of the aryl group. In the present disclosure, the alkyl group in the aralkyl group, the alkylaryl group and the alkylamine group is the same as the above-mentioned examples of the alkyl group. In the present disclosure, the heterocyclic group in the heteroarylamine may be applied to the above-mentioned description of the heteroaryl group. In the present disclosure, the alkenyl group in the aralkenyl group is the same as the above-mentioned examples of the alkenyl group. In the present disclosure, the above-mentioned description of the aryl group may be applied except that the arylene is a divalent group. In the present disclosure, the above-mentioned description of the heterocyclic group can be applied except that the heteroarylene is a divalent group. In the present disclosure, the above-mentioned description of the aryl group or cycloalkyl group may be applied except that the hydrocarbon ring is not a monovalent group but formed by combining two substituent groups. In the present disclosure, the above-mentioned description of the heterocyclic group may be applied, except that the heterocyclic group is not a monovalent group but formed by combining two substituent groups.

Preferably, the compound of Chemical Formula 1 may be represented by any one of the following Chemical Formulas 1-1 to 1-4:

[Chemical Formula 1-1]

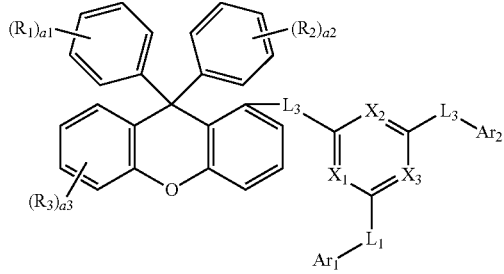

[Chemical Formula 1-2]

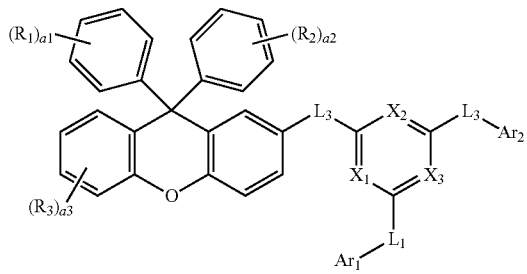

[Chemical Formula 1-3]

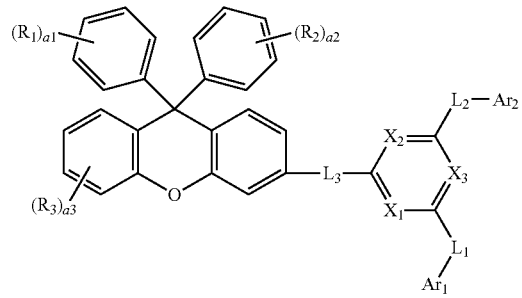

[Chemical Formula 1-4]

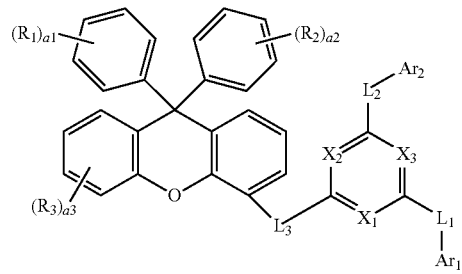

wherein in Chemical Formulas 1-1 to 1-4

$X_1$ to $X_3$, $Ar_1$, $Ar_2$, $L_1$ to $L_3$, $R_1$ to $R_3$ and a1 to a3 are the same as those defined in Chemical Formula 1.

Preferably, $Ar_1$ and $Ar_2$ may be each independently a substituted or unsubstituted $C_{6-20}$ aryl; or a substituted or unsubstituted $C_{2-20}$ heteroaryl containing any one or more selected from the group consisting of N, O and S, wherein $Ar_1$ may be substituted with one, two or three cyano groups.

More preferably, $Ar_1$ and $Ar_2$ may be each independently phenyl, biphenylyl, naphthyl, phenanthrenyl, triphenylenyl, phenyl naphthyl, dimethylfluorenyl, fluoranthenyl, dibenzofuranyl, or dibenzothiophenyl, each of which may be substituted with one, two or three cyano groups.

Preferably, $Ar_4$ may be a substituted or unsubstituted $C_{6-20}$ aryl; or a substituted or unsubstituted $C_{2-20}$ heteroaryl containing any one or more selected from the group consisting of N, O and S, wherein $Ar_4$ may be substituted with one, two or three cyano groups.

More preferably, $Ar_4$ may be phenyl, biphenylyl, or naphthyl, wherein $Ar_1$ may be substituted with one, two or three cyano groups.

Most preferably, $Ar_4$ may be any one selected from the group consisting of the following:

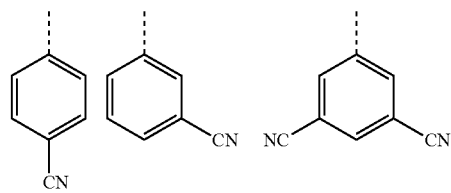

-continued

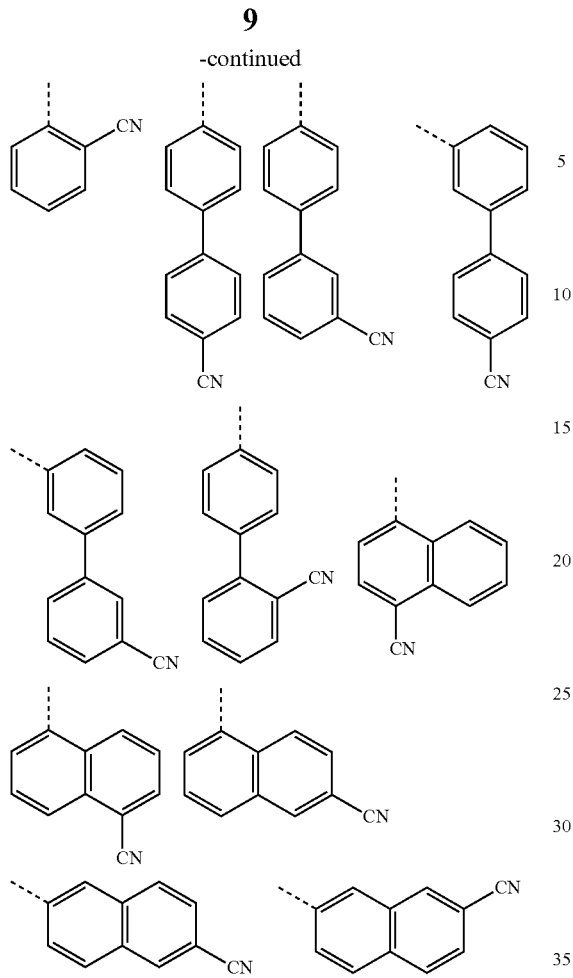

Preferably, $Ar_2$ may be a substituted or unsubstituted $C_{6-20}$ aryl; or a substituted or unsubstituted $C_{2-20}$ heteroaryl containing one or more selected from the group consisting of N, O and S.

More preferably, $Ar_2$ may be phenyl, biphenylyl, naphthyl, phenanthrenyl, triphenylenyl, phenyl naphthyl, dimethylfluorenyl, fluoranthenyl, dibenzofuranyl, or dibenzothiophenyl, and most preferably, $Ar_2$ may be any one selected from the group consisting of the following:

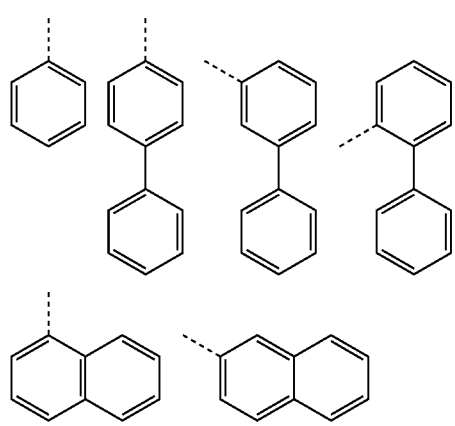

-continued

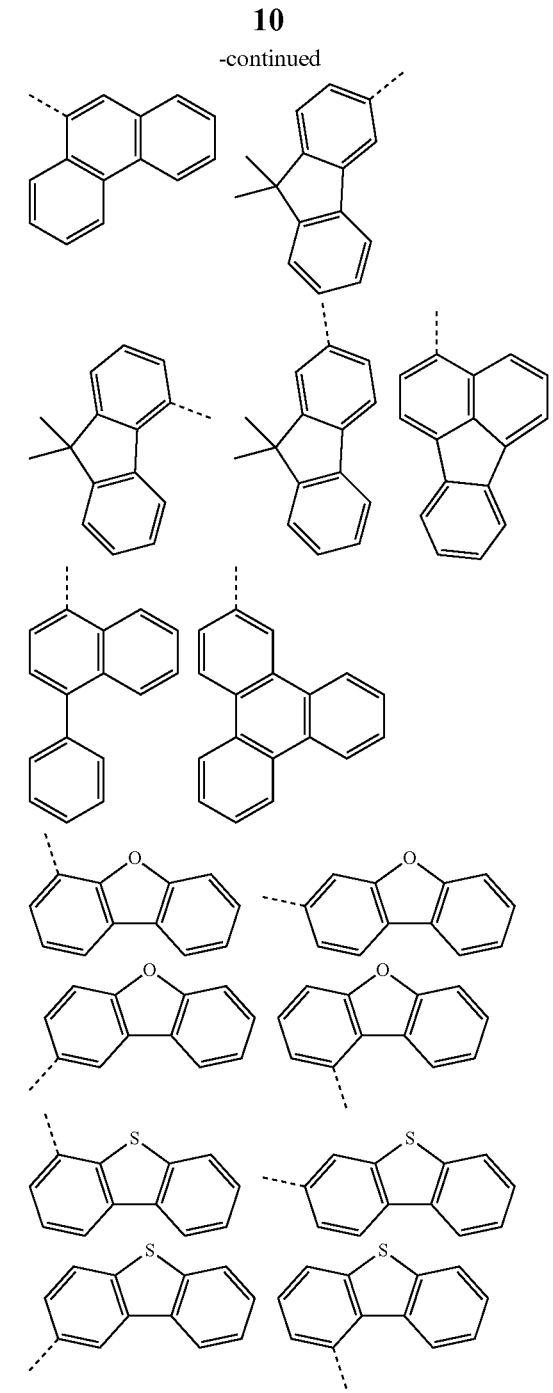

Preferably, $L_1$ to $L_3$ may be each independently a single bond; or a substituted or unsubstituted $C_{6-20}$ arylene.

More preferably, $L_1$ to $L_3$ may be each independently a single bond, phenylene, biphenyldiyl, or naphthyldiyl.

Preferably, $R_1$ to $R_3$ may be each independently hydrogen; deuterium; a substituted or unsubstituted $C_{1-10}$ alkyl; a substituted or unsubstituted $C_{6-20}$ aryl; or a substituted or unsubstituted $C_{2-20}$ heteroaryl containing any one or more selected from the group consisting of N, O and S, or two adjacent groups of $R_1$s, two adjacent groups of $R_2$s, or two adjacent groups of $R_3$s may be linked with each other respectively to form a $C_{6-20}$ aromatic ring or a $C_{2-20}$ heteroaromatic ring containing one or more selected from the group consisting of N, O and S.

More preferably, $R_1$ to $R_3$ may be each independently hydrogen; deuterium; or tertbutyl, or two adjacent groups of $R_1$s, two adjacent groups of $R_2$s, or two adjacent groups of $R_3$s may be linked with each other respectively to form a benzene ring.

Most preferably, $R_1$ and $R_2$ may be each independently hydrogen; deuterium; or tertbutyl, $R_3$ may be hydrogen or deuterium, or two adjacent groups of $R_3$ may be linked with each other to form a benzene ring.

Preferably, a1 and a2 may be each independently an integer of 0 or 1.

Preferably, a3 may be an integer of 0 to 2.

Representative examples of the compound represented by Chemical Formula 1 are as follows:

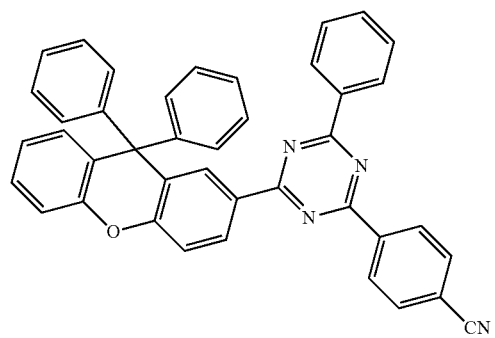

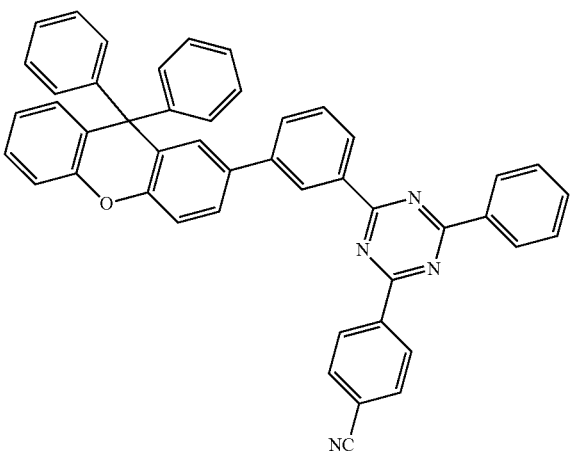

-continued

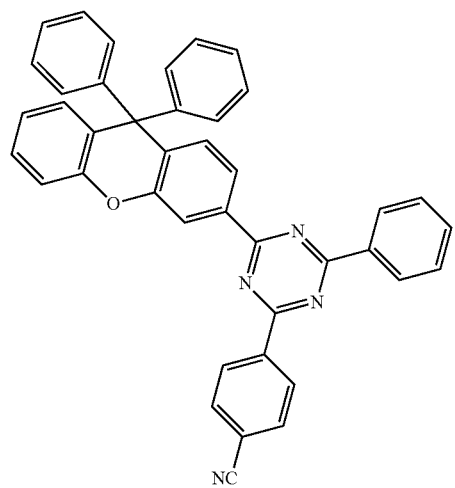

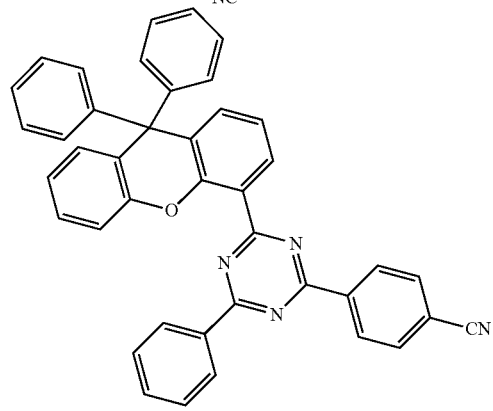

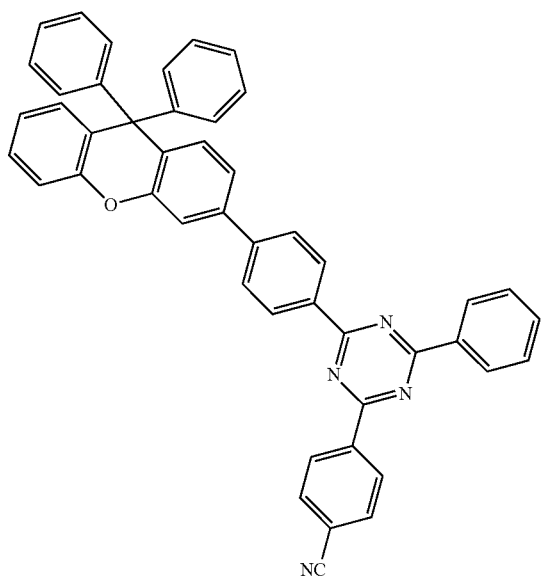
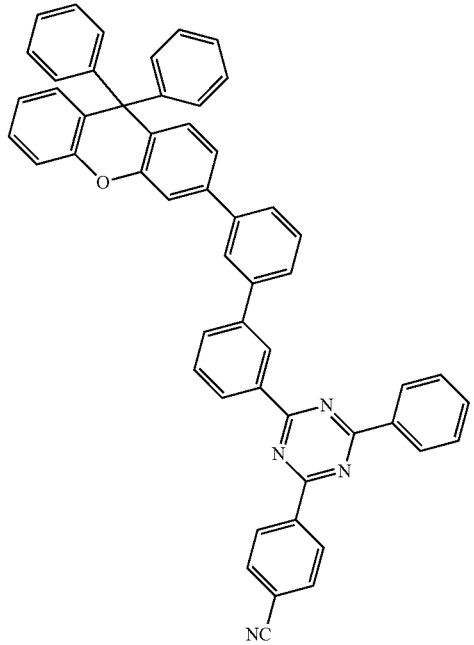
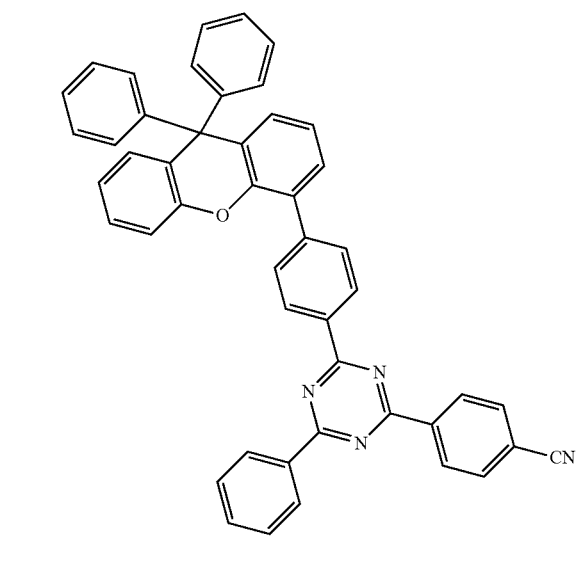
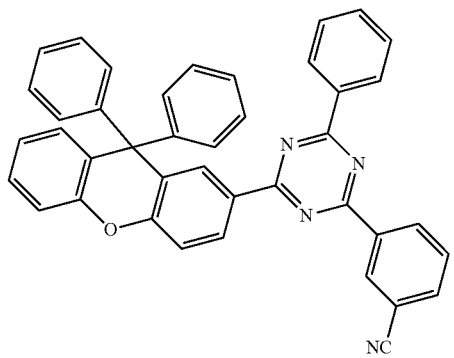

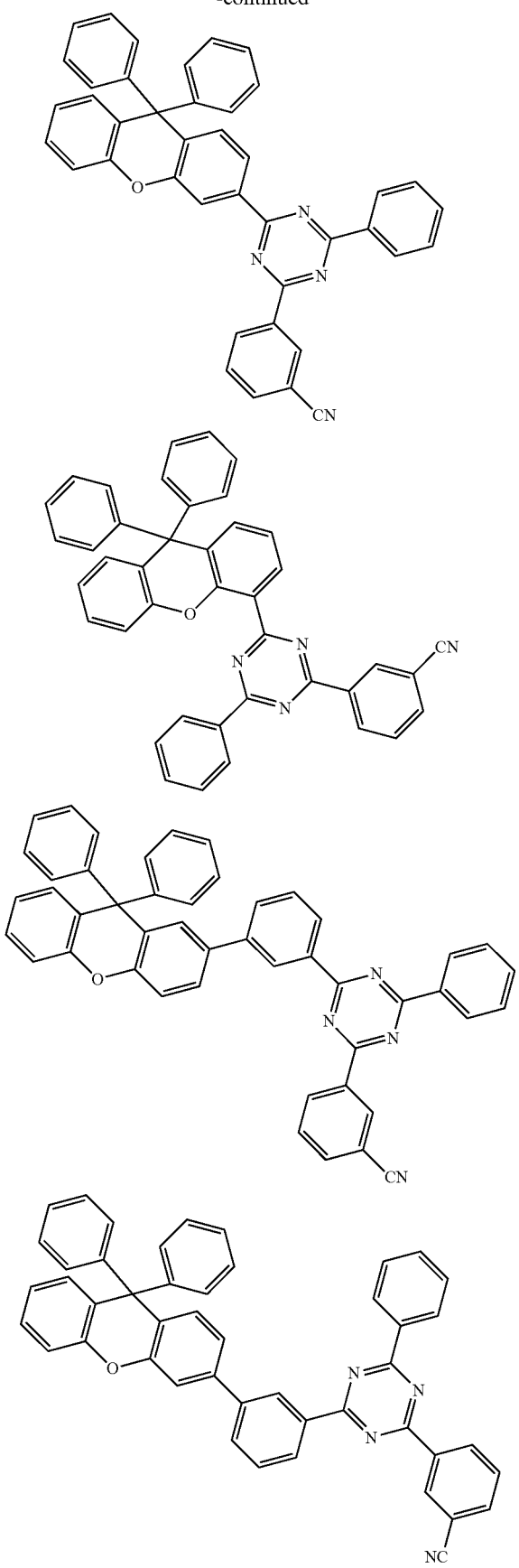
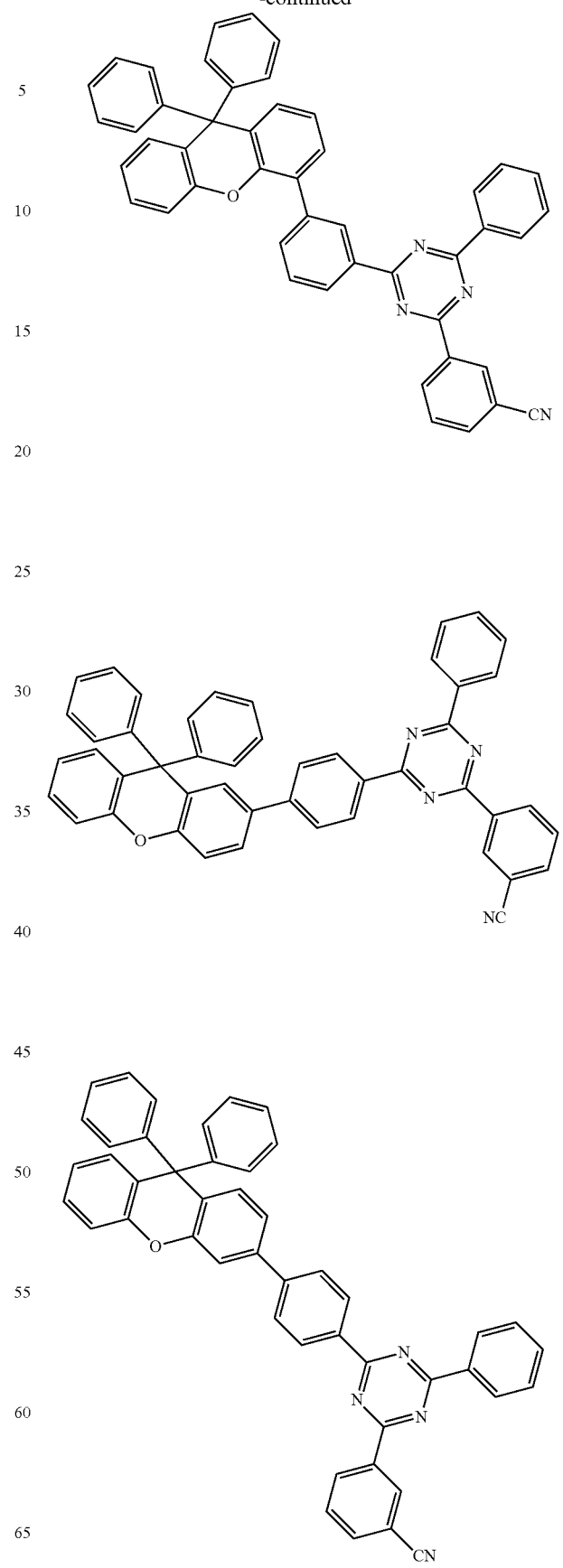

-continued
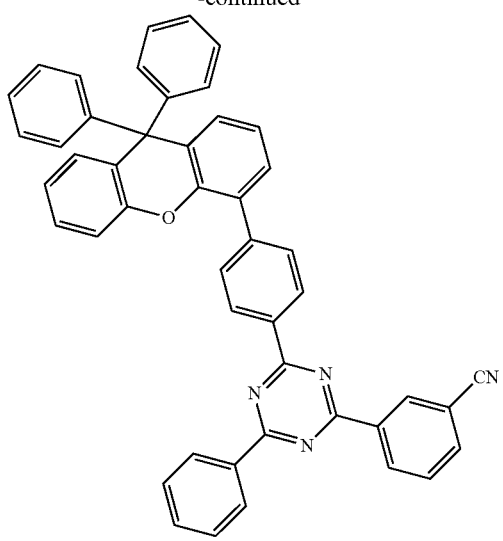
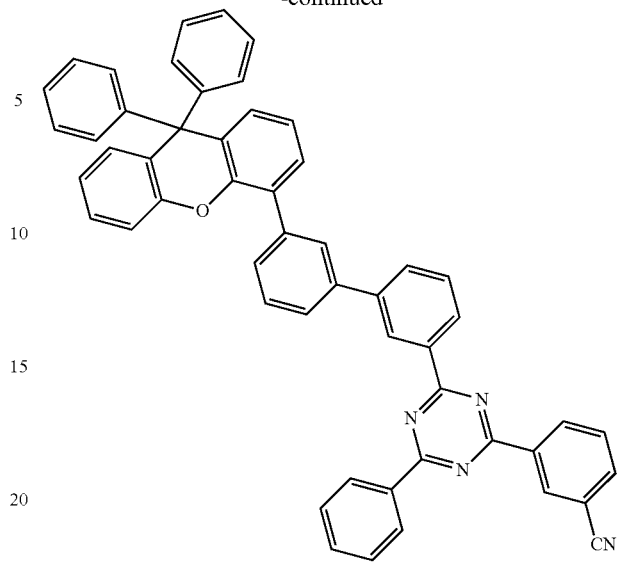
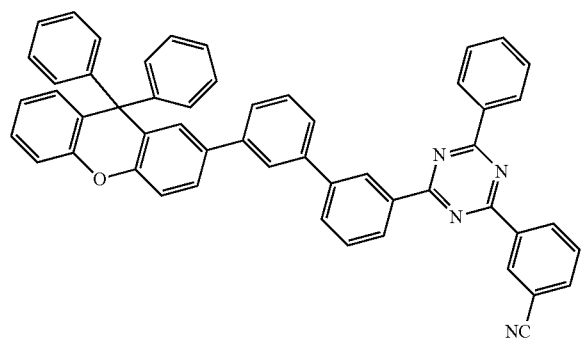
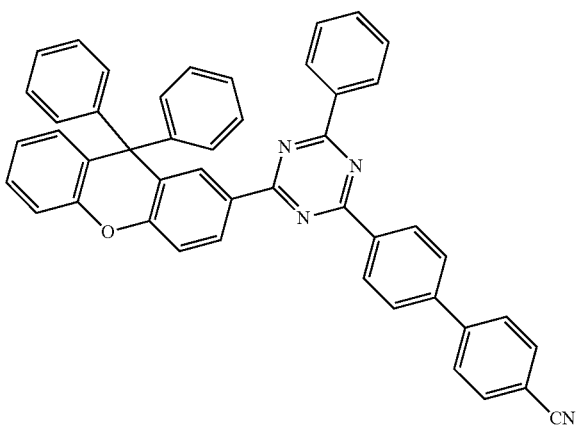
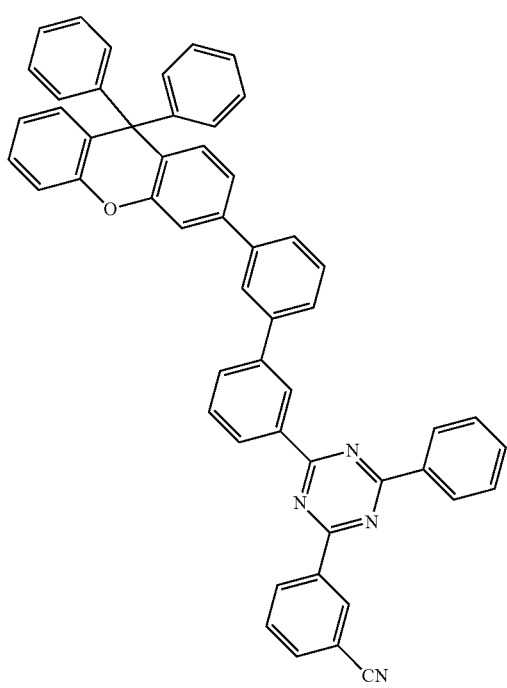
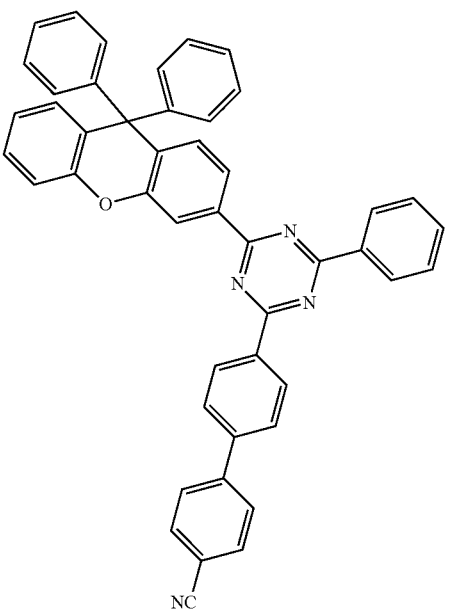

19
-continued
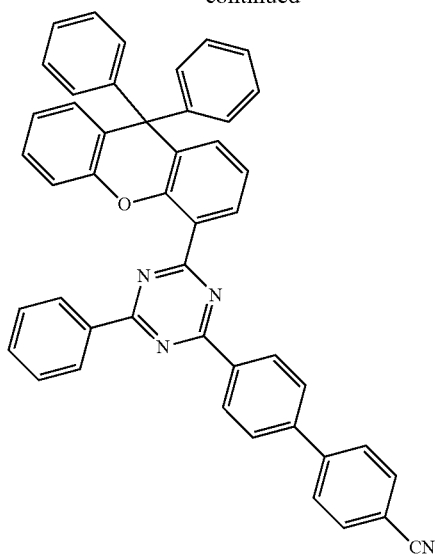
20
-continued
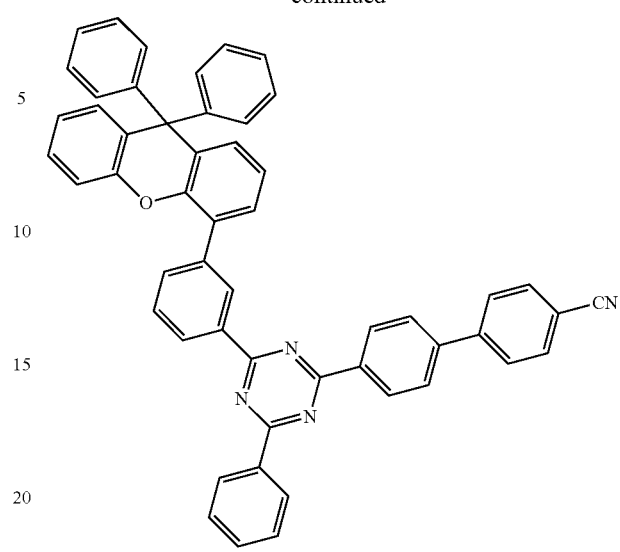
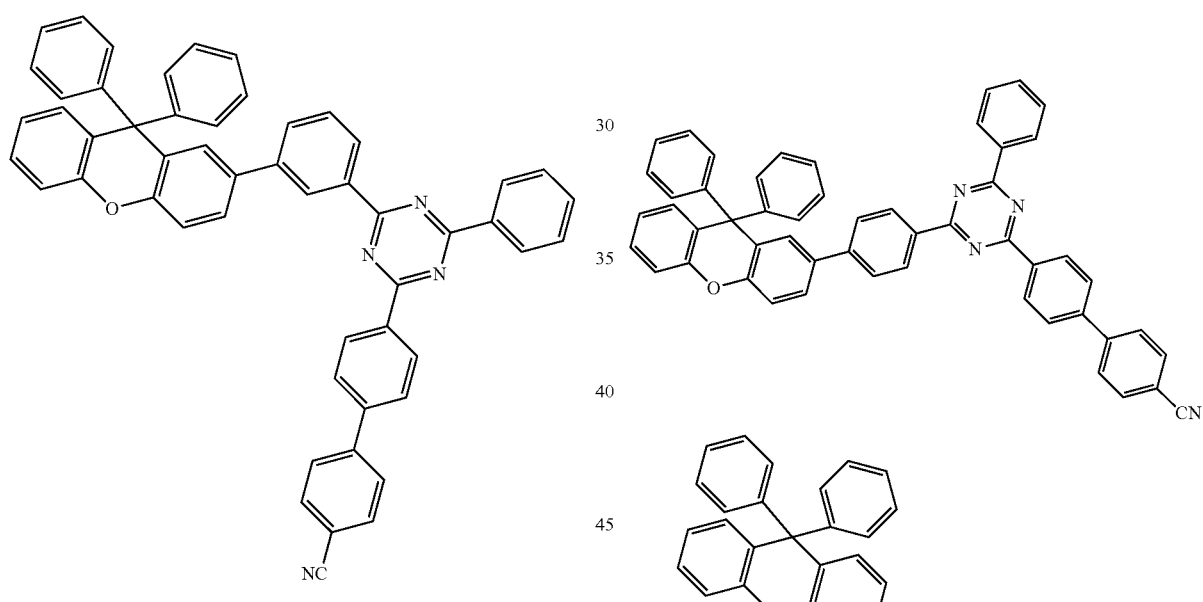
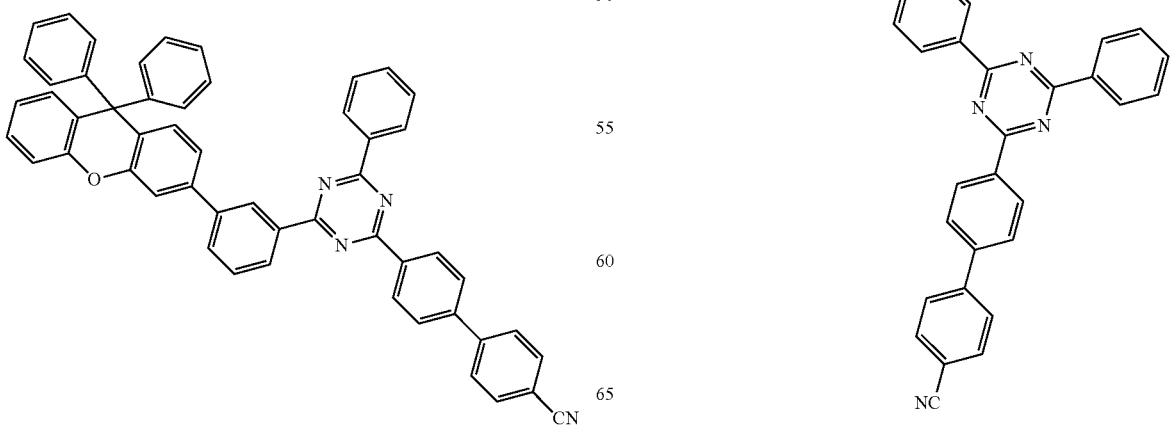

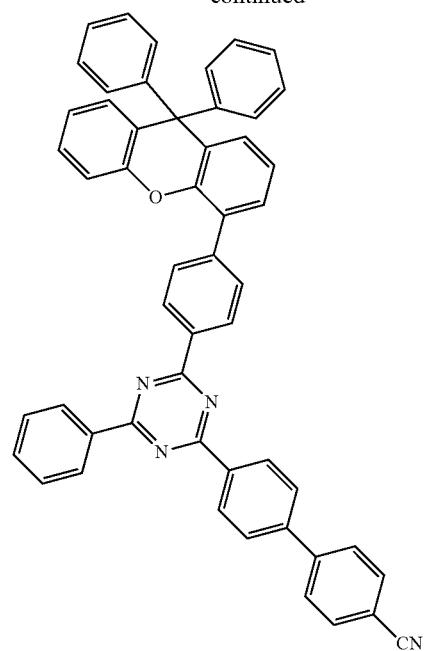
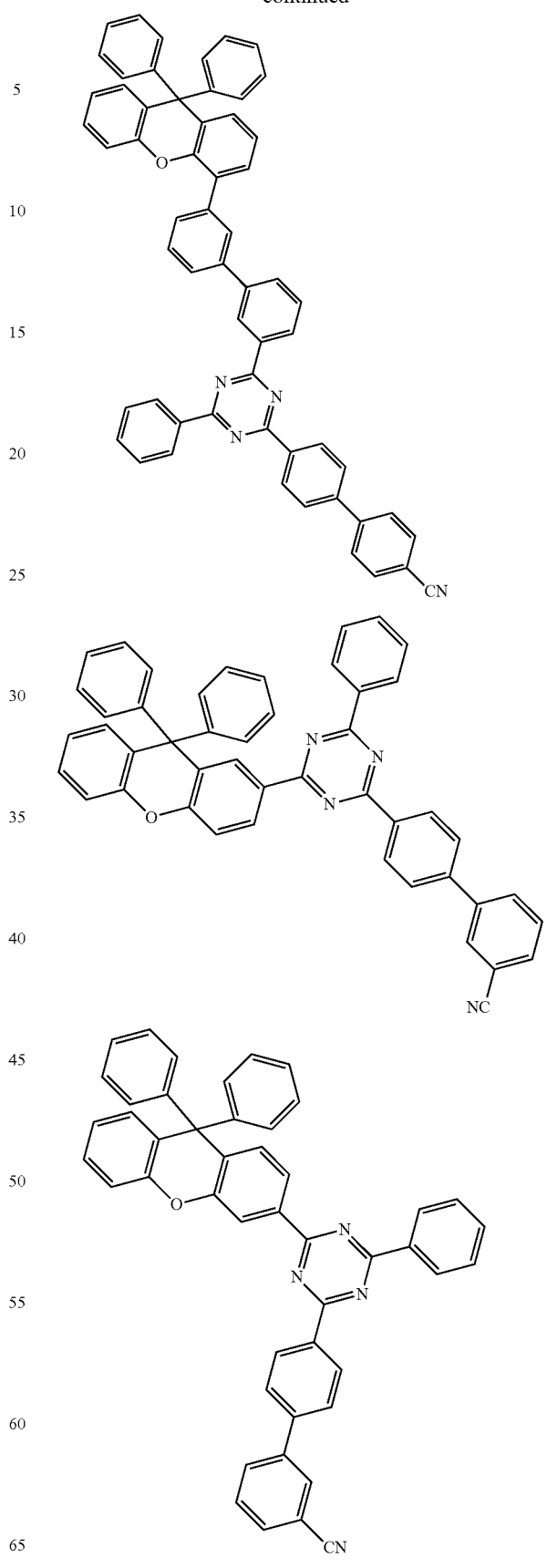

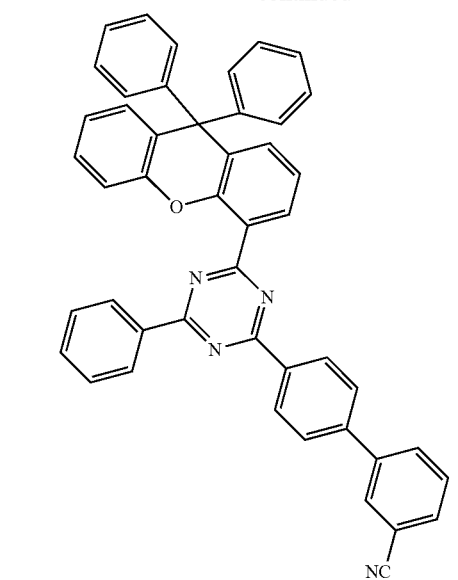
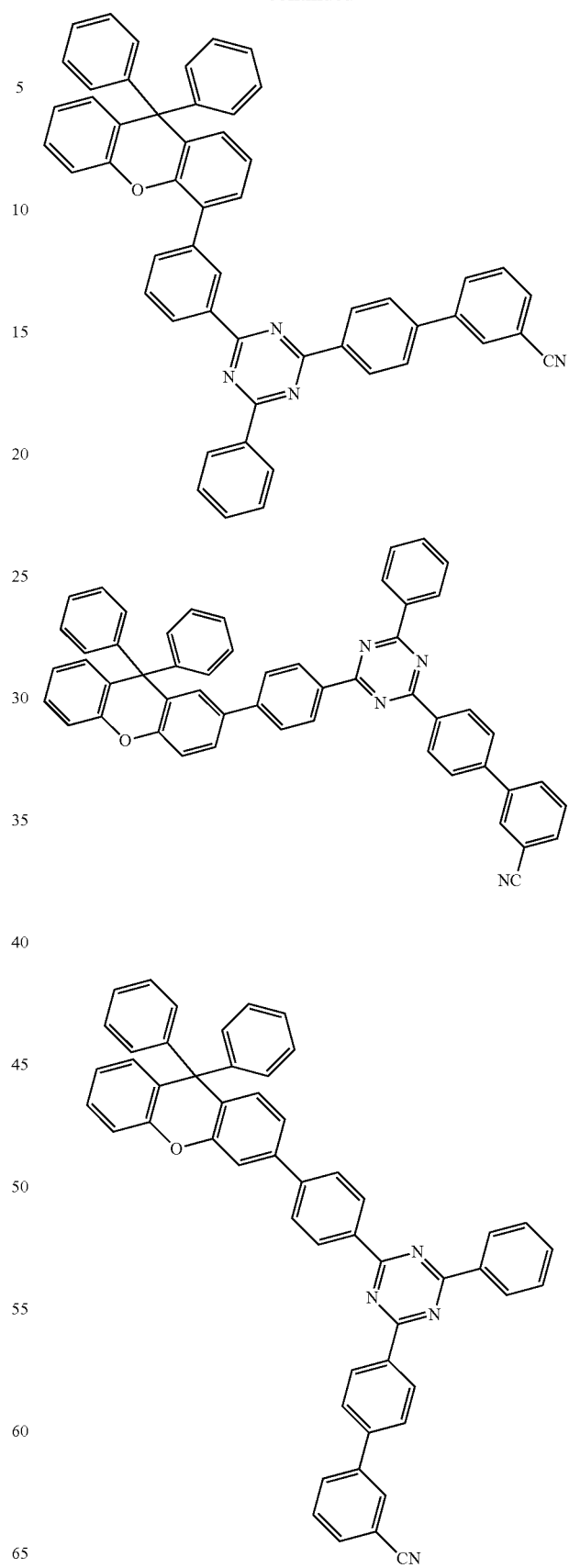

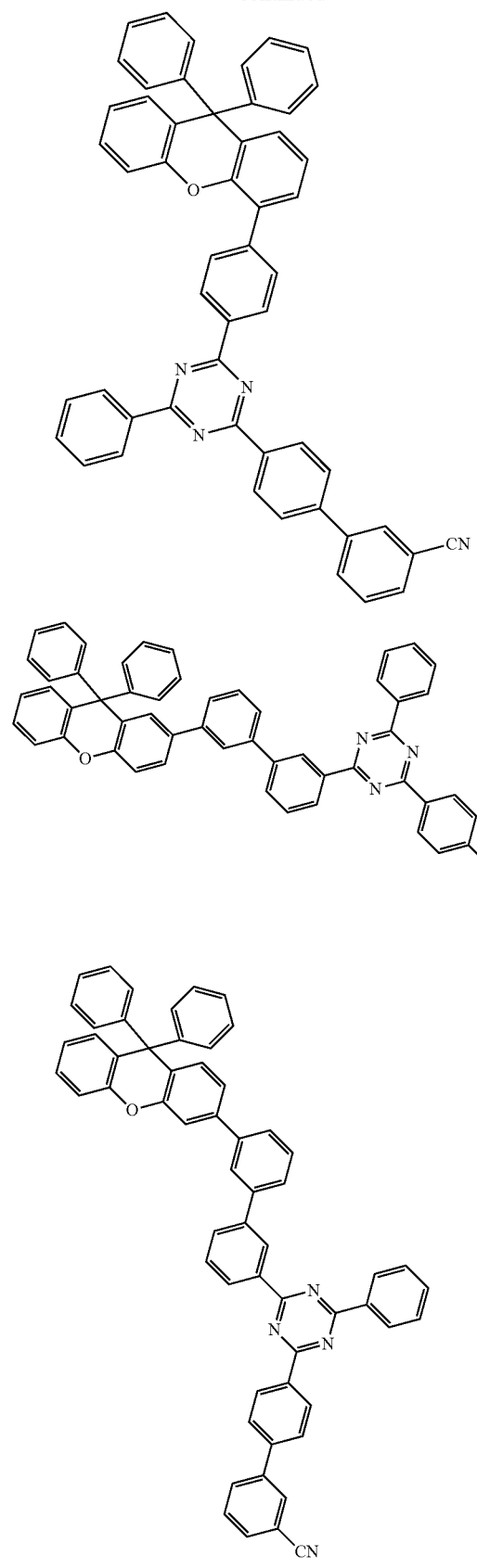
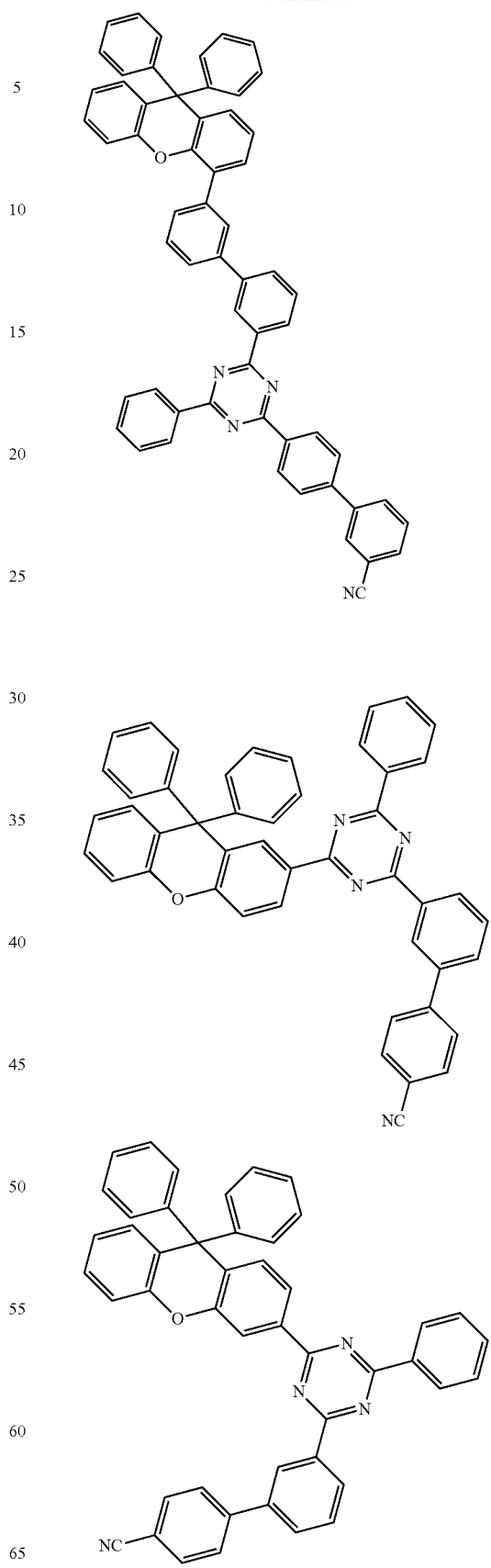

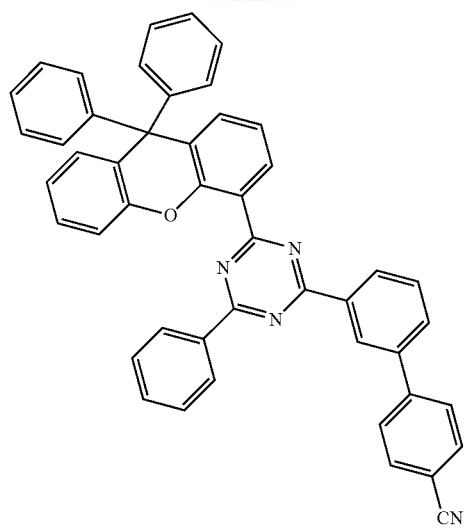
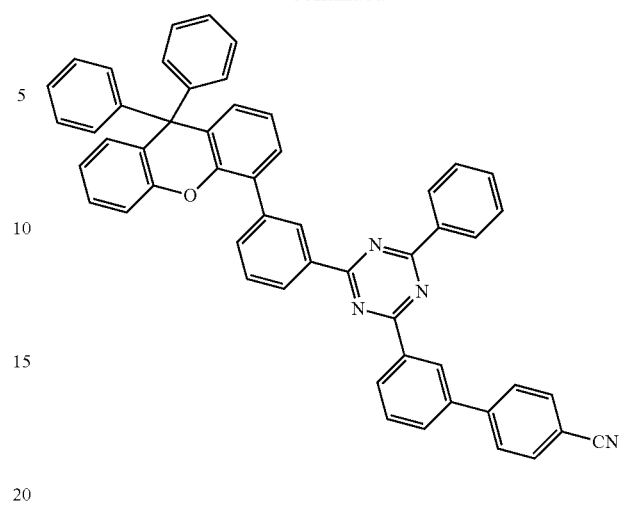
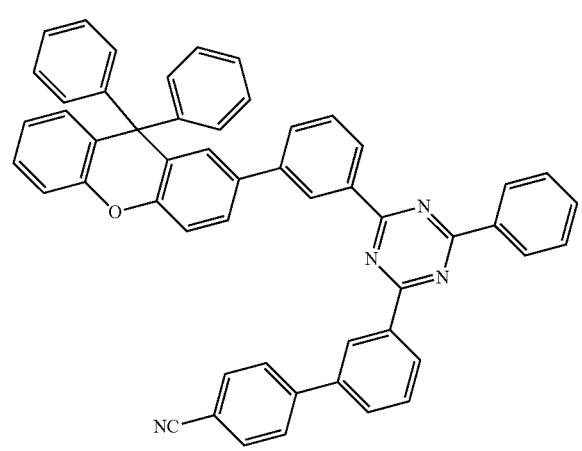
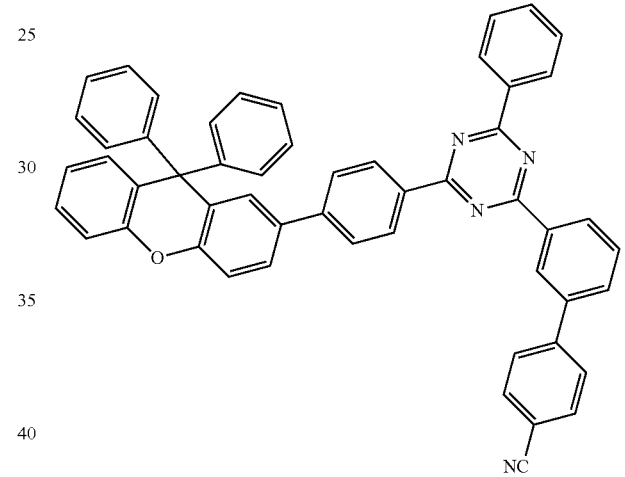
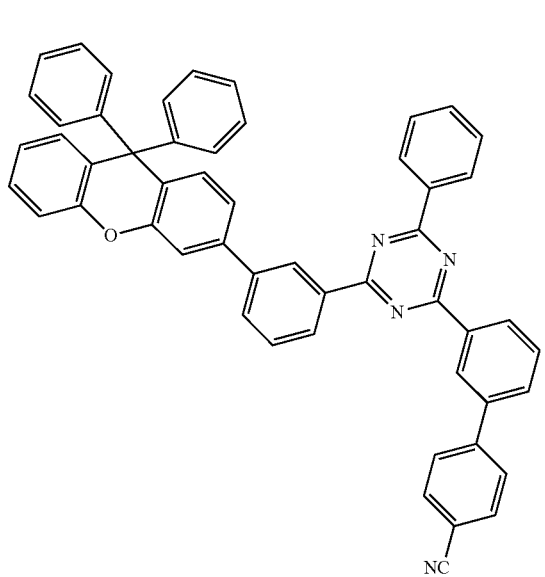
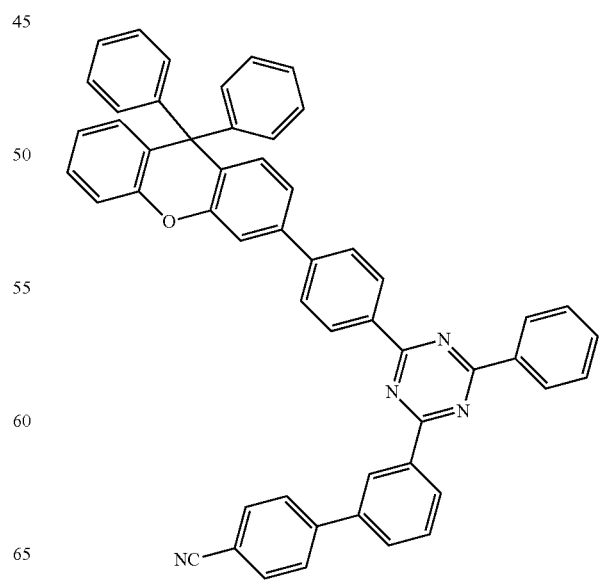

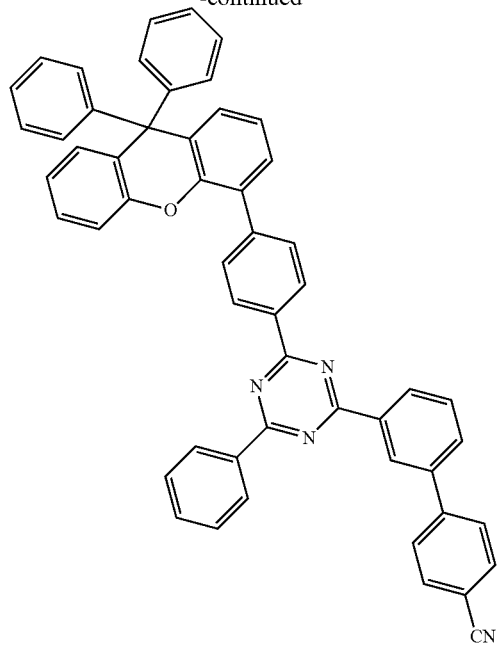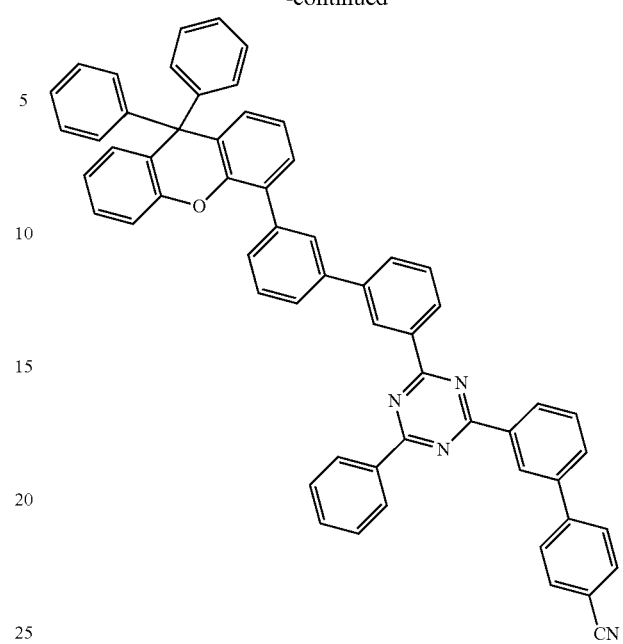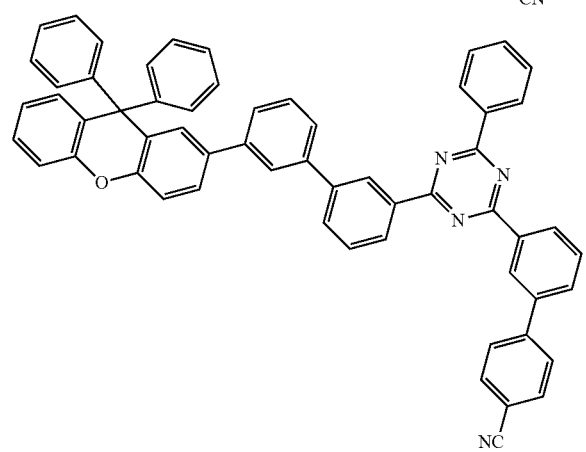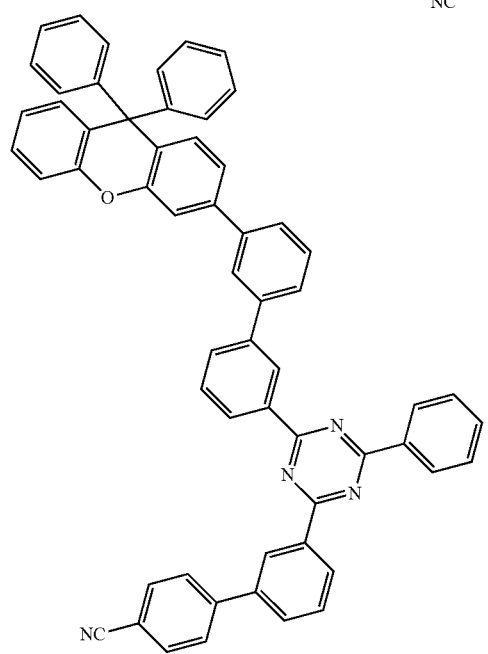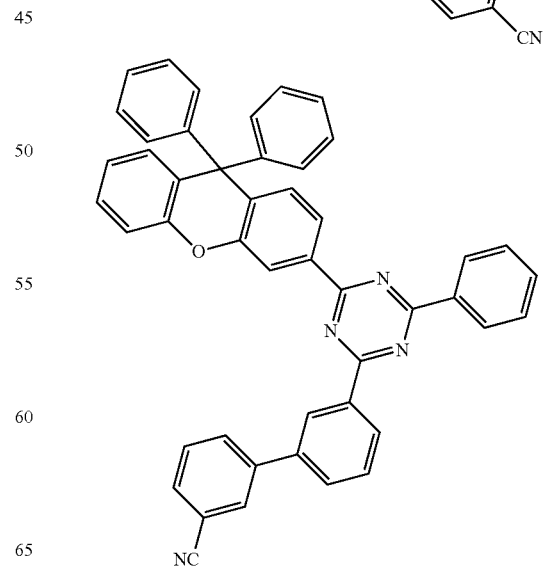

31
-continued
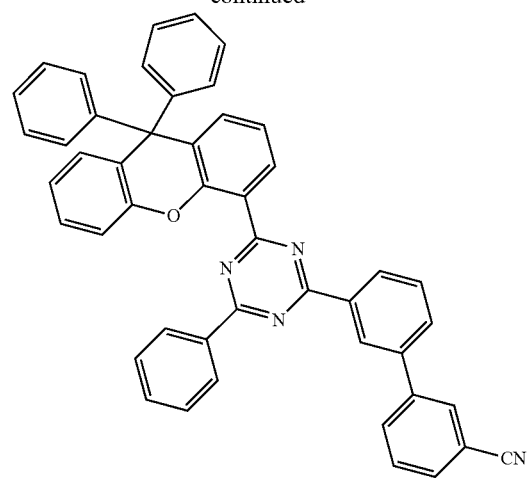
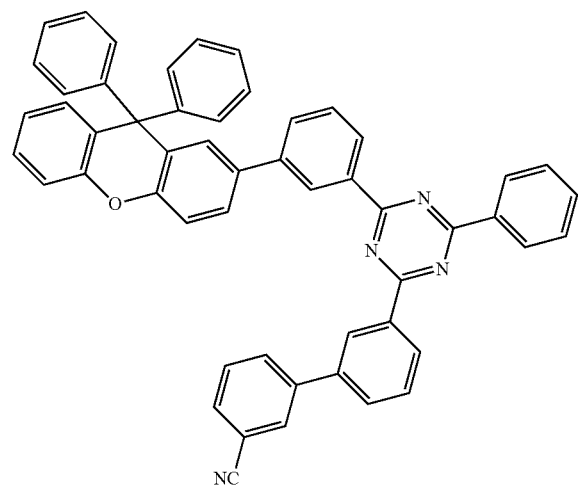
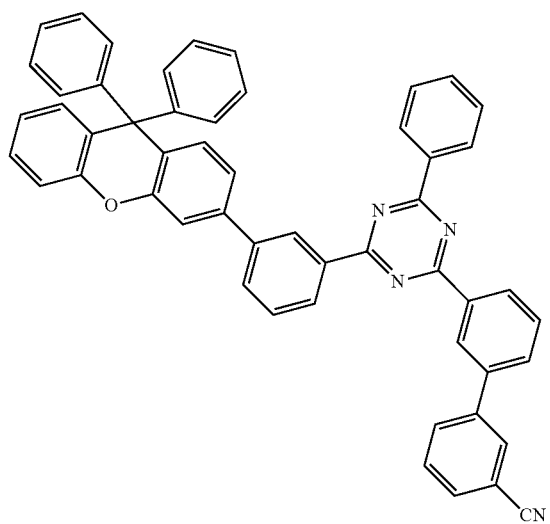
32
-continued
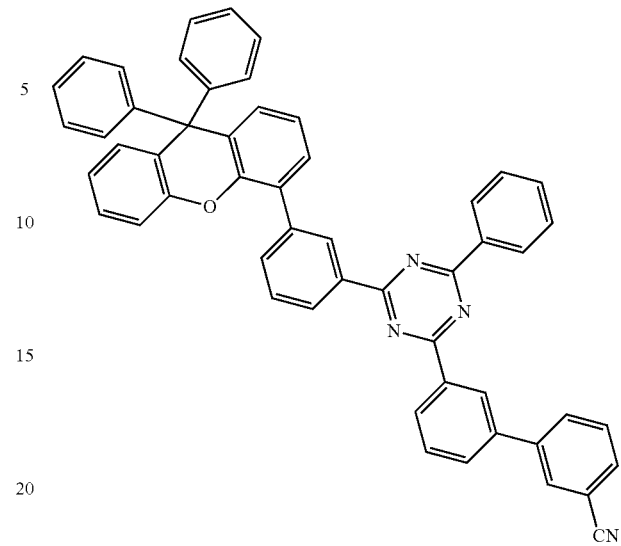
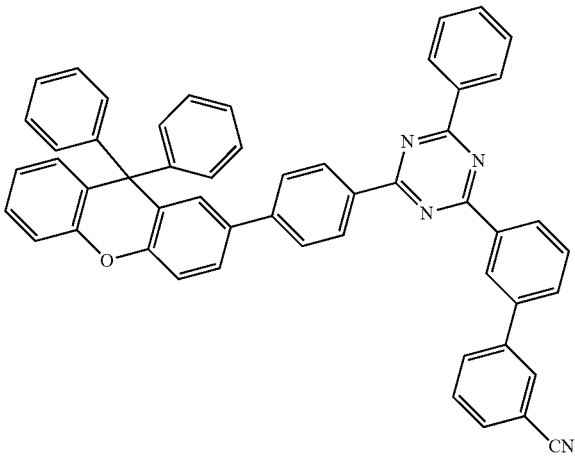
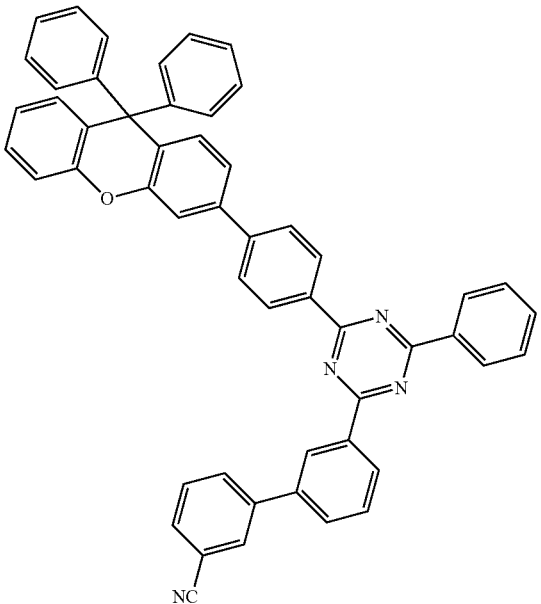

33
-continued
34
-continued
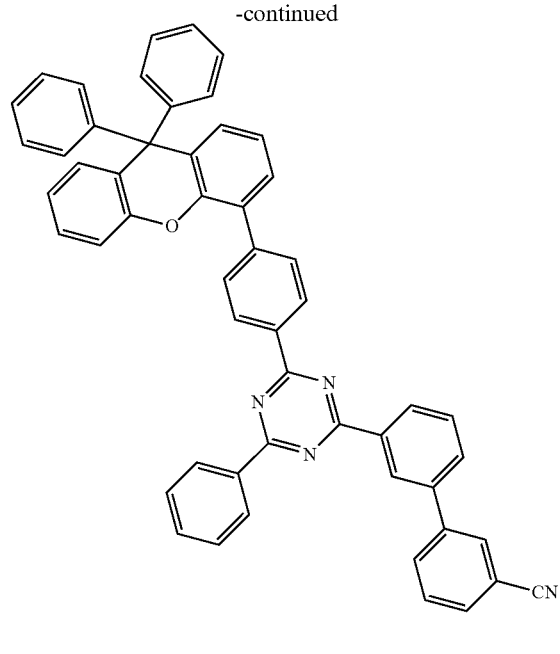
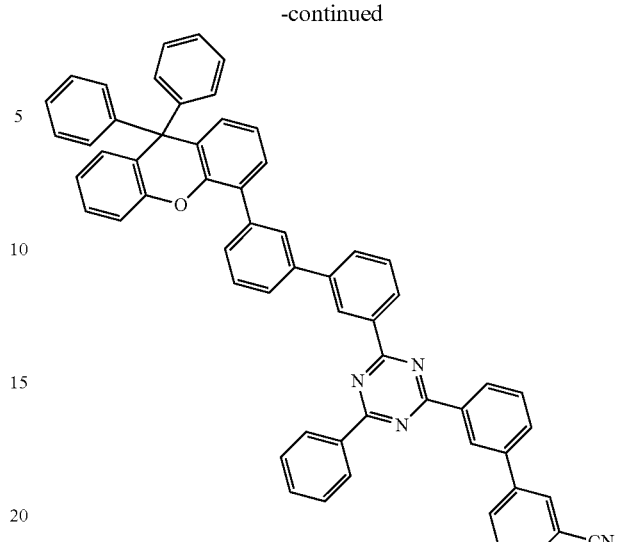
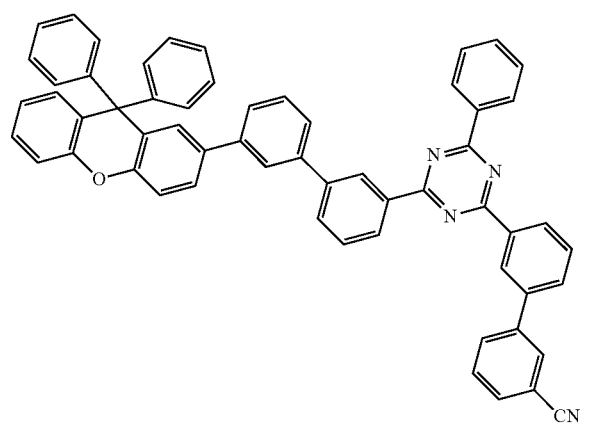
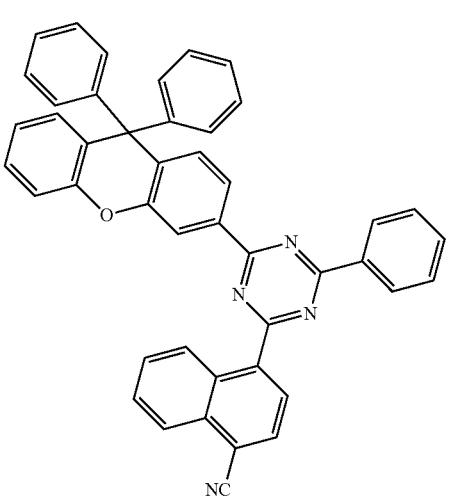
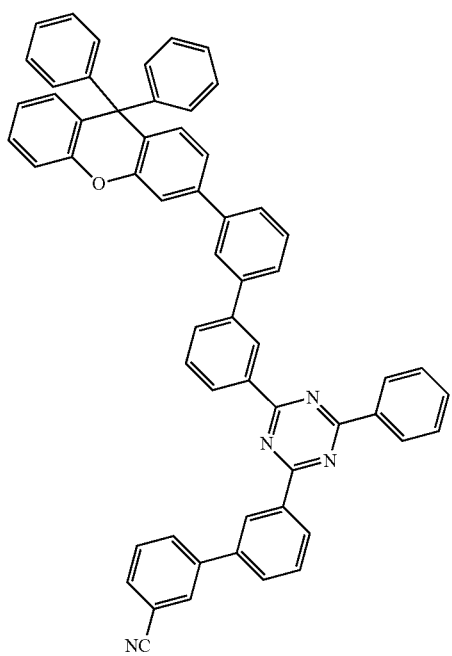

35
-continued
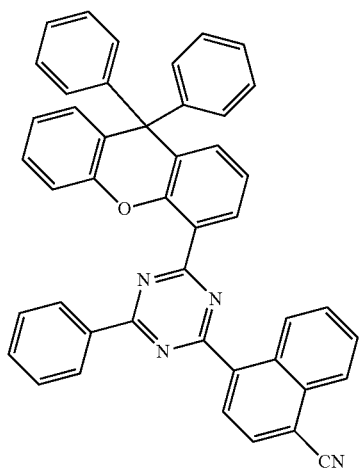
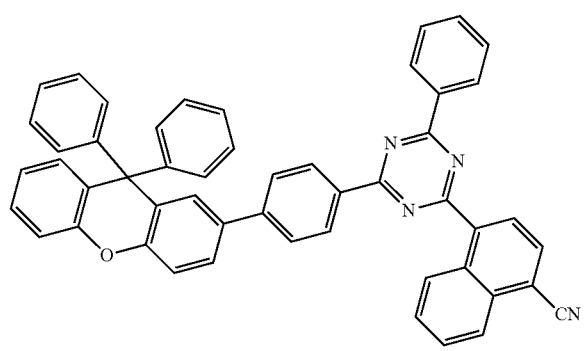
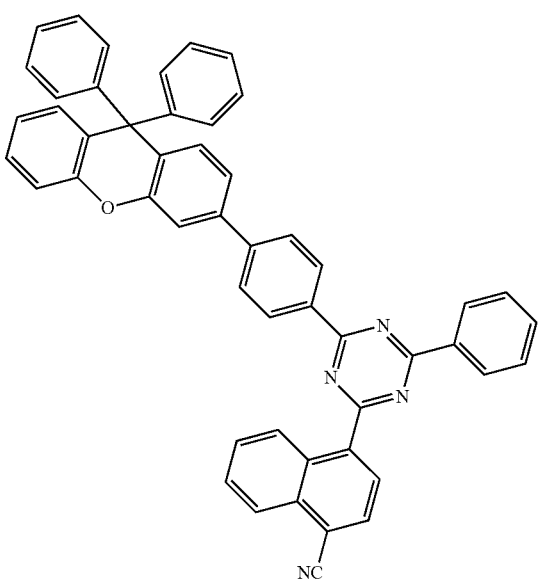
36
-continued
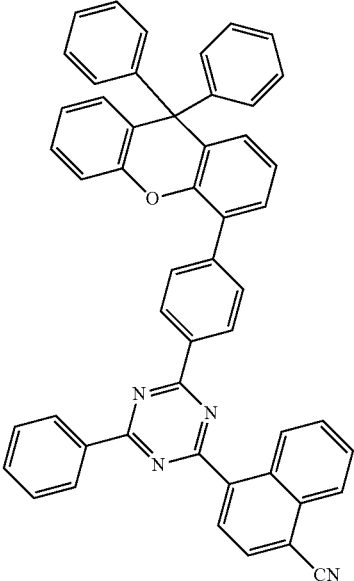
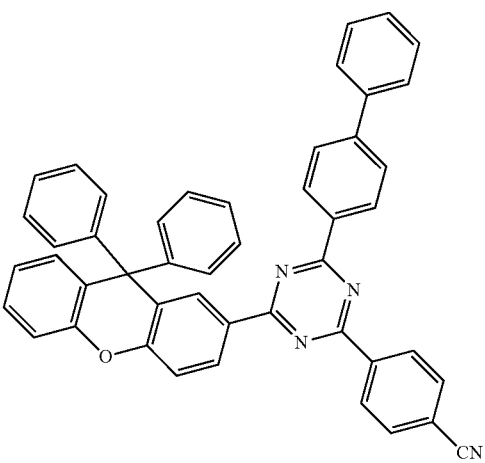
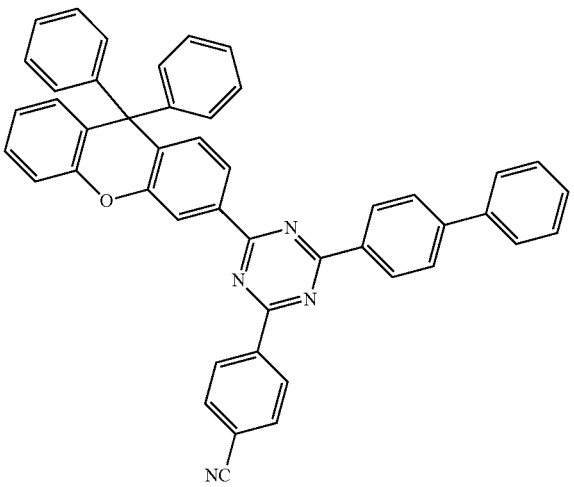

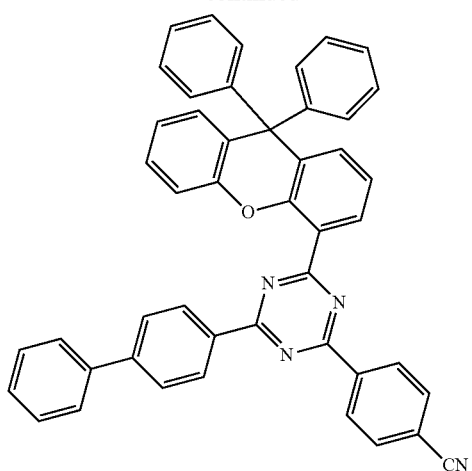
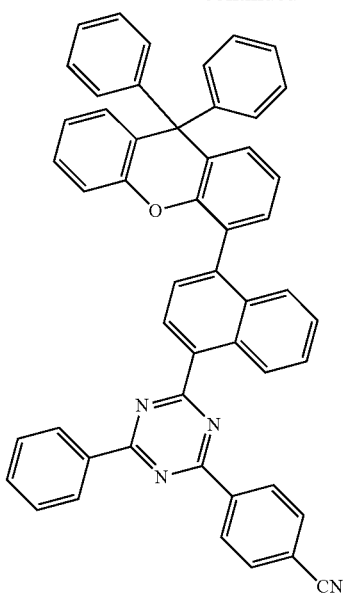
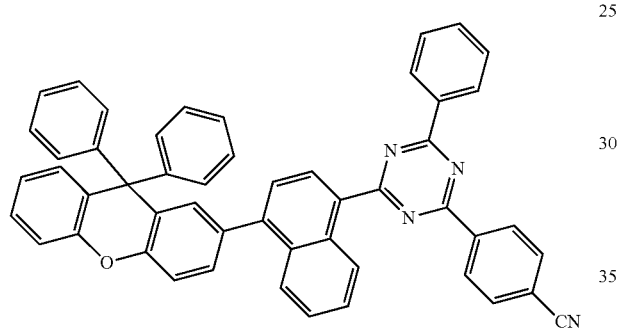
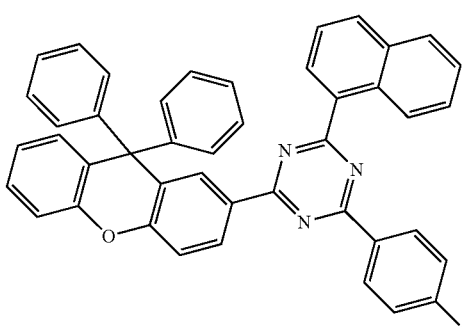
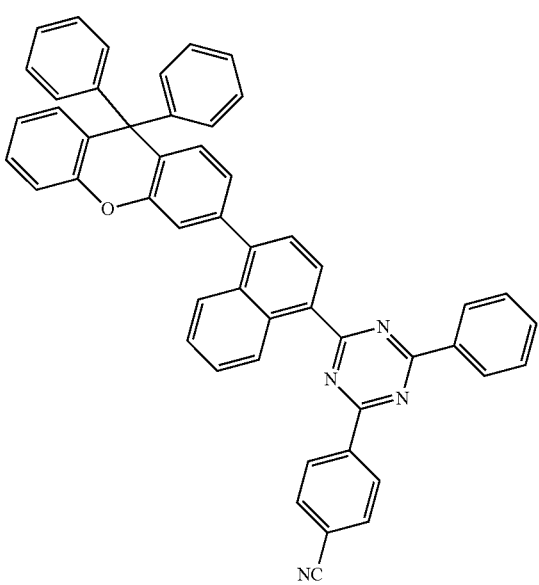
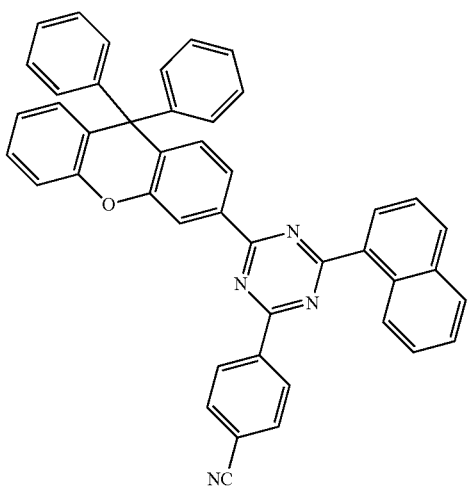

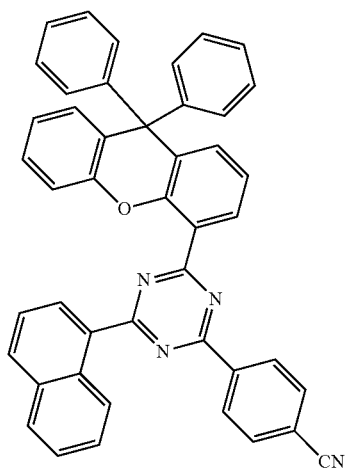
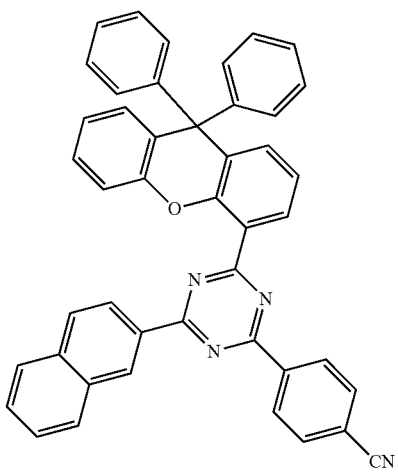
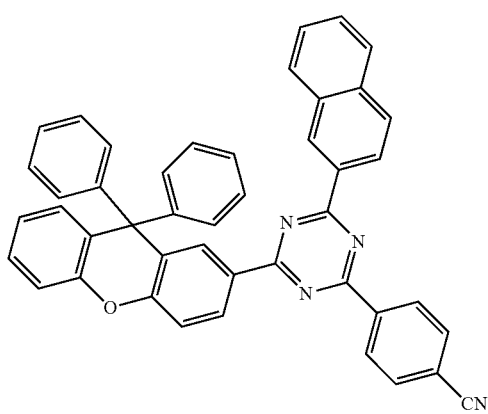
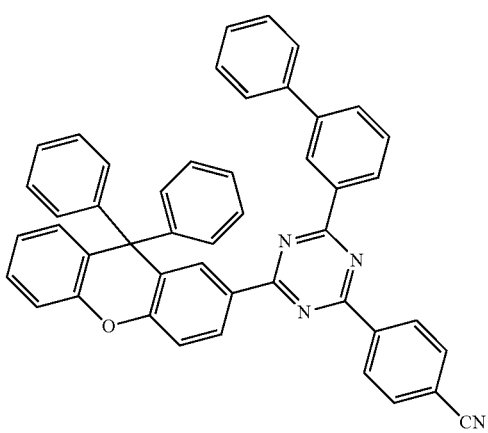
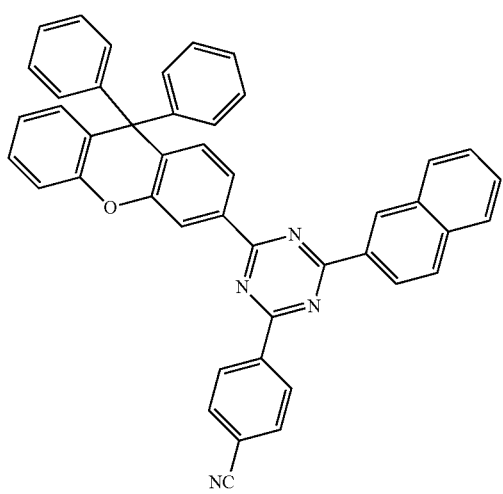
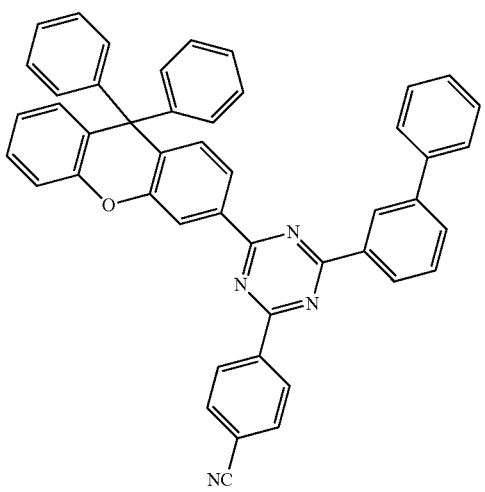

41
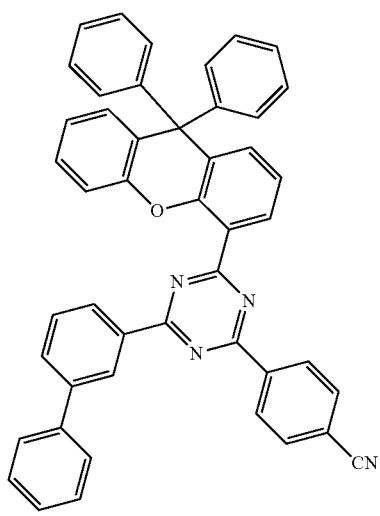
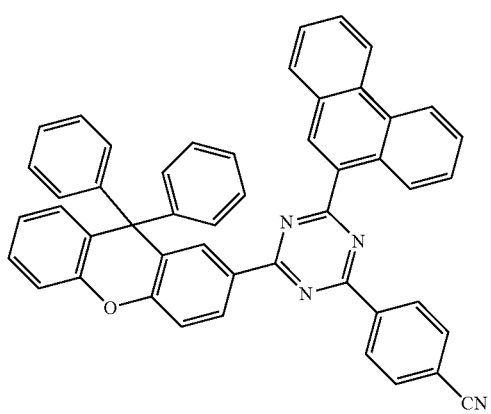
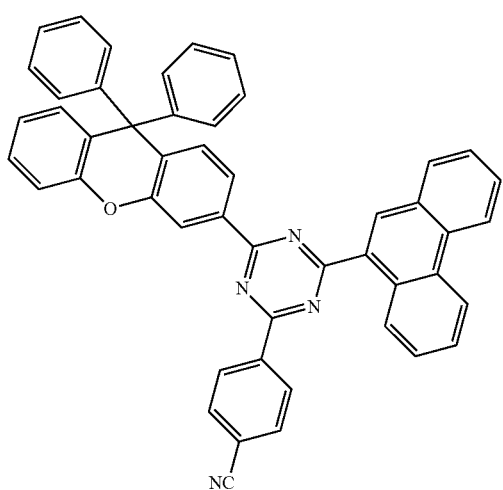
42
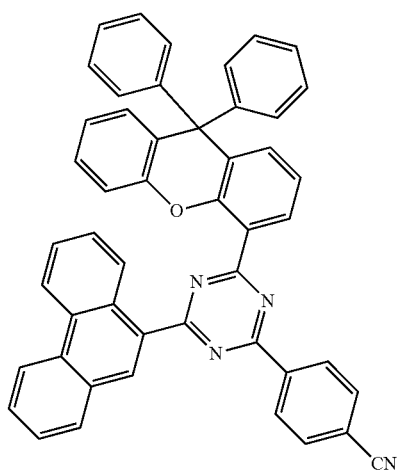
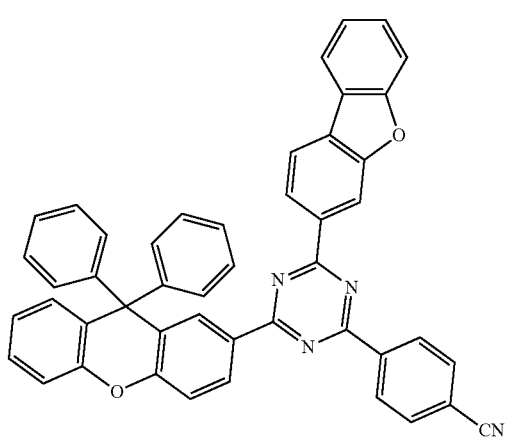
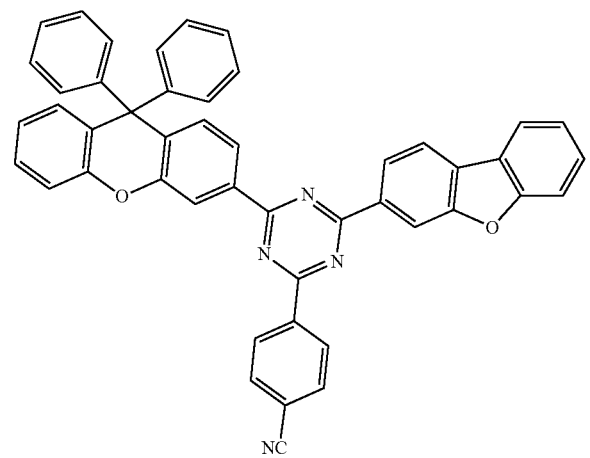

43
-continued
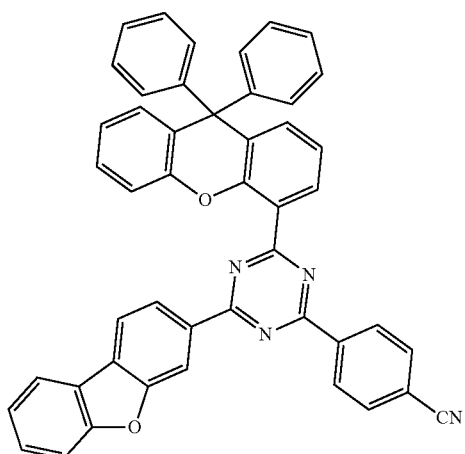
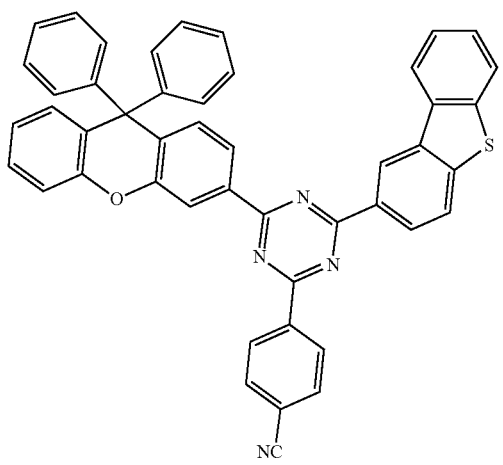
44
-continued
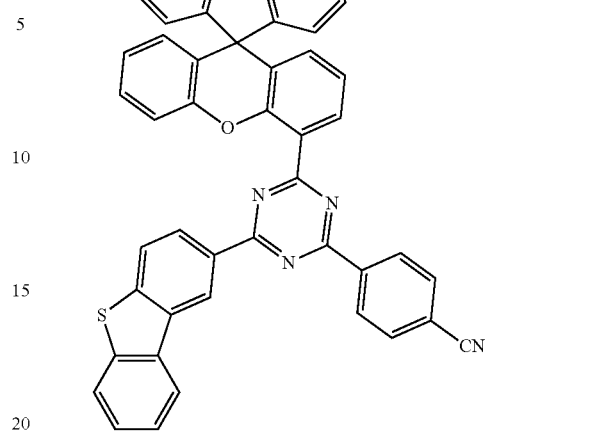
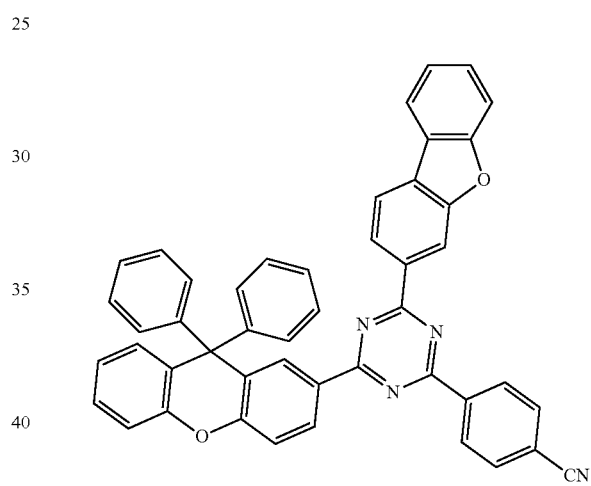
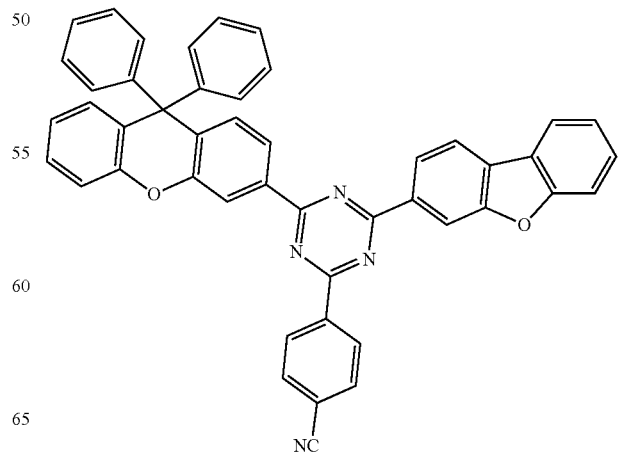

45
-continued
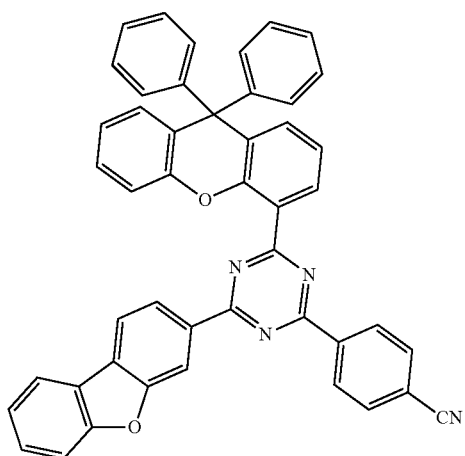
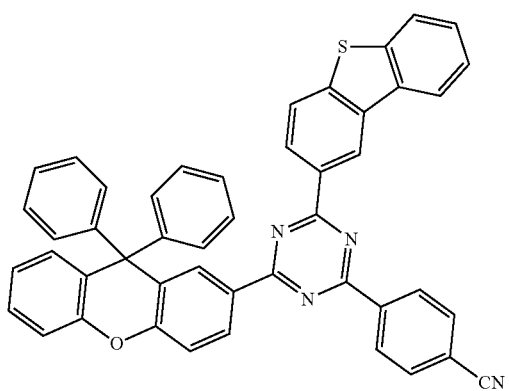
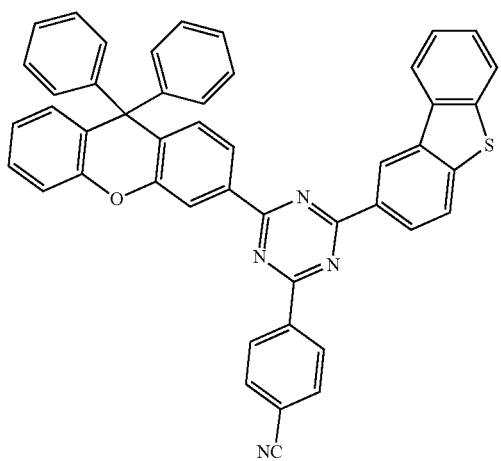
46
-continued
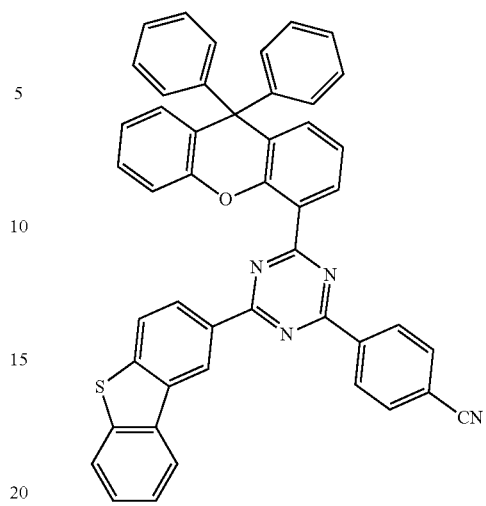
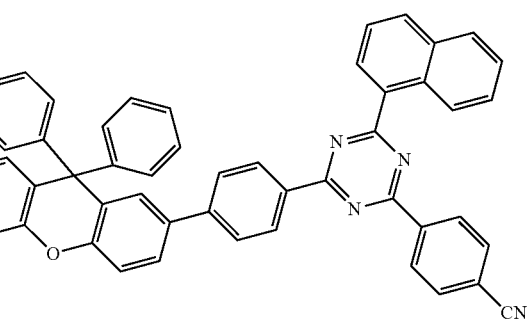
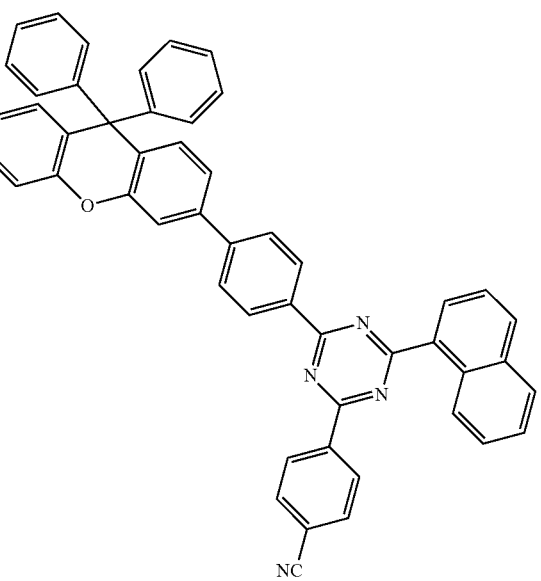

47
-continued
48
-continued
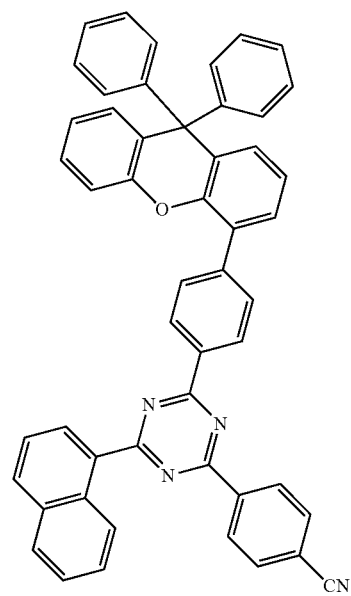
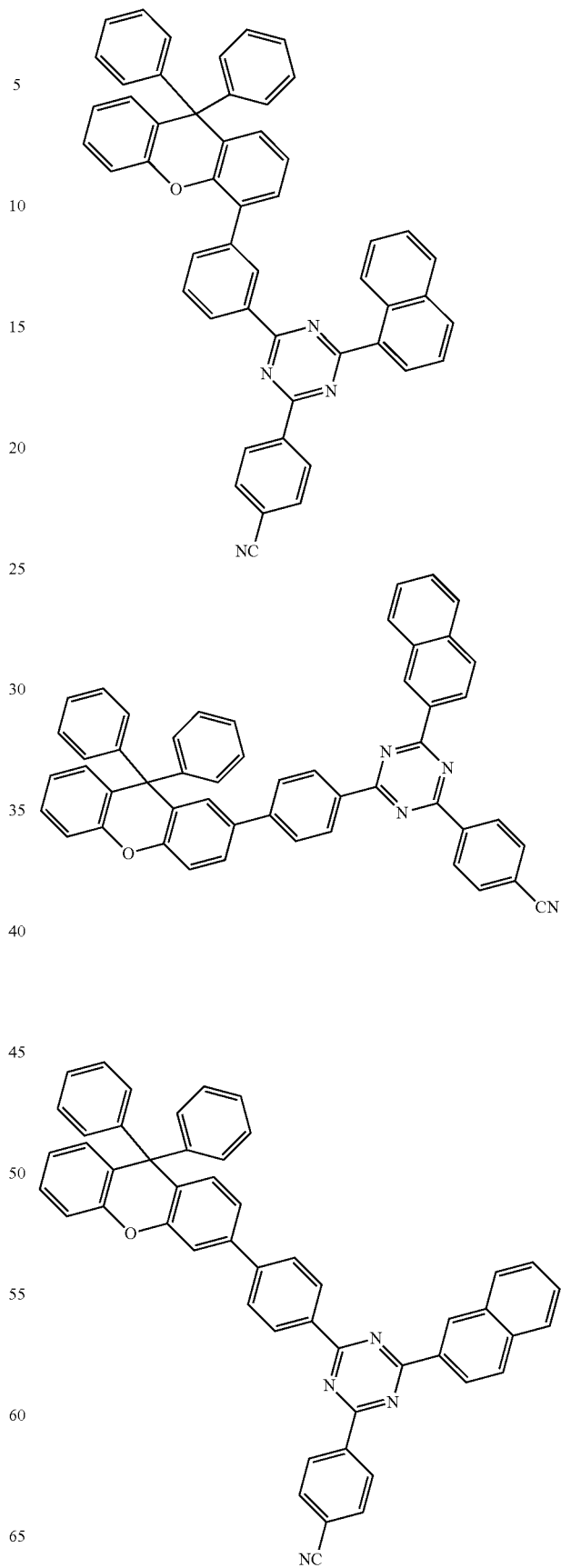

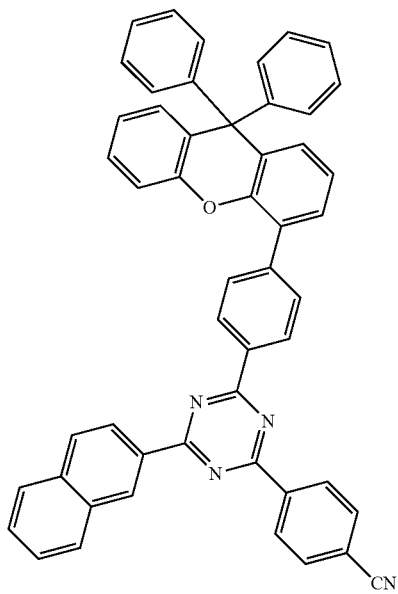
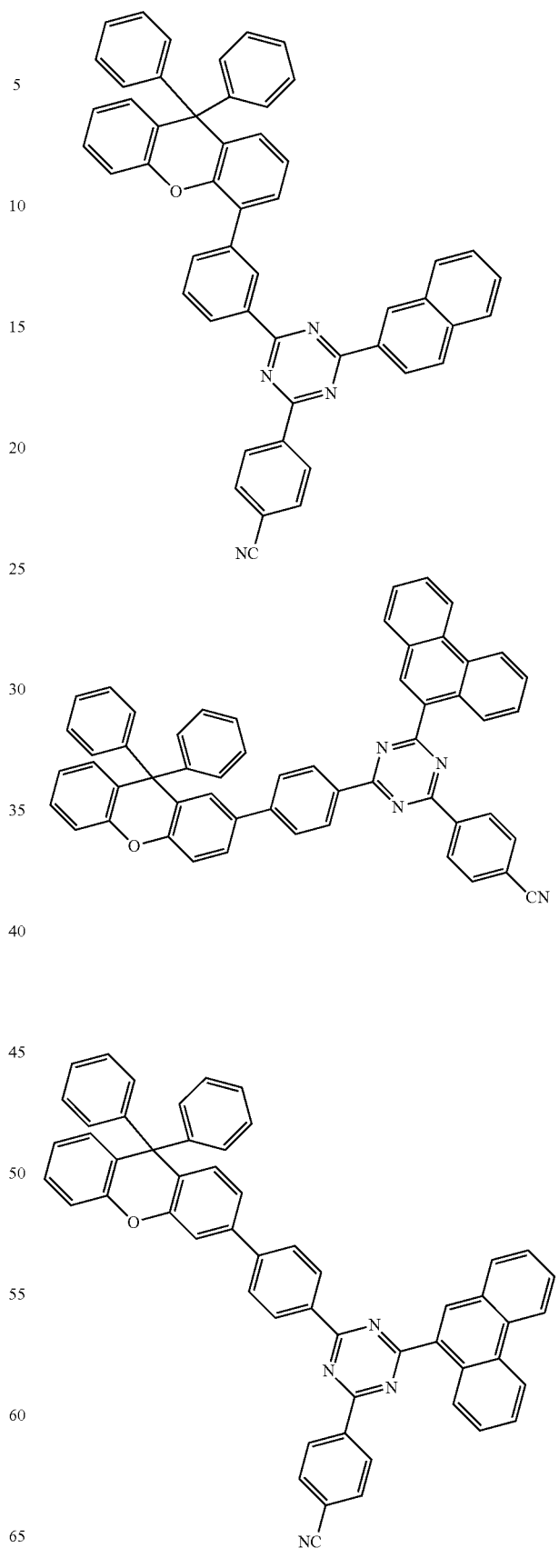

51
-continued
52
-continued
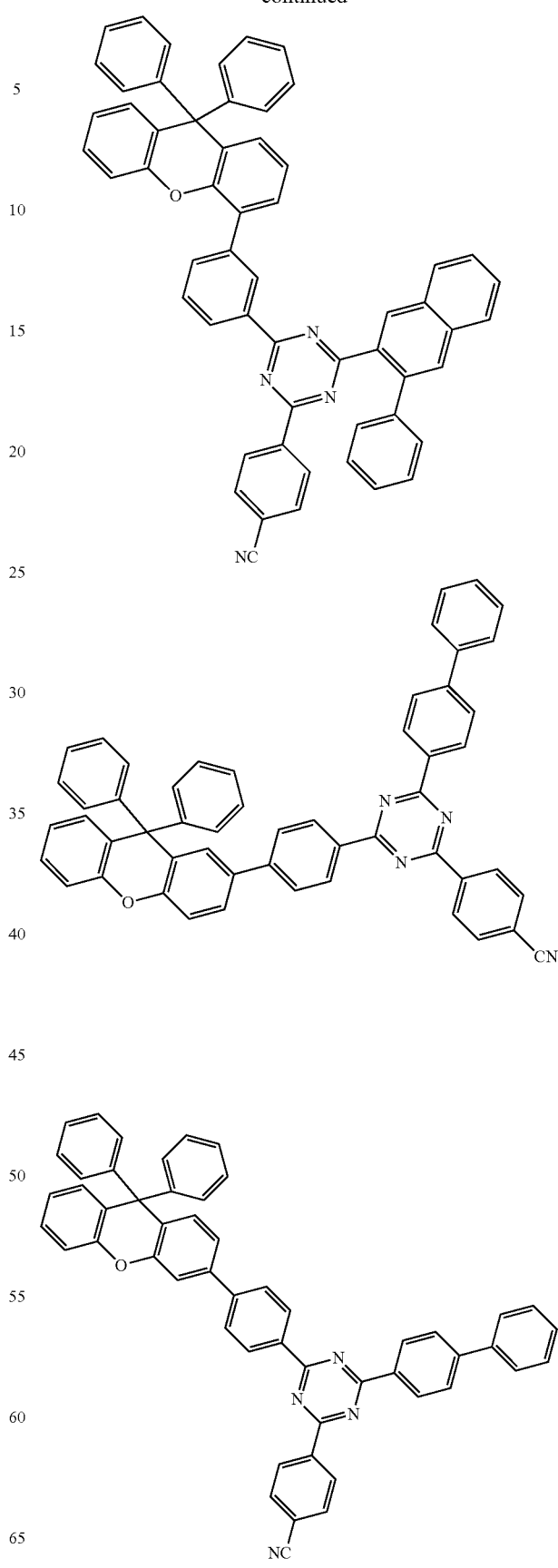

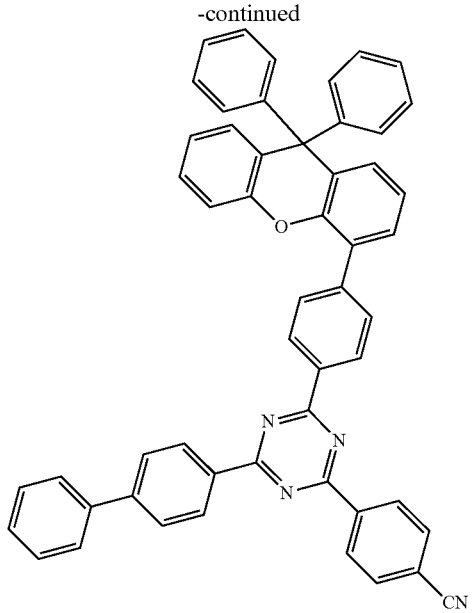
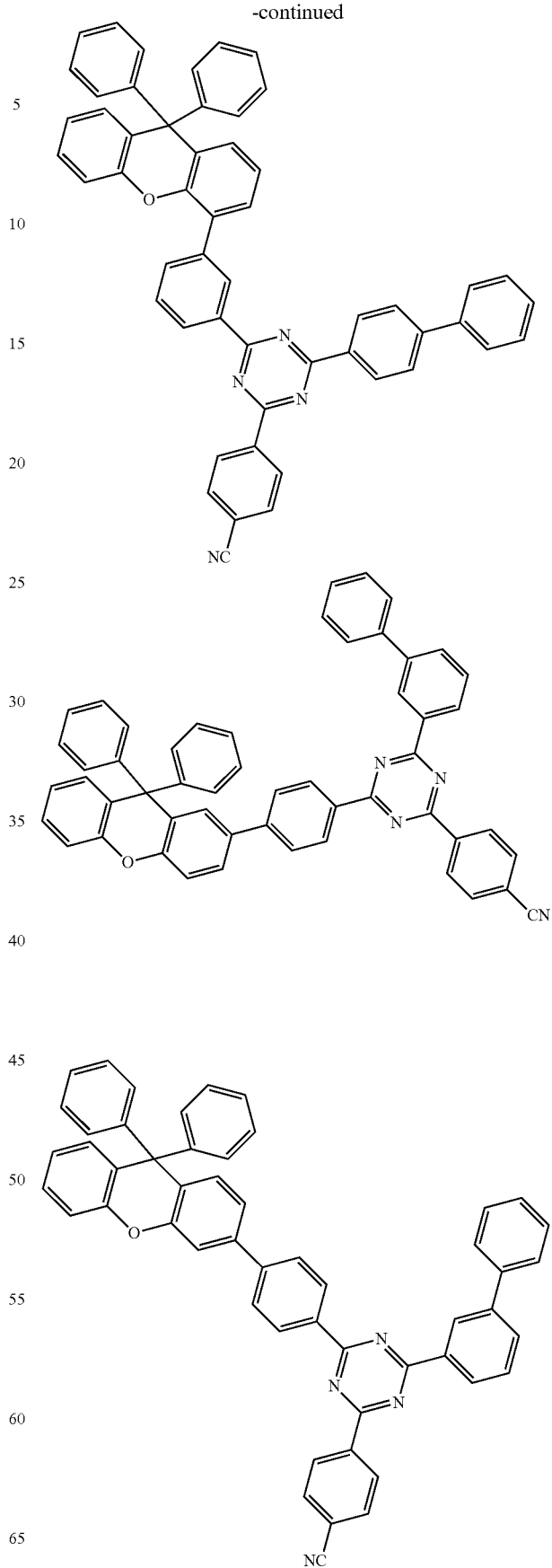

55
-continued
56
-continued
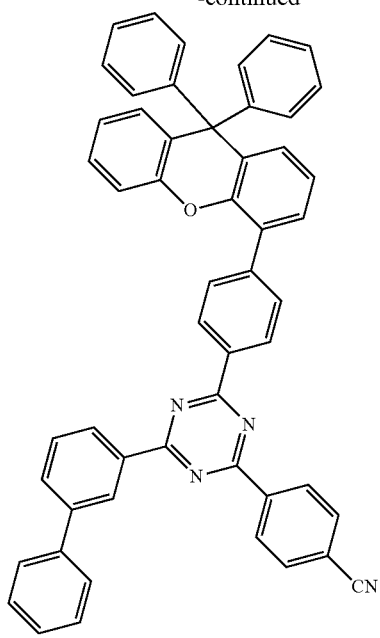
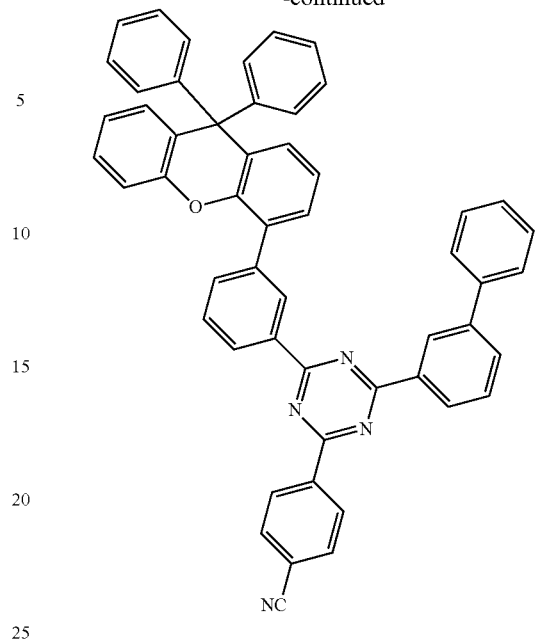
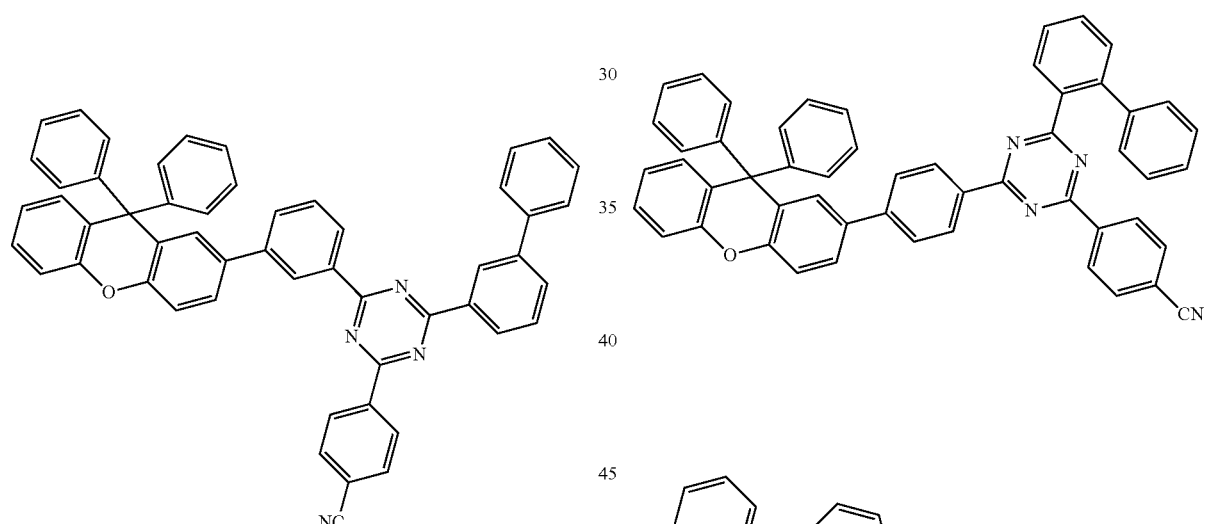
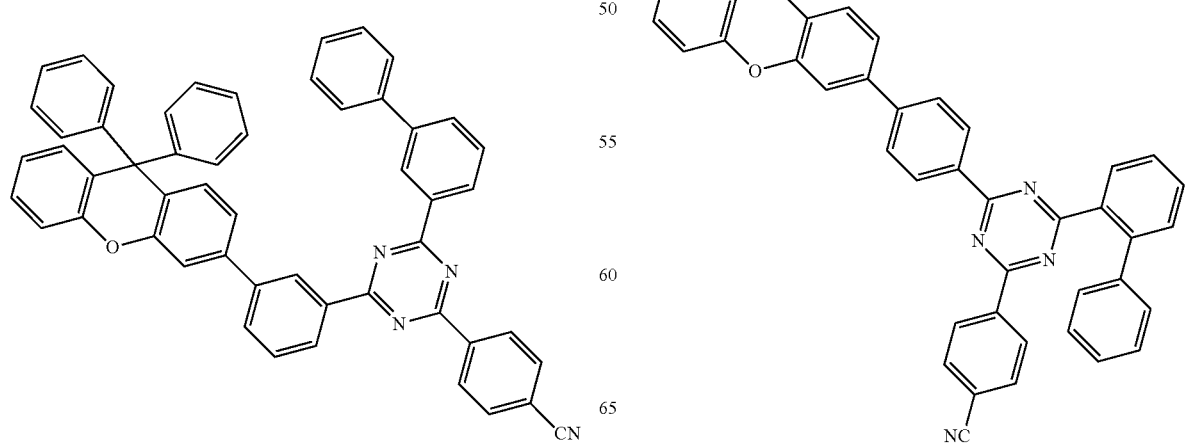

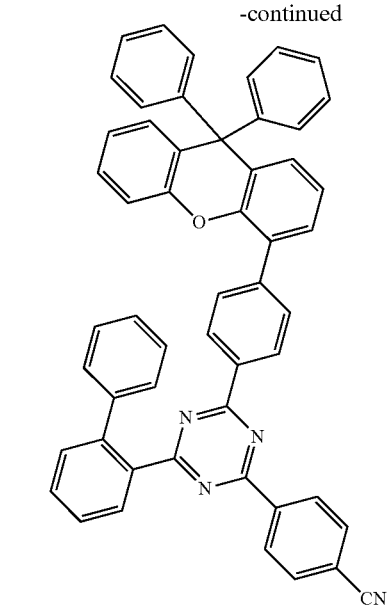
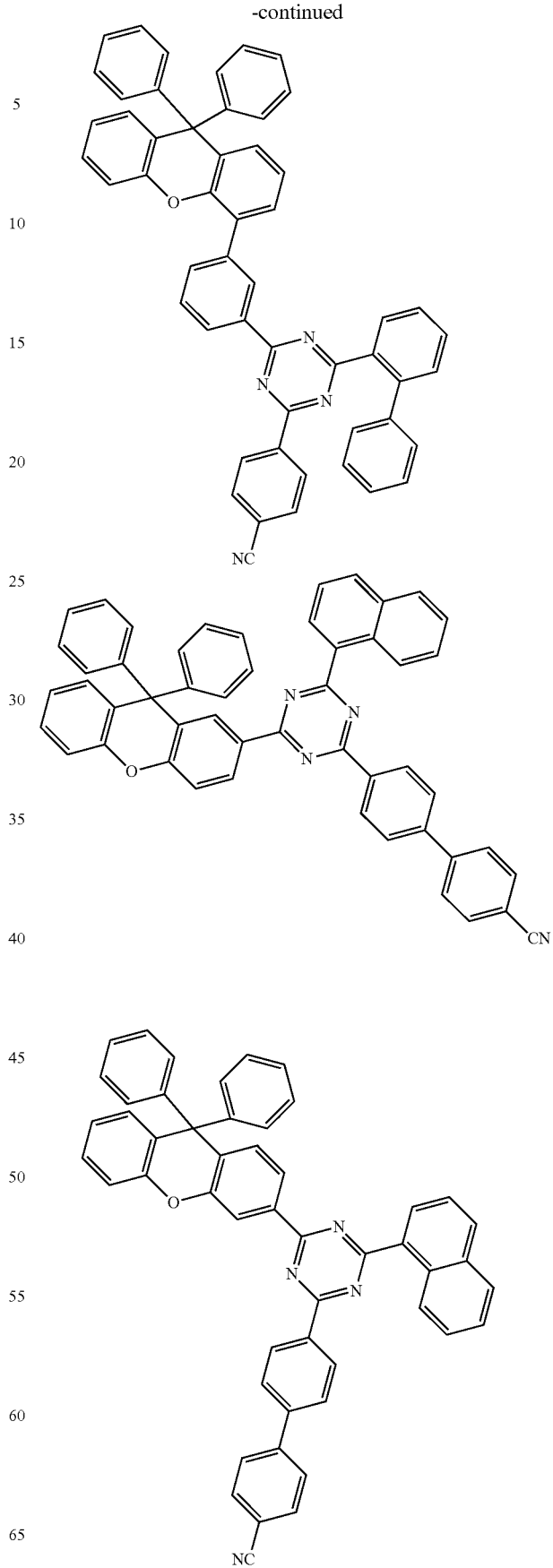

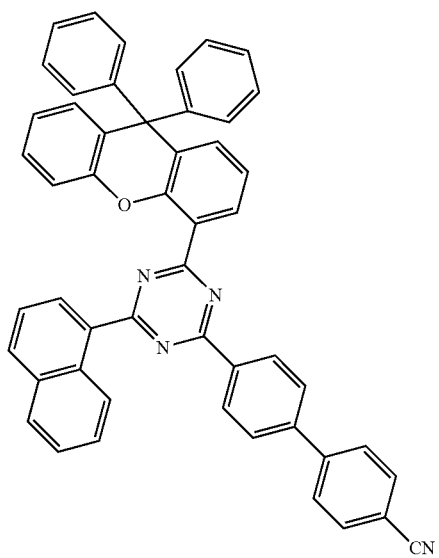
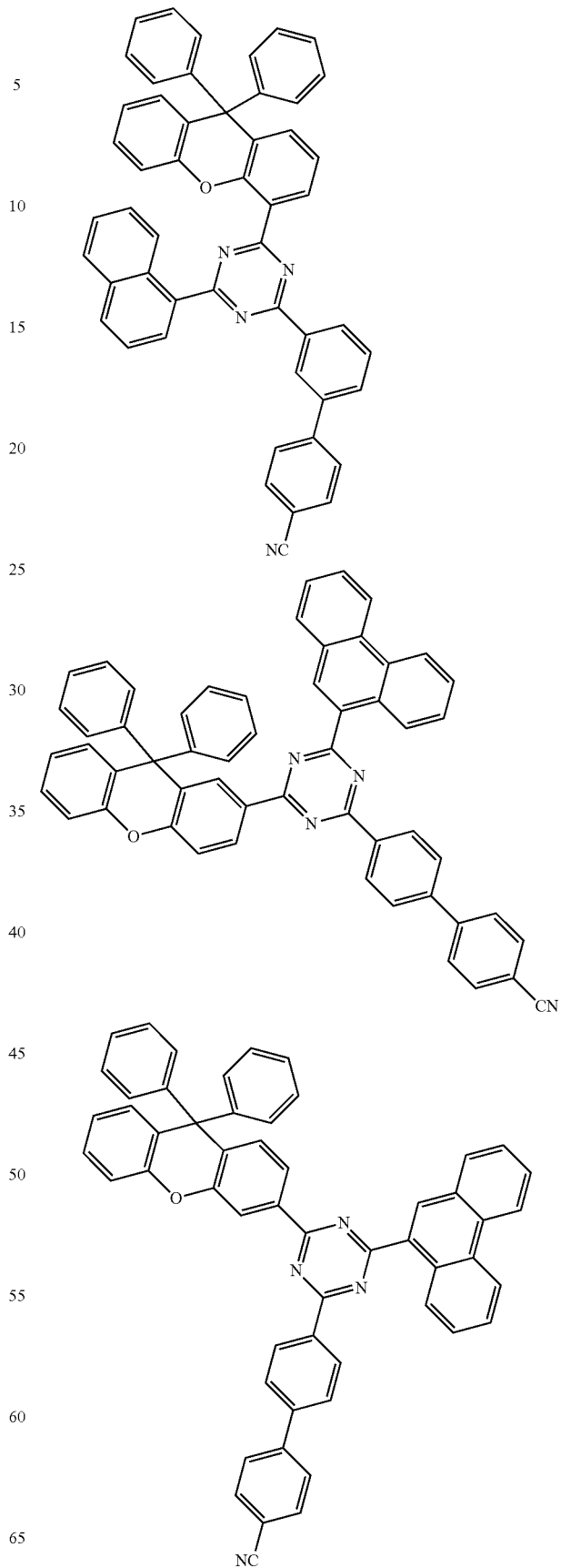

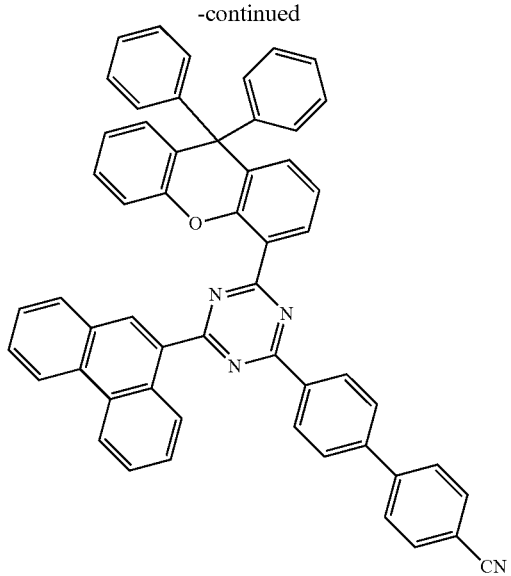
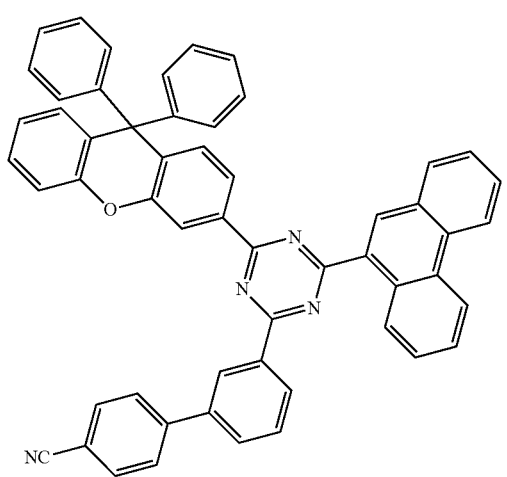
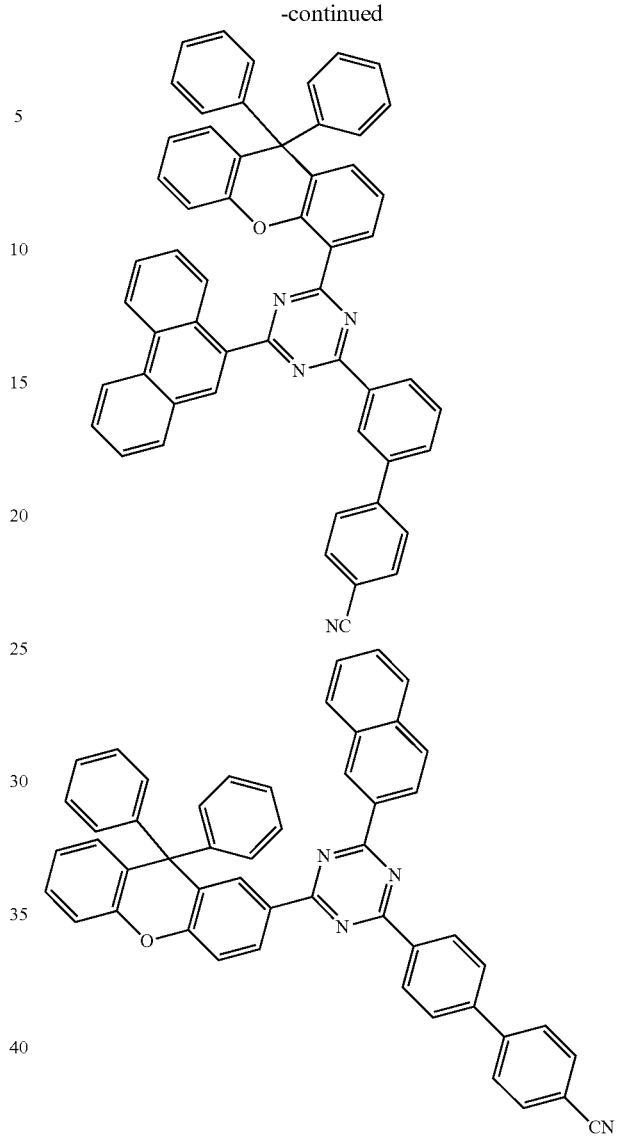

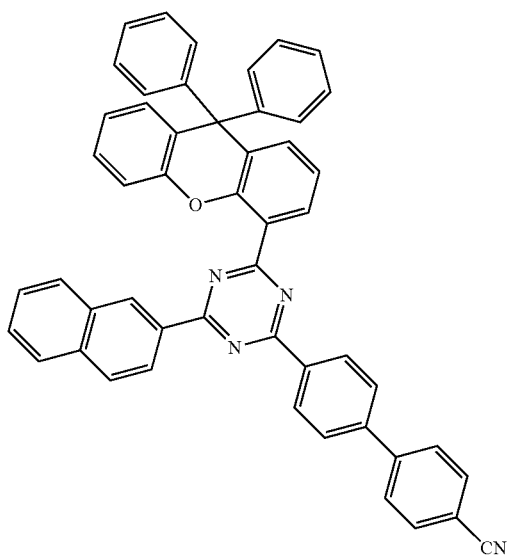
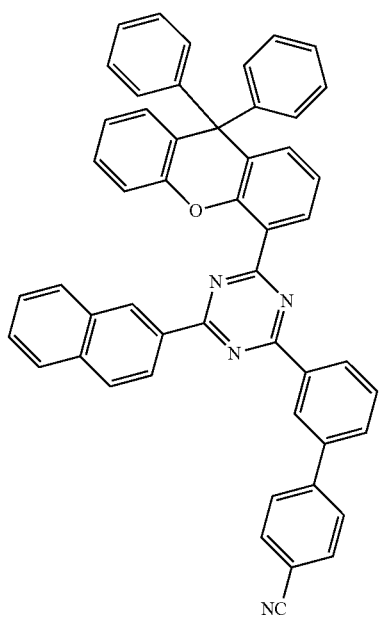
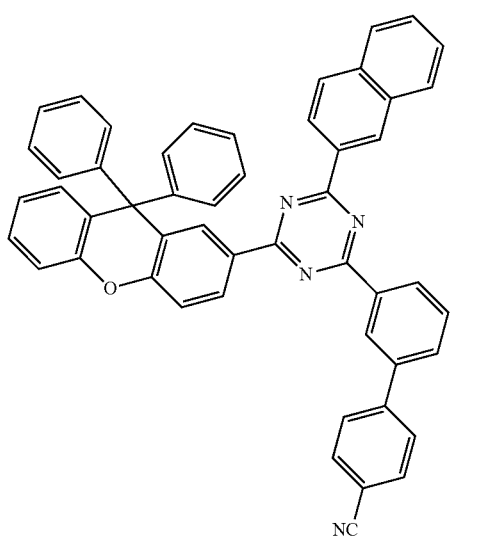
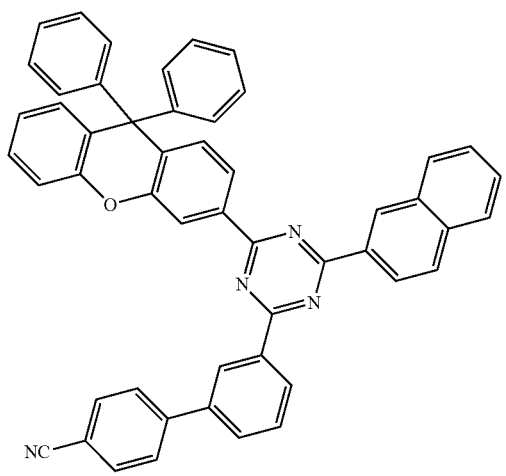
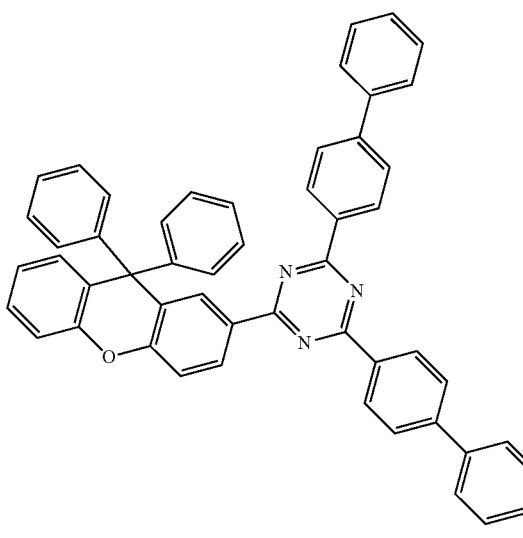

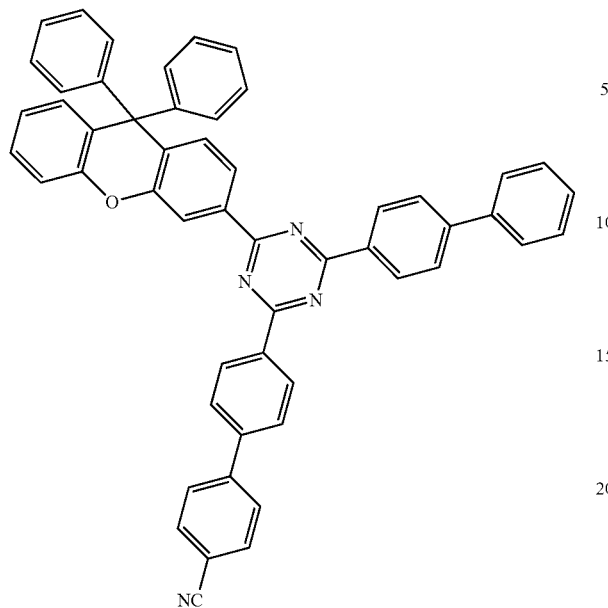
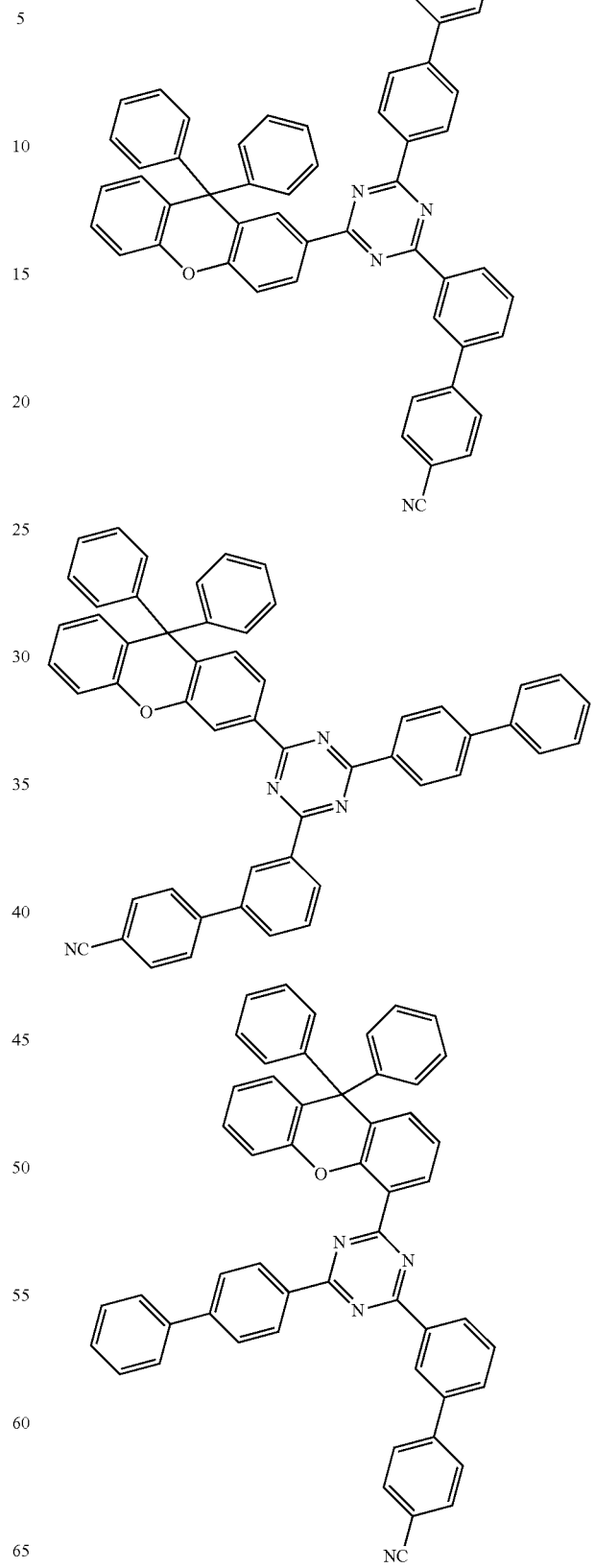

67
-continued
68
-continued
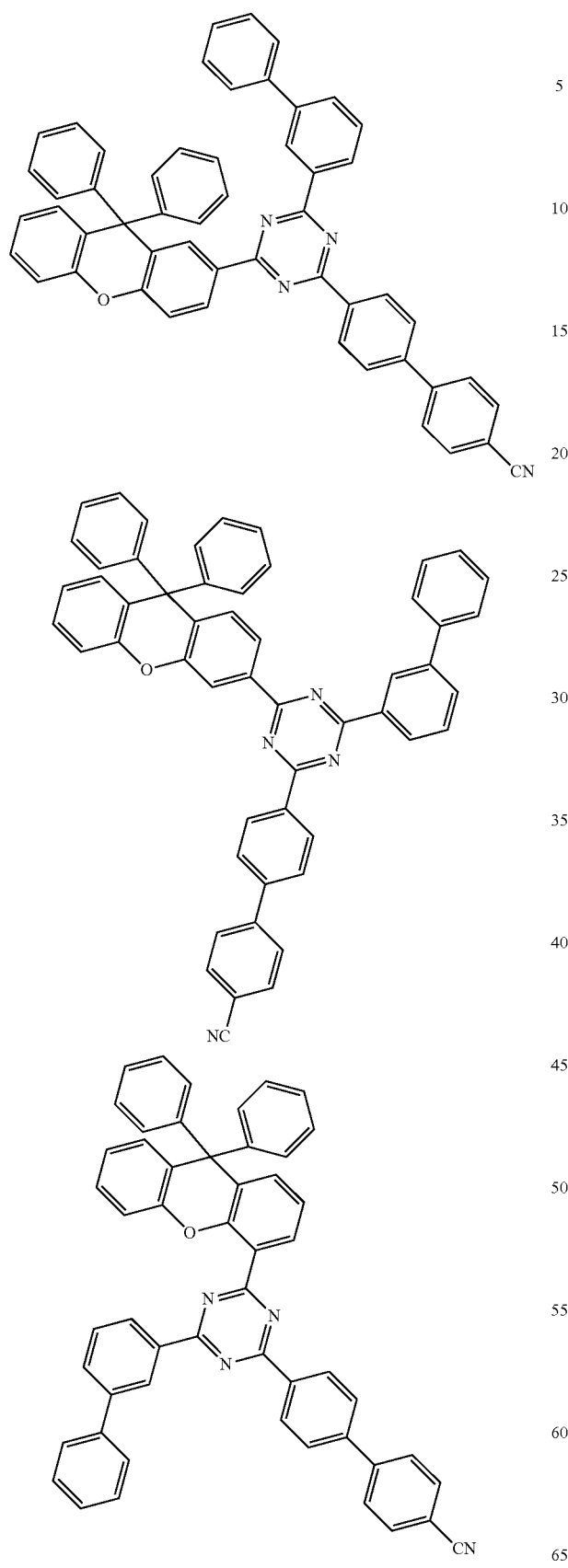
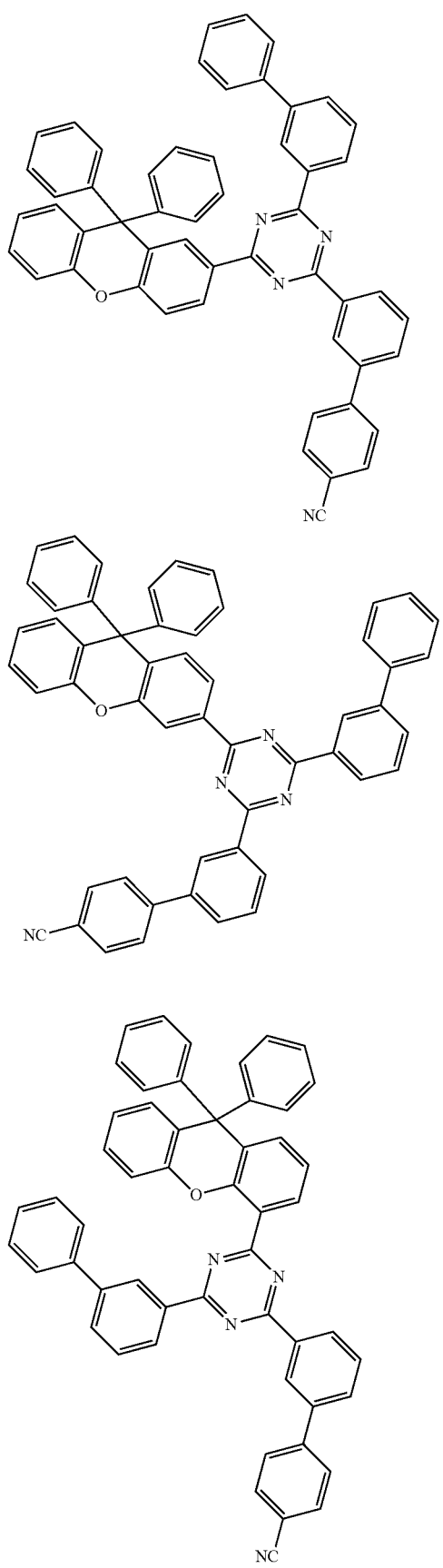

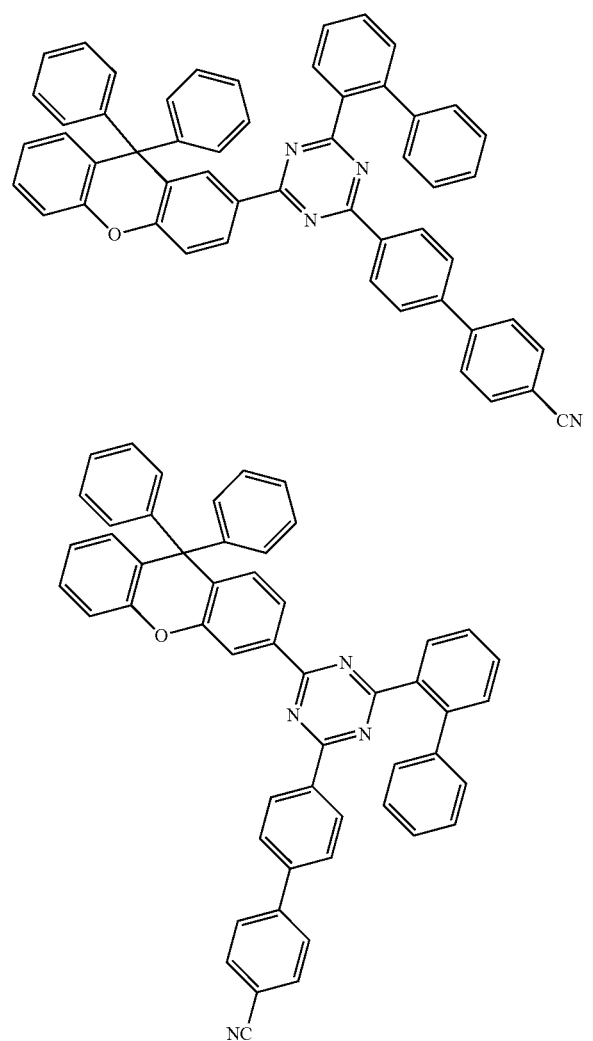
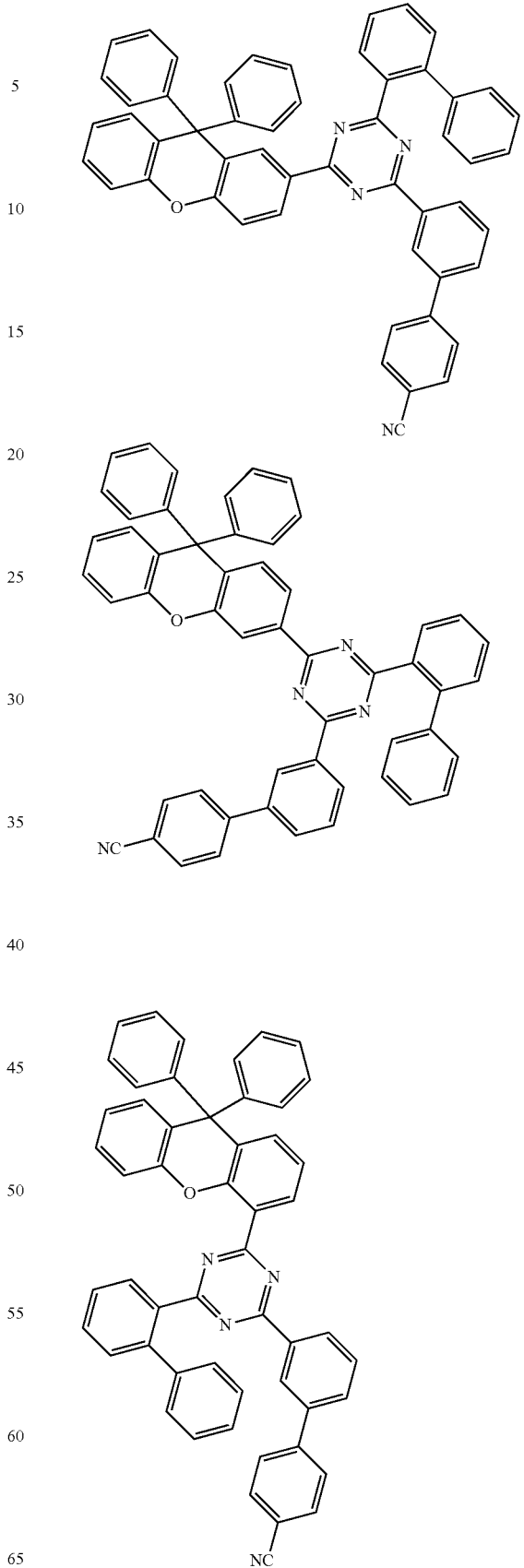

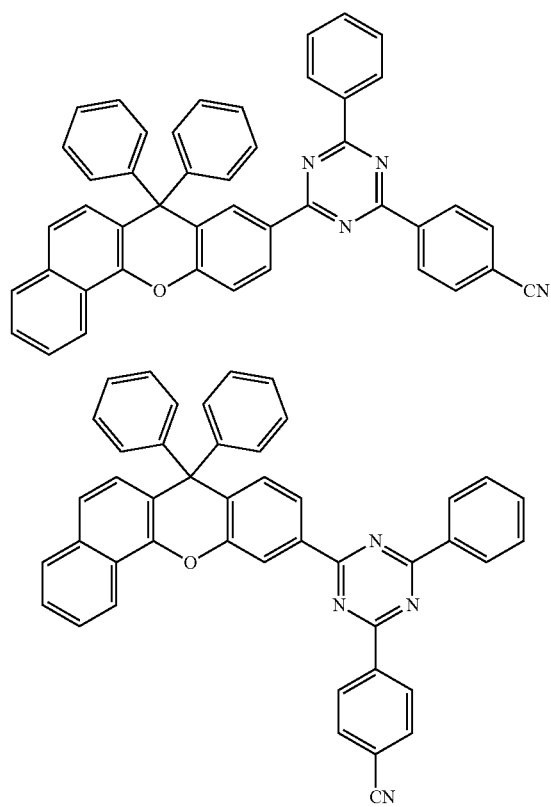
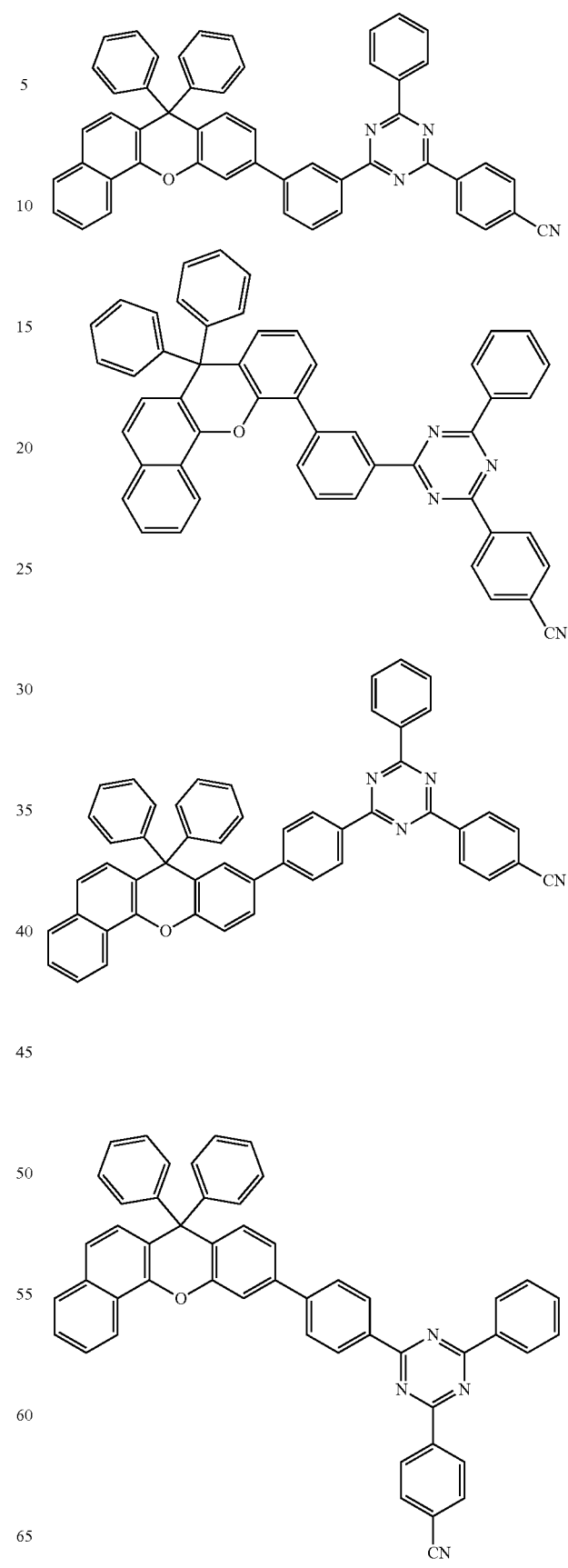

73
-continued
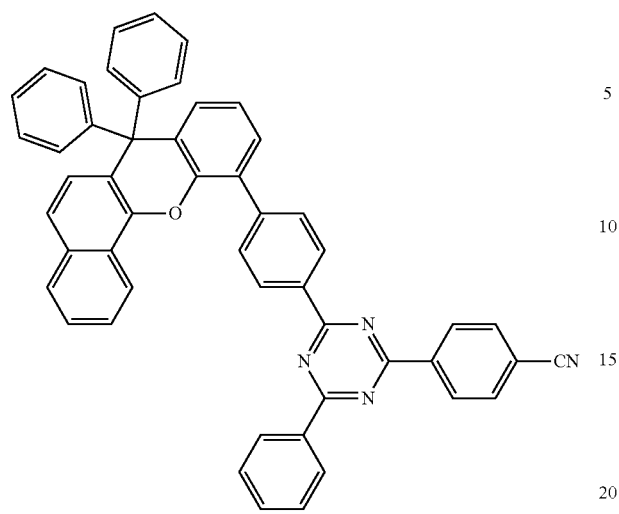
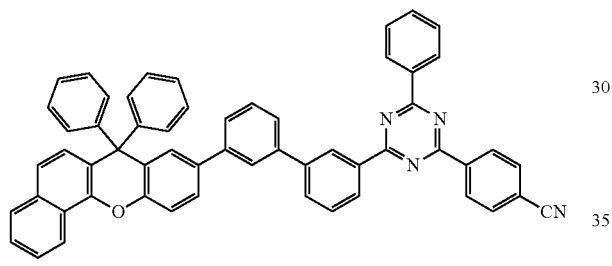
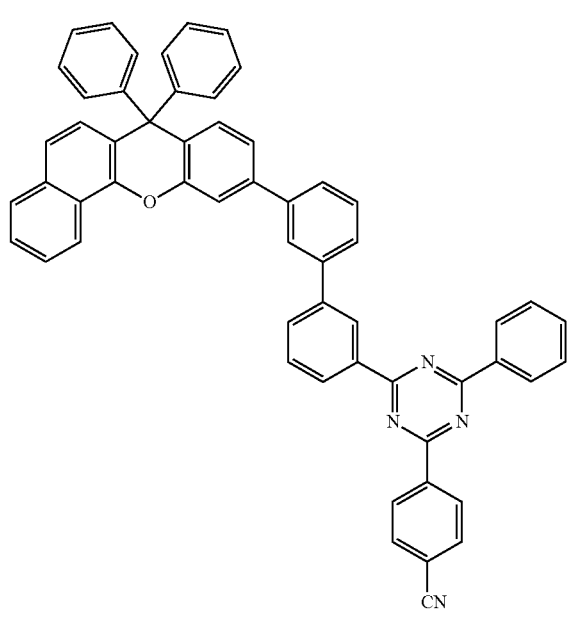
74
-continued
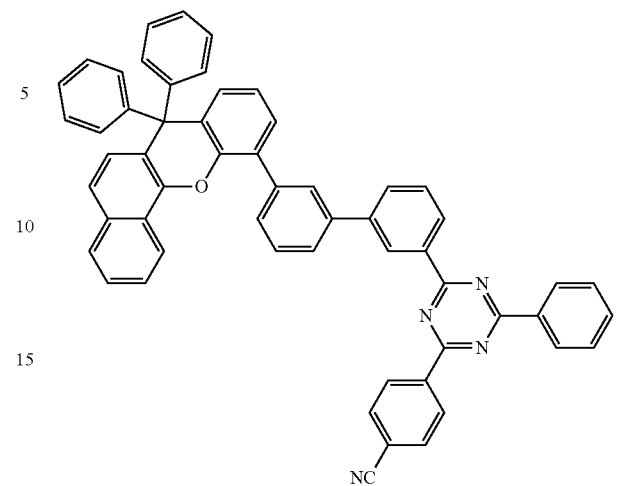
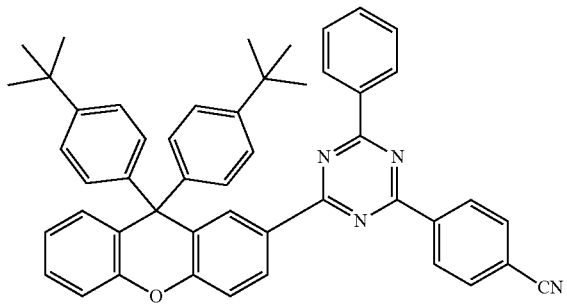
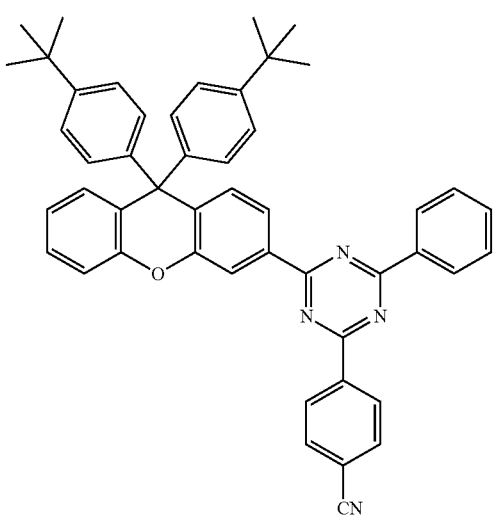

75
-continued
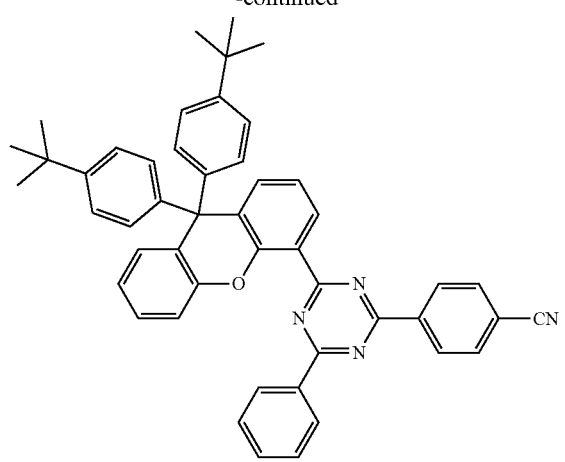
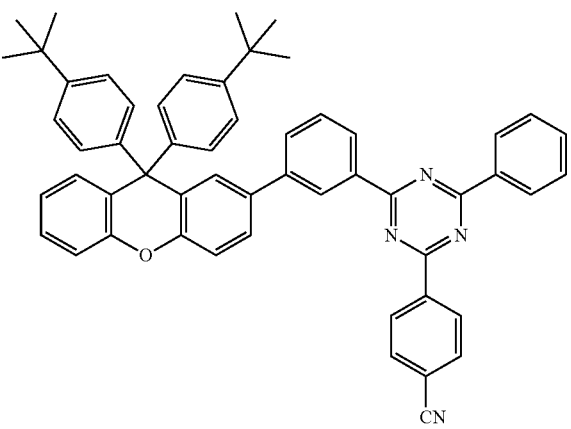
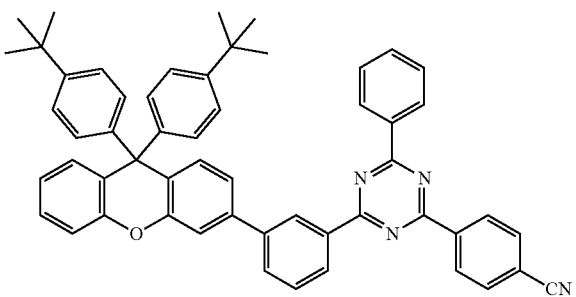
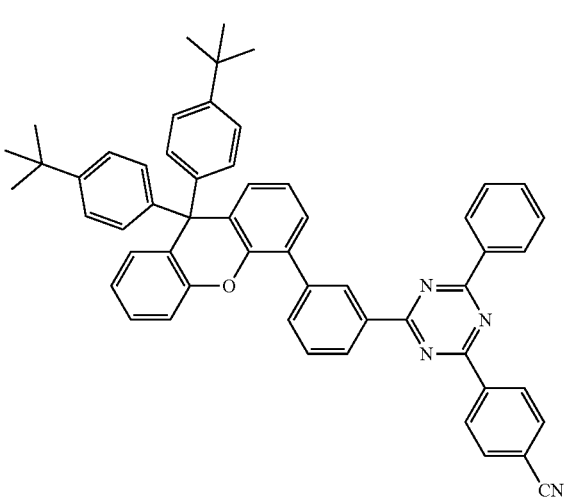
76
-continued
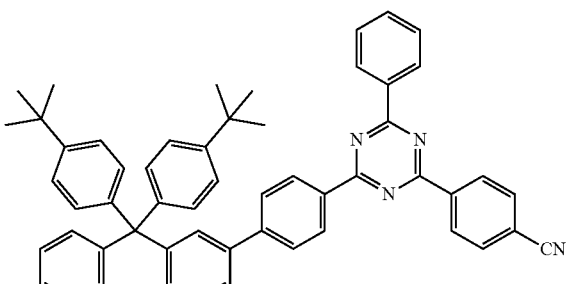
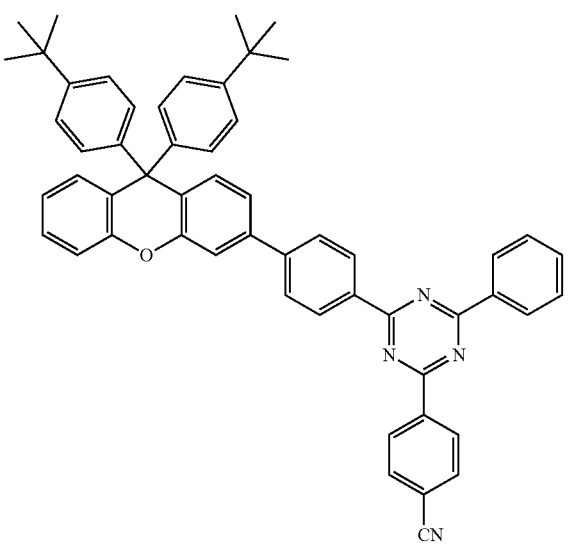
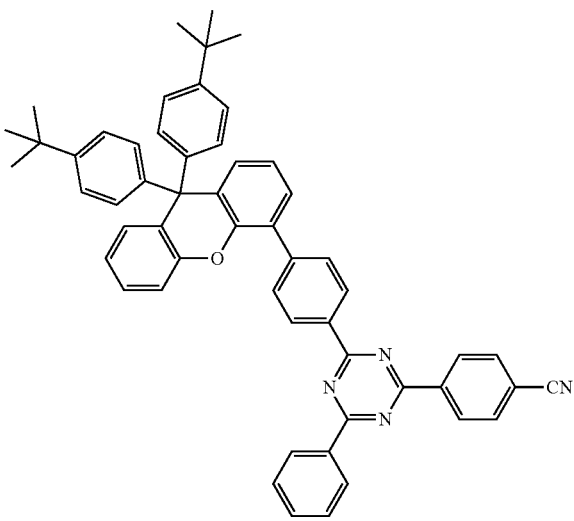
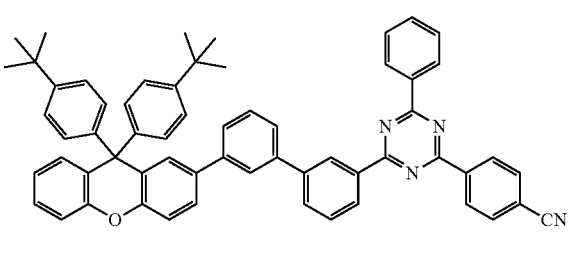

77
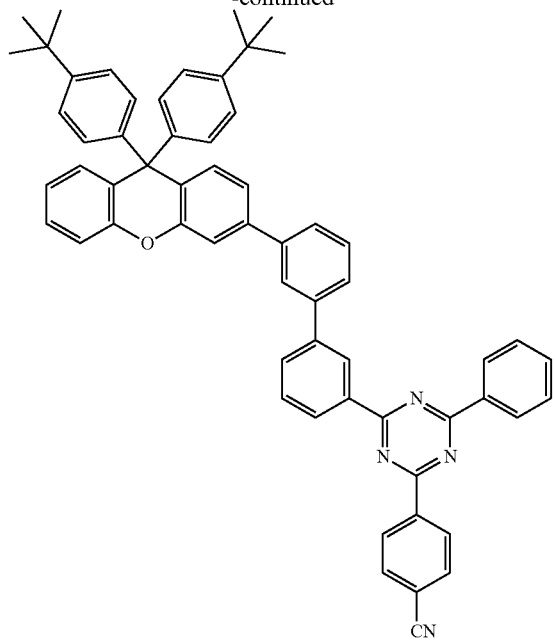
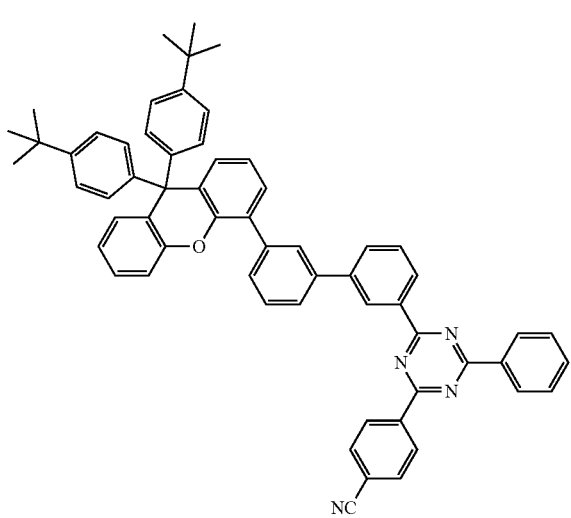
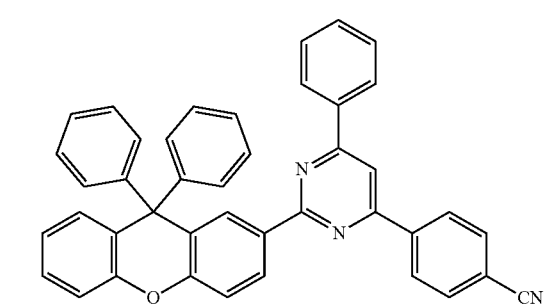
78
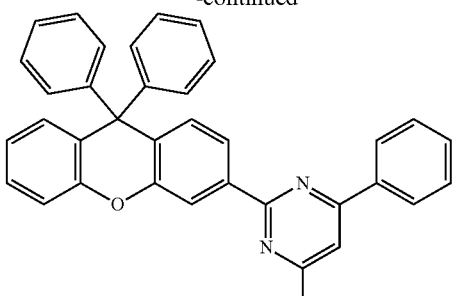
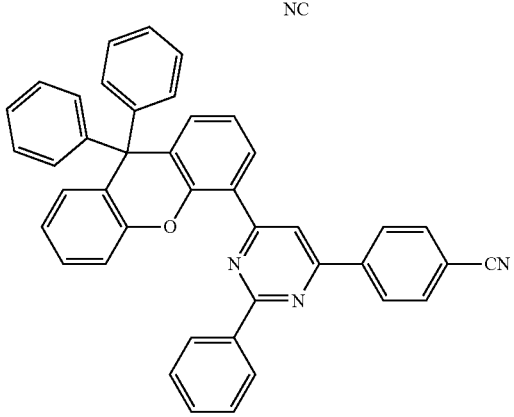
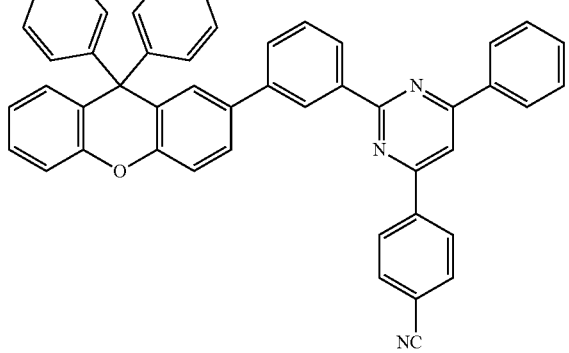
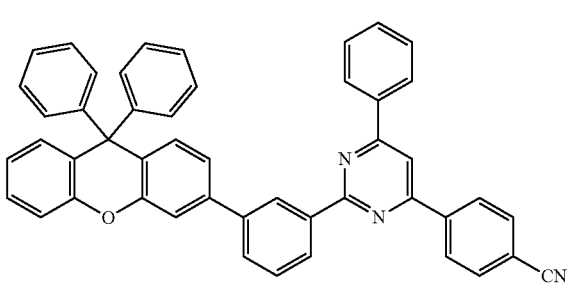

79
-continued
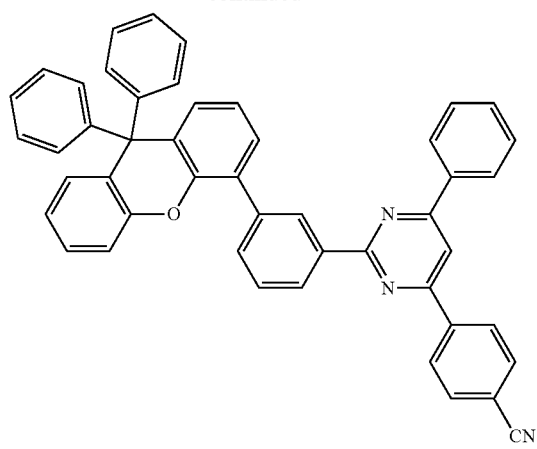
80
-continued
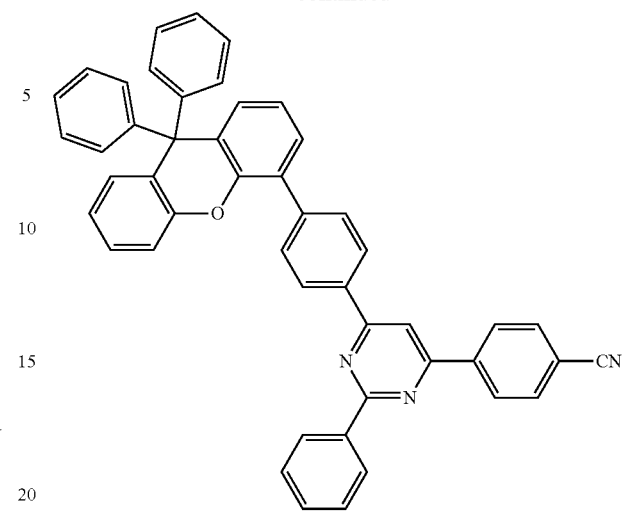
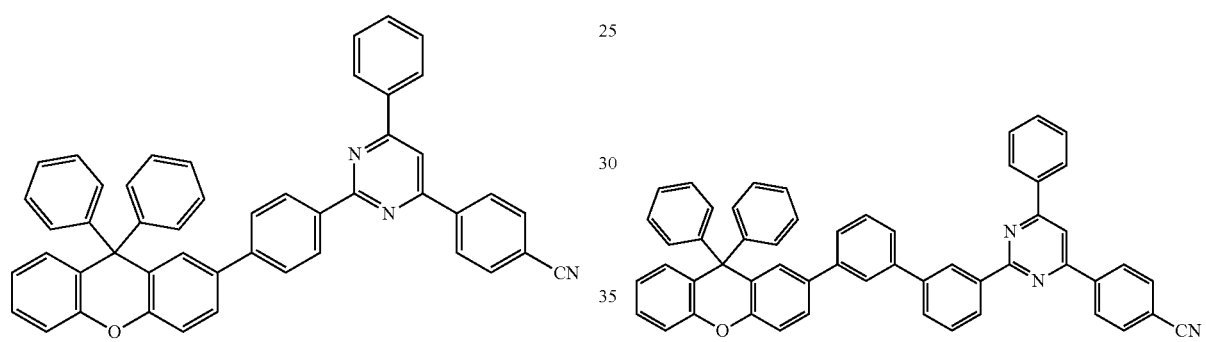
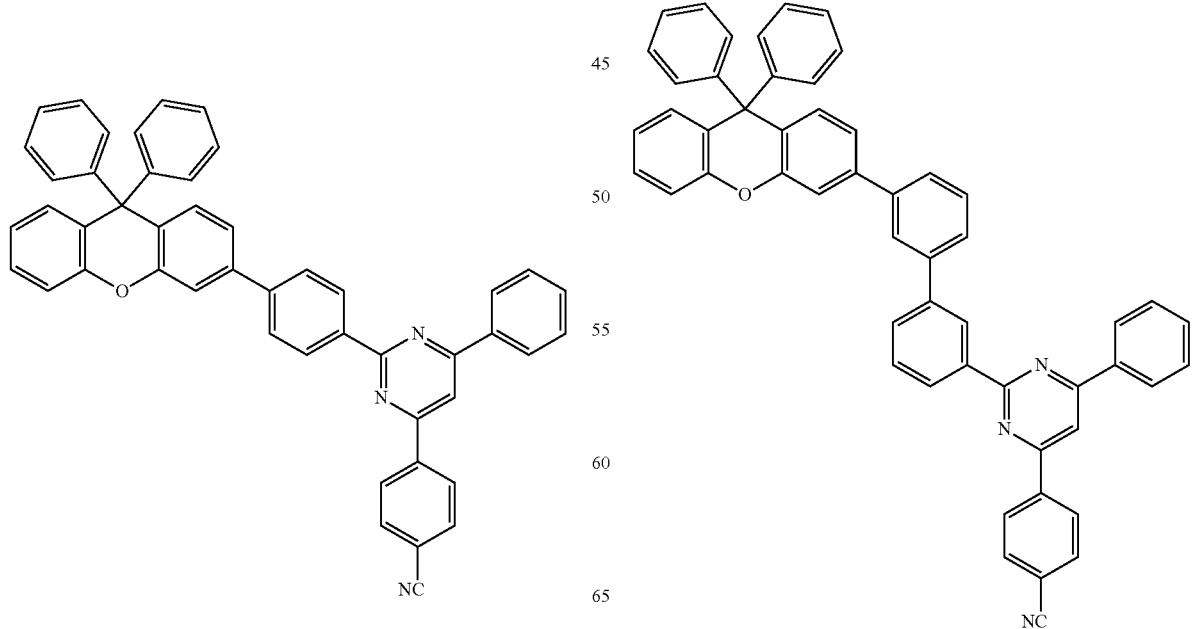

81
-continued
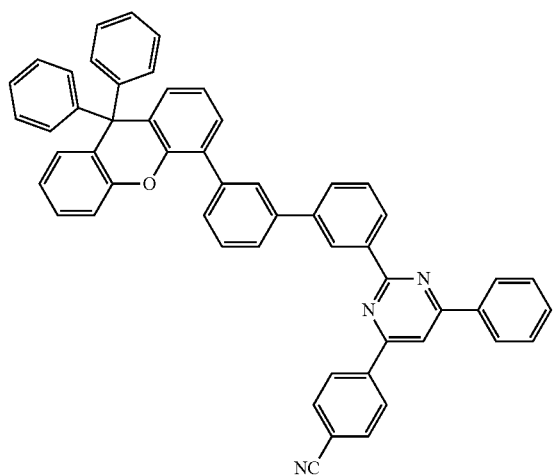
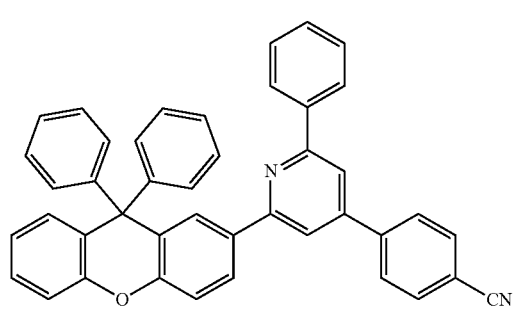
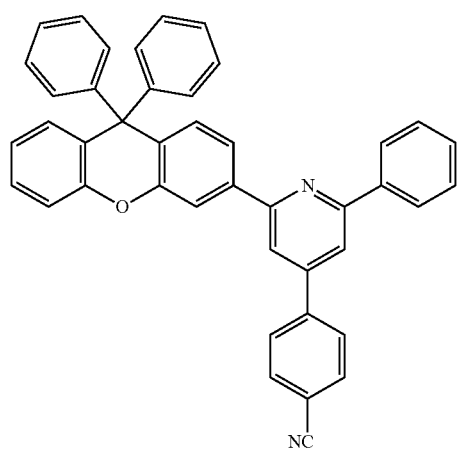
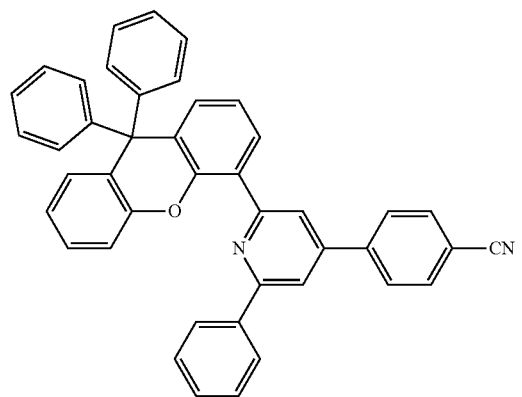
82
-continued
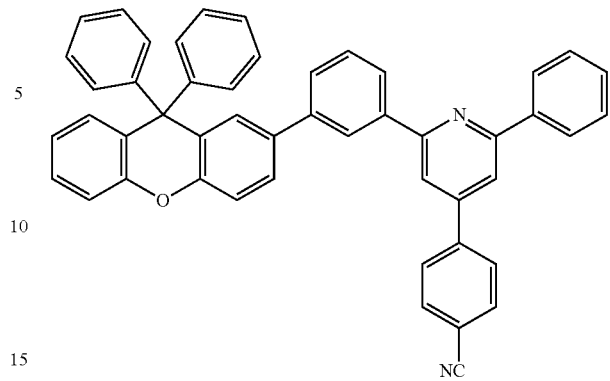
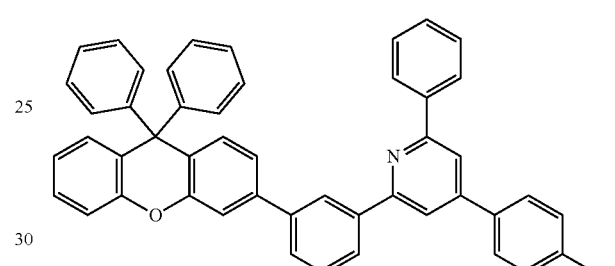
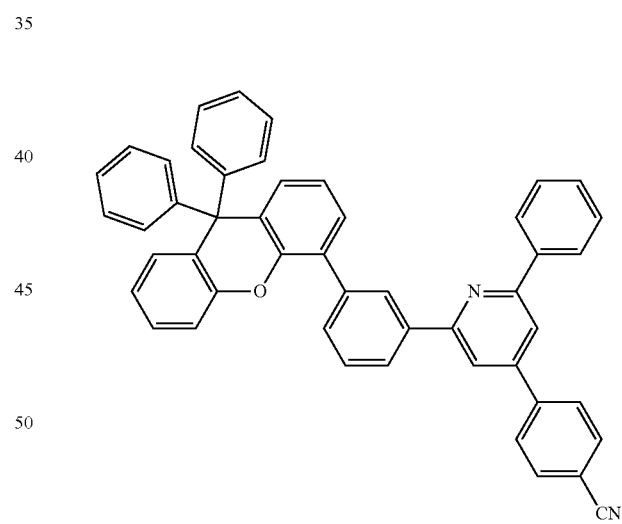
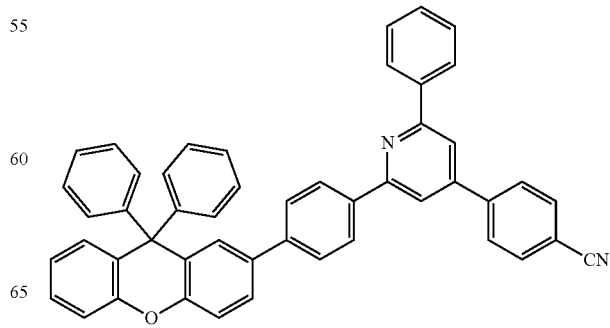

83
-continued
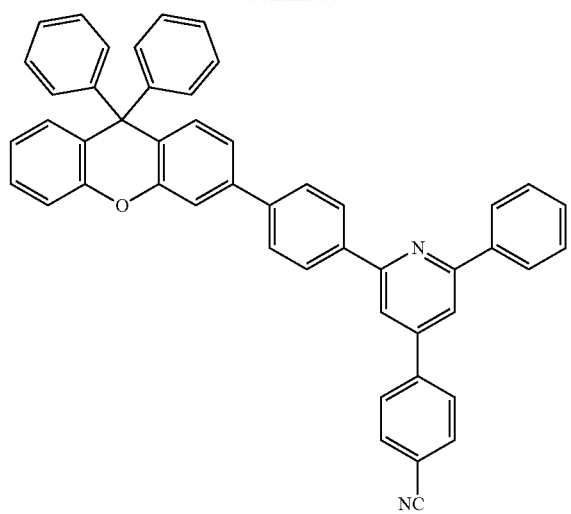
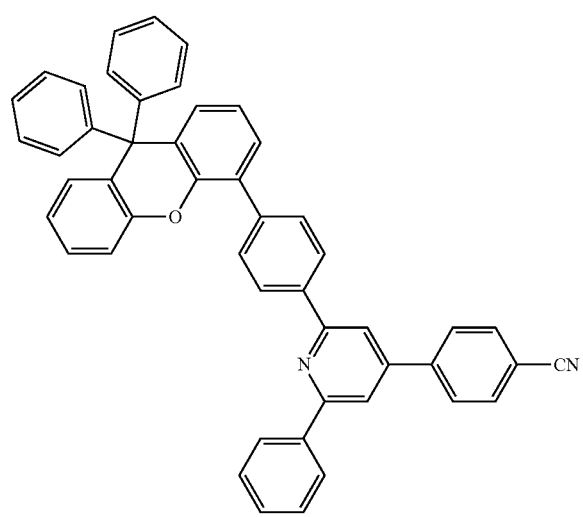
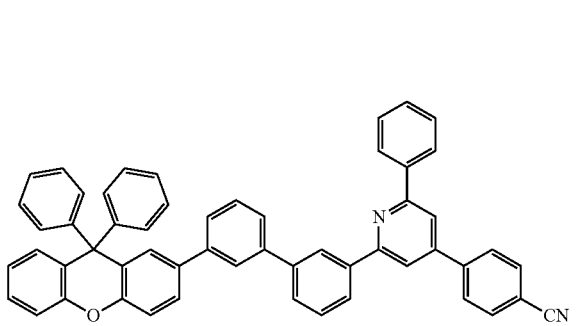
84
-continued
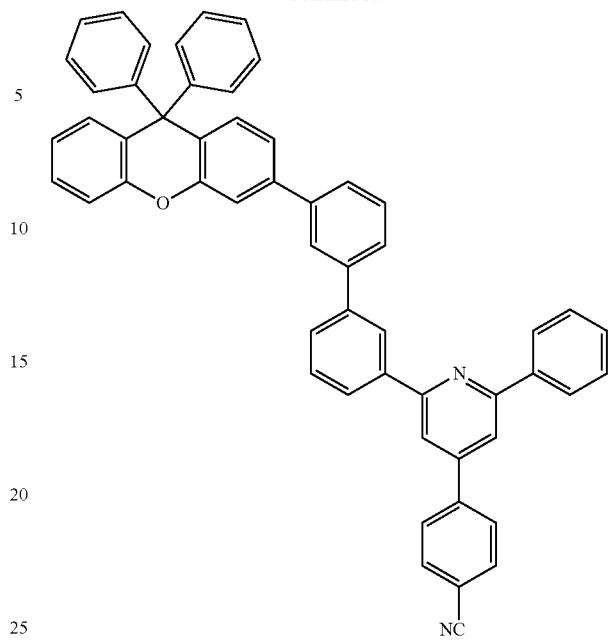
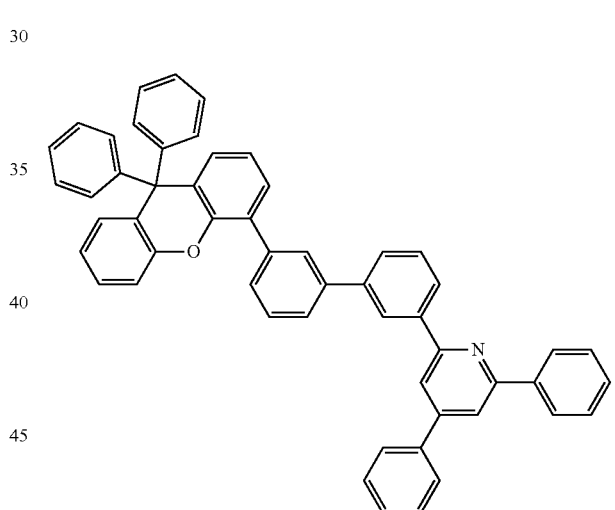
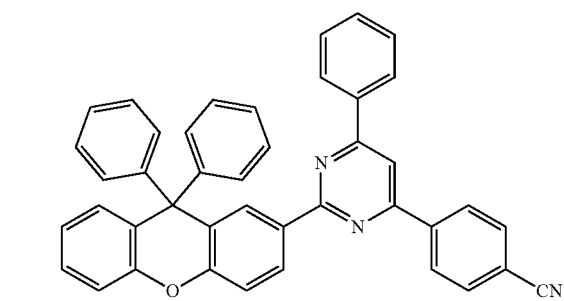

85
-continued
86
-continued
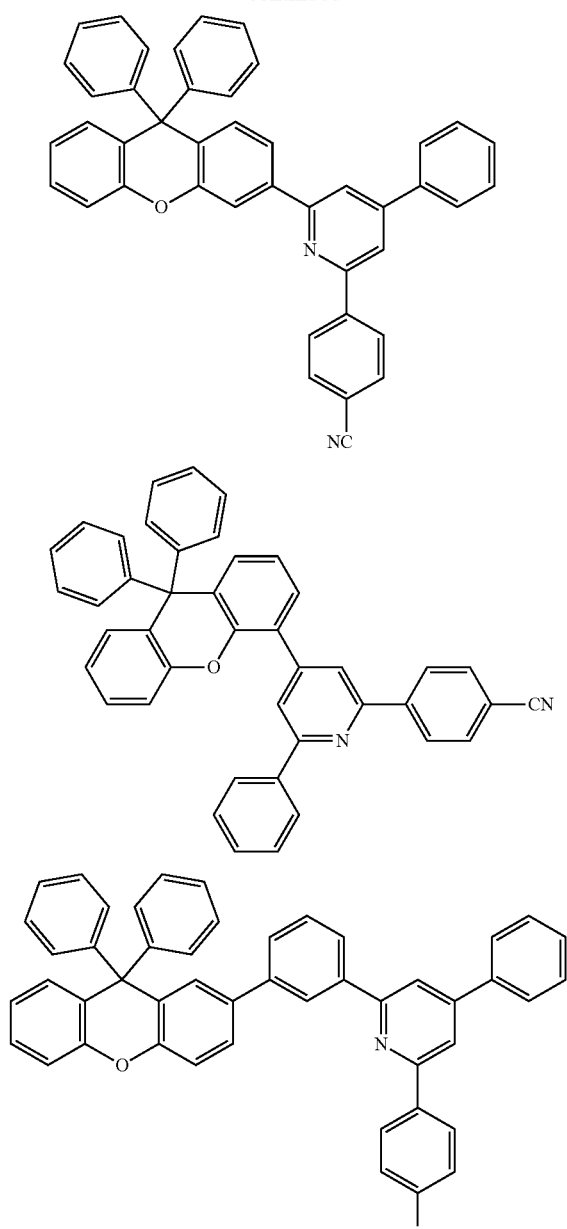
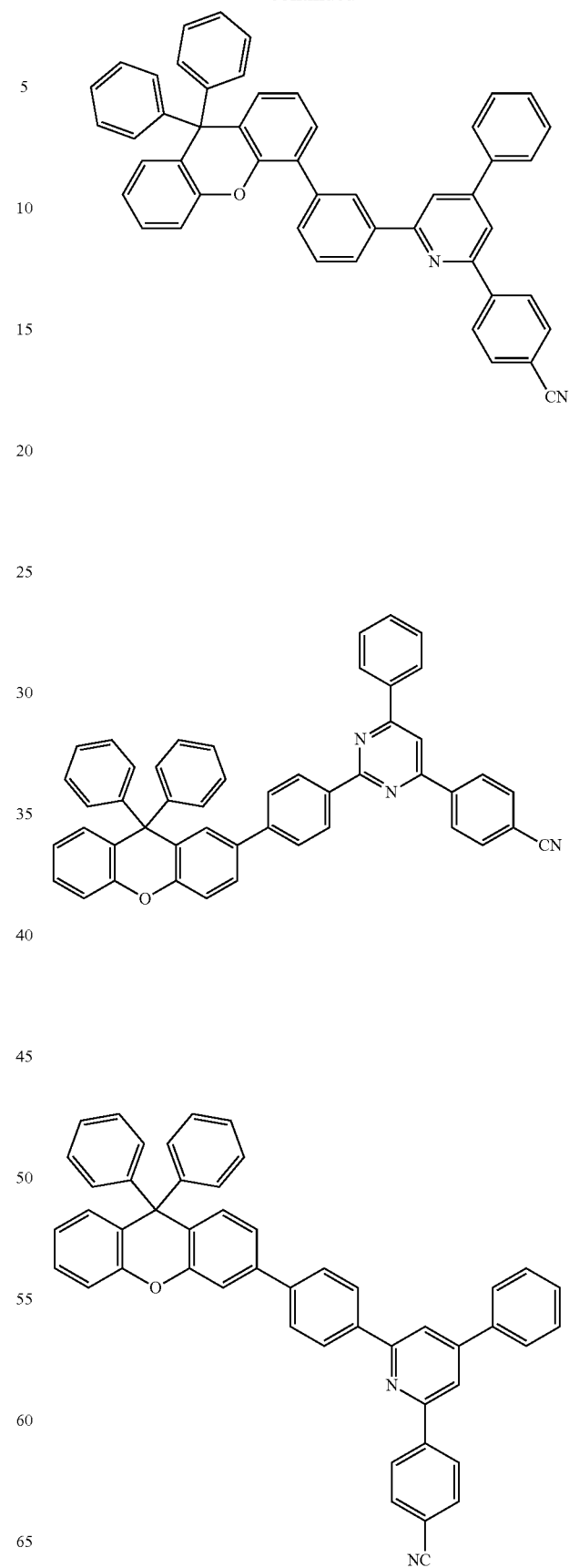

87
-continued
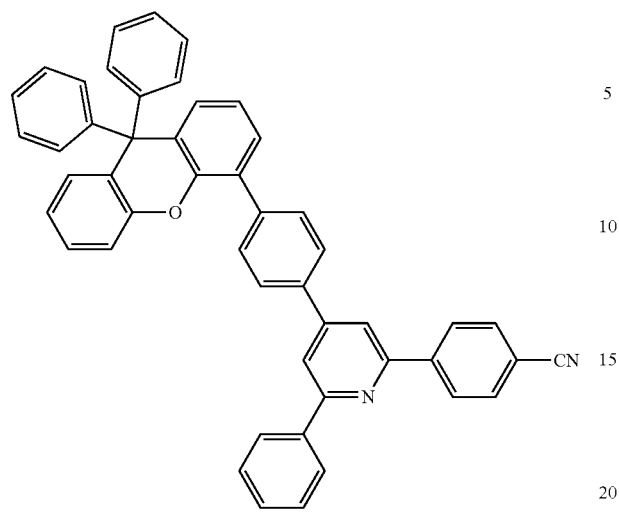
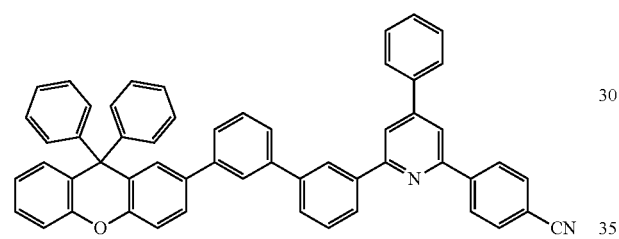
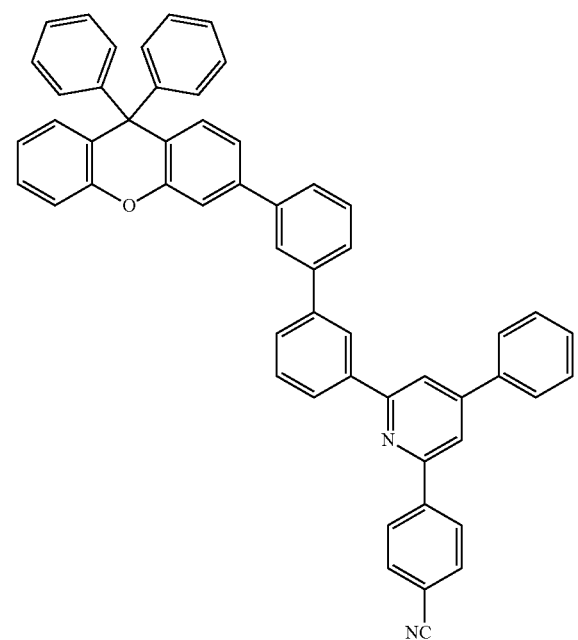
88
-continued
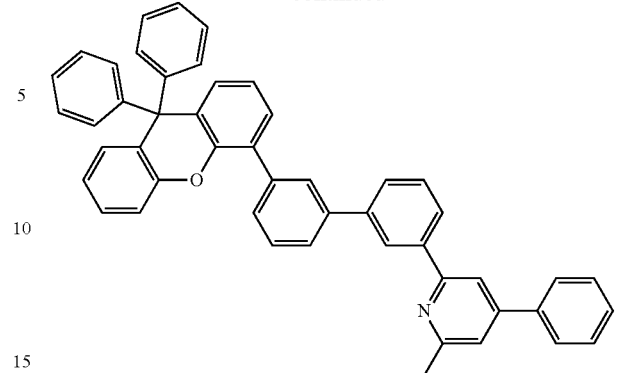
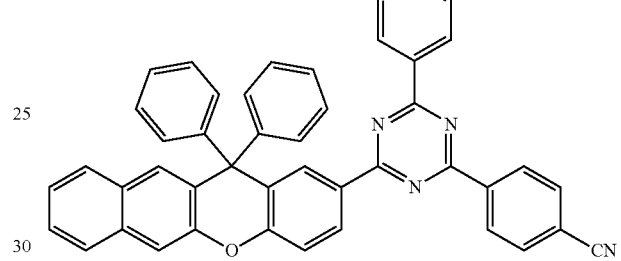
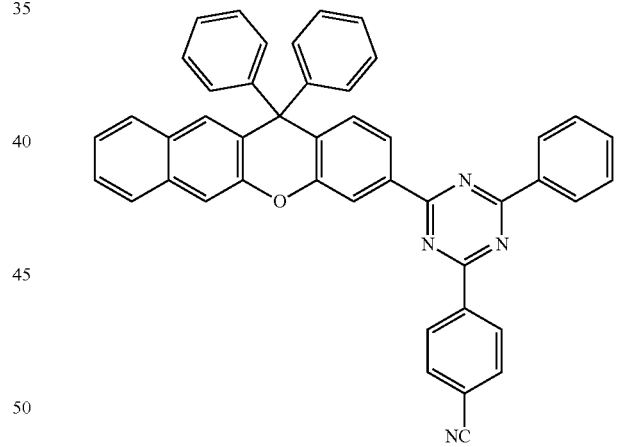
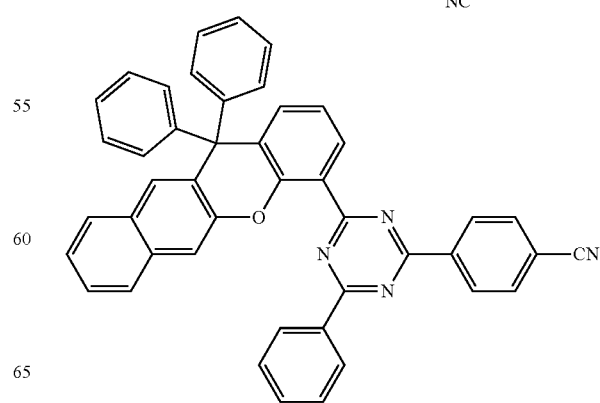

89
-continued
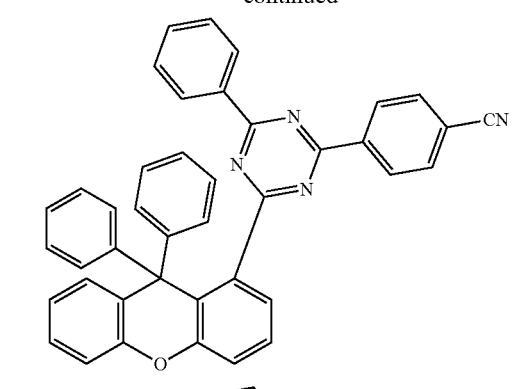
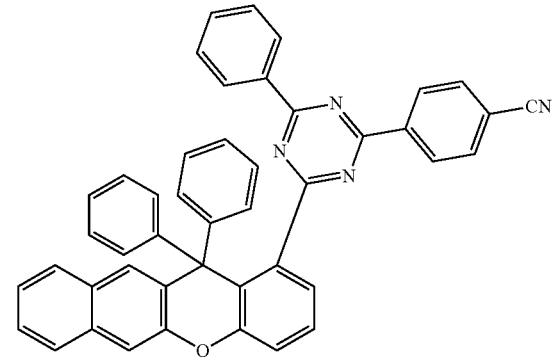
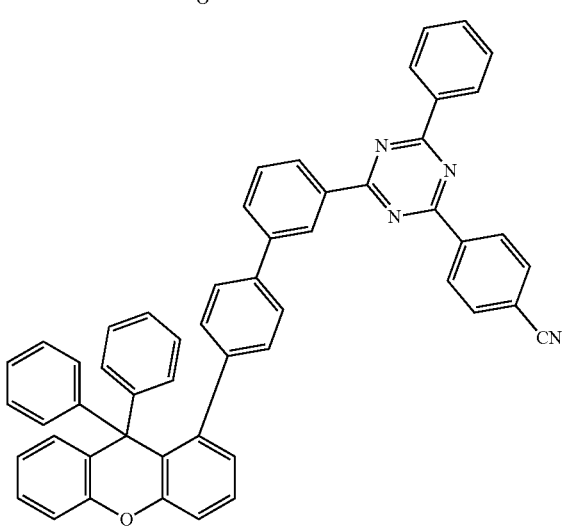
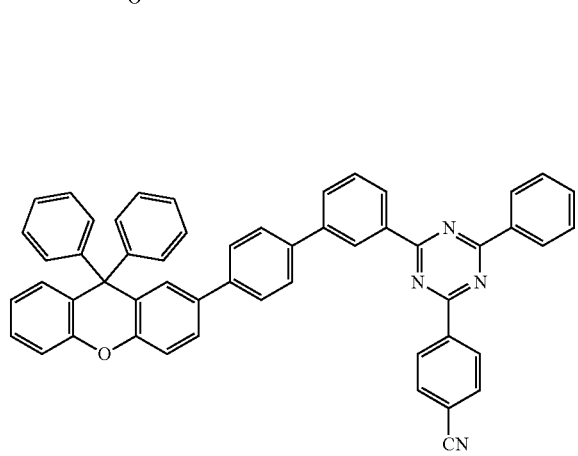
90
-continued
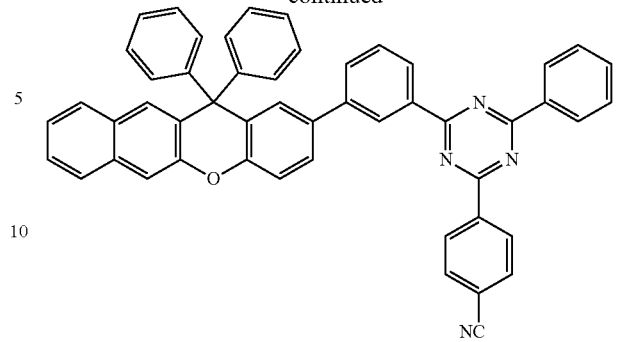
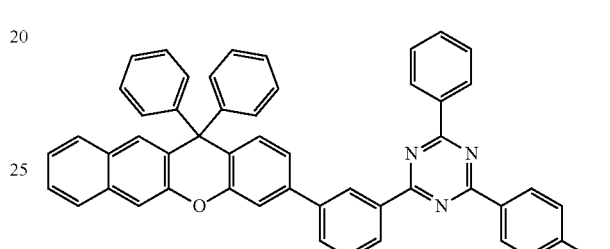
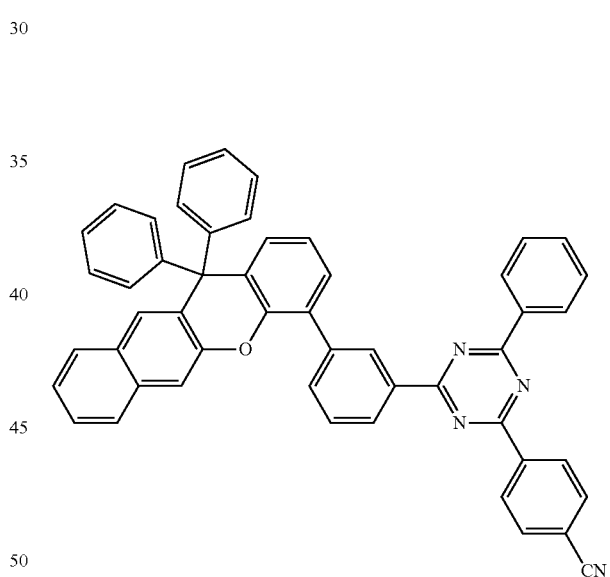
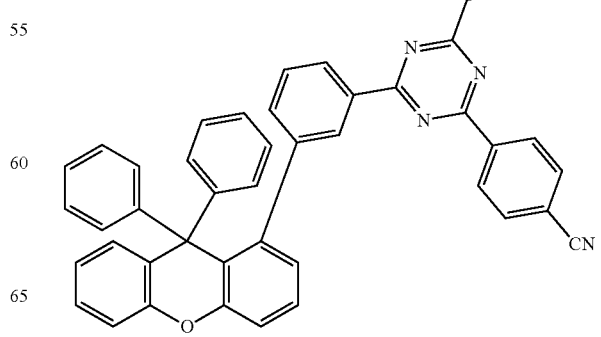

91
-continued
92
-continued
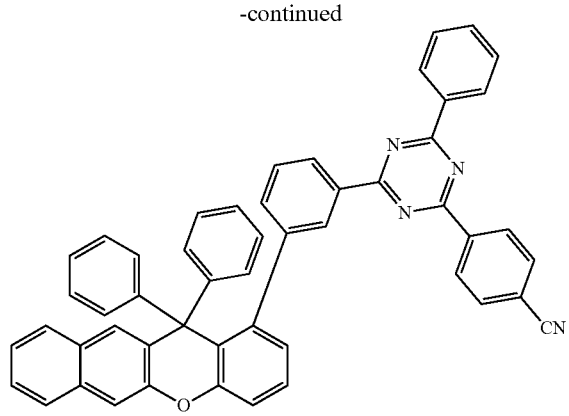
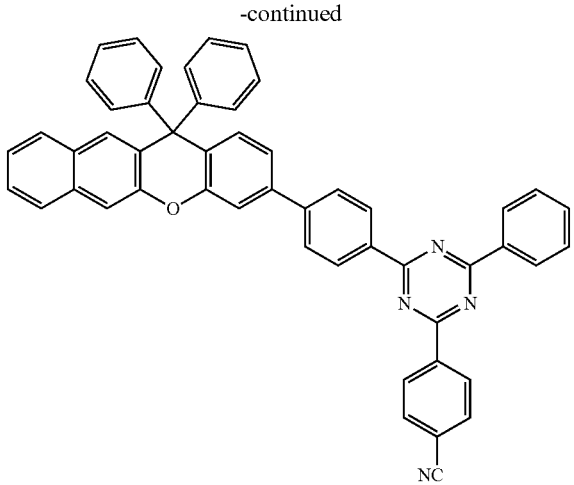
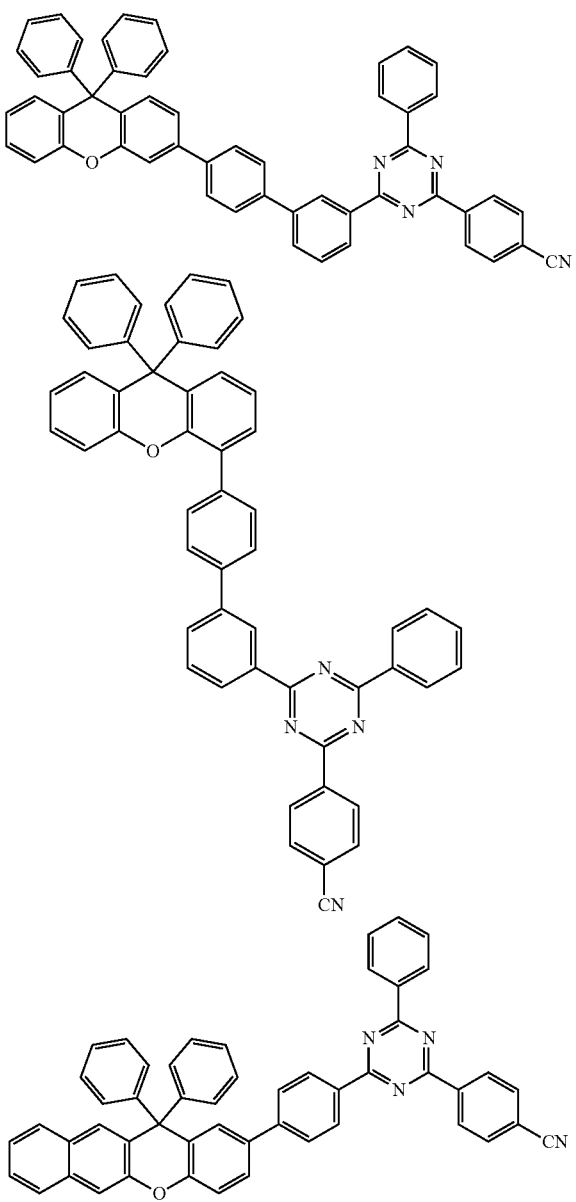
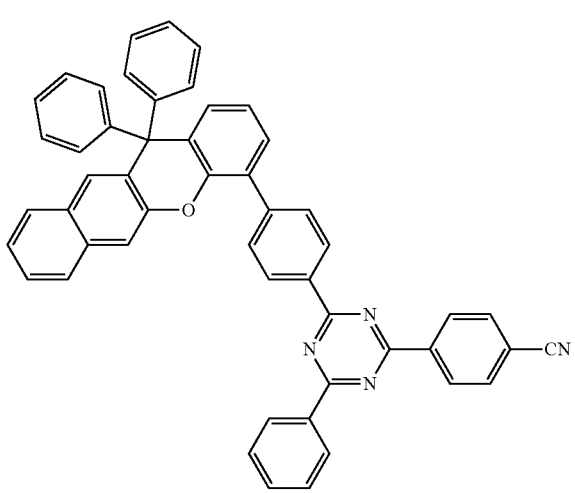

93
-continued
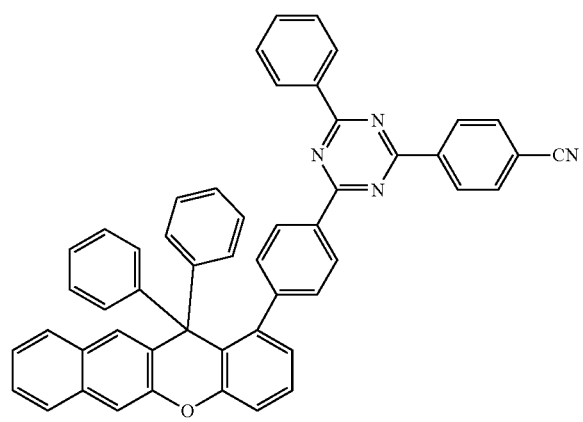
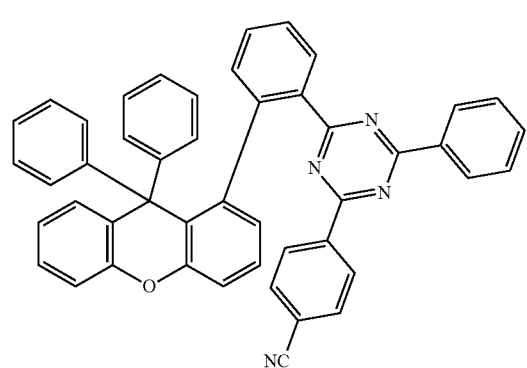
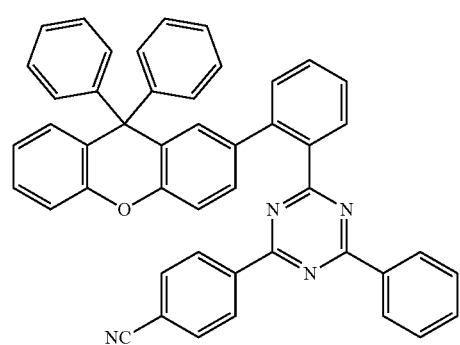
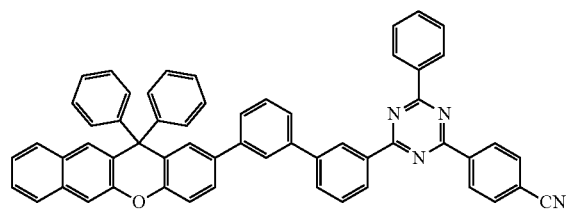
94
-continued
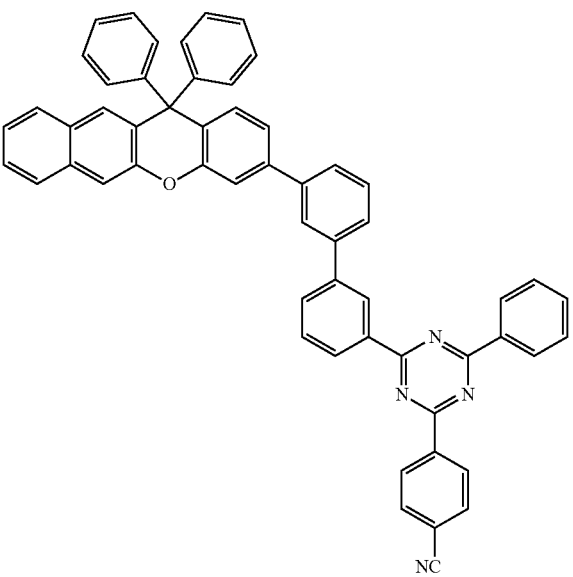
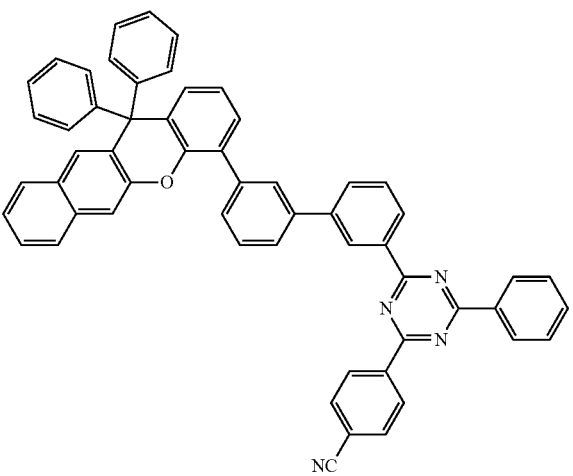
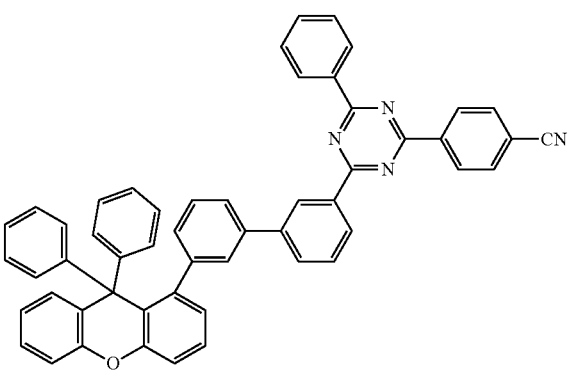

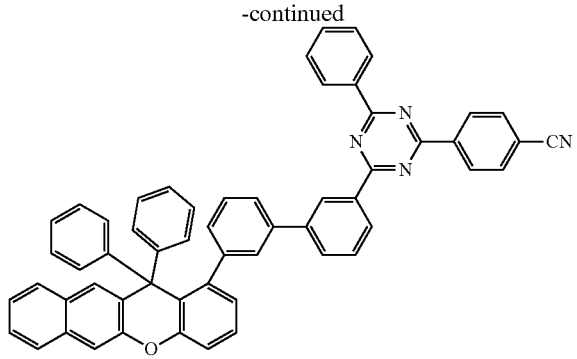
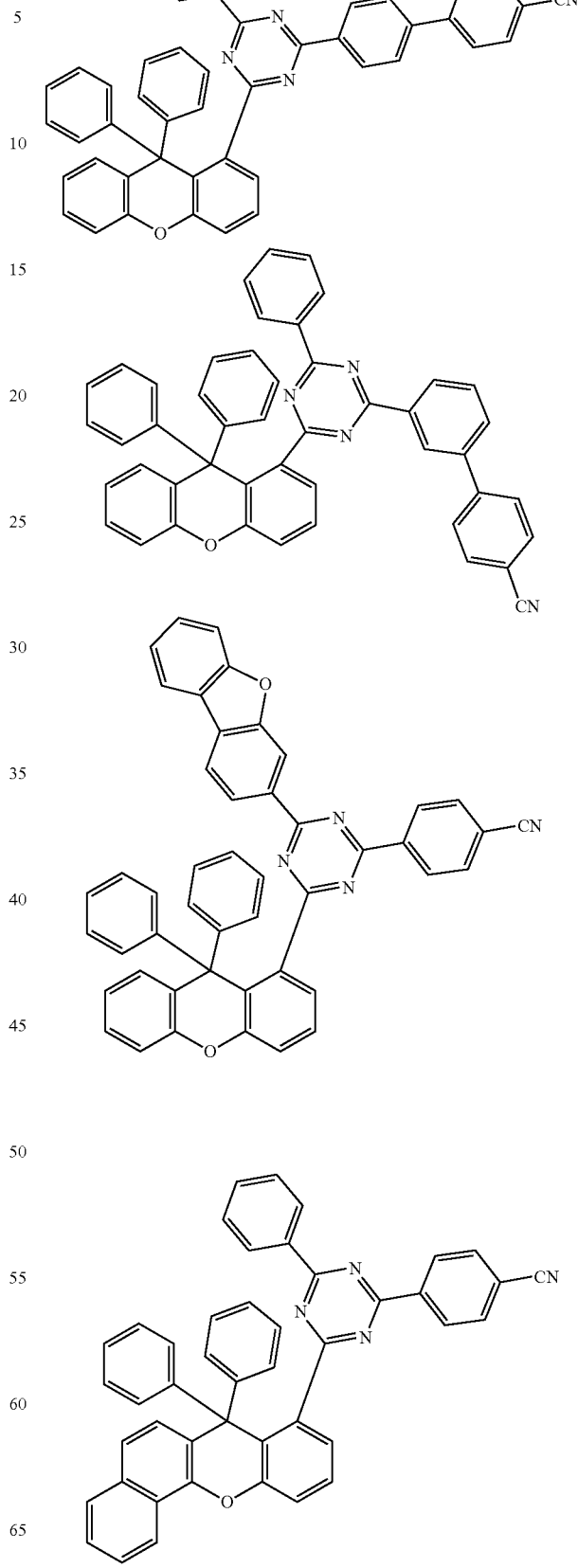

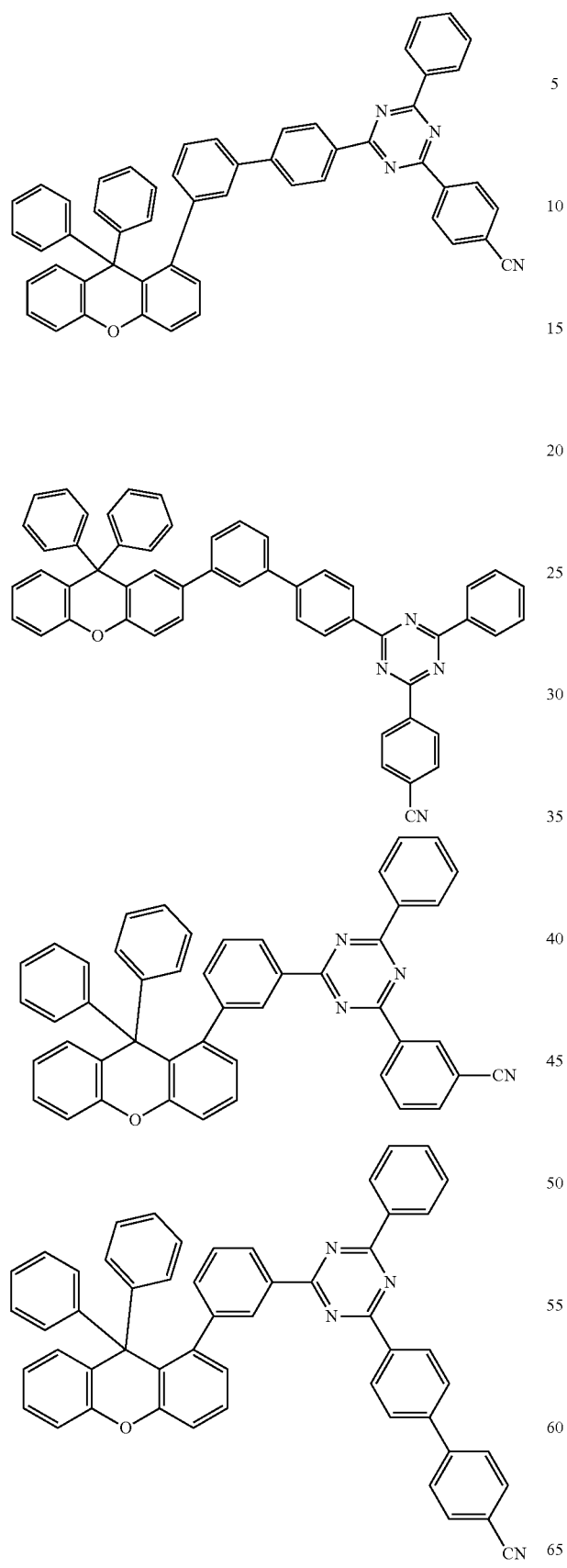
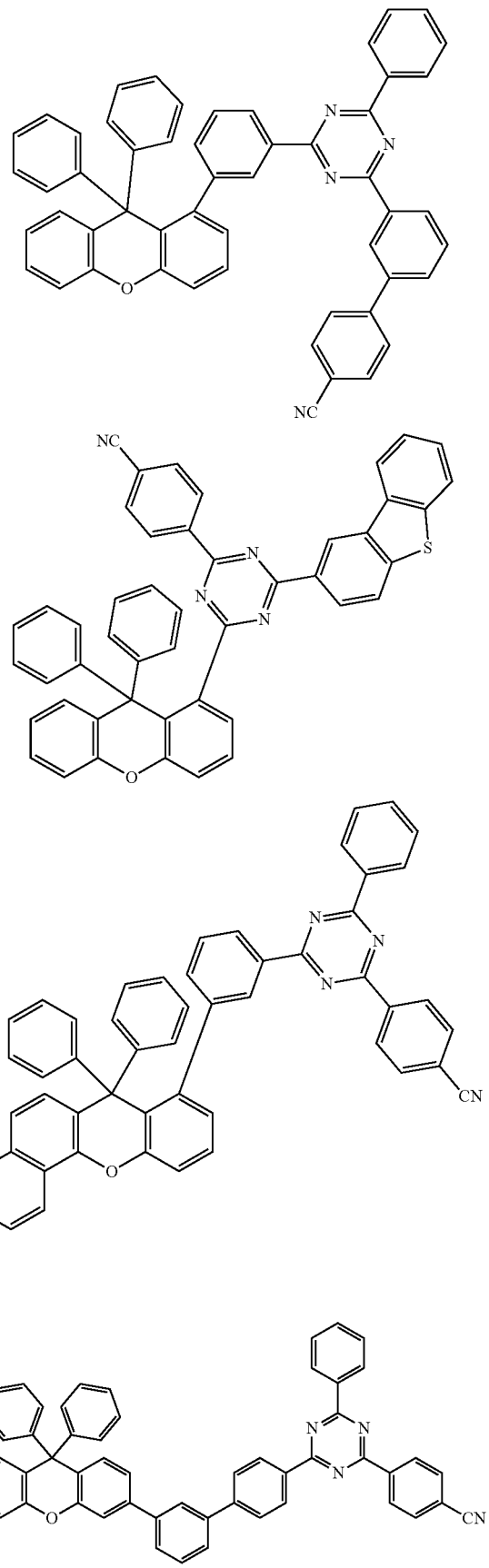

99
-continued
100
-continued
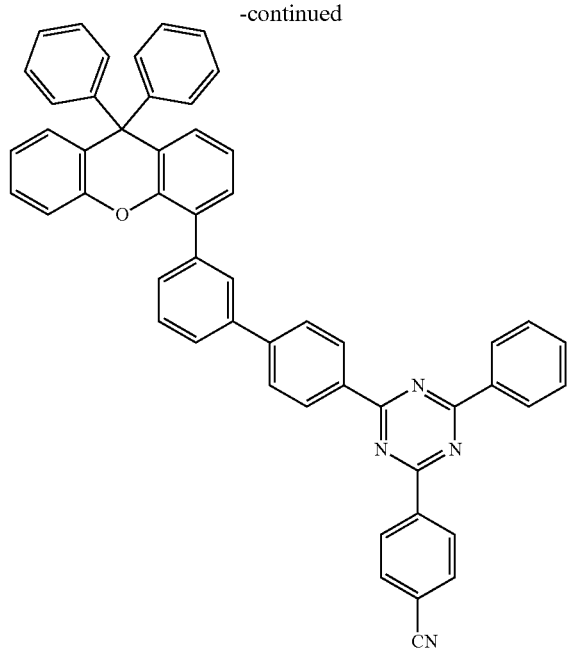
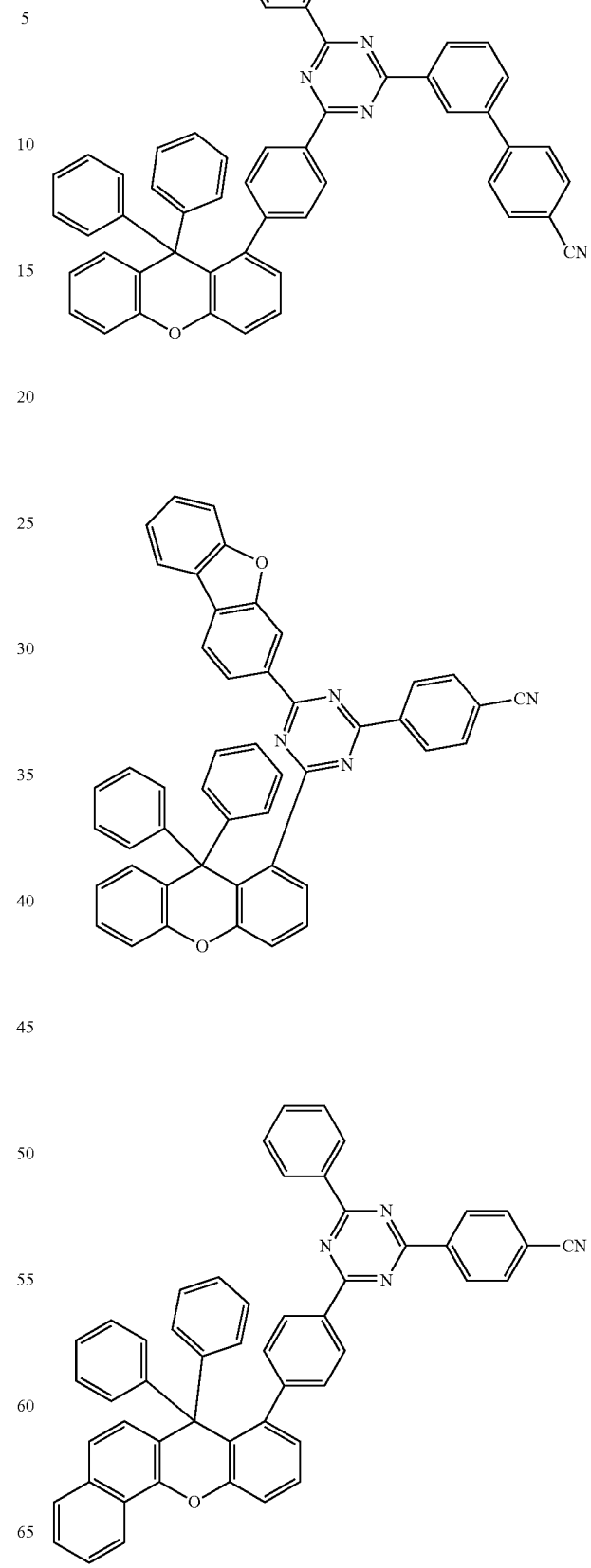

101
-continued
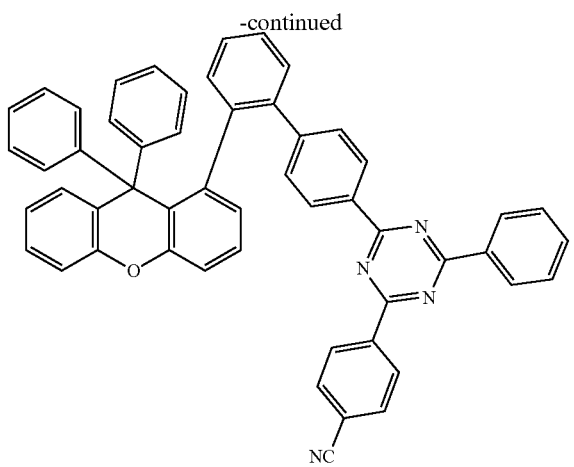
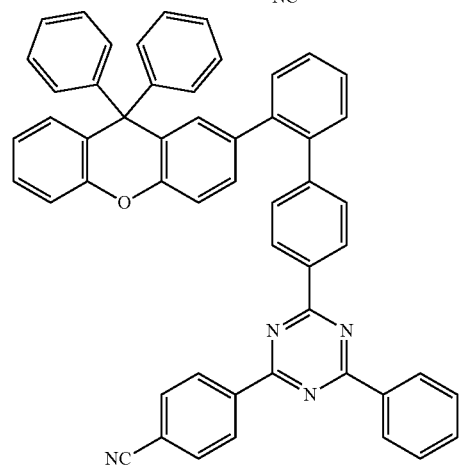
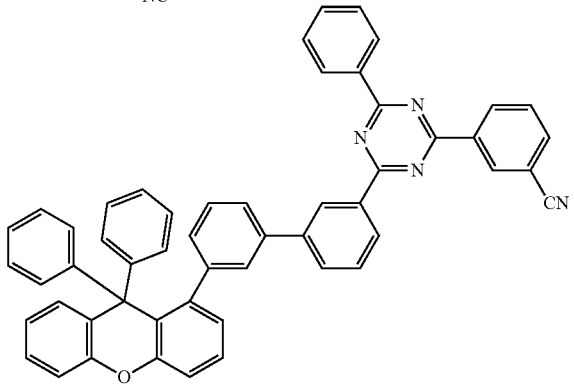
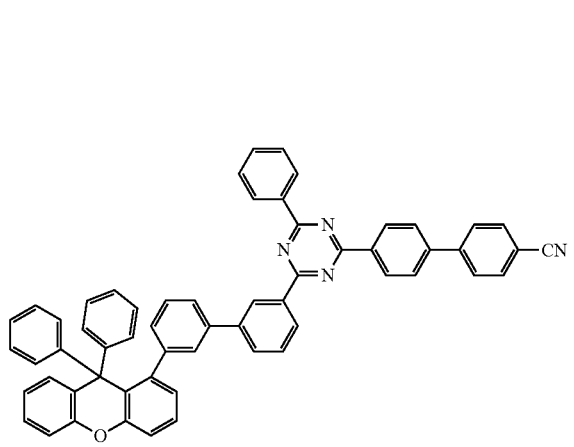
102
-continued
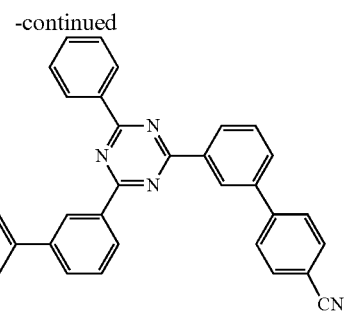
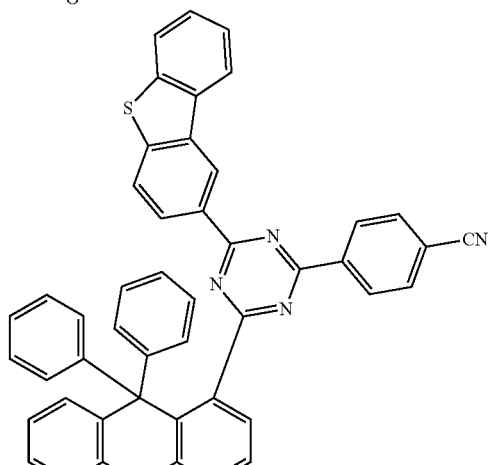
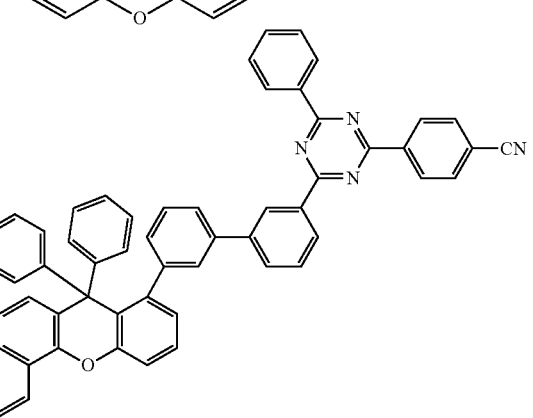
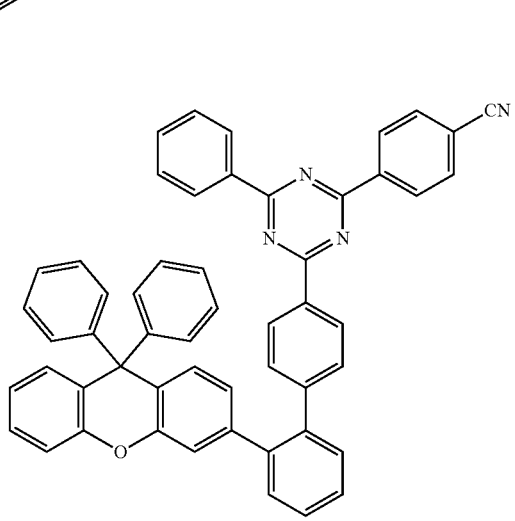

103
-continued
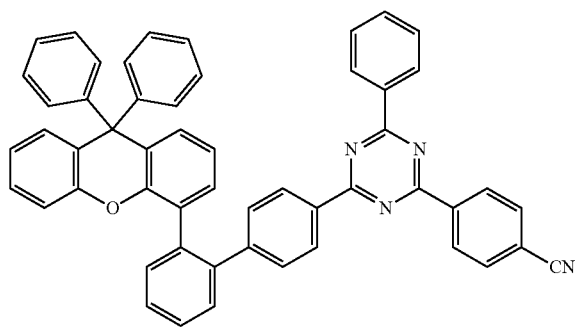
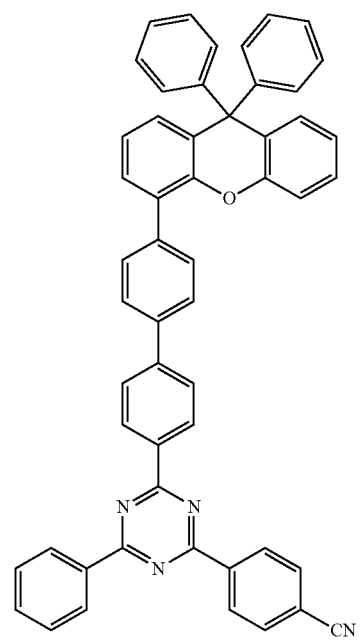
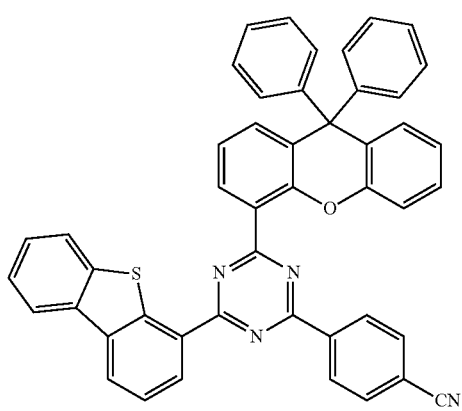 [SMILES: N#Cc1ccc(-c2nc(-c3cccc4c3Oc3ccccc3C4(c3ccccc3)c3ccccc3)nc(-c3cccc4c3sc3ccccc34)n2)cc1]
104
-continued
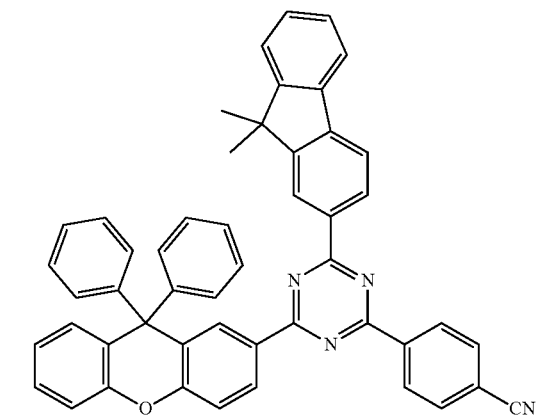
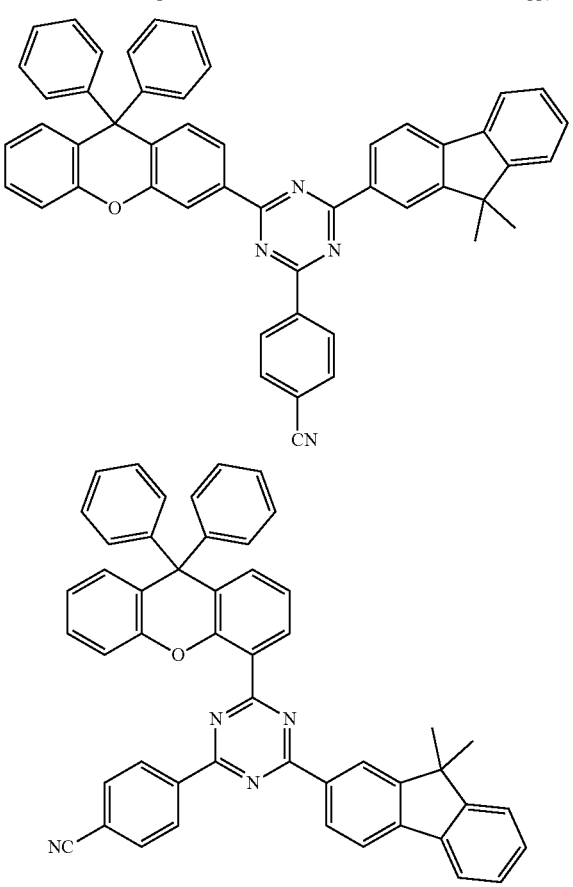
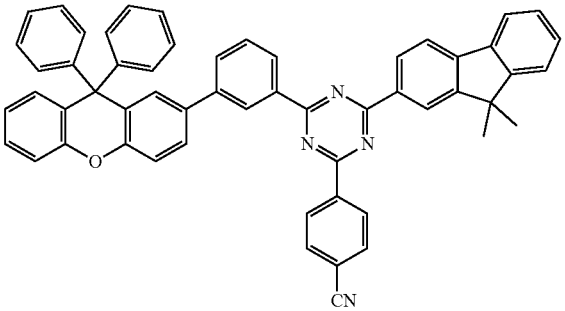

105
-continued
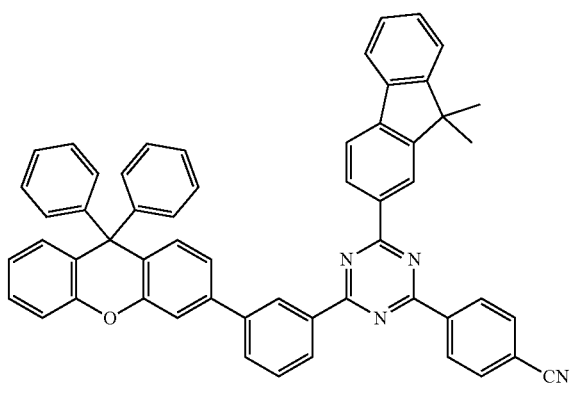
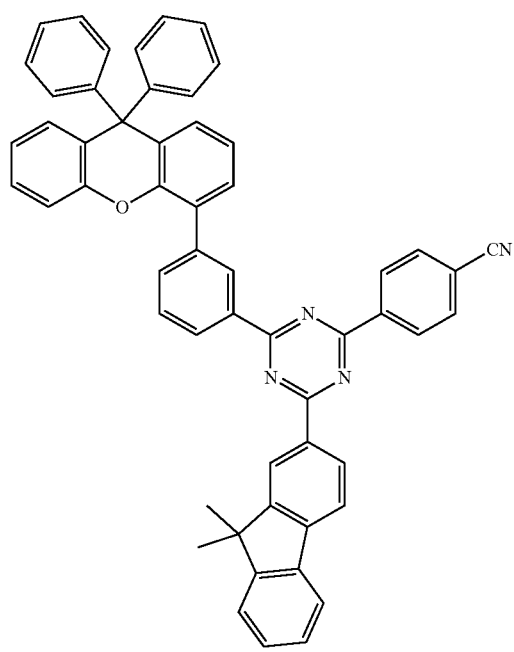
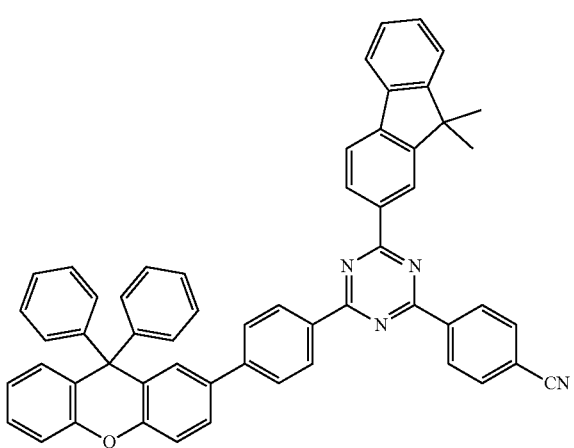
106
-continued
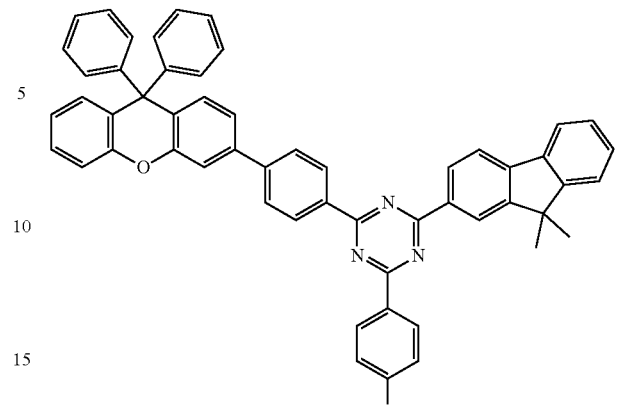
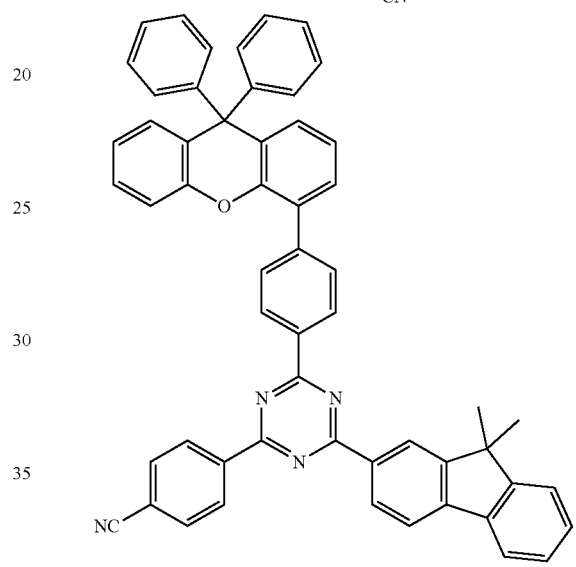
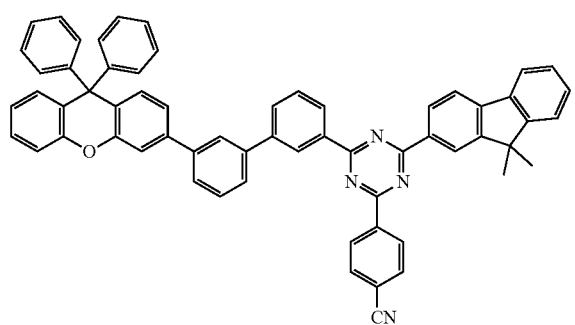

107
-continued
108
-continued
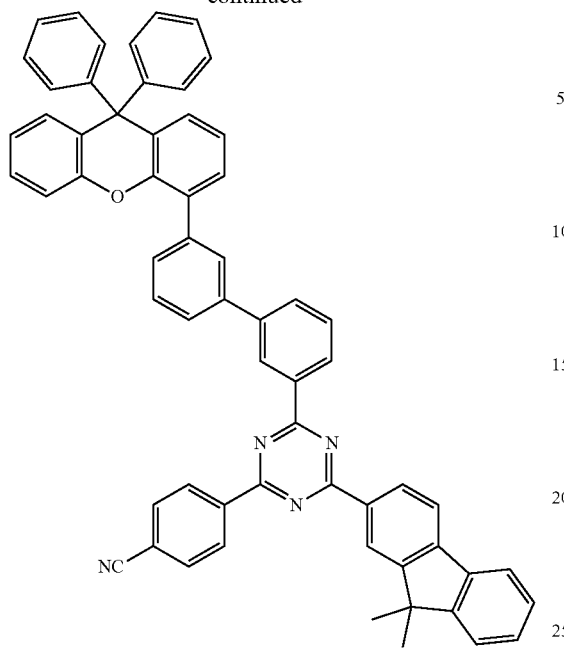
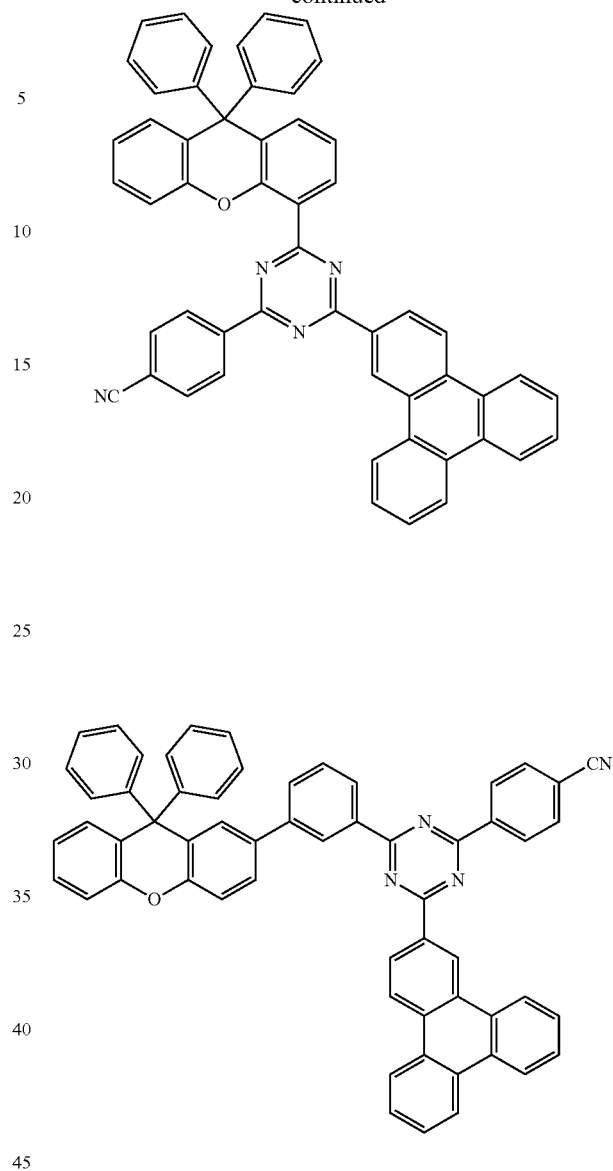
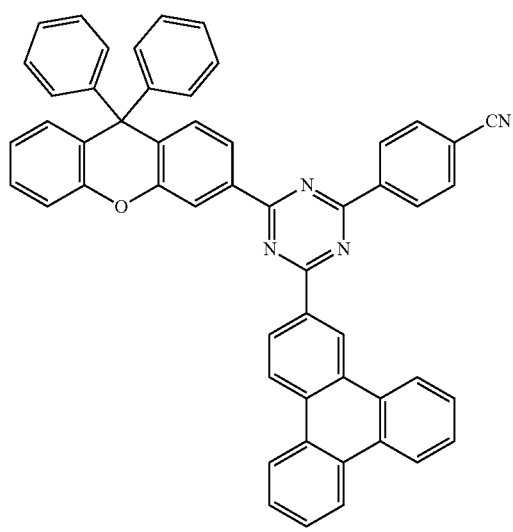

109
-continued
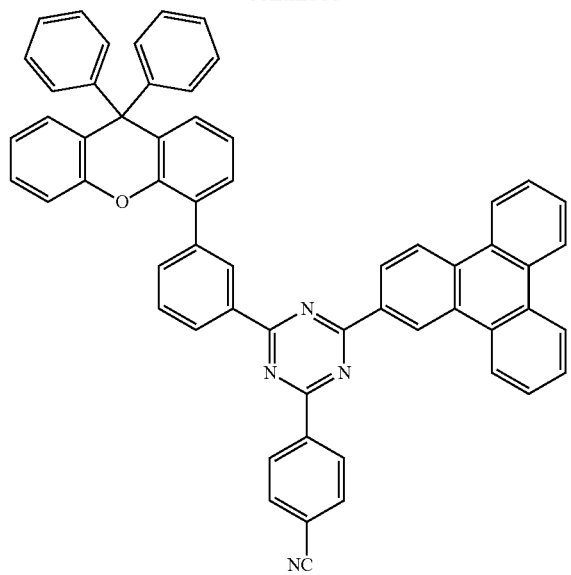
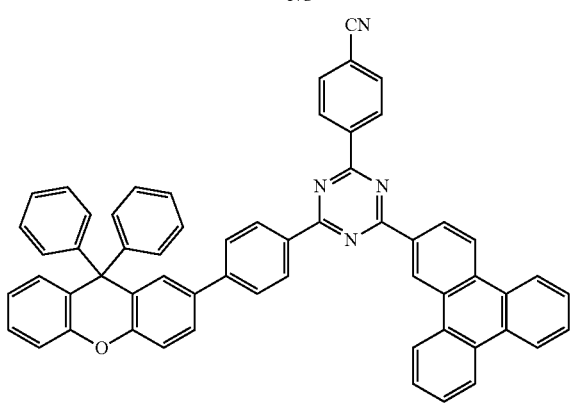
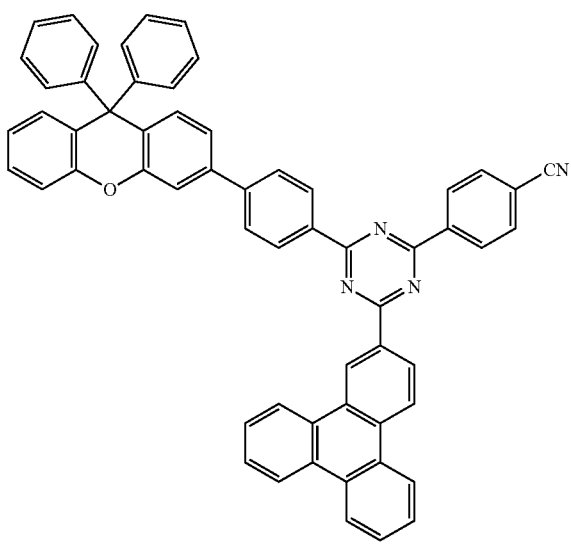
110
-continued
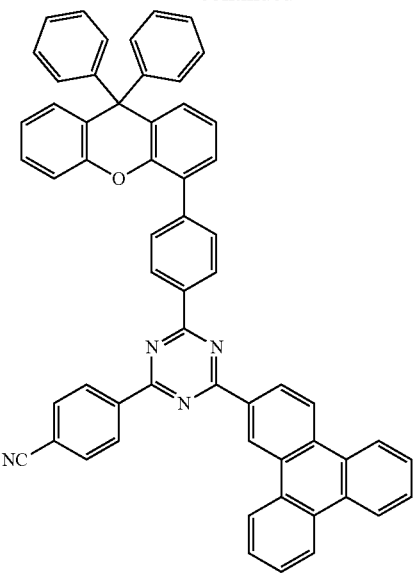
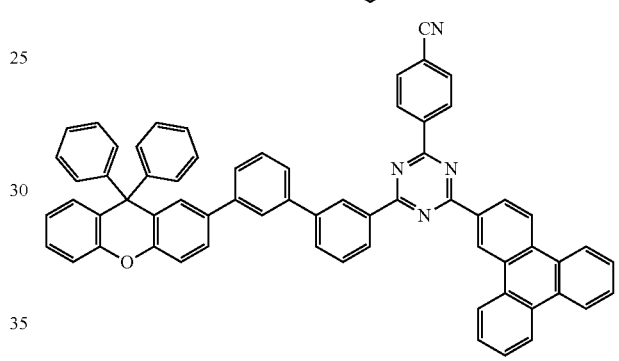
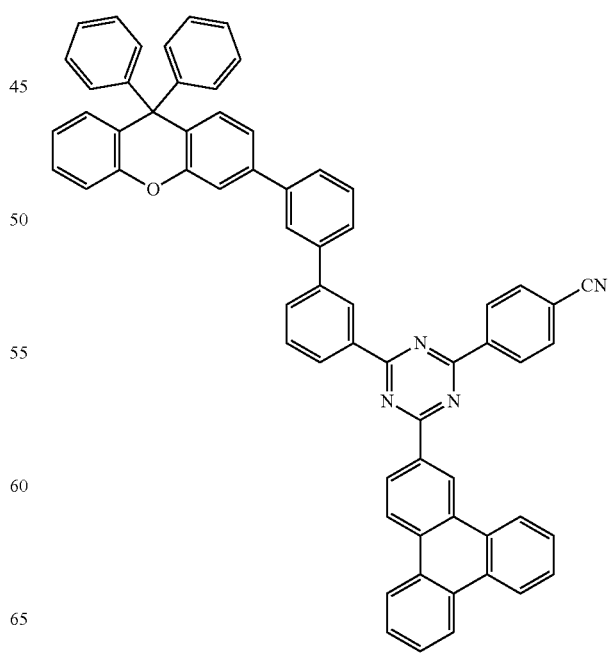

111
-continued
112
-continued
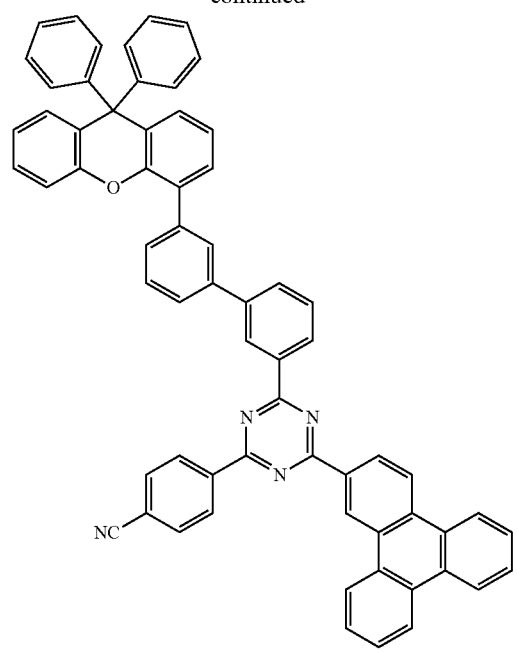
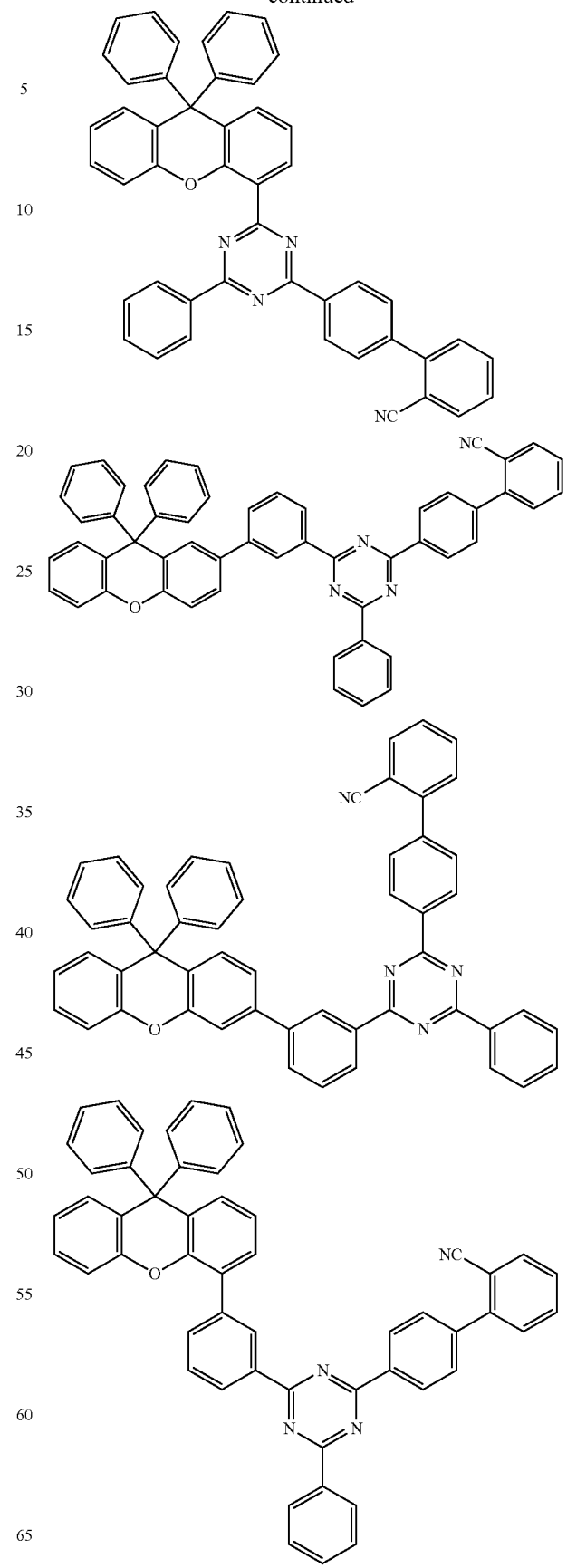

113
-continued
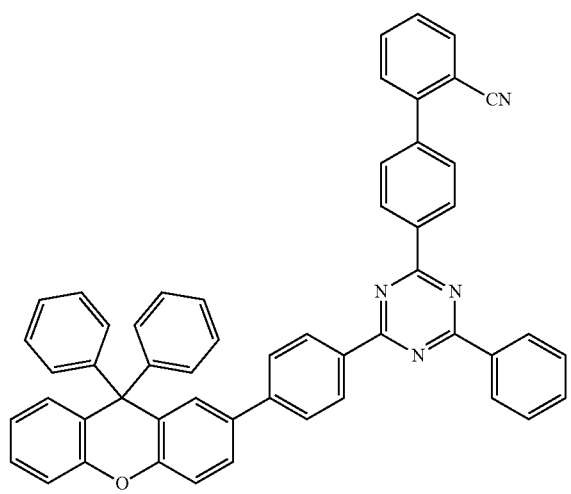
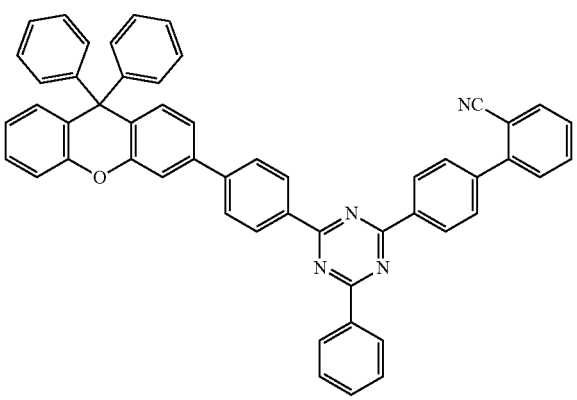
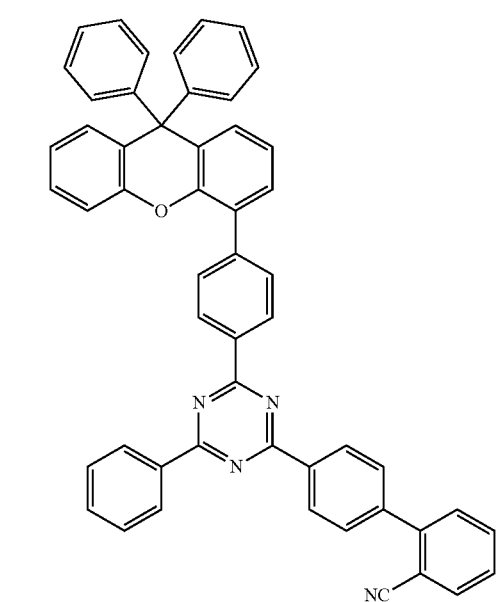
114
-continued
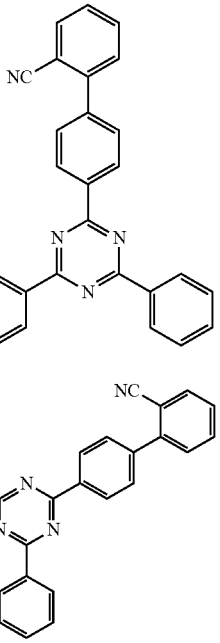
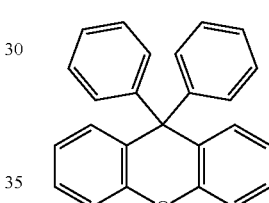
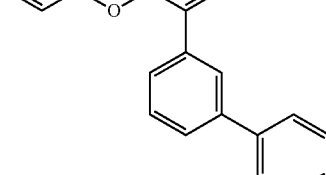
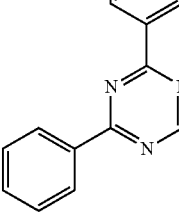
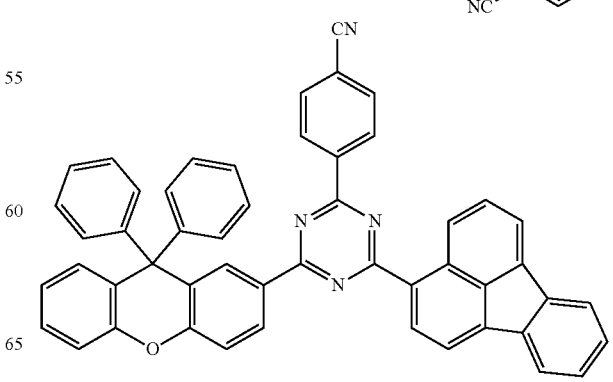

115
-continued
116
-continued
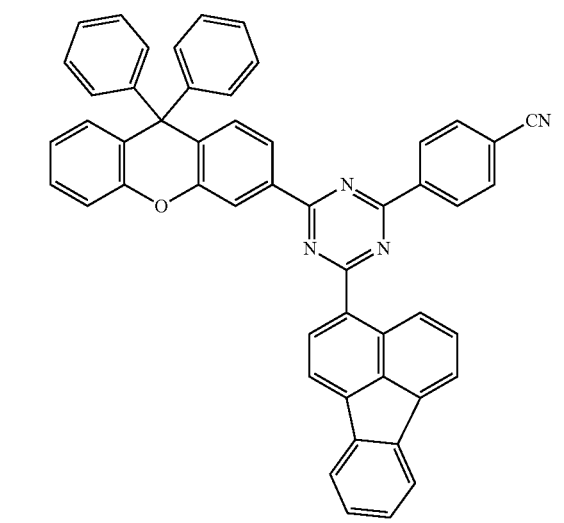
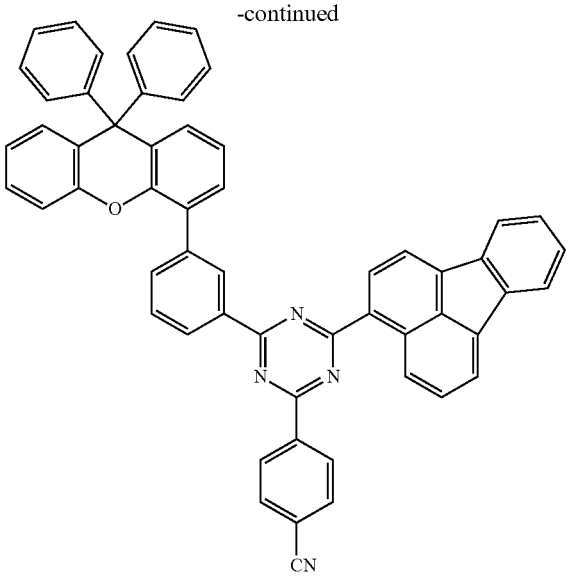

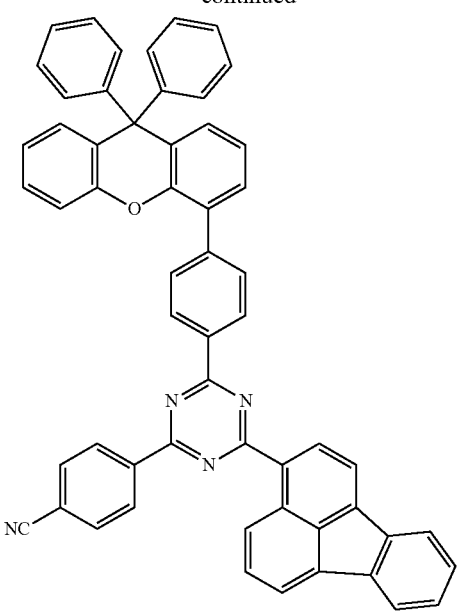
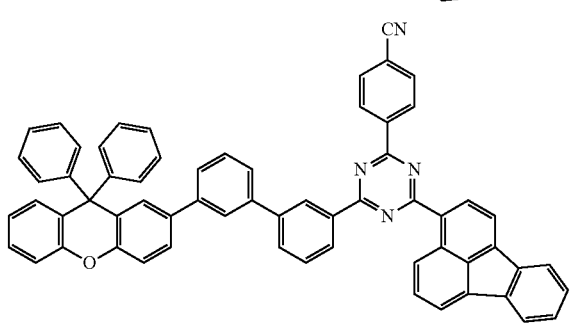
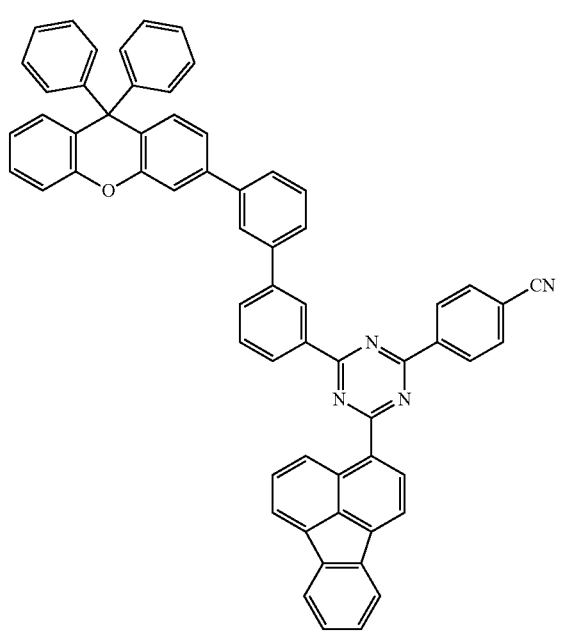

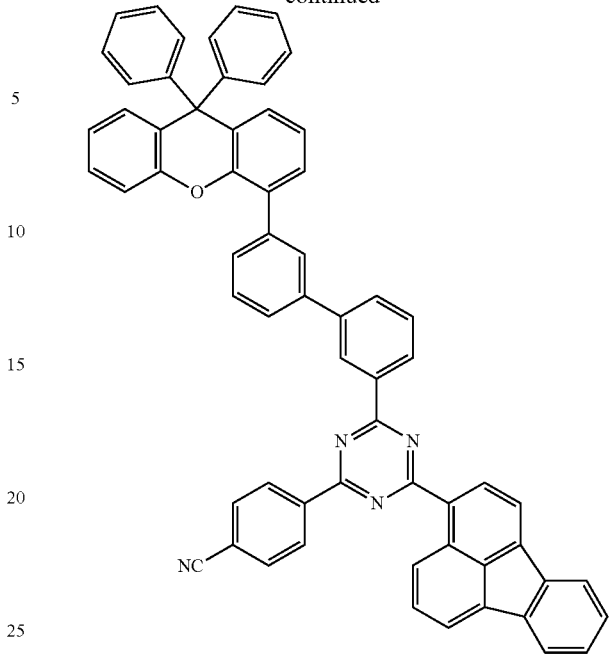

The compound represented by Chemical Formula 1 can be prepared, for example, by the preparation method as shown in the following Reaction Scheme 1, and the other compounds can be prepared in a similar manner.

[Reaction Scheme 1]

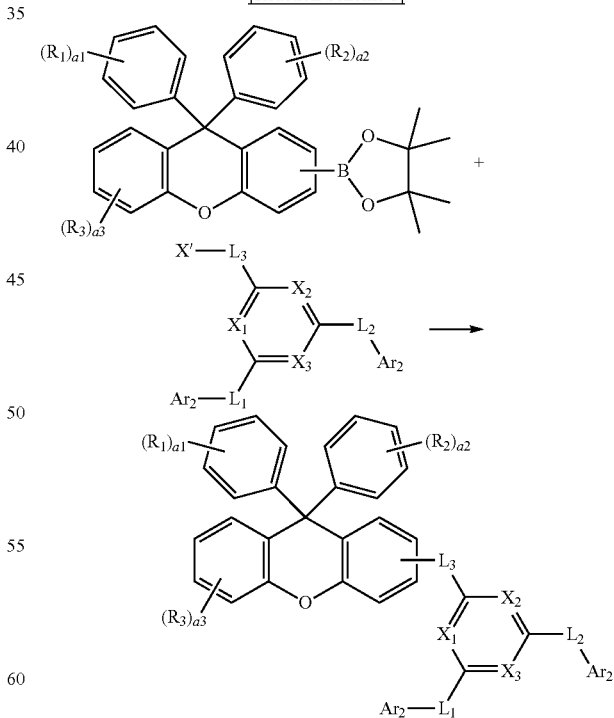

In Reaction Scheme 1, $X_1$ to $X_3$, $Ar_1$, $Ar_2$, $L_1$ to $L_3$, $R_1$ to $R_3$, a1, a2 and a3 are the same as those defined in Chemical Formula 1, and X is halogen, and preferably X' is chloro or bromo.

Reaction Scheme 1 includes a Suzuki coupling reaction, which is preferably carried out in the presence of a palladium catalyst and a base, and a reactive group for the Suzuki coupling reaction can be modified as known in the art. The above preparation method may be further embodied in Preparation Examples described hereinafter.

In addition, the present disclosure provides an organic light emitting device comprising the compound represented by Chemical Formula 1. In one example, the present disclosure provides an organic light emitting device comprising: a first electrode; a second electrode that is provided to face the first electrode; and an organic material layer including one or more layers that are provided between the first electrode and the second electrode, wherein one or more layers of the organic material layer include the compound represented by Chemical Formula 1.

The organic material layer of the organic light emitting device of the present disclosure may have a single-layer structure, or it may have a multilayered structure in which two or more organic material layers are stacked. For example, the organic light emitting device of the present disclosure may have a structure comprising a hole injection layer, a hole transport layer, a light emitting layer, an electron transport layer, an electron injection layer and the like as the organic material layer. However, the structure of the organic light emitting device is not limited thereto, and it may include a smaller number of layers of the organic material layer.

Further, the organic material layer may include a hole injection layer, a hole transport layer, or a layer for simultaneously performing hole injection and transport, wherein the hole injection layer, the hole transport layer, or the layer for simultaneously performing hole injection and transport may include the compound represented by Chemical Formula 1.

Further, the organic material layer may include a light emitting layer, wherein the light emitting layer may include the compound represented by Chemical Formula 1.

Further, the organic material layer may include a hole blocking layer, an electron transport layer, an electron injection layer, or a layer for simultaneously performing electron transport and electron injection, wherein the hole blocking layer, the electron transport layer, the electron injection layer, or the layer for simultaneously performing electron transport and electron injection may include the compound represented by Chemical Formula 1.

Further, the organic material layer may include a light emitting layer and an electron injection and transport layer, wherein the light emitting layer or the electron injection and transport layer may include the compound represented by Chemical Formula 1.

Further, the organic light emitting device according to the present disclosure may be a normal type organic light emitting device in which an anode, one or more organic material layers, and a cathode are sequentially stacked on a substrate. Further, the organic light emitting device according to the present disclosure may be an inverted type organic light emitting device in which a cathode, one or more organic material layers, and an anode are sequentially stacked on a substrate. Further, the structure of the organic light emitting device according to an embodiment of the present disclosure is illustrated in FIGS. 1 and 2.

FIG. 1 shows an example of an organic light emitting device comprising a substrate 1, an anode 2, a light emitting layer 3, and a cathode 4. In such a structure, the compound represented by Chemical Formula 1 may be included in the light emitting layer. FIG. 2 shows an example of an organic light emitting device comprising a substrate 1, an anode 2, a hole injection layer 5, a hole transport layer 6, an electron blocking layer 7, a light emitting layer 3, a hole blocking layer 8, an electron transport layer 9, an electron injection layer 10, and a cathode 4. In such a structure, the compound represented by Chemical Formula 1 may be included in at least one of the light emitting layer, the hole blocking layer, the electron transport layer and the electron injection layer.

The organic light emitting device according to the present disclosure may be manufactured by materials and methods known in the art, except that at least one of the organic material layers includes the compound represented by Chemical Formula 1. Further, when the organic light emitting device includes a plurality of organic material layers, the organic material layers may be formed of the same material or different materials.

For example, the organic light emitting device according to the present disclosure can be manufactured by sequentially stacking a first electrode, an organic material layer and a second electrode on a substrate. In this case, the organic light emitting device may be manufactured by depositing a metal, metal oxides having conductivity, or an alloy thereof on the substrate using a PVD (physical vapor deposition) method such as a sputtering method or an e-beam evaporation method to form an anode, forming organic material layers including the hole injection layer, the hole transport layer, the light emitting layer and the electron transport layer thereon, and then depositing a material that can be used as the cathode thereon. In addition to such a method, the organic light emitting device may be manufactured by sequentially depositing a cathode material, an organic material layer and an anode material on a substrate.

Further, the compound represented by Chemical Formula 1 may be formed into an organic layer by a solution coating method as well as a vacuum deposition method at the time of manufacturing an organic light emitting device. Herein, the solution coating method means a spin coating, a dip coating, a doctor blading, an inkjet printing, a screen printing, a spray method, a roll coating, or the like, but is not limited thereto.

In addition to such a method, the organic light emitting device may be manufactured by sequentially depositing a cathode material, an organic material layer and an anode material on a substrate (International Publication WO2003/012890). However, the manufacturing method is not limited thereto.

As an example, the first electrode is an anode, and the second electrode is a cathode, or alternatively, the first electrode is a cathode and the second electrode is an anode.

As the anode material, generally, a material having a large work function is preferably used so that holes can be smoothly injected into the organic material layer. Specific examples of the anode material include metals such as vanadium, chrome, copper, zinc, and gold, or an alloy thereof; metal oxides such as zinc oxides, indium oxides, indium tin oxides (ITO), and indium zinc oxides (IZO); a combination of metals and oxides, such as ZnO:Al or $SnO_2$:Sb; conductive compounds such as poly(3-methylthiophene), poly[3,4-(ethylene-1,2-dioxy)thiophene](PEDOT), polypyrrole, and polyaniline, and the like, but are not limited thereto.

As the cathode material, generally, a material having a small work function is preferably used so that electrons can be easily injected into the organic material layer. Specific examples of the cathode material include metals such as magnesium, calcium, sodium, potassium, titanium, indium, yttrium, lithium, gadolinium, aluminum, silver, tin, and lead, or an alloy thereof; a multilayered structure material such as LiF/Al or LiO$_2$/Al, and the like, but are not limited thereto.

The hole injection layer is a layer for injecting holes from the electrode, and the hole injection material is preferably a compound which has a capability of transporting the holes, thus has a hole injecting effect in the anode and an excellent hole injecting effect to the light emitting layer or the light emitting material, prevents excitons produced in the light emitting layer from moving to a electron injection layer or the electron injection material, and further is excellent in the ability to form a thin film. It is preferable that a HOMO (highest occupied molecular orbital) of the hole injection material is between the work function of the anode material and a HOMO of a peripheral organic material layer. Specific examples of the hole injection material include metal porphyrine, oligothiophene, an arylamine-based organic material, a hexanitrilehexaazatriphenylene-based organic material, a quinacridone-based organic material, a perylene-based organic material, anthraquinone, polyaniline and polythiophene-based conductive polymer, and the like, but are not limited thereto.

The hole transport layer is a layer that receives holes from a hole injection layer and transports the holes to the light emitting layer. The hole transport layer is suitably a material having large mobility to the holes, which may receive holes from the anode or the hole injection layer and transfer the holes to the light emitting layer. Specific examples thereof include an arylamine-based organic material, a conductive polymer, a block copolymer in which a conjugate portion and a non-conjugate portion are present together, and the like, but are not limited thereto.

The electron blocking layer is a layer provided between the hole transport layer and the light emitting layer in order to prevent the electrons injected in the cathode from being transferred to the hole transport layer without being recombined in the light emitting layer, which may also be referred to as an electron inhibition layer. The electron blocking layer is preferably a material having the smaller electron affinity than the electron transport layer.

The light emitting material is preferably a material which may receive holes and electrons transported from a hole transport layer and an electron transport layer, respectively, and combine the holes and the electrons to emit light in a visible ray region, and has good quantum efficiency to fluorescence or phosphorescence. Specific examples of the light emitting material include an 8-hydroxy-quinoline aluminum complex (Alq$_3$); a carbazole-based compound; a dimerized styryl compound; BAlq; a 10-hydroxybenzoquinoline-metal compound; a benzoxazole, benzthiazole and benzimidazole-based compound; a poly(p-phenylenevinylene)(PPV)-based polymer; a spiro compound; polyfluorene, lubrene, and the like, but are not limited thereto.

The light emitting layer may include a host material and a dopant material. The host material may be a fused aromatic ring derivative, a heterocycle-containing compound or the like. Specific examples of the fused aromatic ring derivatives include anthracene derivatives, pyrene derivatives, naphthalene derivatives, pentacene derivatives, phenanthrene compounds, fluoranthene compounds, and the like. Examples of the heterocyclic-containing compounds include carbazole derivatives, dibenzofuran derivatives, ladder-type furan compounds, pyrimidine derivatives, and the like, but are not limited thereto. Preferably, the compound represented by Chemical Formula 1 may be included as a host material.

Examples of the dopant material include an aromatic amine derivative, a styrylamine compound, a boron complex, a fluoranthene compound, a metal complex, and the like. Specifically, the aromatic amine derivative is a substituted or unsubstituted fused aromatic ring derivative having an arylamino group, and examples thereof include pyrene, anthracene, chrysene, periflanthene and the like, which have an arylamino group. The styrylamine compound is a compound where at least one arylvinyl group is substituted in substituted or unsubstituted arylamine, in which one or two or more substituent groups selected from the group consisting of an aryl group, a silyl group, an alkyl group, a cycloalkyl group, and an arylamino group are substituted or unsubstituted. Specific examples thereof include styrylamine, styryldiamine, styryltriamine, styryltetramine, and the like, but are not limited thereto. Further, the metal complex includes an iridium complex, a platinum complex, and the like, but is not limited thereto.

The hole blocking layer is a layer provided between the electron transport layer and the light emitting layer in order to prevent the holes injected in the anode from being transferred to the electron transport layer without being recombined in the light emitting layer, which may also be referred to as a hole inhibition layer. The hole blocking layer is preferably a material having the large ionization energy. Preferably, the compound represented by Chemical Formula 1 may be included as a material of the hole blocking layer.

The electron transport layer is a layer which receives electrons from an electron injection layer and transports the electrons to a light emitting layer, and an electron transport material is suitably a material which may receive electrons well from a cathode and transfer the electrons to a light emitting layer, and has a large mobility for electrons. Specific examples of the electron transport material include: an Al complex of 8-hydroxyquinoline; a complex including Alq$_3$; an organic radical compound; a hydroxyflavone-metal complex, and the like, but are not limited thereto. The electron transport layer may be used with any desired cathode material, as used according to the related art. In particular, appropriate examples of the cathode material are a typical material which has a low work function, followed by an aluminum layer or a silver layer. Specific examples thereof include cesium, barium, calcium, ytterbium, and samarium, in each case followed by an aluminum layer or a silver layer. Preferably, the compound represented by Chemical Formula 1 may be included as a material of the electron transport layer.

The electron injection layer is a layer which injects electrons from an electrode, and is preferably a compound which has a capability of transporting electrons, has an effect of injecting electrons from a cathode and an excellent effect of injecting electrons into a light emitting layer or a light emitting material, prevents excitons produced from the light emitting layer from moving to a hole injection layer, and is also excellent in the ability to form a thin film. Specific examples of the electron injection layer include fluorenone, anthraquinodimethane, diphenoquinone, thiopyran dioxide, oxazole, oxadiazole, triazole, imidazole, perylenetetracarboxylic acid, fluorenylidene methane, anthrone, and the like, and derivatives thereof, a metal complex compound, a nitrogen-containing 5-membered ring derivative, and the like, but are not limited thereto. Preferably, the compound represented by Chemical Formula 1 may be included as a material of the electron injection layer.

Examples of the metal complex compound include 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato)gallium, bis(10-hydroxybenzo[h]quinolinato)beryllium, bis(10-hydroxybenzo[h]quinolinato)zinc, bis(2-methyl-8-quinolinato)chlorogallium, bis(2-methyl-8-quinolinato)(o-cresolato)gallium, bis(2-methyl-8-quinolinato)(1-naphtholato)aluminum, bis(2-methyl-8-quinolinato)(2-naphtholato)gallium, and the like, but are not limited thereto.

On the other hand, in the present disclosure, the "electron injection and transport layer" is a layer that performs both the roles of the electron injection layer and the electron transport layer, and the materials that perform the roles of each layer may be used alone or in combination, without being limited thereto. Preferably, the compound represented by Chemical Formula 1 may be included as a material of the electron injection and transport layer.

The organic light emitting device according to the present disclosure may be a front-side emission type, a back-side emission type, or a dual emission type according to the material to be used.

In addition, the compound represented by Chemical Formula 1 may be included in an organic solar cell or an organic transistor in addition to an organic light emitting device.

The preparation of the compound represented by Chemical Formula 1 and the organic light emitting device including the same will be specifically described in the following Examples. However, the following Examples are provided for exemplifying the present disclosure, and the scope of the present disclosure is not limited thereby.

PREPARATION EXAMPLES

Preparation Example 1: Preparation of Compound 1

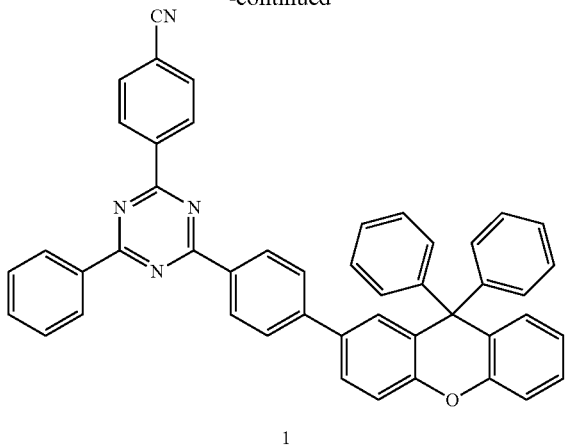

Compound A (7.50 g, 16.31 mmol) and Compound a-1 (6.01 g, 15.53 mmol) were completely dissolved in 280 ml of tetrahydrofuran in a 500 mL round bottom flask under nitrogen atmosphere, to which a 2M aqueous potassium carbonate solution (140 ml) was added and tetrakis-(triphenylphosphine)palladium (0.54 g, 0.47 mmol) was added, and then the resulting mixture was heated and stirred for 4 hours. The temperature was lowered to normal temperature, the aqueous layer was removed, and the resulting product was dried over anhydrous magnesium sulfate, then concentrated under reduced pressure, and recrystallized with 210 ml of tetrahydrofuran to prepare Compound 1 (8.26 g, 72%).

MS:[M+H]$^+$=667

Preparation Example 2: Preparation of Compound 2

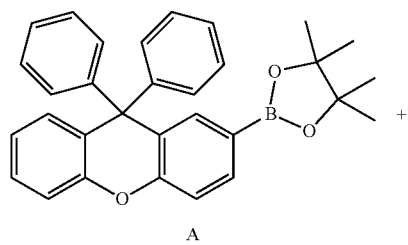

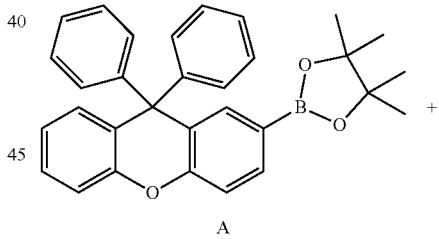

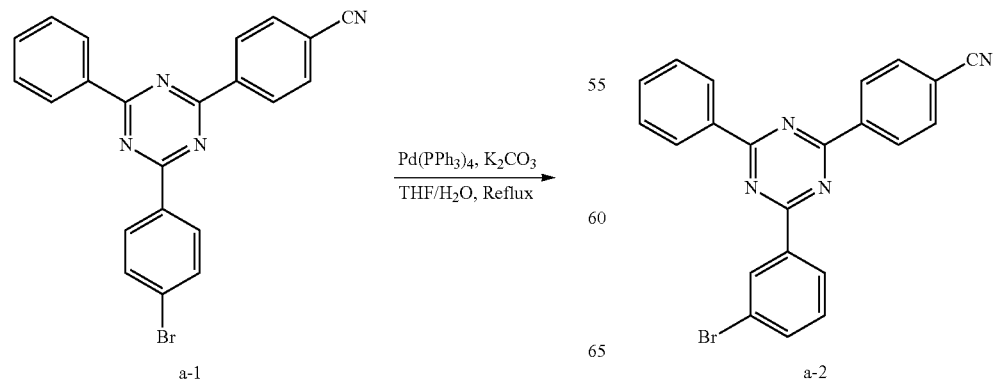

-continued

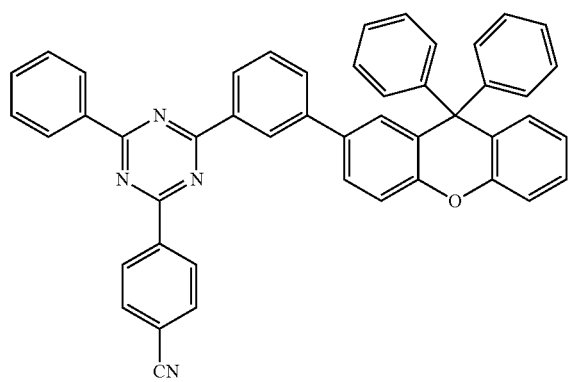

2

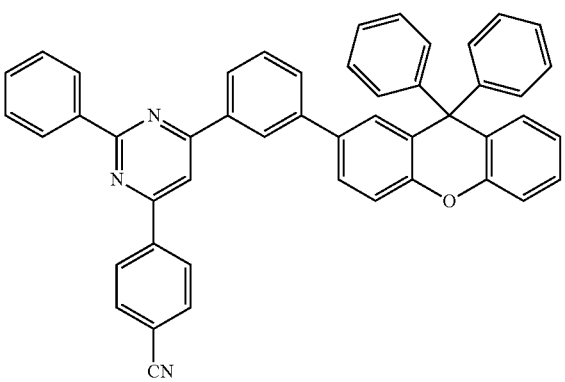

3

Compound A (7.50 g, 16.31 mmol) and Compound a-2 (6.01 g, 15.53 mmol) were completely dissolved in 280 ml of tetrahydrofuran in a 500 mL round bottom flask under nitrogen atmosphere, to which a 2M aqueous potassium carbonate solution (140 ml) was added and tetrakis-(triphenylphosphine)palladium (0.54 g, 0.47 mmol) was added, and then the resulting mixture was heated and stirred for 4 hours. The temperature was lowered to normal temperature, the aqueous layer was removed, and the resulting product was dried over anhydrous magnesium sulfate, then concentrated under reduced pressure, and recrystallized with 280 ml of ethylacetate to prepare Compound 2 (6.86 g, 59%).

MS:[M+H]$^+$=667

Compound A (7.50 g, 16.31 mmol) and Compound a-3 (6.01 g, 15.53 mmol) were completely dissolved in 280 ml of tetrahydrofuran in a 500 mL round bottom flask under nitrogen atmosphere, to which a 2M aqueous potassium carbonate solution (140 ml) was added and tetrakis-(triphenylphosphine)palladium (0.54 g, 0.47 mmol) was added, and then the resulting mixture was heated and stirred for 4 hours. The temperature was lowered to normal temperature, the aqueous layer was removed, and the resulting product was dried over anhydrous magnesium sulfate, then concentrated under reduced pressure, and recrystallized with 250 ml of ethylacetate to prepare Compound 3 (6.52 g, 57%).

MS:[M+H]$^+$=666

Preparation Example 3: Preparation of Compound 3

Preparation Example 4: Preparation of Compound 4

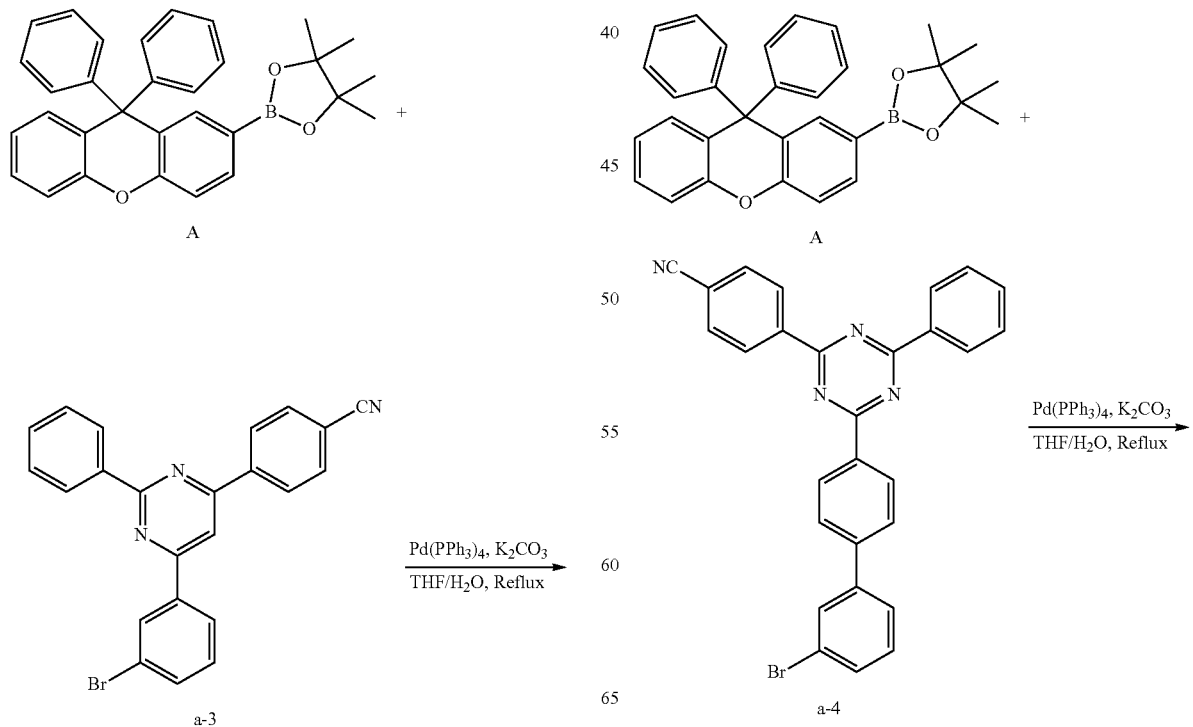

-continued

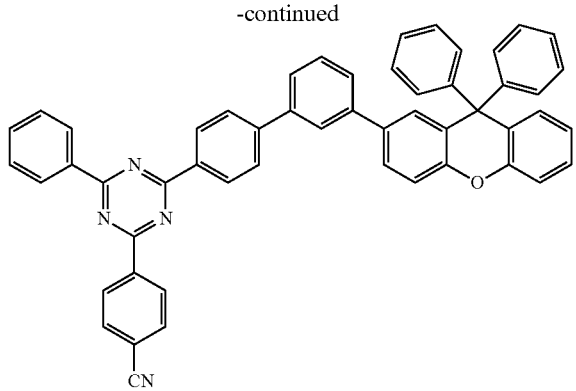

4

-continued

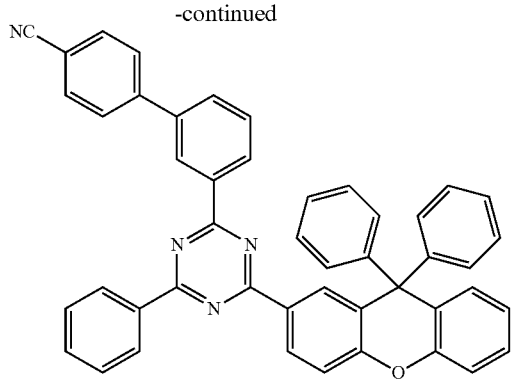

5

Compound A (7.50 g, 16.31 mmol) and Compound a-4 (6.01 g, 15.53 mmol) were completely dissolved in 280 ml of tetrahydrofuran in a 500 mL round bottom flask under nitrogen atmosphere, to which a 2M aqueous potassium carbonate solution (140 ml) was added and tetrakis-(triphenylphosphine)palladium (0.54 g, 0.47 mmol) was added, and then the resulting mixture was heated and stirred for 4 hours. The temperature was lowered to normal temperature, the aqueous layer was removed, and the resulting product was dried over anhydrous magnesium sulfate, then concentrated under reduced pressure, and recrystallized with 230 ml of ethylacetate to prepare Compound 4 (631 g, 55%).

MS:[M+H]$^+$=743

Preparation Example 5: Preparation of Compound 5

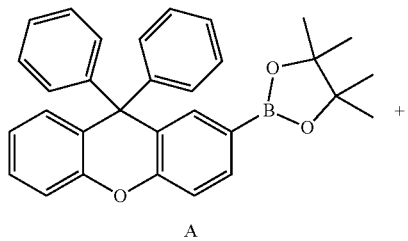

Compound A (7.51 g, 16.32 mmol) and Compound a-5 (5.53 g, 15.54 mmol) were completely dissolved in 280 ml of tetrahydrofuran in a 500 mL round bottom flask under nitrogen atmosphere, to which a 2M aqueous potassium carbonate solution (140 ml) was added and tetrakis-(triphenylphosphine)palladium (0.54 g, 0.47 mmol) was added, and then the resulting mixture was heated and stirred for 4 hours. The temperature was lowered to normal temperature, the aqueous layer was removed, and the resulting product was dried over anhydrous magnesium sulfate, then concentrated under reduced pressure, and recrystallized with 180 ml of ethylacetate to prepare Compound 5 (5.97 g, 60%),

MS:[M+H]$^+$=667

Preparation Example 6: Preparation of Compound 6

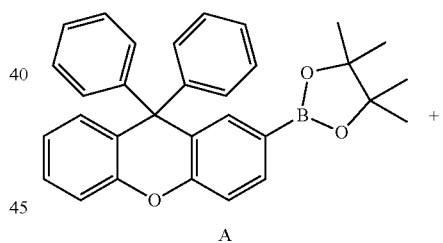

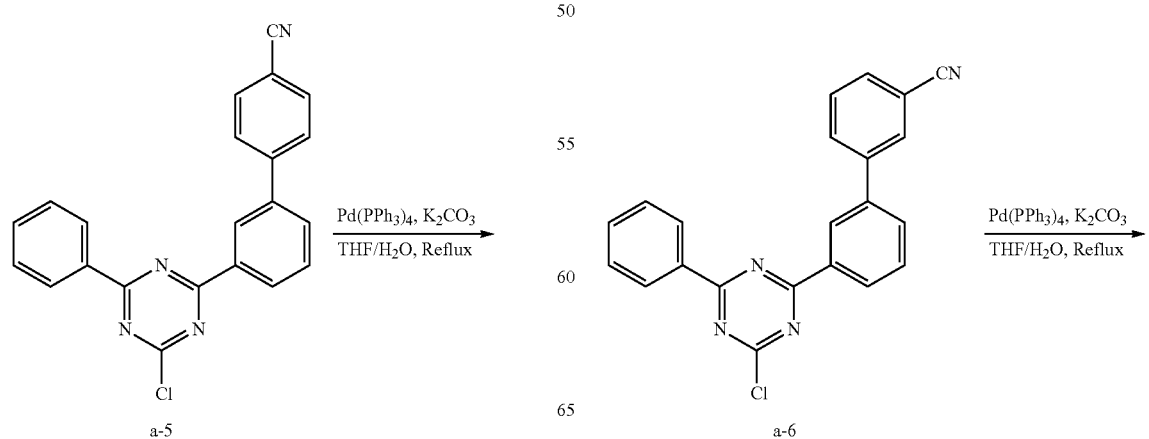

-continued

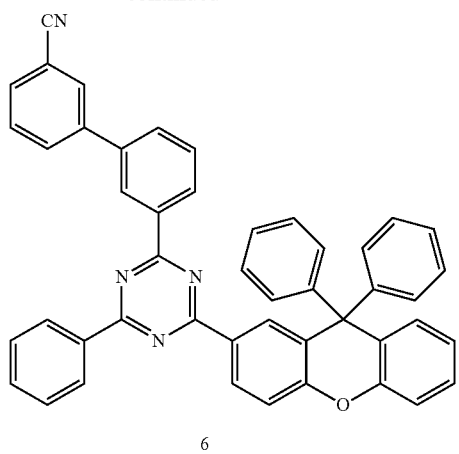

6

Compound A (7.50 g, 16.29 mmol) and Compound a-6 (5.54 g, 15.52 mmol) were completely dissolved in 280 ml of tetrahydrofuran in a 500 mL round bottom flask under nitrogen atmosphere, to which a 2M aqueous potassium carbonate solution (140 ml) was added and tetrakis-(triphenylphosphine)palladium (0.54 g, 0.47 mmol) was added, and then the resulting mixture was heated and stirred for 4 hours. The temperature was lowered to normal temperature, the aqueous layer was removed, and the resulting product was dried over anhydrous magnesium sulfate, then concentrated under reduced pressure, and recrystallized with 210 ml of ethylacetate to prepare Compound 6 (5.97 g, 60%).

MS:[M+H]$^+$=667

Preparation Example 7: Preparation of Compound 7

-continued

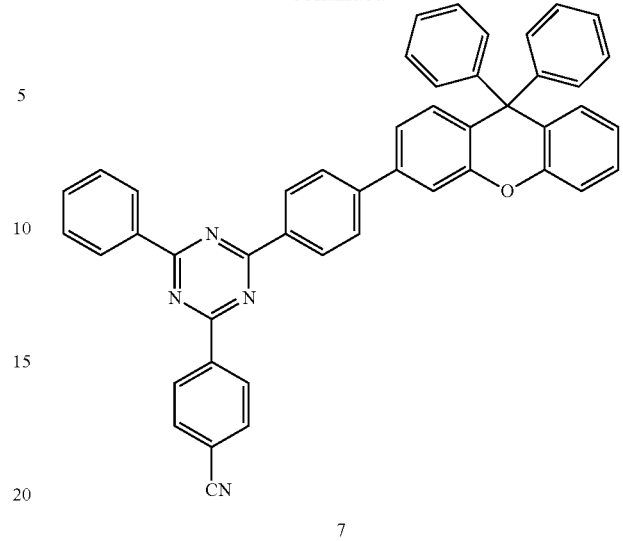

7

Compound B (7.50 g, 16.31 mmol) and Compound a-1 (6.01 g, 15.53 mmol) were completely dissolved in 280 ml of tetrahydrofuran in a 500 mL round bottom flask under nitrogen atmosphere, to which a 2M aqueous potassium carbonate solution (140 ml) was added and tetrakis-(triphenylphosphine)palladium (0.54 g, 0.47 mmol) was added, and then the resulting mixture was heated and stirred for 4 hours. The temperature was lowered to normal temperature, the aqueous layer was removed, and the resulting product was dried over anhydrous magnesium sulfate, then concentrated under reduced pressure, and recrystallized with 210 ml of tetrahydrofuran to prepare Compound 7 (7.16 g, 72%).

MS:[M+H]$^+$=667

Preparation Example 8: Preparation of Compound 8

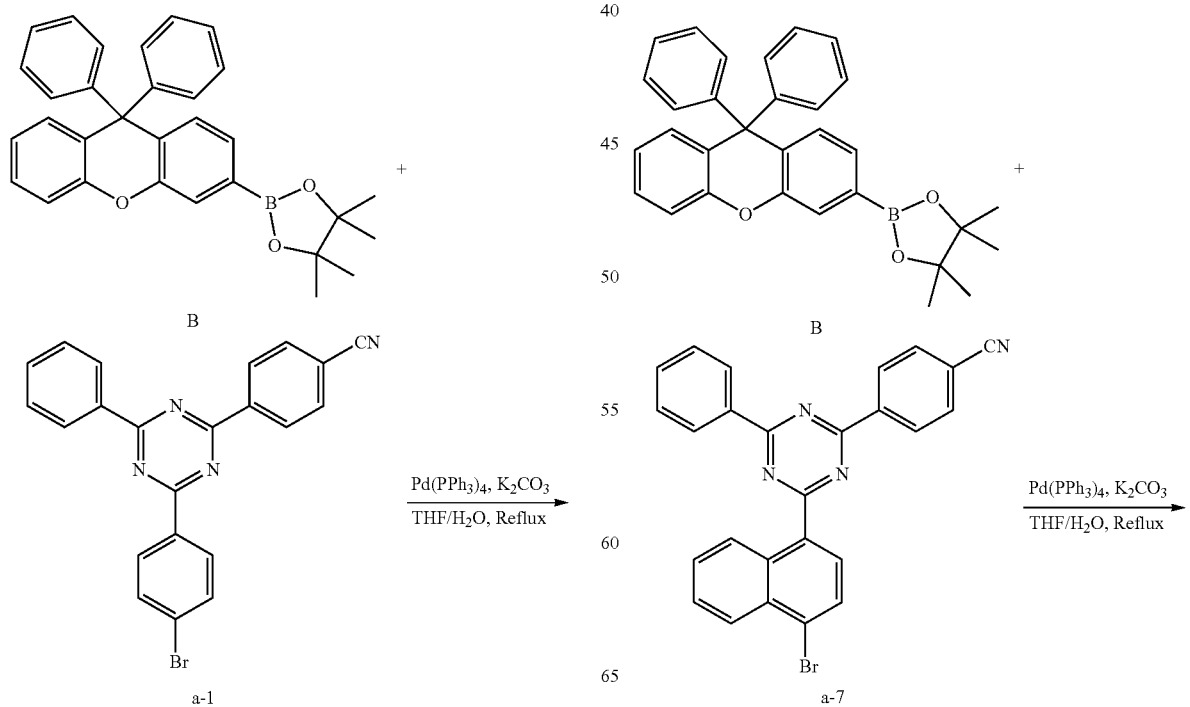

-continued

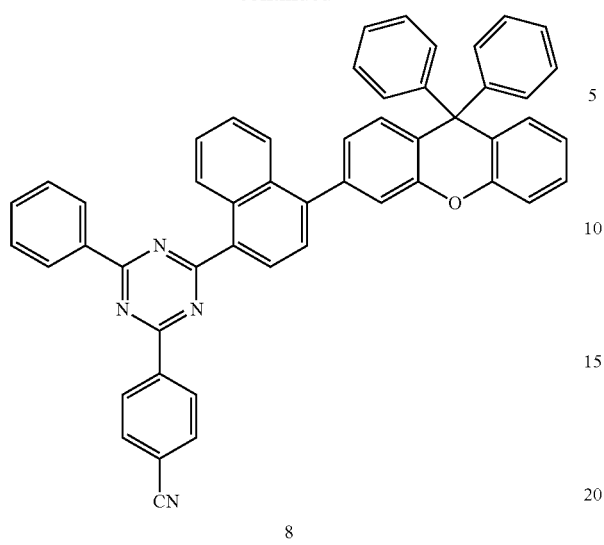

8

Compound B (7.50 g, 16.31 mmol) and Compound a-7 (5.70 g, 15.53 mmol) were completely dissolved in 280 ml of tetrahydrofuran in a 500 mL round bottom flask under nitrogen atmosphere, to which a 2M aqueous potassium carbonate solution (140 ml) was added and tetrakis-(triphenylphosphine)palladium (0.54 g, 0.47 mmol) was added, and then the resulting mixture was heated and stirred for 4 hours. The temperature was lowered to normal temperature, the aqueous layer was removed, and the resulting product was dried over anhydrous magnesium sulfate, then concentrated under reduced pressure, and recrystallized with 210 ml of ethylacetate to prepare Compound 8 (8.22 g, 79%).

MS:[M+H]$^+$=717

Preparation Example 9: Preparation of Compound 9

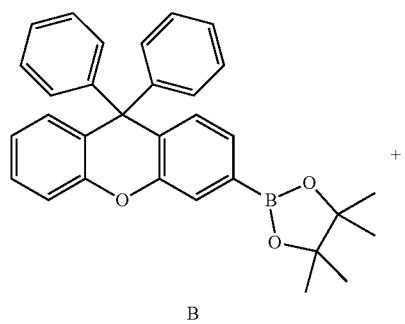

B

+

-continued

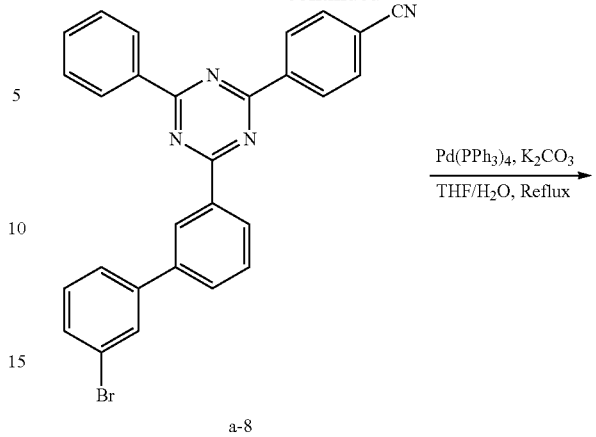

a-8

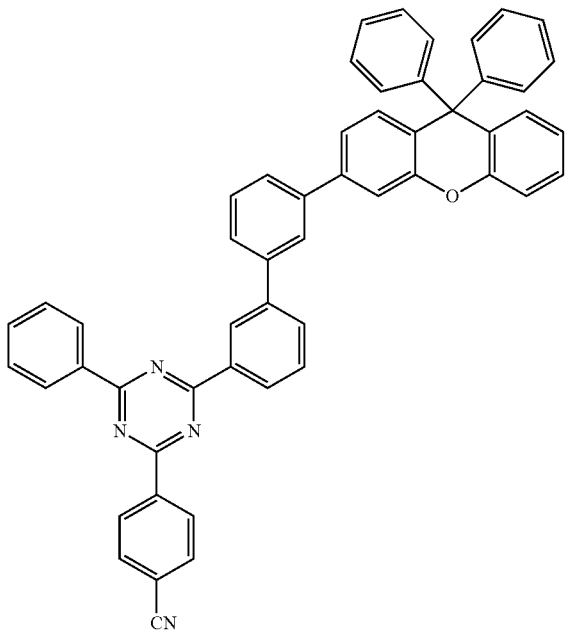

9

Compound B (7.50 g, 16.31 mmol) and Compound a-8 (5.70 g, 15.53 mmol) were completely dissolved in 280 ml of tetrahydrofuran in a 500 mL round bottom flask under nitrogen atmosphere, to which a 2M aqueous potassium carbonate solution (140 ml) was added and tetrakis-(triphenylphosphine)palladium (0.54 g, 0.47 mmol) was added, and then the resulting mixture was heated and stirred for 4 hours. The temperature was lowered to normal temperature, the aqueous layer was removed, and the resulting product was dried over anhydrous magnesium sulfate, then concentrated under reduced pressure, and recrystallized with 240 ml of ethylacetate to prepare Compound 9 (8.22 g, 79%).

MS:[M+H]$^+$=743

Preparation Example 10: Preparation of Compound 10

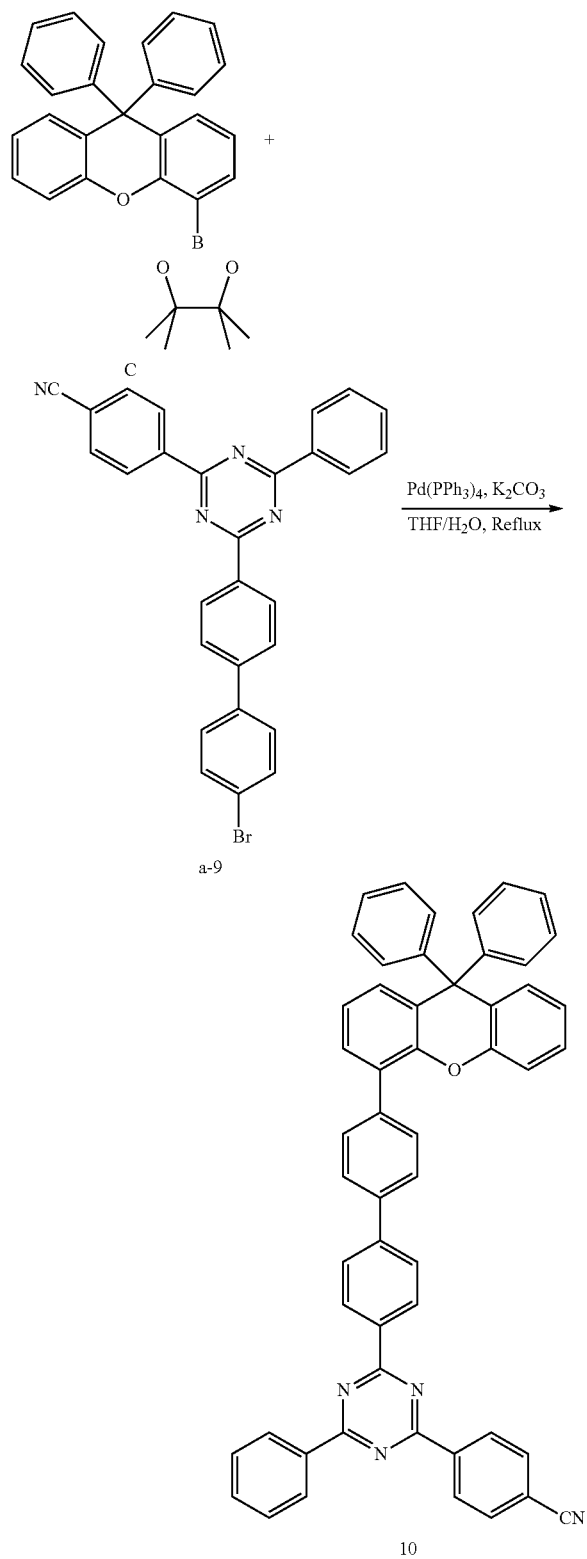

Compound C (7.50 g, 16.31 mmol) and Compound a-9 (5.70 g, 15.53 mmol) were completely dissolved in 280 ml of tetrahydrofuran in a 500 mL round bottom flask under nitrogen atmosphere, to which a 2M aqueous potassium carbonate solution (140 ml) was added and tetrakis-(triphenylphosphine)palladium (0.54 g, 0.47 mmol) was added, and then the resulting mixture was heated and stirred for 4 hours. The temperature was lowered to normal temperature, the aqueous layer was removed, and the resulting product was dried over anhydrous magnesium sulfate, then concentrated under reduced pressure, and recrystallized with 260 ml of ethylacetate to prepare Compound 10 (8.22 g, 79%).
MS:[M+H]$^+$=743

Preparation Example 11: Preparation of Compound 11

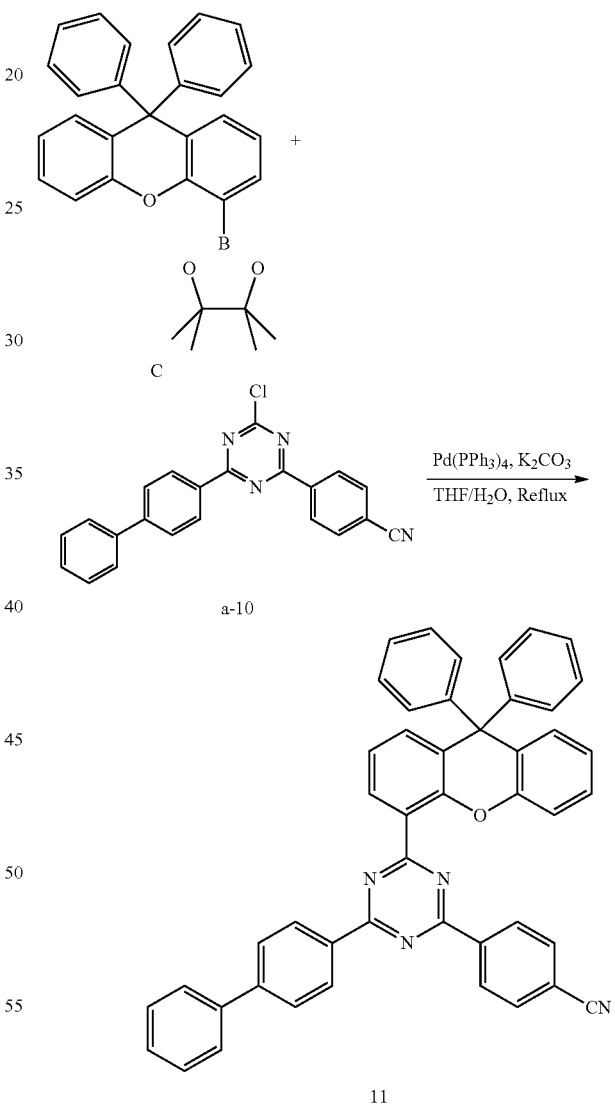

Compound C (7.50 g, 16.31 mmol) and Compound a-10 (4.91 g, 15.54 mmol) were completely dissolved in 280 ml of tetrahydrofuran in a 500 mL round bottom flask under nitrogen atmosphere, to which a 2M aqueous potassium carbonate solution (140 ml) was added and tetrakis-(triphenylphosphine)palladium (0.54 g, 0.47 mmol) was added, and then the resulting mixture was heated and stirred for 4 hours. The temperature was lowered to normal temperature, the aqueous layer was removed, and the resulting product was dried over anhydrous magnesium sulfate, then concentrated under reduced pressure, and recrystallized with 230 ml of ethylacetate to prepare Compound 11 (5.97 g, 60%).

MS:[M+H]$^+$=667

Preparation Example 12: Preparation of Compound 12

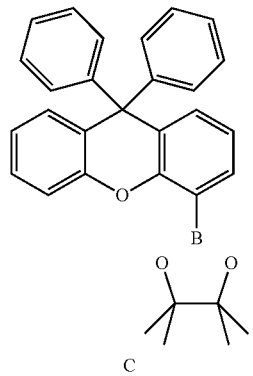

C

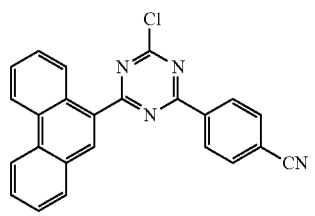

a-11

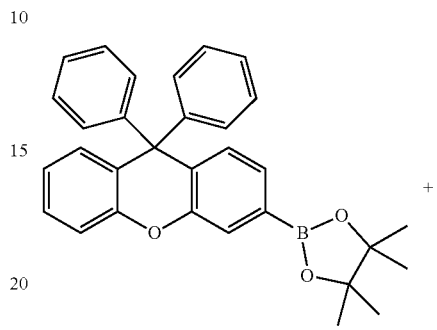

12

Compound C (7.50 g, 16.31 mmol) and Compound a-11 (4.91 g, 15.54 mmol) were completely dissolved in 280 ml of tetrahydrofuran in a 500 mL round bottom flask under nitrogen atmosphere, to which a 2M aqueous potassium carbonate solution (140 ml) was added and tetrakis-(triphenylphosphine)palladium (0.54 g, 0.47 mmol) was added, and then the resulting mixture was heated and stirred for 4 hours. The temperature was lowered to normal temperature, the aqueous layer was removed, and the resulting product was dried over anhydrous magnesium sulfate, then concentrated under reduced pressure, and recrystallized with 230 ml of ethylacetate to prepare Compound 12 (5.97 g, 60%).

MS:[M+H]$^+$=691

Preparation Example 13: Preparation of Compound 13

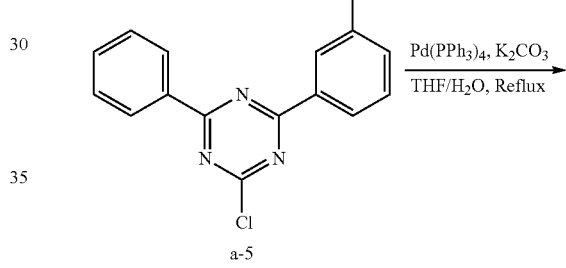

a-5

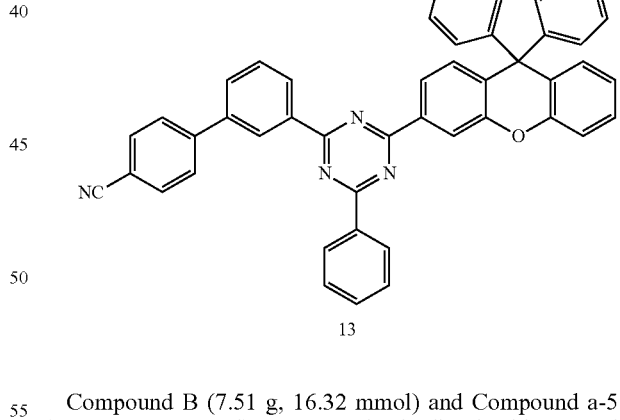

13

Compound B (7.51 g, 16.32 mmol) and Compound a-5 (5.33 g, 15.54 mmol) were completely dissolved in 280 ml of tetrahydrofuran in a 500 mL round bottom flask under nitrogen atmosphere, to which a 2M aqueous potassium carbonate solution (140 ml) was added and tetrakis-(triphenylphosphine)palladium (0.54 g, 0.47 mmol) was added, and then the resulting mixture was heated and stirred for 4 hours. The temperature was lowered to normal temperature, the aqueous layer was removed, and the resulting product was dried over anhydrous magnesium sulfate, then concentrated under reduced pressure, and recrystallized with 180 ml of ethylacetate to prepare Compound 13 (5.97 g, 60%).

MS:[M+H]$^+$=667

Preparation Example 14: Preparation of Compound 14

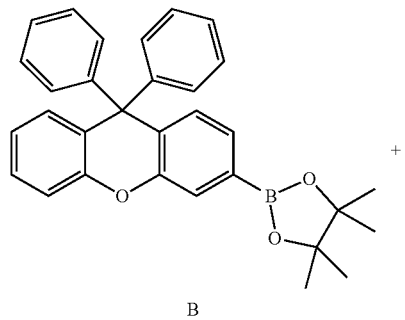

B

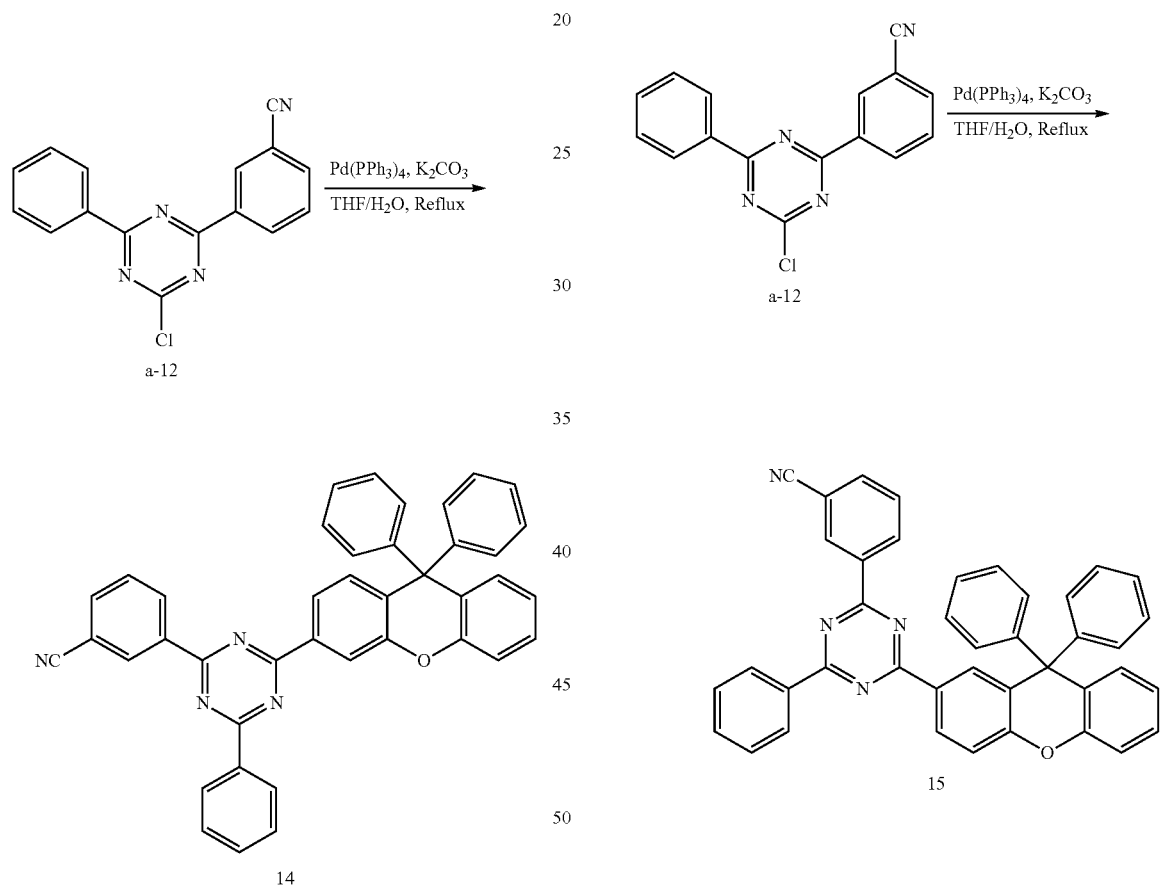

Compound B (7.51 g, 16.32 mmol) and Compound a-12 (5.33 g, 15.54 mmol) were completely dissolved in 280 ml of tetrahydrofuran in a 500 mL round bottom flask under nitrogen atmosphere, to which a 2M aqueous potassium carbonate solution (140 ml) was added and tetrakis-(triphenylphosphine)palladium (0.54 g, 0.47 mmol) was added, and then the resulting mixture was heated and stirred for 4 hours. The temperature was lowered to normal temperature, the aqueous layer was removed, and the resulting product was dried over anhydrous magnesium sulfate, then concentrated under reduced pressure, and recrystallized with 180 ml of ethylacetate to prepare Compound 14 (5.97 g, 60%).

MS:[M+H]$^+$=591

Preparation Example 15: Preparation of Compound 15

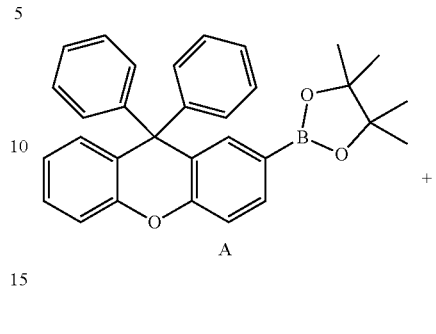

A

Compound A (7.51 g, 16.32 mmol) and Compound a-12 (5.33 g, 15.54 mmol) were completely dissolved in 280 ml of tetrahydrofuran in a 500 mL round bottom flask under nitrogen atmosphere, to which a 2M aqueous potassium carbonate solution (140 ml) was added and tetrakis-(triphenylphosphine)palladium (0.54 g, 0.47 mmol) was added, and then the resulting mixture was heated and stirred for 4 hours. The temperature was lowered to normal temperature, the aqueous layer was removed, and the resulting product was dried over anhydrous magnesium sulfate, then concentrated under reduced pressure, and recrystallized with 180 ml of ethylacetate to prepare Compound 15 (5.97 g, 60%).

MS:[M+H]$^+$=591

Preparation Example 16: Preparation of Compound 16

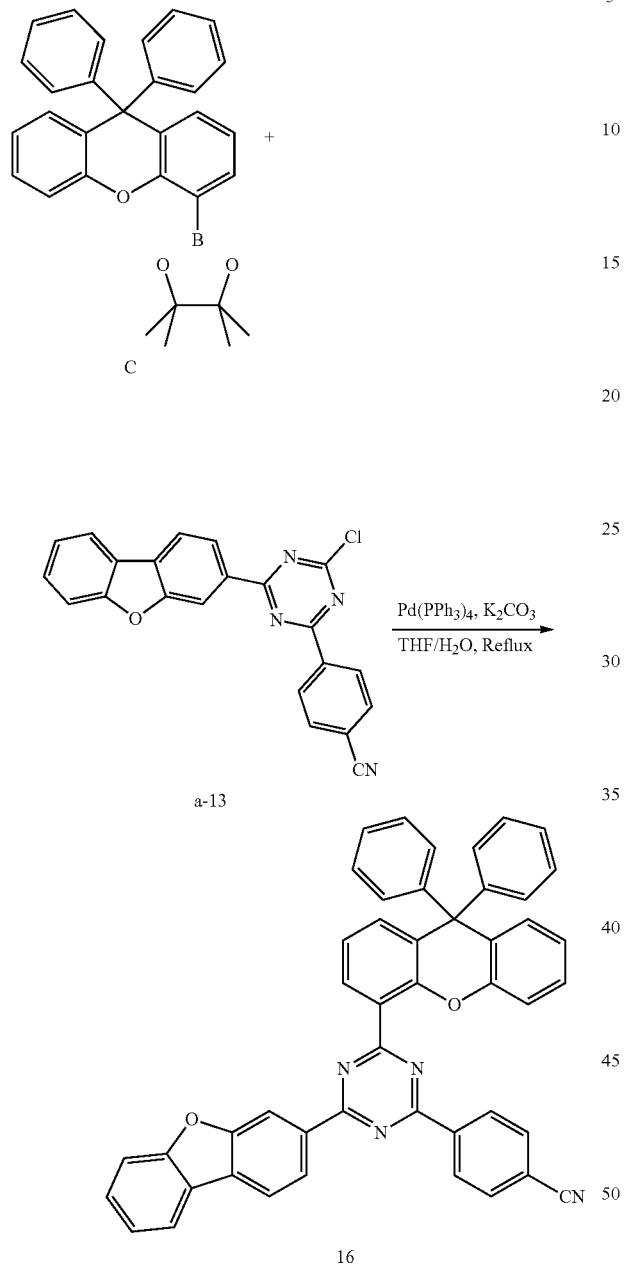

a-13

16

Compound C (7.50 g, 16.31 mmol) and Compound a-13 (4.91 g, 15.54 mmol) were completely dissolved in 280 ml of tetrahydrofuran in a 500 mL round bottom flask under nitrogen atmosphere, to which a 2M aqueous potassium carbonate solution (140 ml) was added and tetrakis-(triphenylphosphine)palladium (0.54 g, 0.47 mmol) was added, and then the resulting mixture was heated and stirred for 4 hours. The temperature was lowered to normal temperature, the aqueous layer was removed, and the resulting product was dried over anhydrous magnesium sulfate, then concentrated under reduced pressure, and recrystallized with 230 ml of ethylacetate to prepare Compound 16 (5.97 g, 60%).

MS:[M+H]$^+$=681

Preparation Example 17: Preparation of Compound 17

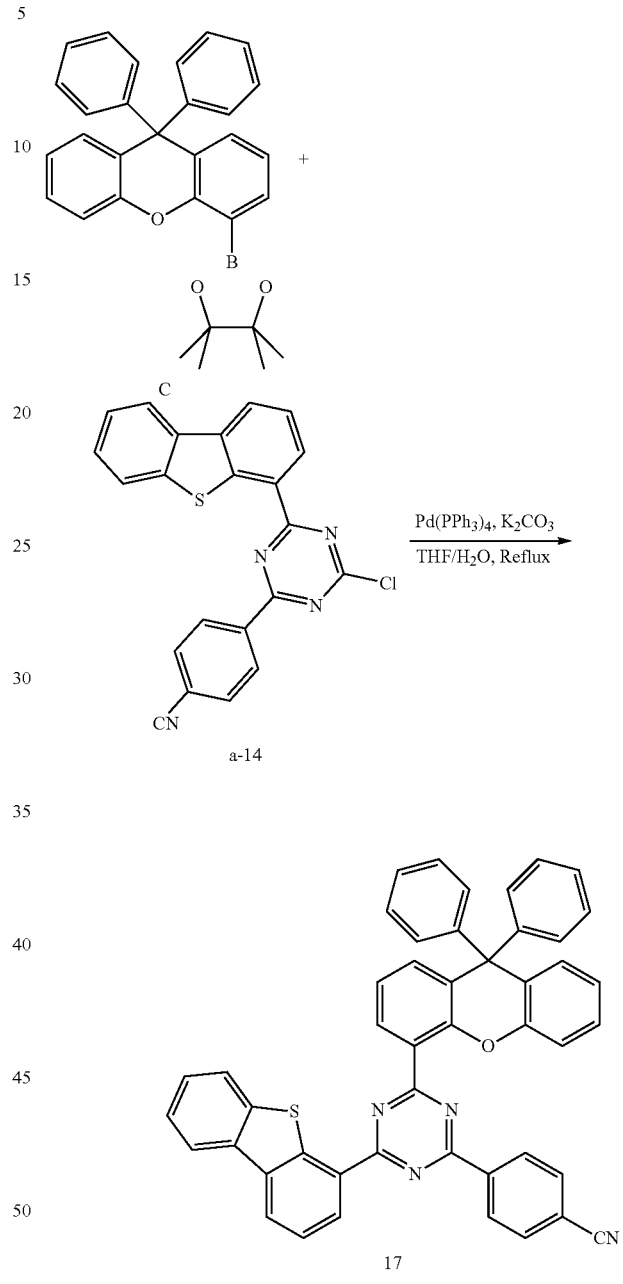

a-14

17

Compound C (7.50 g, 16.31 mmol) and Compound a-14 (4.91 g, 15.54 mmol) were completely dissolved in 280 ml of tetrahydrofuran in a 500 mL round bottom flask under nitrogen atmosphere, to which a 2M aqueous potassium carbonate solution (140 ml) was added and tetrakis-(triphenylphosphine)palladium (0.54 g, 0.47 mmol) was added, and then the resulting mixture was heated and stirred for 4 hours. The temperature was lowered to normal temperature, the aqueous layer was removed, and the resulting product was dried over anhydrous magnesium sulfate, then concentrated under reduced pressure, and recrystallized with 230 ml of ethylacetate to prepare Compound 17 (5.97 g, 60%).

MS:[M+H]$^+$=697

Preparation Example 18: Preparation of Compound 18

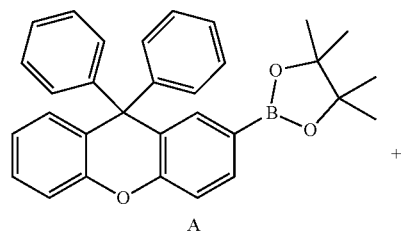
A

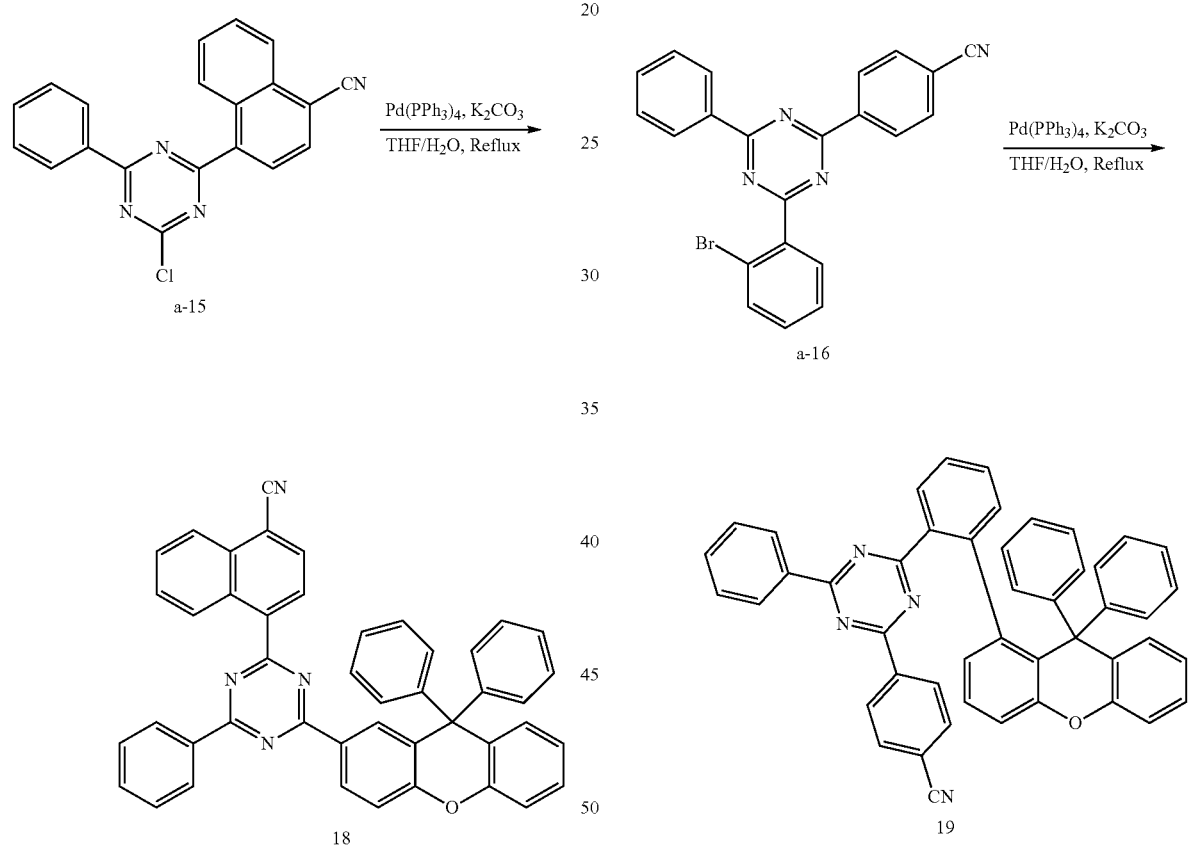

Compound A (8.11 g, 17.63 mmol) and Compound a-15 (5.74 g, 16.75 mmol) were completely dissolved in 280 ml of tetrahydrofuran in a 500 mL round bottom flask under nitrogen atmosphere, to which a 2M aqueous potassium carbonate solution (140 ml) was added and tetrakis-(triphenylphosphine)palladium (0.61 g, 0.53 mmol) was added, and then the resulting mixture was heated and stirred for 5 hours. The temperature was lowered to normal temperature, the aqueous layer was removed, and the resulting product was dried over anhydrous magnesium sulfate, then concentrated under reduced pressure, and recrystallized with 250 ml of ethylacetate to prepare Compound 18 (6.88 g, 61%).

MS:[M+H]$^+$=641

Preparation Example 19: Preparation of Compound 19

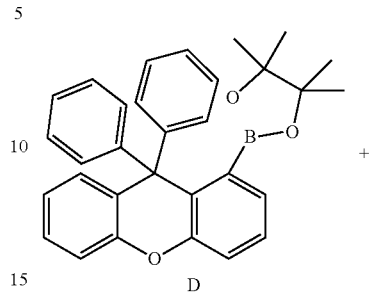
D

Compound D (9.37 g, 20.37 mmol) and Compound a-16 (7.63 g, 18.52 mmol) were completely dissolved in 280 ml of tetrahydrofuran in a 500 mL round bottom flask under nitrogen atmosphere, to which a 2M aqueous potassium carbonate solution (140 ml) was added and tetrakis-(triphenylphosphine)palladium (0.64 g, 0.56 mmol) was added, and then the resulting mixture was heated and stirred for 4 hours. The temperature was lowered to normal temperature, the aqueous layer was removed, and the resulting product was dried over anhydrous magnesium sulfate, then concentrated under reduced pressure, and recrystallized with 210 ml of tetrahydrofuran to prepare Compound 19 (7.11 g, 58%).

MS:[M+H]$^+$=667

Preparation Example 20: Preparation of Compound 20

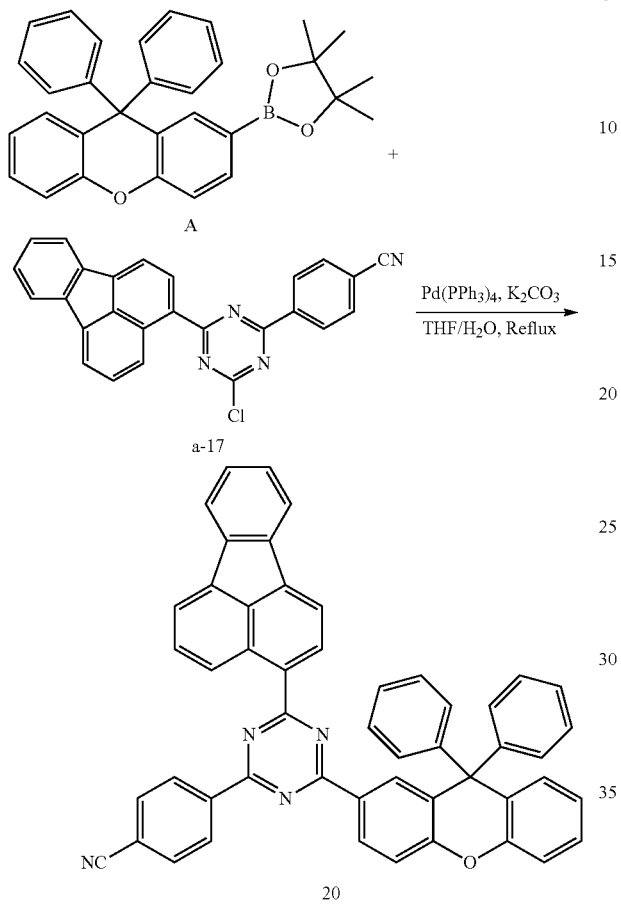

Compound A (8.57 g, 18.64 mmol) and Compound a-17 (6.66 g, 16.20 mmol) were completely dissolved in 280 ml of tetrahydrofuran in a 500 mL round bottom flask under nitrogen atmosphere, to which a 2M aqueous potassium carbonate solution (140 ml) was added and tetrakis-(triphenylphosphine)palladium (0.56 g, 0.49 mmol) was added, and then the resulting mixture was heated and stirred for 5 hours. The temperature was lowered to normal temperature, the aqueous layer was removed, and the resulting product was dried over anhydrous magnesium sulfate, then concentrated under reduced pressure, and recrystallized with 240 ml of ethylacetate to prepare Compound 20 (7.16 g, 62%).

MS:[M+H]$^+$=715

EXAMPLES

Example 1-1

A glass substrate thinly coated with indium tin oxide (ITO) to have a thickness of 1,000 Å was put into distilled water in which a detergent was dissolved, and ultrasonically washed. In this case, a product manufactured by Fischer Co. was used as the detergent, and distilled water twice filtered using a filter manufactured by Millipore Co. was used as the distilled water. After the ITO was washed for 30 minutes, ultrasonic washing was conducted twice repeatedly using distilled water for 10 minutes. After the washing using distilled water was completed, ultrasonic washing was conducted using isopropyl alcohol, acetone, and methanol solvents, and drying was conducted, and then the substrate was transferred to a plasma cleaner. In addition, the substrate was cleaned using oxygen plasma for 5 minutes, and then transferred to a vacuum evaporator.

On the ITO transparent electrode which is the anode thus prepared, the following compound HI1 and the following compound HI2 were thermally vacuum deposited at a molar ratio of 98:2 to have a thickness of 100 Å, thereby forming a hole injection layer. The following compound HT1 (1150 Å) was vacuum deposited on the hole injection layer to form a hole transport layer. Subsequently, the following compound EB1 was vacuum deposited to a thickness of 50 Å on the hole transport layer to form an electron blocking layer. Subsequently, the following compound BH and the following compound BD were vacuum deposited at a weight ratio of 50:1 on the electron blocking layer to a thickness of 200 Å to form a light emitting layer. The Compound 5 previously prepared was vacuum deposited to a thickness of 50 Å on the light emitting layer to form a hole blocking layer. Then, the following compound ET1 and the following compound LiQ were vacuum deposited at a weight ratio of 1:1 on the hole blocking layer to form an electron injection and transport layer with a thickness of 30 Å. Lithium fluoride (LiF) and aluminum were sequentially deposited to have a thickness of 12 Å and 1,000 Å, respectively, on the electron injection and transport layer, thereby forming a cathode.

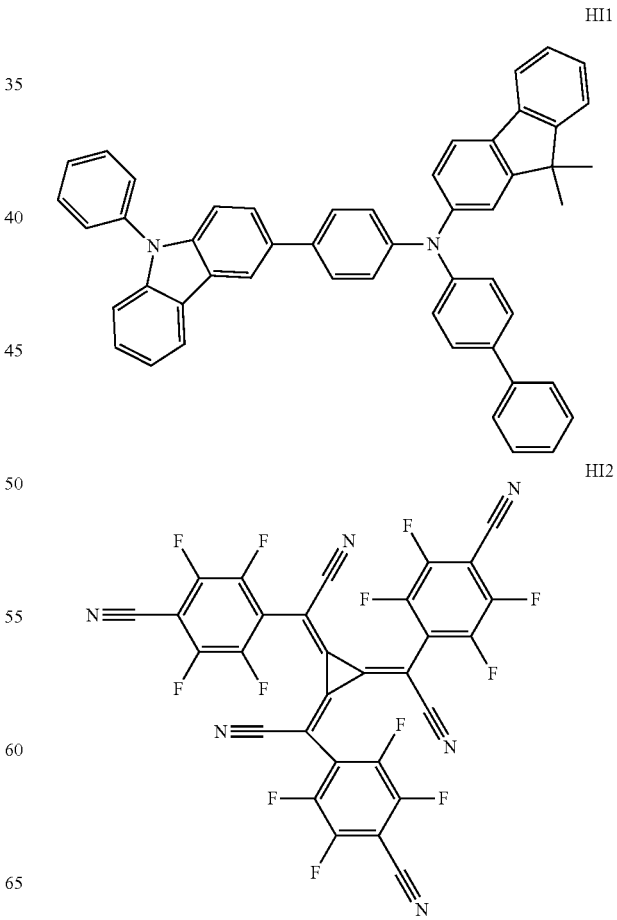

HT1

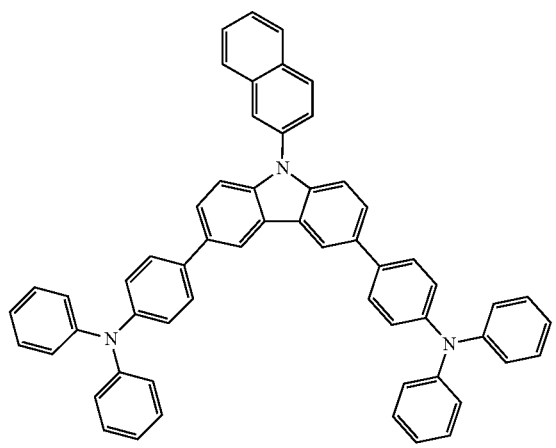

EB1

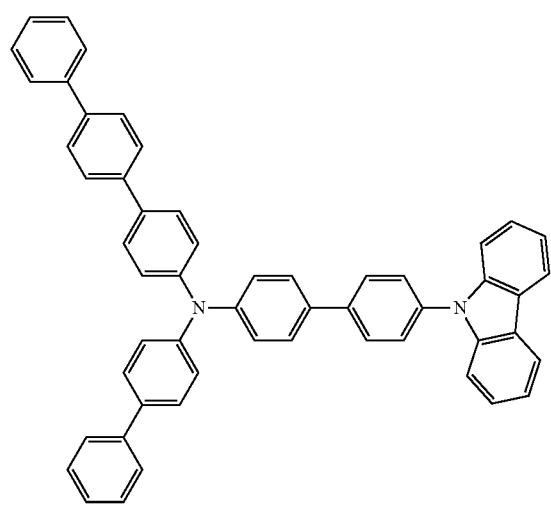

BH

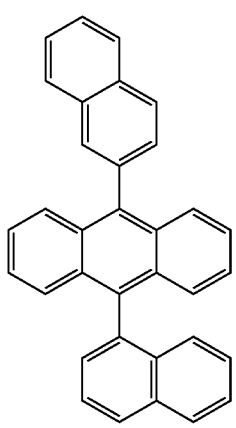

BD

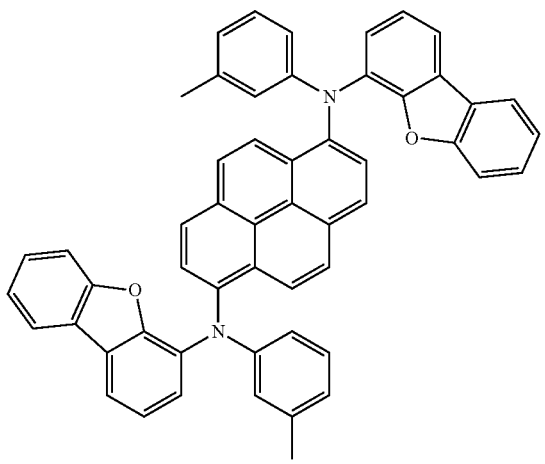

ET1

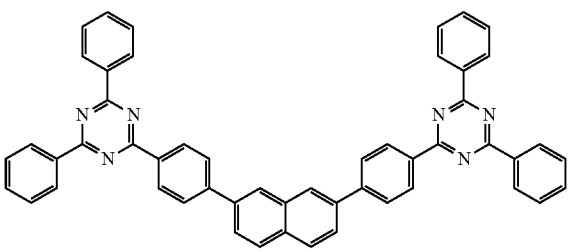

LiQ

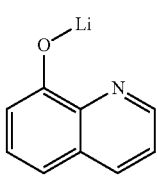

In the above-mentioned process, the vapor deposition rate of the organic material was maintained at 0.4 to 0.7 Å/sec, the deposition rates of lithium fluoride and aluminum of the cathode were maintained at 0.3 Å/sec and at 2 Å/sec, respectively, and the degree of vacuum during the deposition was maintained at $2 \times 10^{-7}$ to $5 \times 10^{-6}$ torr, thereby manufacturing an organic light emitting device.

Example 1-2 to Example 1-12

An organic light emitting device was manufactured in the same manner as in Example 1-1, except that the compounds shown in Table 1 below were used instead of Compound 5.

Comparative Example 1-1 to Comparative Example 1-3

An organic light emitting device was manufactured in the same manner as in Example 1-1, except that the compounds shown in Table 1 below were used instead of the compound of Preparation Example 1. The compounds of HB2, HB3 and HB4 used in Table 1 below were as follows:

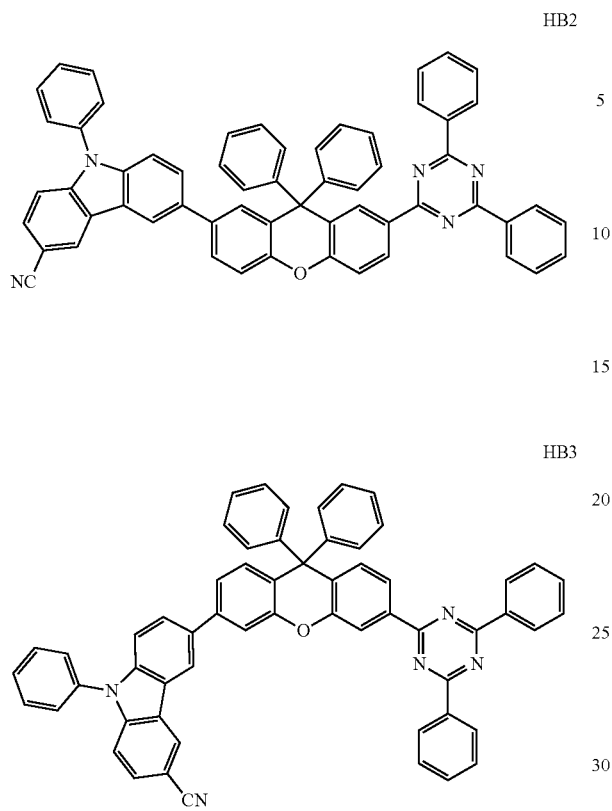

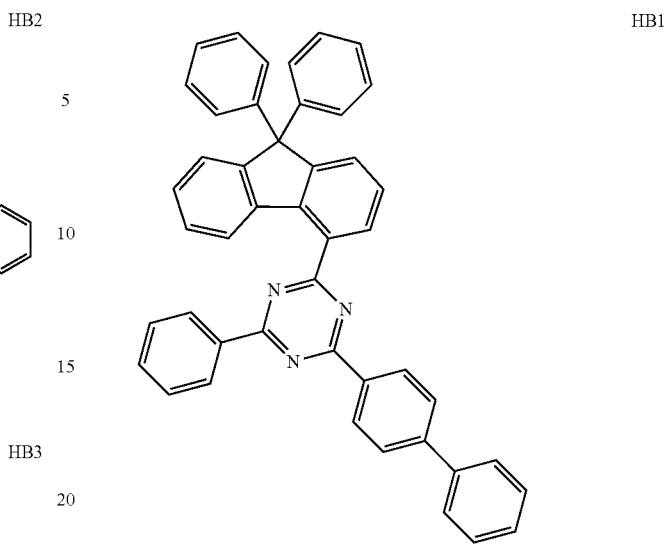

Comparative Example 2-1 to Comparative Example 2-3

An organic light emitting device was manufactured in the same manner as in Example 1-1, except that the compound HB1 was used instead of Compound 5, and the compounds shown in Table 2 below were used instead of Compound ET1. The compounds of ET2, ET3 and ET4 used in Table 2 below were as follows:

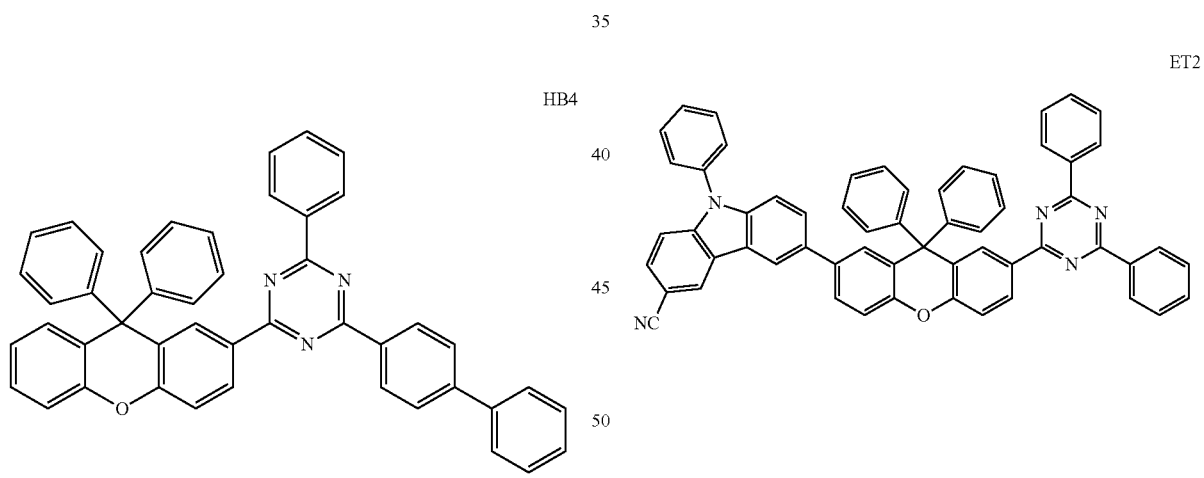

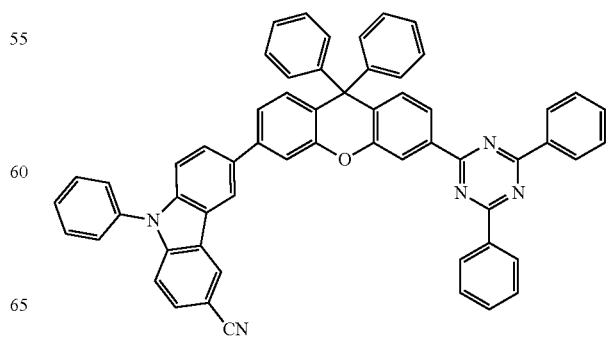

Example 2-1 to Example 2-8

An organic light emitting device was manufactured in the same manner as in Example 1-1, except that the following compound HB1 was used instead of Compound 5, and the compounds shown in Table 2 were used instead of Compound ET1.

-continued

ET4

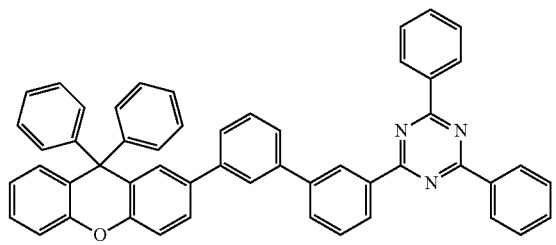

EXPERIMENTAL EXAMPLE

Experimental Example 1

The voltage, efficiency, color coordinate, and lifetime were measured by applying a current of 20 mA/cm² to the organic light emitting devices manufactured in Examples 1-1 to 1-12 and Comparative Examples 1-1 to 1-3, and the results are shown in Table 1 below. T95 means the time required for the luminance to be reduced to 95% of the initial luminance (1600 nit).

TABLE 1

| | Compound (hole blocking layer) | Voltage (V@ 20 mA/cm²) | Efficiency (cd/A@20 mA/cm²) | Color coordinate (x, y) | T95 (hr) |
|---|---|---|---|---|---|
| Example 1-1 | Compound 5 | 4.06 | 6.92 | (0.144, 0.142) | 300 |
| Example 1-2 | Compound 6 | 4.07 | 6.96 | (0.144, 0.143) | 305 |
| Example 1-3 | Compound 11 | 4.24 | 6.84 | (0.143, 0.143) | 280 |
| Example 1-4 | Compound 12 | 4.29 | 6.83 | (0.145, 0.142) | 285 |
| Example 1-5 | Compound 13 | 4.18 | 6.89 | (0.144, 0.141) | 295 |
| Example 1-6 | Compound 14 | 4.14 | 6.88 | (0.145, 0.143) | 285 |
| Example 1-7 | Compound 15 | 4.13 | 6.87 | (0.144, 0.141) | 280 |
| Example 1-8 | Compound 16 | 4.31 | 6.66 | (0.145, 0.142) | 260 |
| Example 1-9 | Compound 17 | 4.35 | 6.63 | (0.145, 0.143) | 265 |
| Example 1-10 | Compound 18 | 4.23 | 6.85 | (0.145, 0.144) | 275 |
| Example 1-11 | Compound 19 | 4.27 | 6.71 | (0.145, 0.143) | 275 |
| Example 1-12 | Compound 20 | 4.31 | 6.68 | (0.145, 0.144) | 270 |
| Comparative Example 1-1 | Compound HB2 | 5.12 | 5.85 | (0.145, 0.145) | 185 |
| Comparative Example 1-2 | Compound HB3 | 5.06 | 5.94 | (0.146, 0.146) | 190 |
| Comparative Example 1-3 | Compound HB4 | 4.51 | 6.27 | (0.146, 0.147) | 240 |

As shown in Table 1 above, in the case of an organic light emitting device manufactured by using the compound of the present disclosure as a material of the hole blocking layer, the organic light emitting device exhibits excellent characteristics in terms of efficiency, driving voltage, and/or stability (lifetime).

The organic light emitting device according to an embodiment of the present disclosure exhibited lower voltage, higher efficiency and longer lifetime characteristics than the organic light emitting devices manufactured by using, as a material of the hole blocking layer, Compounds HB1 and HB2 in which an azine-based substituent does not contain cyano and a parent nucleus and cyano are linked by carbazole or the like as a linker or a compound HB3 in which an azine-based substituent does not contain cyano.

Experimental Example 2

The voltage, efficiency, color coordinate, and lifetime were measured by applying a current of 20 mA/cm² to the organic light emitting devices manufactured in Examples 2-1 to 2-8 and Comparative Examples 2-1 to 2-3, and the results are shown in Table 2 below. T95 means the time required for the luminance to be reduced to 95% of the initial luminance (1600 nit).

TABLE 2

| | Compound (Electron transport layer) | Voltage (V@ 20 mA/cm²) | Efficiency (cd/A@20 mA/cm²) | Color coordinate (x, y) | T95 (hr) |
|---|---|---|---|---|---|
| Example 2-1 | Compound 1 | 4.10 | 6.94 | (0.145, 0.146) | 315 |
| Example 2-2 | Compound 2 | 4.13 | 6.95 | (0.146, 0.142) | 305 |
| Example 2-3 | Compound 3 | 4.42 | 6.66 | (0.147, 0.148) | 285 |
| Example 2-4 | Compound 4 | 4.14 | 6.97 | (0.145, 0.144) | 320 |
| Example 2-5 | Compound 7 | 4.26 | 6.88 | (0.146, 0.142) | 325 |
| Example 2-6 | Compound 8 | 4.27 | 6.89 | (0.146, 0.147) | 310 |
| Example 2-7 | Compound 9 | 4.25 | 6.85 | (0.147, 0.146) | 315 |
| Example 2-8 | Compound 10 | 4.31 | 6.73 | (0.146, 0.148) | 285 |
| Comparative Example 2-1 | Compound ET2 | 4.89 | 5.12 | (0.145, 0.147) | 230 |
| Comparative Example 2-2 | Compound ET3 | 4.95 | 5.33 | (0.146, 0.148) | 215 |
| Comparative Example 2-3 | Compound ET4 | 4.57 | 6.37 | (0.145, 0.146) | 255 |

As shown in Table 2, in the case of an organic light emitting device manufactured by using the compound of the present disclosure as a material for the electron transport layer, the organic light emitting device exhibits excellent characteristics in terms of efficiency, driving voltage and/or stability.

An organic light emitting device according to an embodiment of the present disclosure exhibited characteristics of lower voltage, higher efficiency and longer lifetime than the organic light emitting devices manufactured by using, as a material of the electron transport layer, Compounds ET1 and ET2 in which an azine-based substituent does not contain cyano, and a parent nucleus and cyano are linked by carbazole or the like as a linker, or Compound ET3 in which an azine-based substituent does not contain cyano.

DESCRIPTION OF REFERENCE NUMERALS

1: substrate

2: anode

3: light emitting layer

4: cathode

5: hole injection layer

6: hole transport layer

7: electron blocking layer

8: hole blocking layer

9: electron transport layer

10: electron injection layer

What is claimed is:

1. A compound represented by the following Chemical Formula 1:

[Chemical Formula 1]

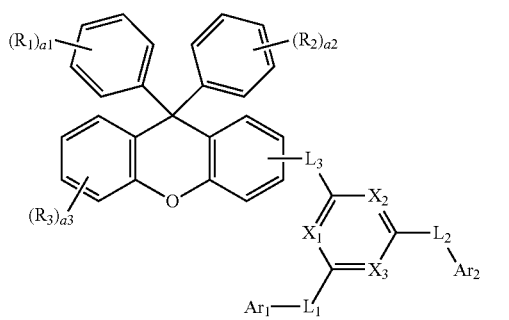

wherein in Chemical Formula 1, $X_1$ to $X_3$ are each independently N or CH, and at least one of $X_1$ to $X_3$ is N, $Ar_1$ and $Ar_2$ are each independently a substituted or unsubstituted $C_{6-60}$ aryl; or a substituted or unsubstituted $C_{2-60}$ heteroaryl containing one or more selected from the group consisting of N, O and S, and $Ar_1$ is substituted with one, two or three cyano groups, $L_1$ to $L_3$ are each independently a single bond; or a substituted or unsubstituted $C_{6-60}$ arylene, $R_1$ to $R_3$ are each independently hydrogen; deuterium; halogen; cyano; nitro; amino; a substituted or unsubstituted $C_{1-60}$ alkyl; a substituted or unsubstituted $C_{3-60}$ cycloalkyl; a substituted or unsubstituted $C_{2-60}$ alkenyl; a substituted or unsubstituted $C_{6-60}$ aryl; or a substituted or unsubstituted $C_{2-60}$ heteroaryl containing one or more selected from the group consisting of N, O and S, or two adjacent groups of $R_1$s, two adjacent groups of $R_2$s, or two adjacent groups of $R_3$s are linked with each other respectively to form a $C_{6-60}$ aromatic ring or a $C_{2-60}$ heteroaromatic ring containing any one or more selected from the group consisting of N, O and S, a1 and a2 are each independently an integer of 0 to 5, and a3 is an integer of 0 to 4.

2. The compound of claim 1, wherein the compound of Chemical Formula 1 is represented by any one of the following Chemical Formulas 1-1 to 1-4:

[Chemical Formula 1-1]

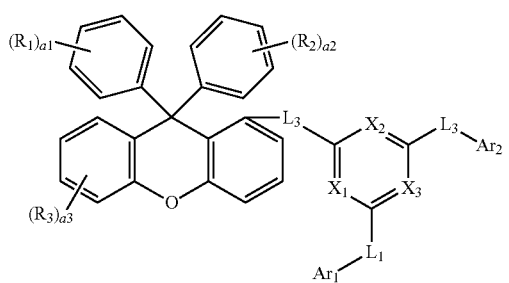

[Chemical Formula 1-2]

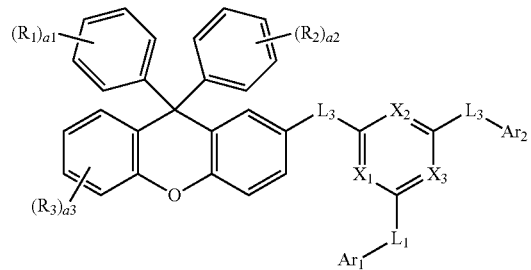

[Chemical Formula 1-3]

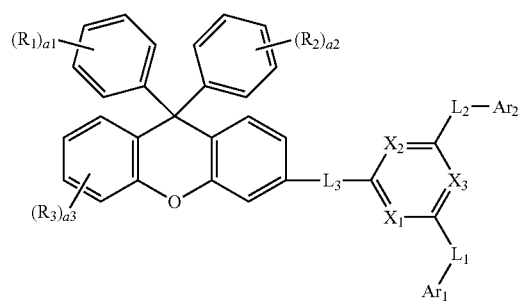

[Chemical Formula 1-4]

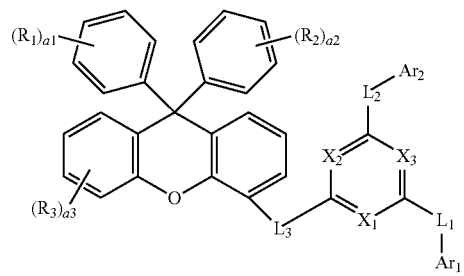

wherein in Chemical Formulas 1-1 to 1-4, $X_1$ to $X_3$, $Ar_1$, $Ar_2$, $L_1$ to $L_3$, $R_1$ to $R_3$ and a1 to a3 are the same as those defined in claim 1.

3. The compound of claim 1, wherein $Ar_1$ and $Ar_2$ are each independently phenyl, biphenylyl, naphthyl, phenanthrenyl, triphenylenyl, phenyl naphthyl, dimethylfluorenyl, fluoranthenyl, dibenzofuranyl, or dibenzothiophenyl, and wherein $Ar_1$ is substituted with one, two or three cyano groups.

4. The compound of claim 1, wherein $Ar^1$ is phenyl, biphenylyl, or naphthyl, and wherein $Ar_1$ is substituted with one, two or three cyano groups.

5. The compound of claim 1, wherein $Ar_1$ is any one selected from the group consisting of the following:

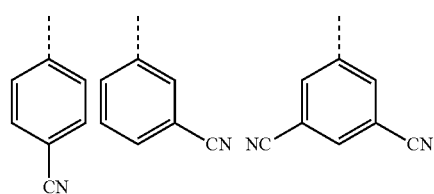

6. The compound of claim 1, wherein
Ar$_2$ is any one selected from the group consisting of the following:

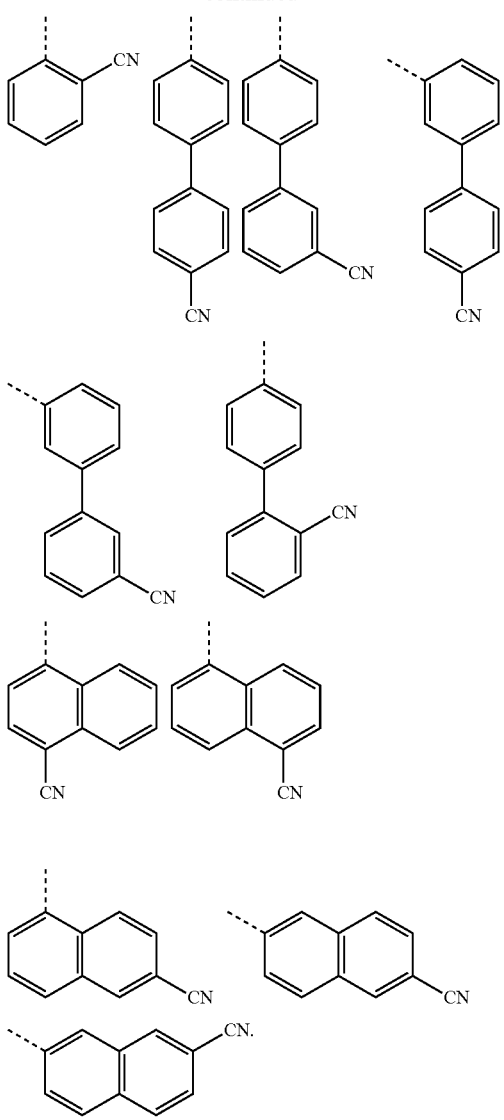
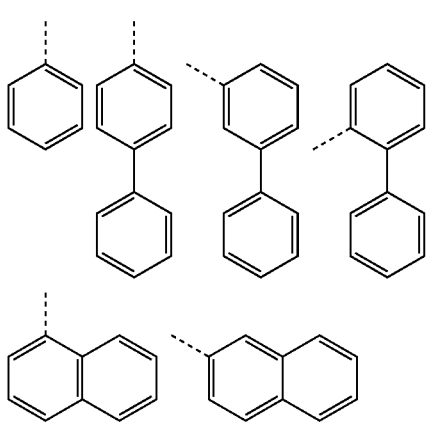
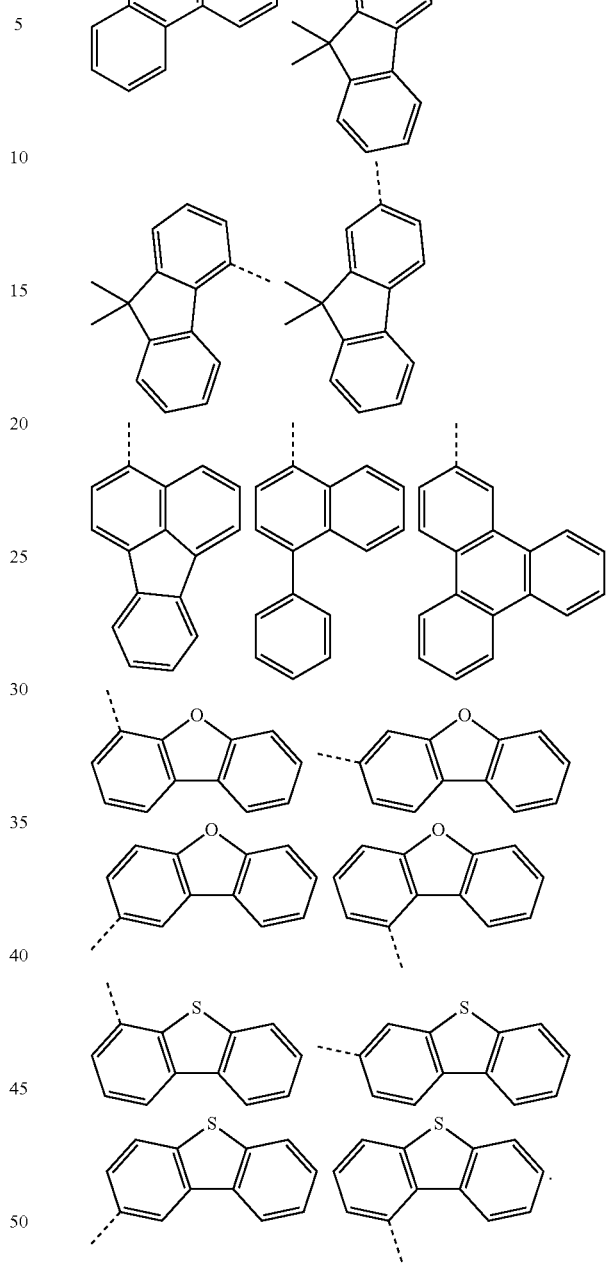

7. The compound of claim 1, wherein:
L$_1$ to L$_3$ are each independently a single bond, phenylene, biphenyldiyl, or naphthyldiyl.

8. The compound of claim 1, wherein
R$_1$ to R$_3$ are each independently hydrogen; deuterium; or tertbutyl, or two adjacent groups of R$_1$s, two adjacent groups of R$_2$s, or two adjacent groups of R$_3$s are linked with each other respectively to form a benzene ring.

9. The compound of claim 1, wherein
the compound represented by Chemical Formula 1 is any one selected from the group consisting of the following:

155
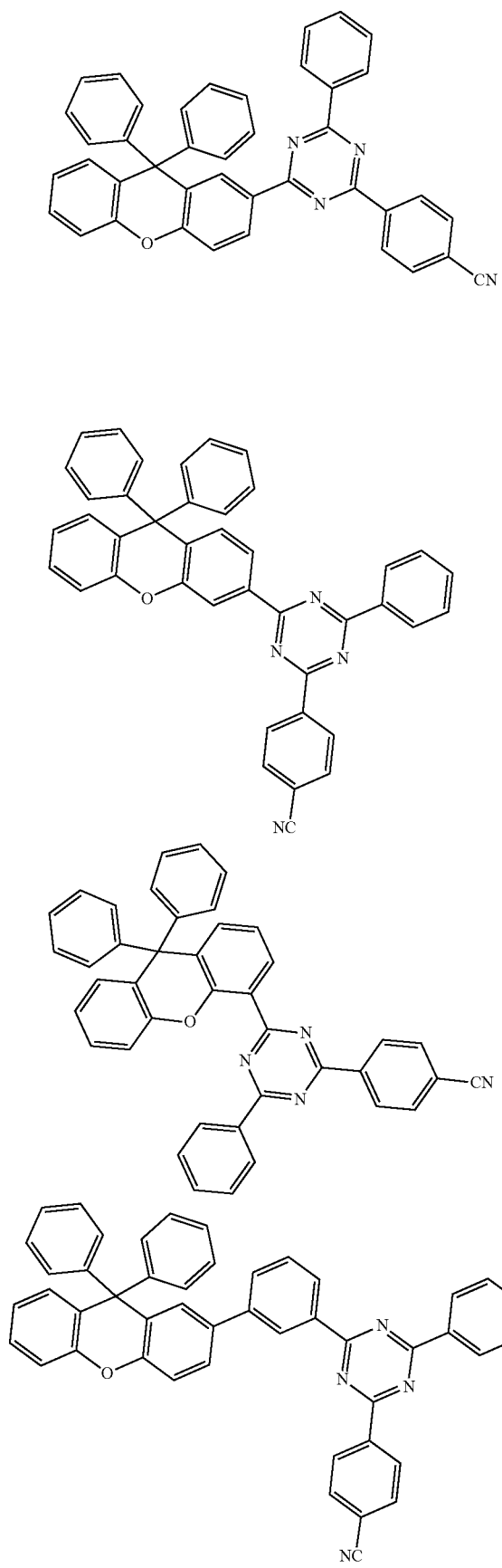
156
-continued
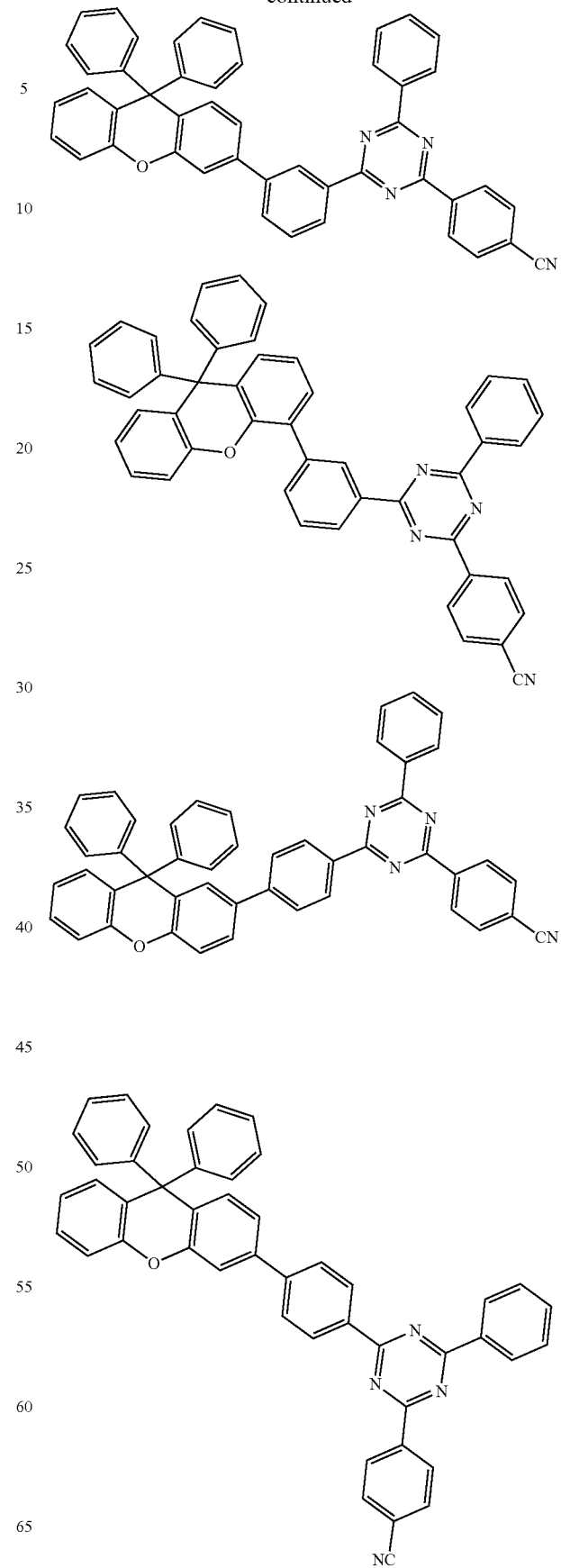

157
-continued
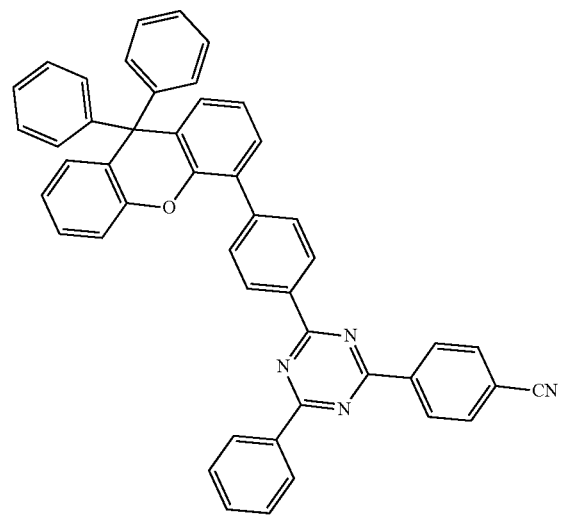
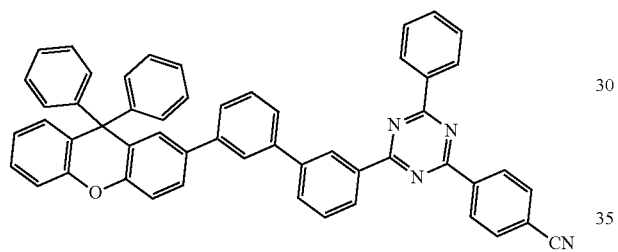
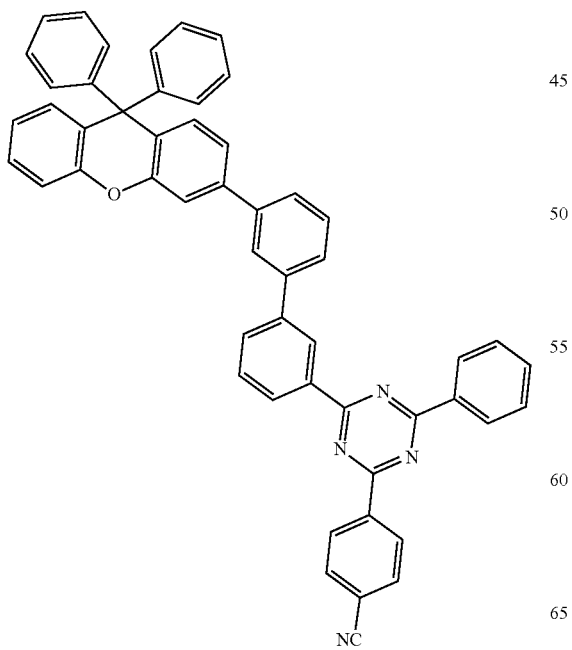
158
-continued
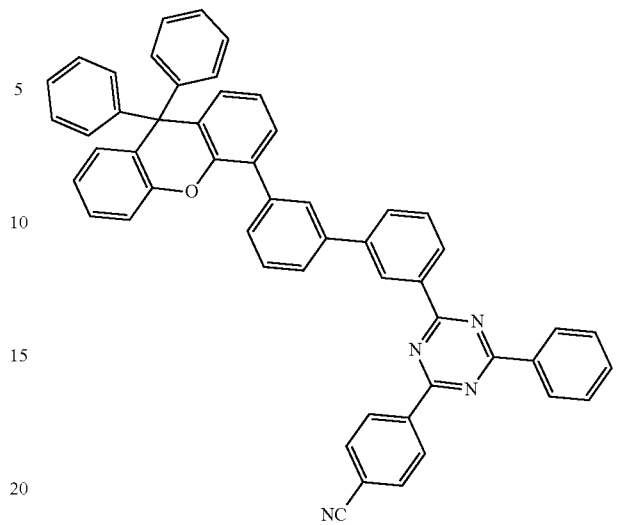
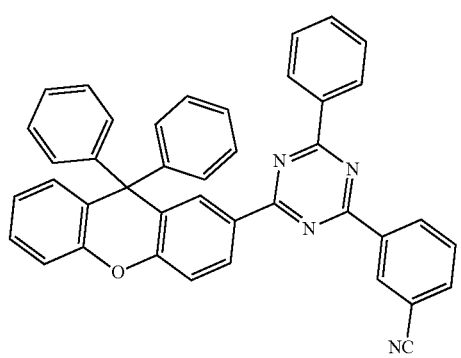
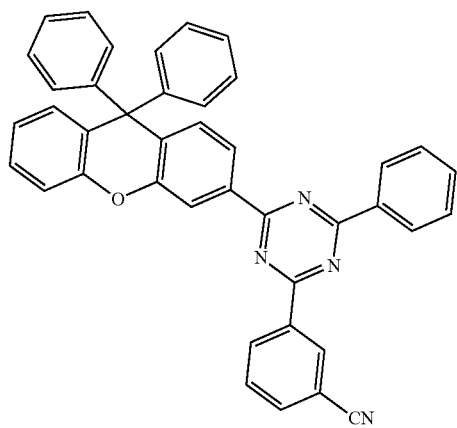
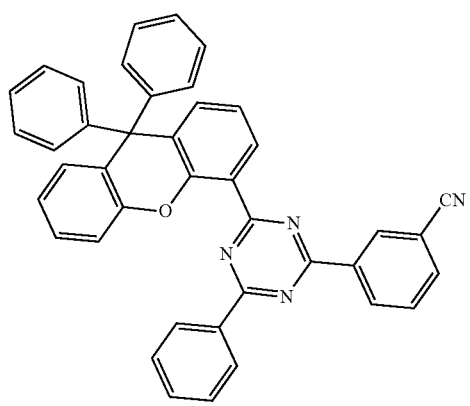

159
-continued
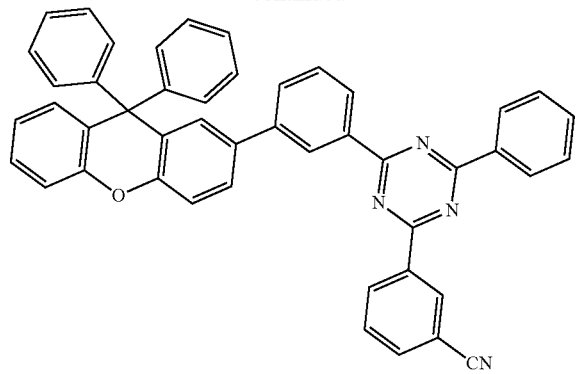
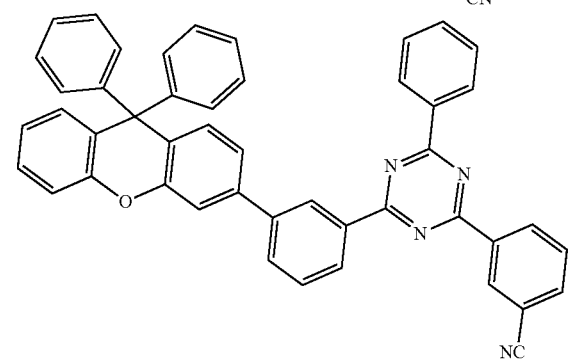
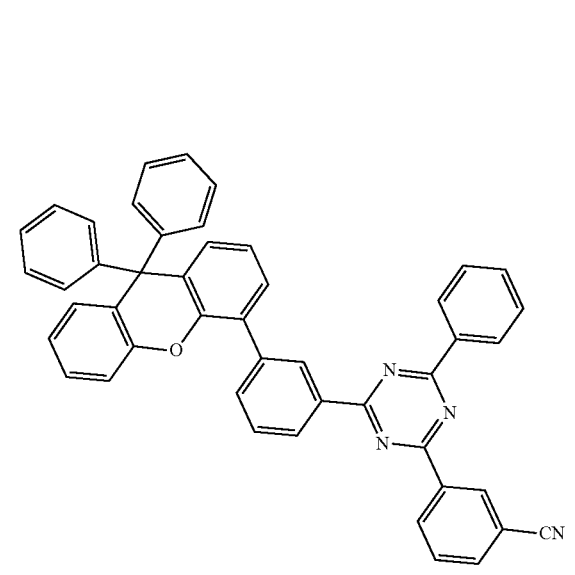
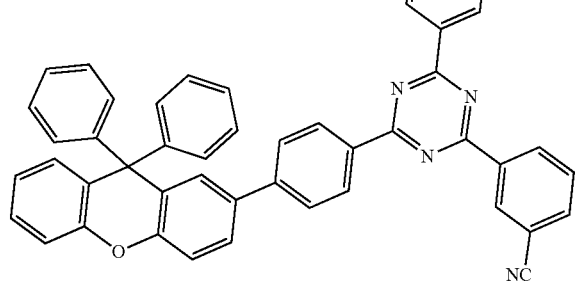
160
-continued
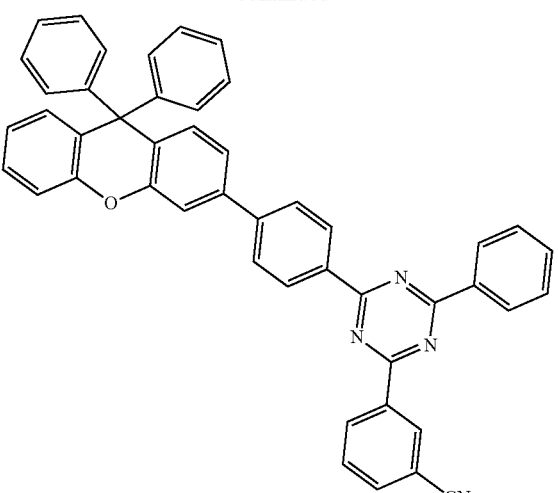
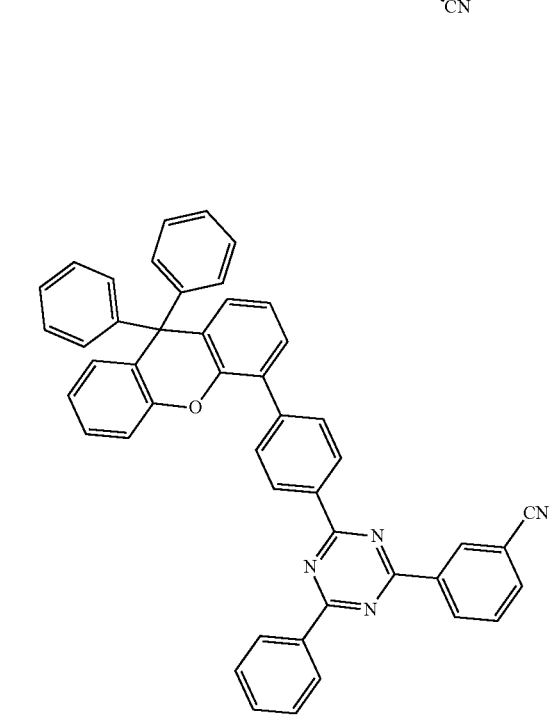
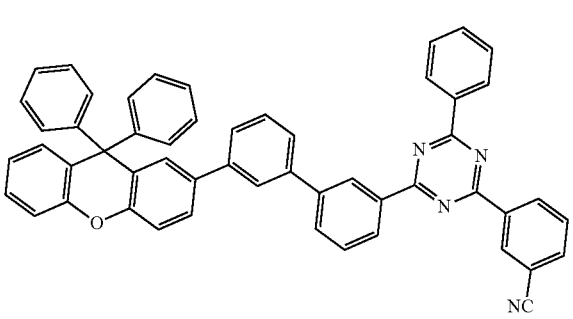

161
-continued
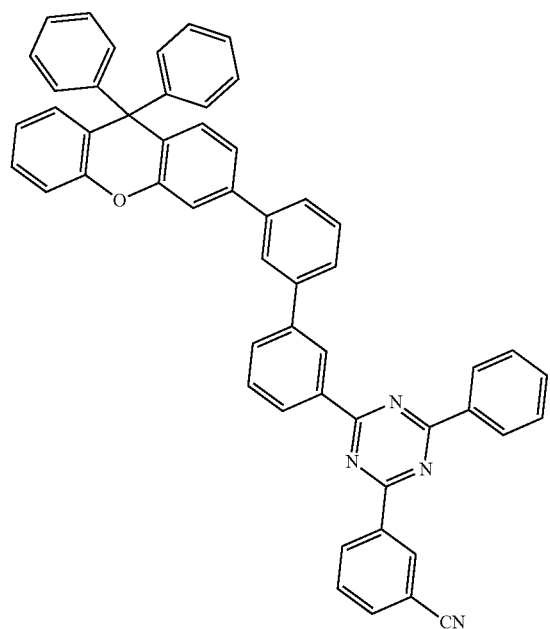
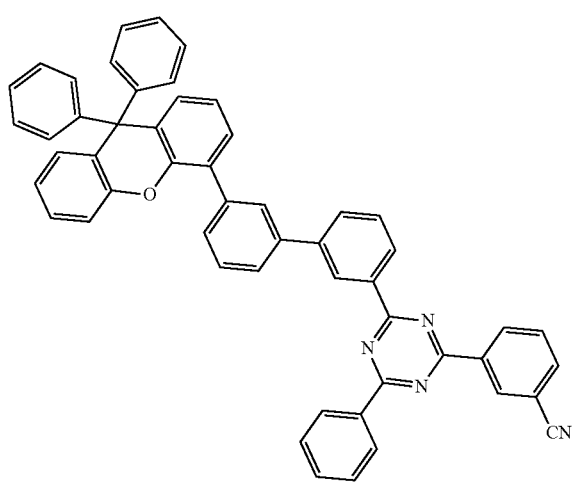
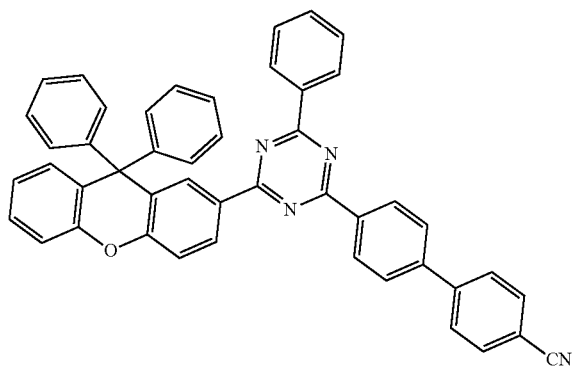
162
-continued
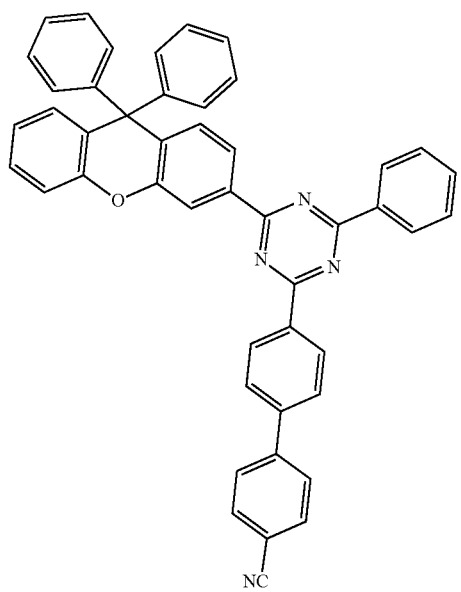
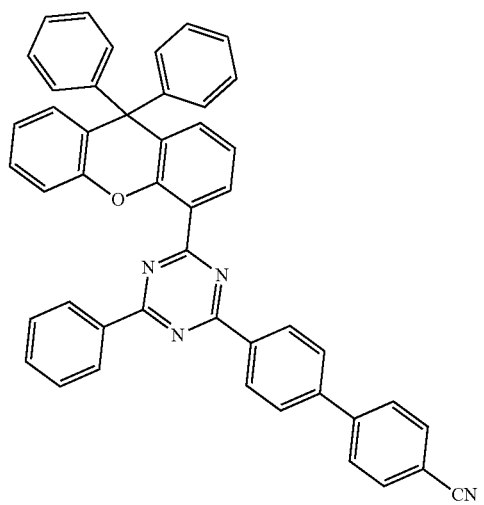
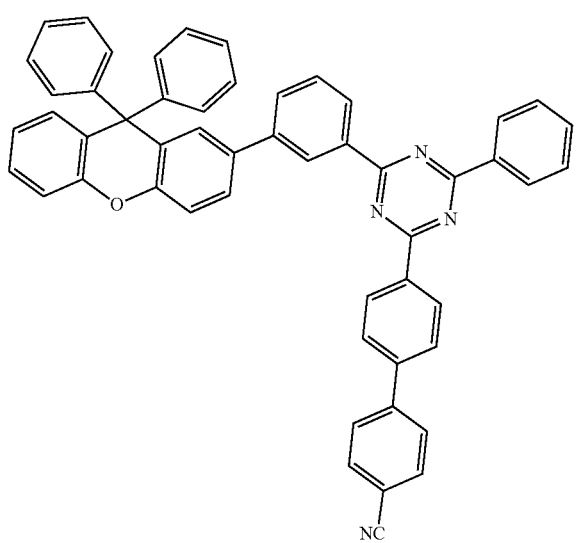

163
-continued
164
-continued
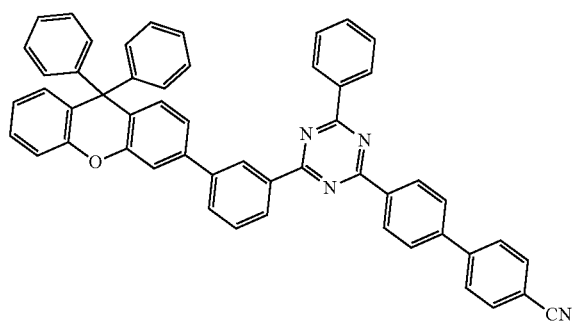
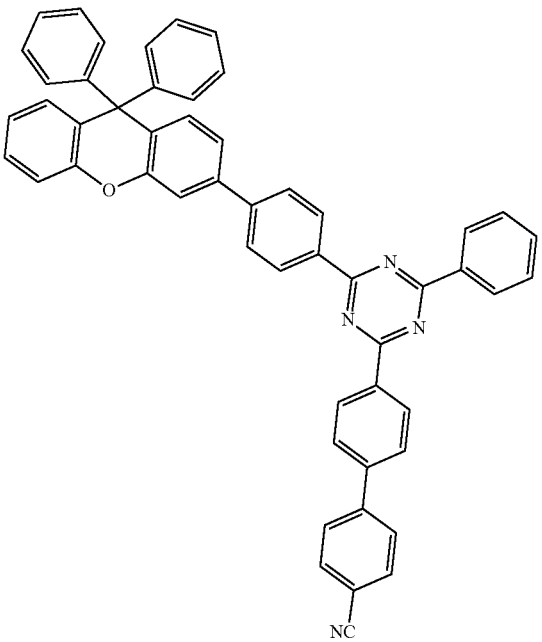
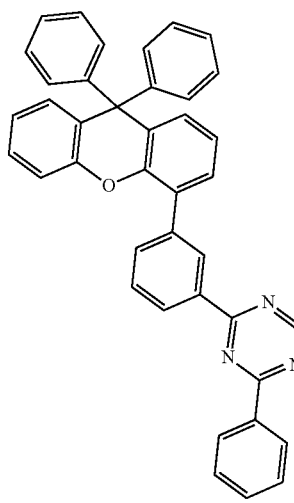
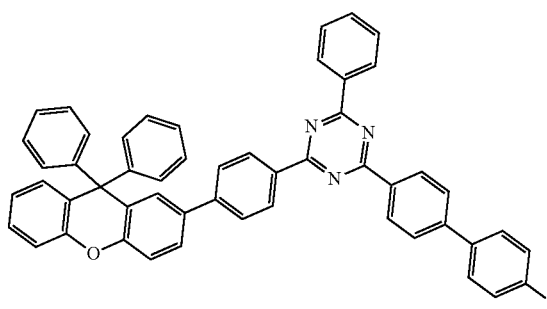
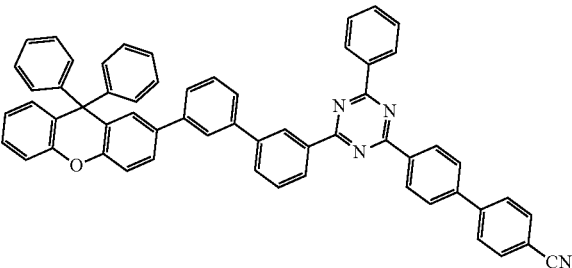

165
-continued
166
-continued
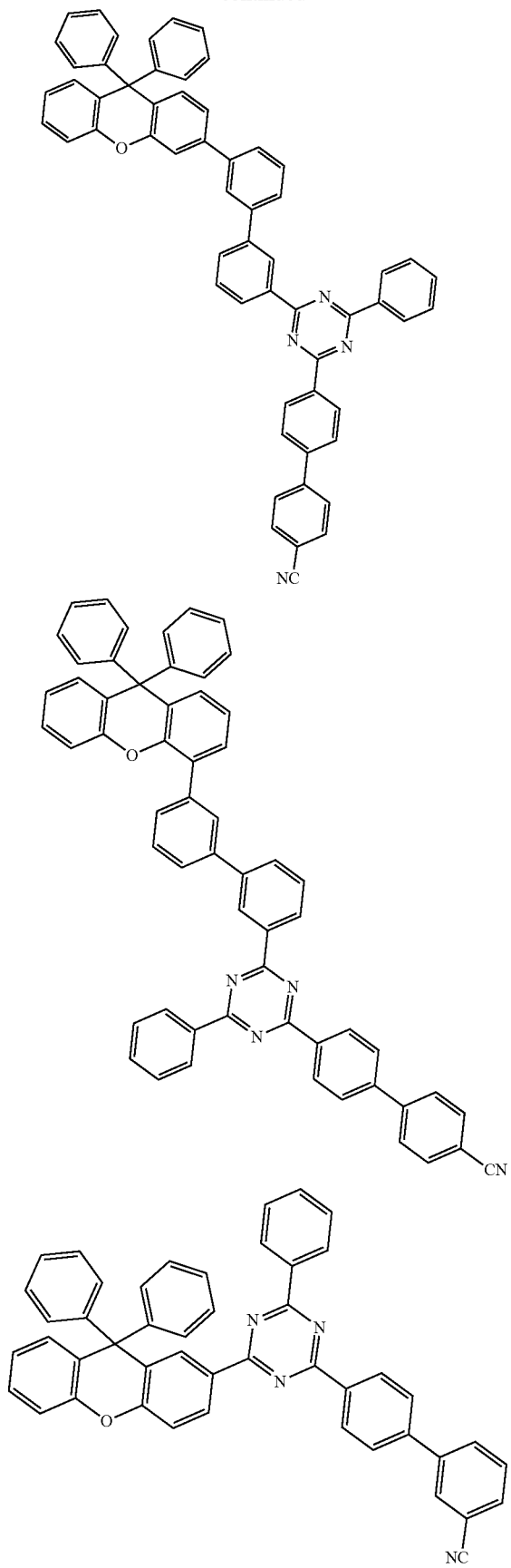
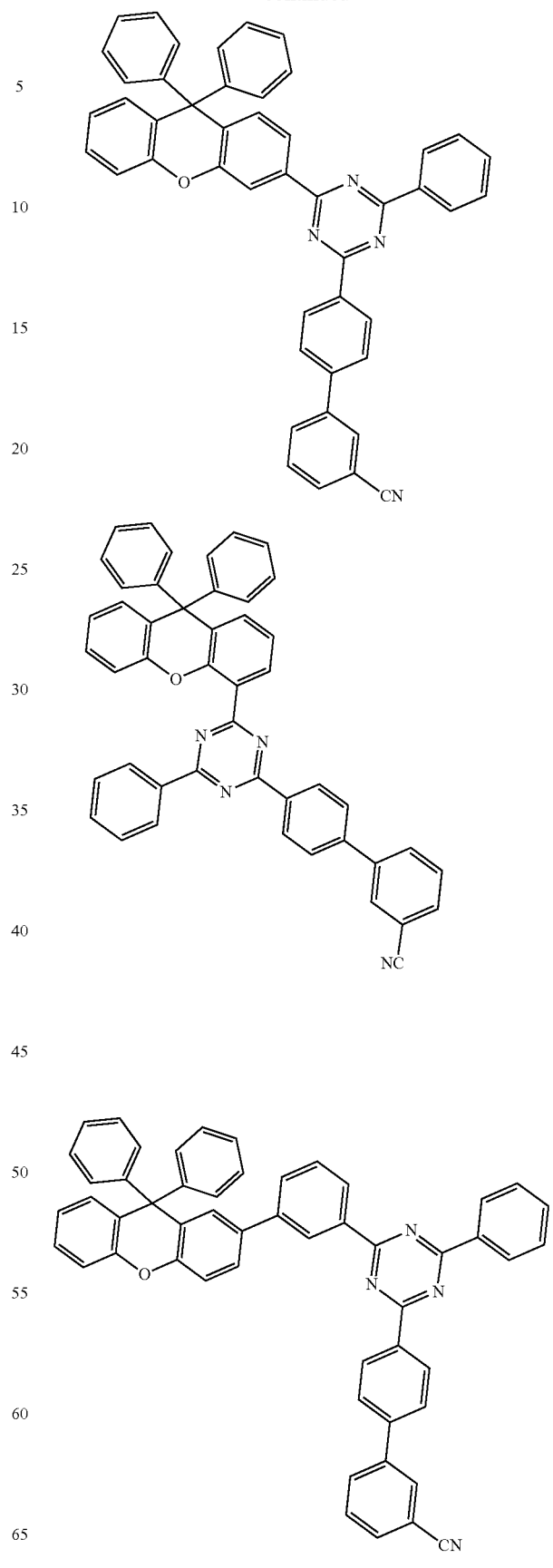

167
-continued
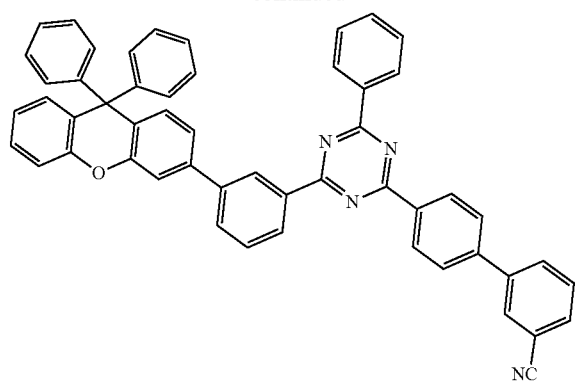
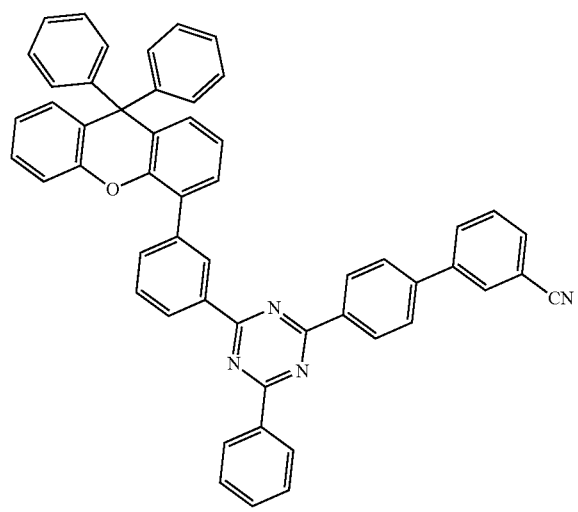
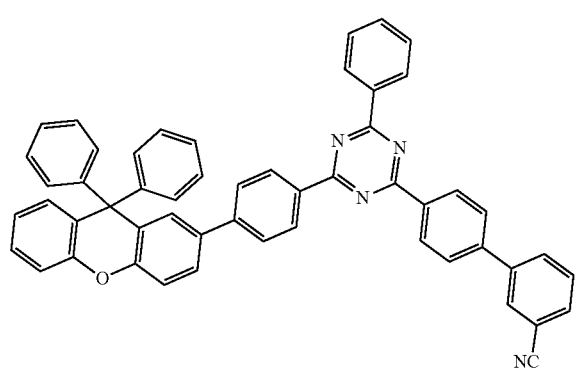
168
-continued
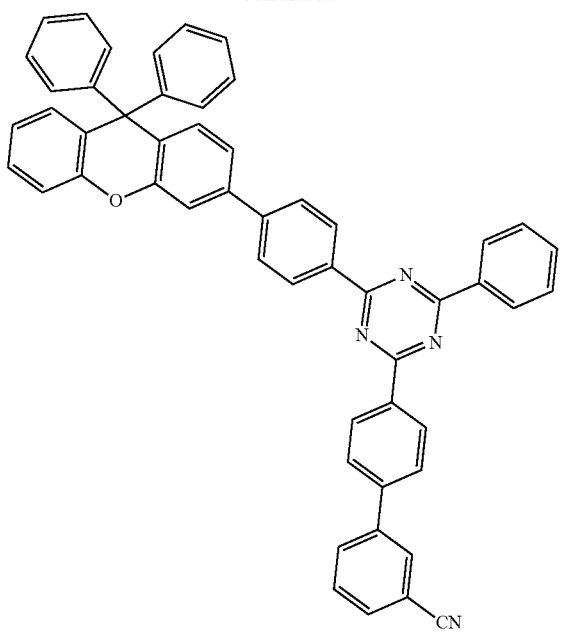
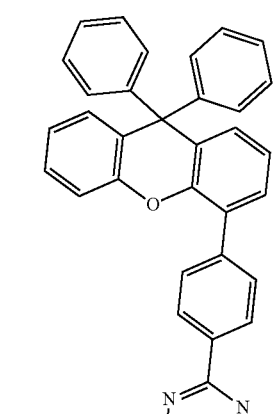

169
-continued
170
-continued
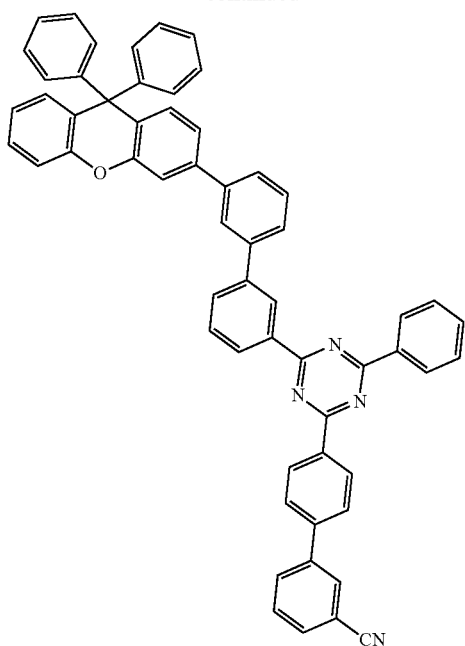
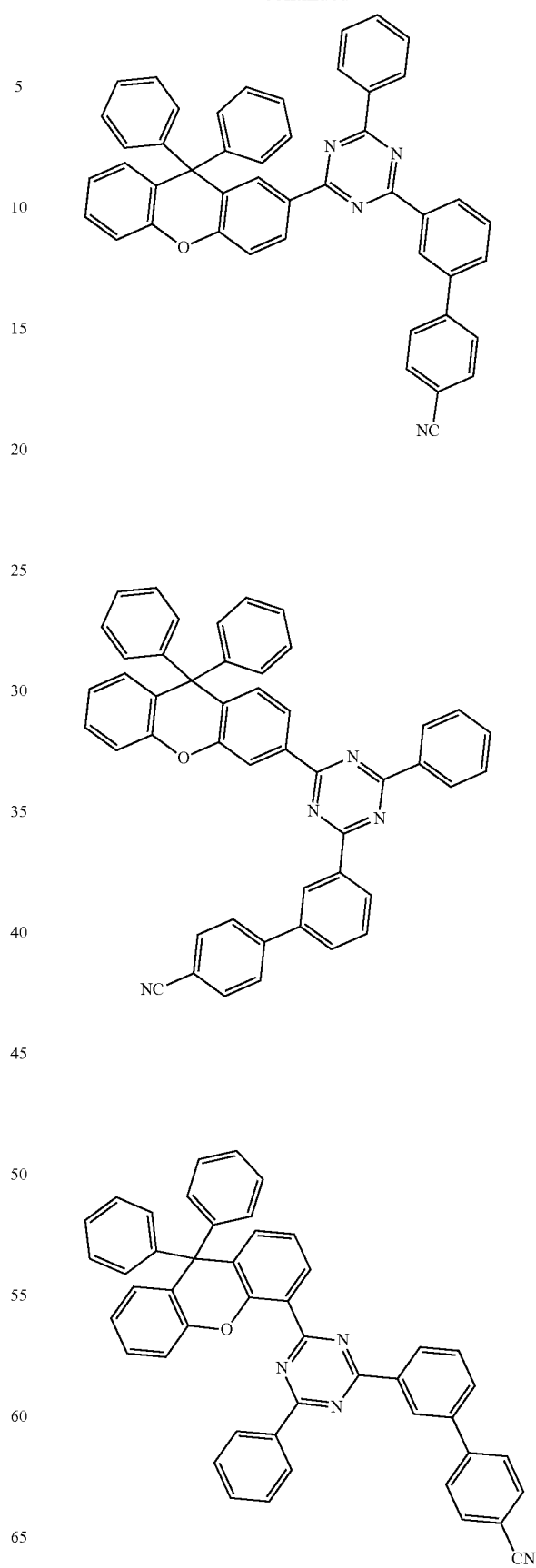

171
-continued
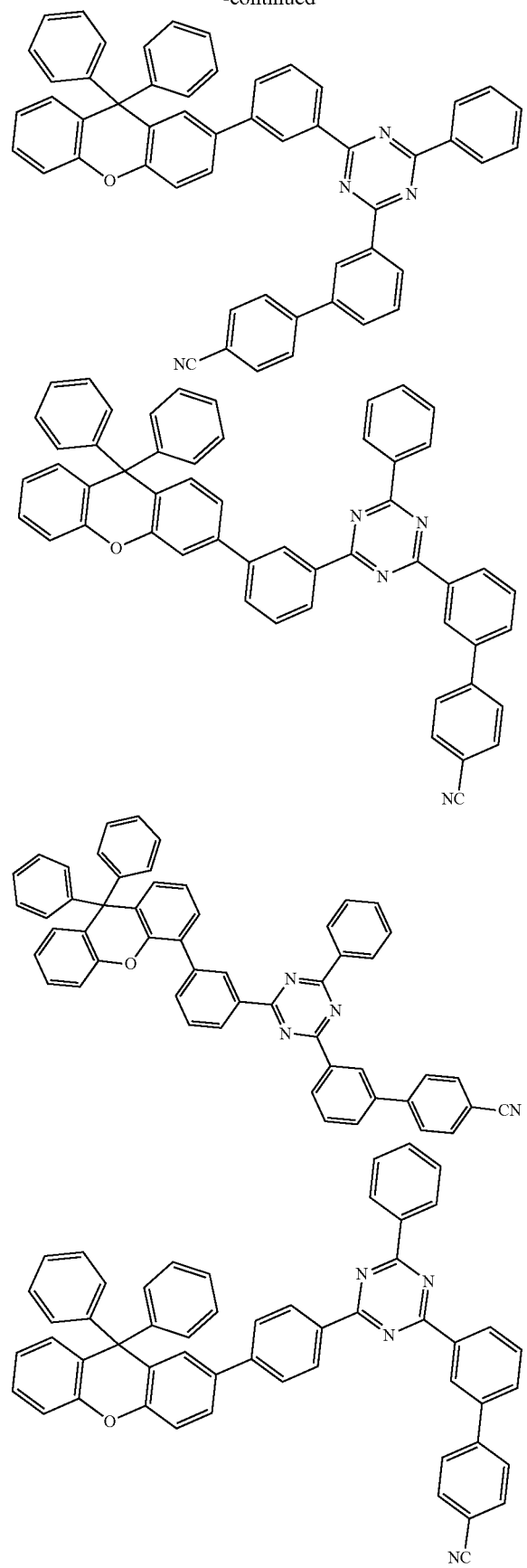
172
-continued
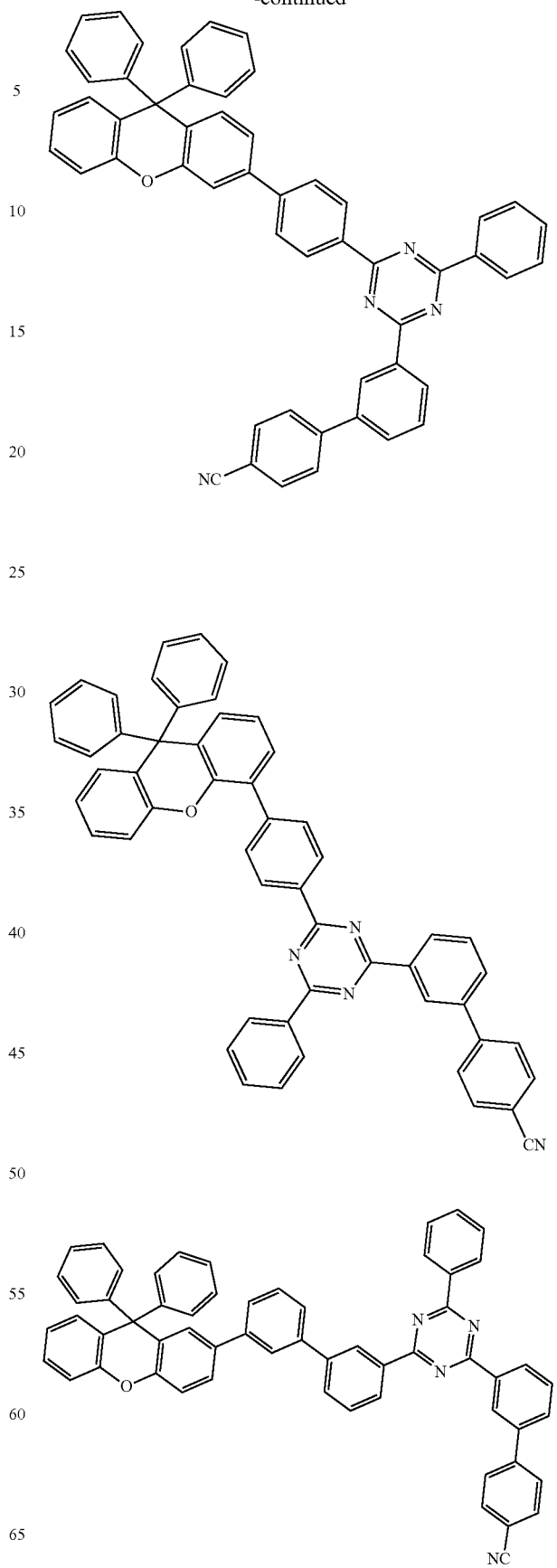

173
-continued
174
-continued
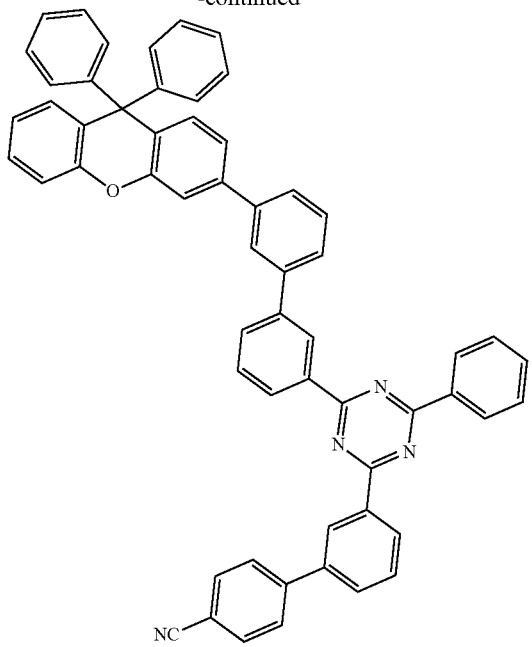
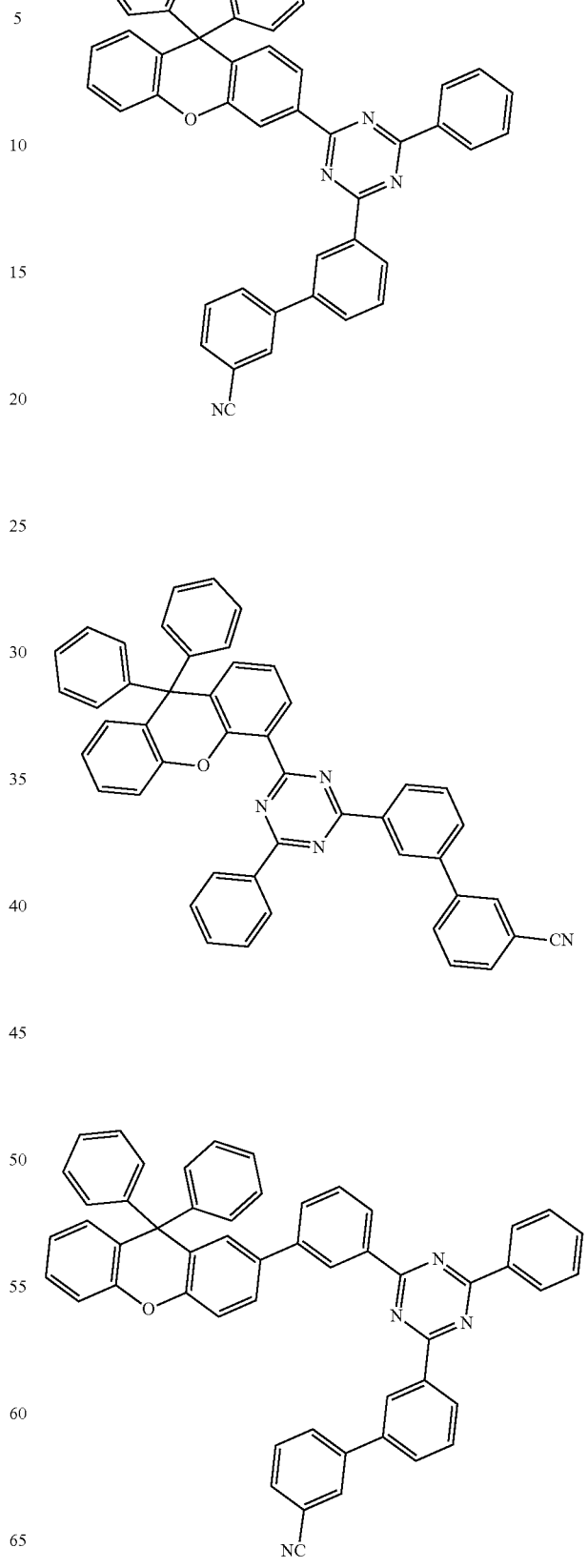

175
-continued
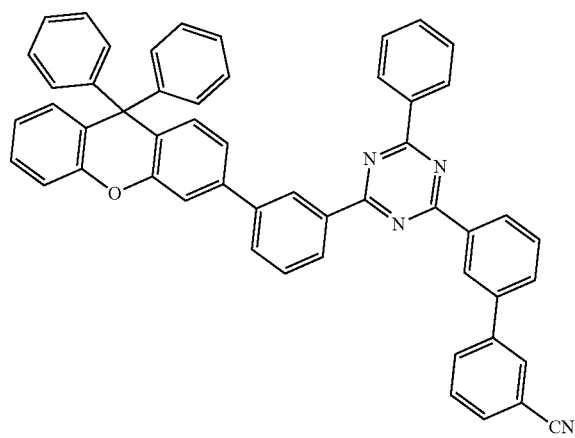
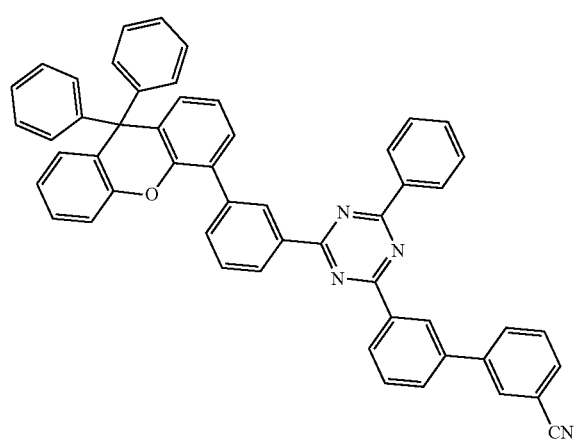
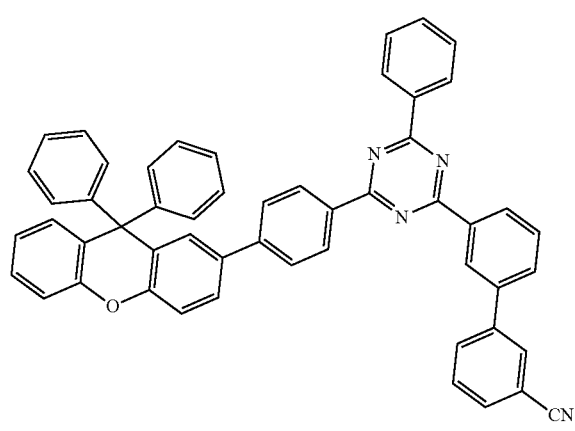
176
-continued
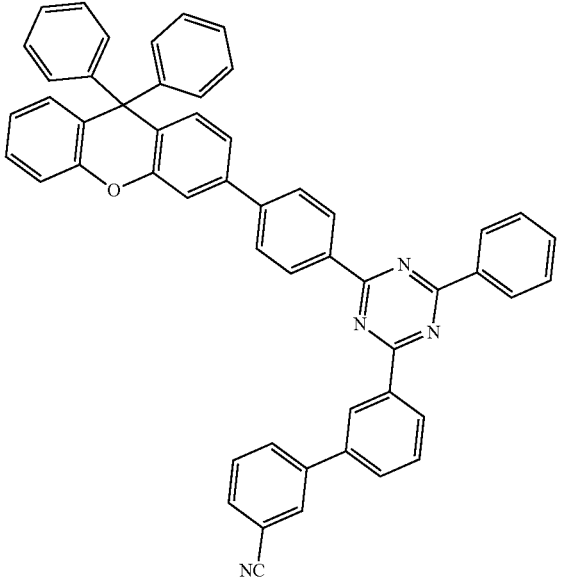
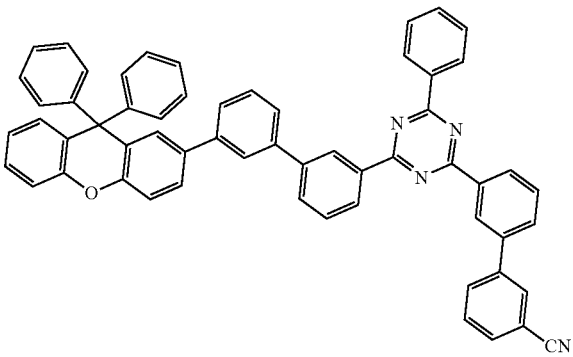

177
-continued
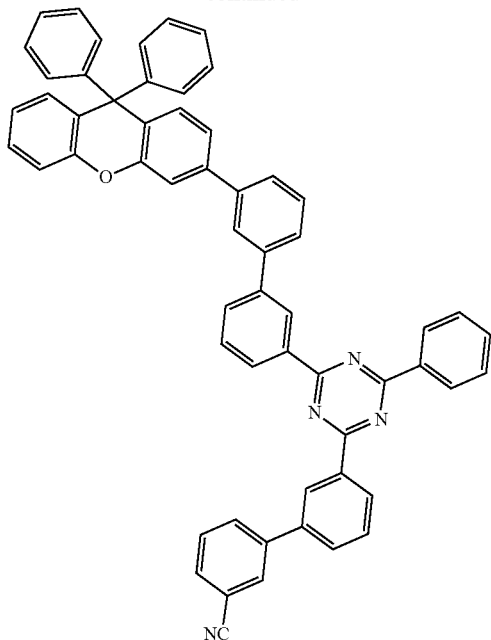
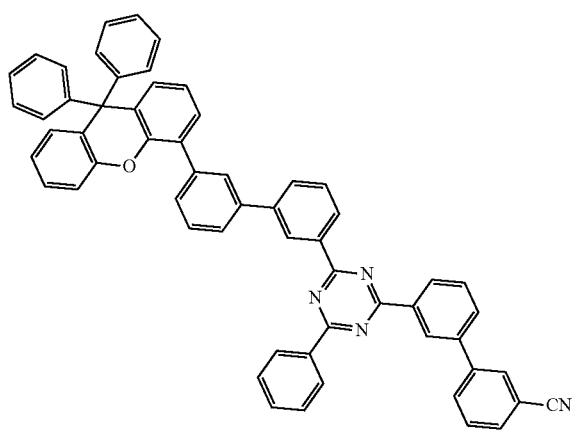
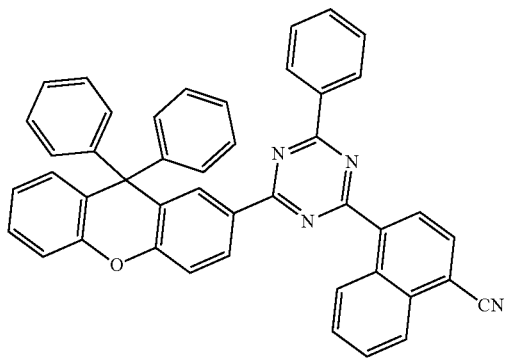
178
-continued
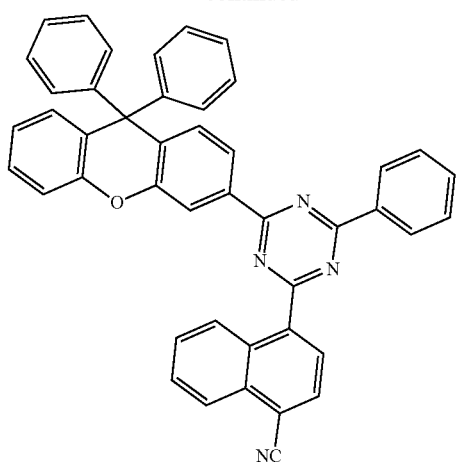
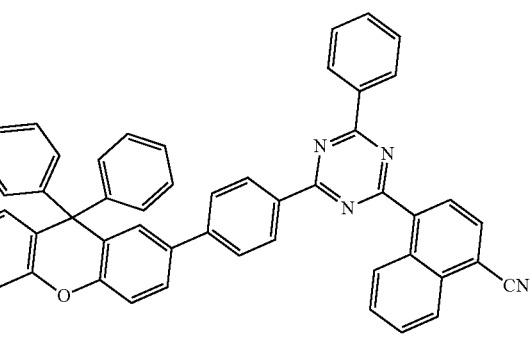

179
-continued
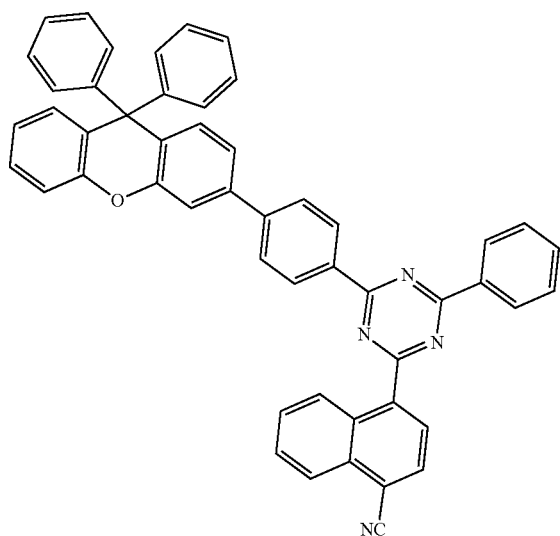
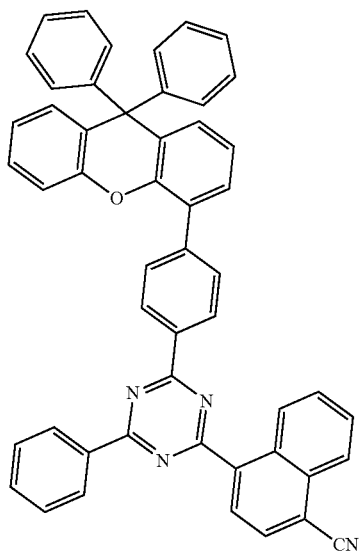
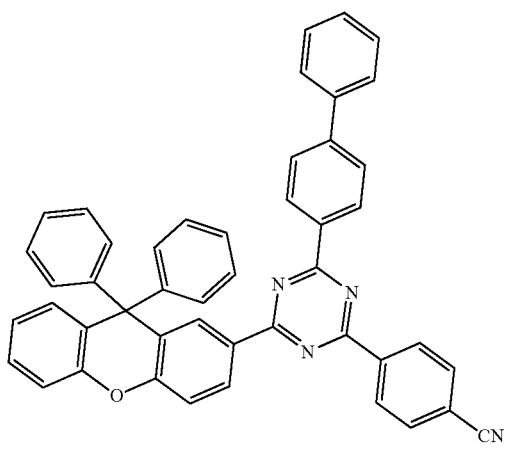
180
-continued
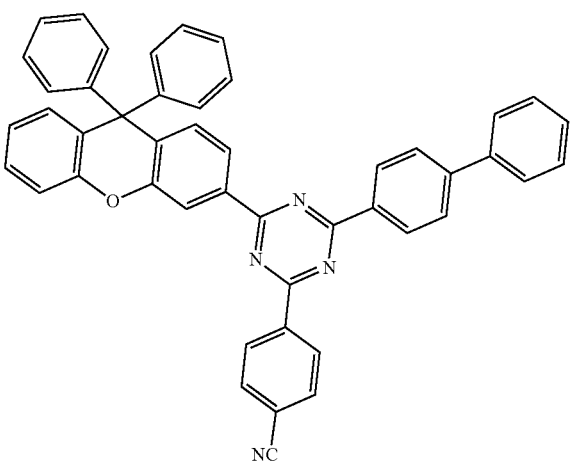
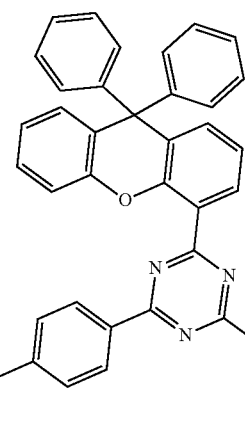
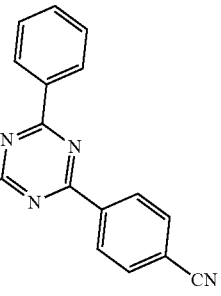

181
-continued
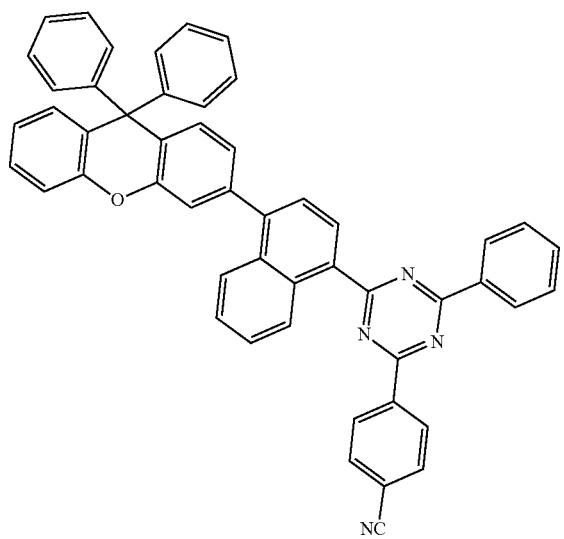
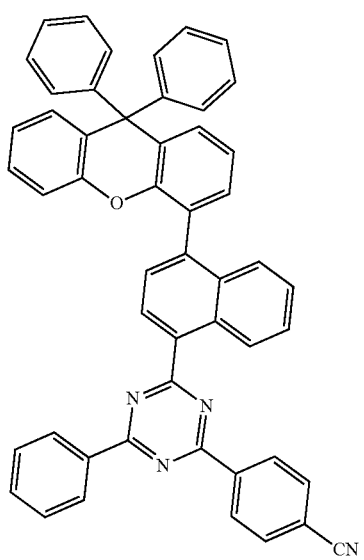
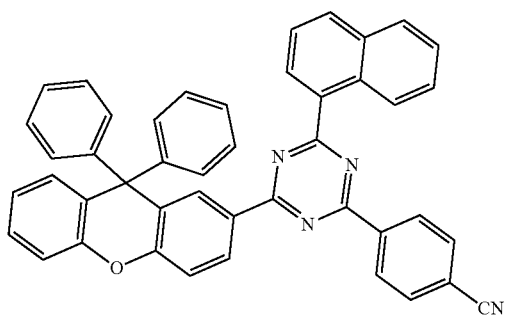
182
-continued
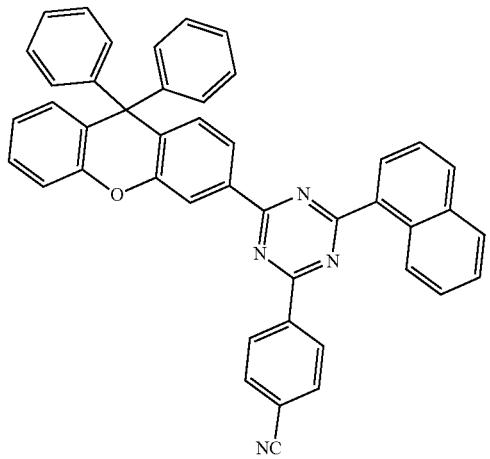
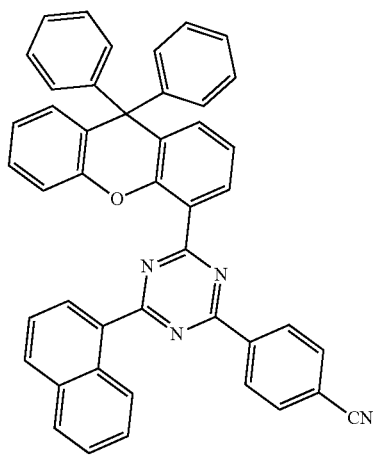
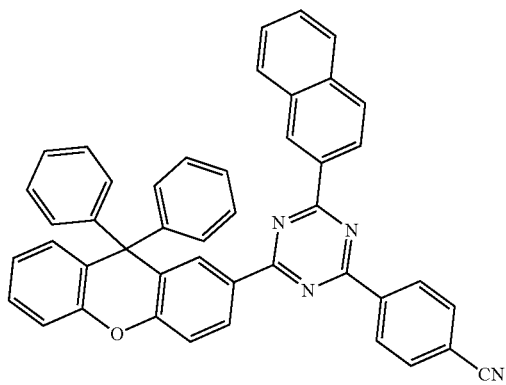

183
-continued
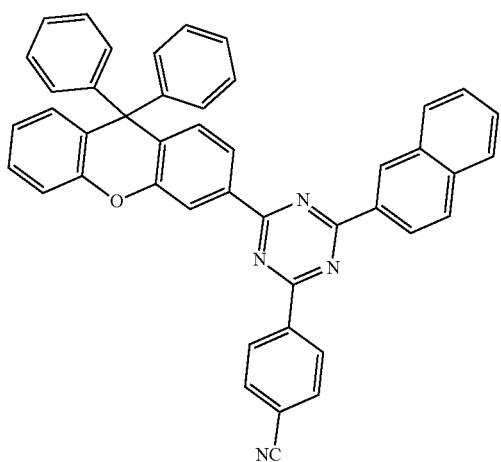
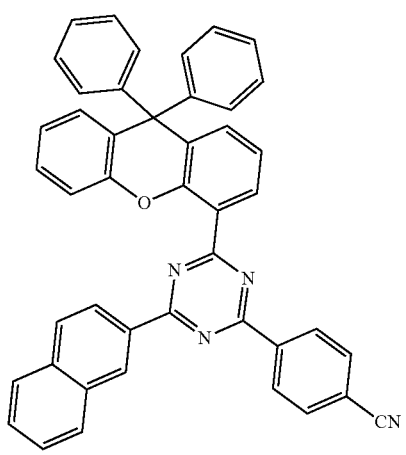
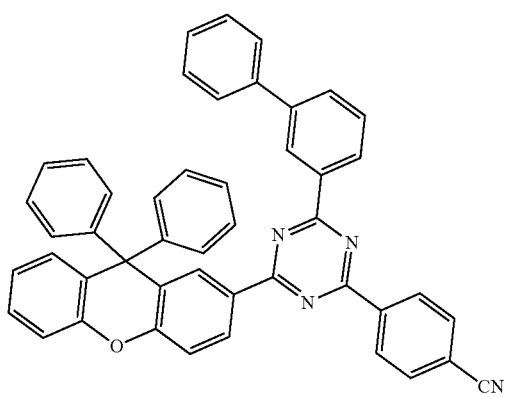
184
-continued
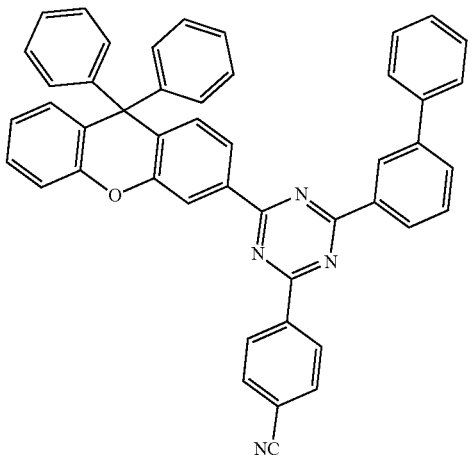
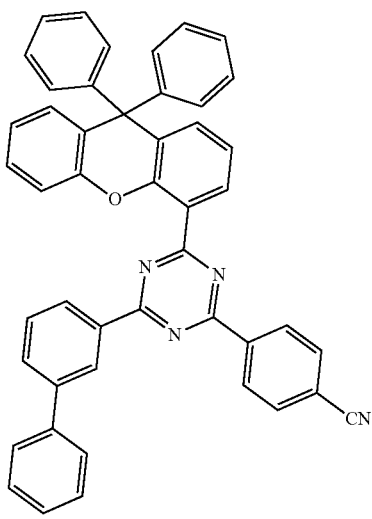
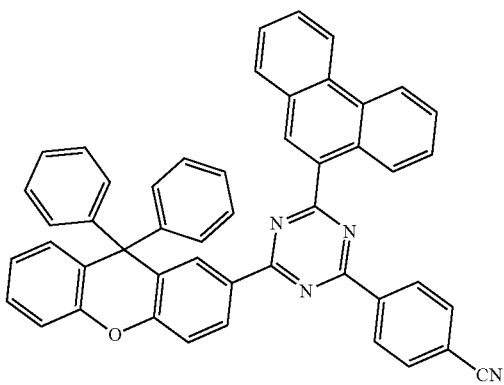

185
-continued
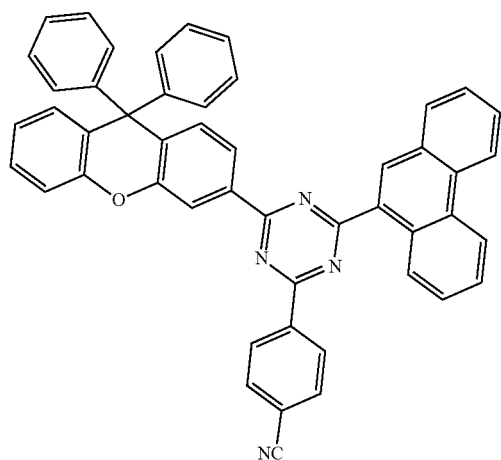
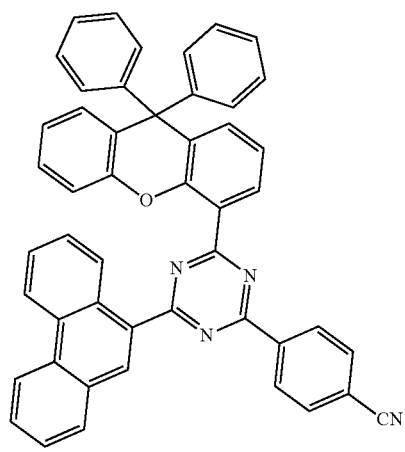
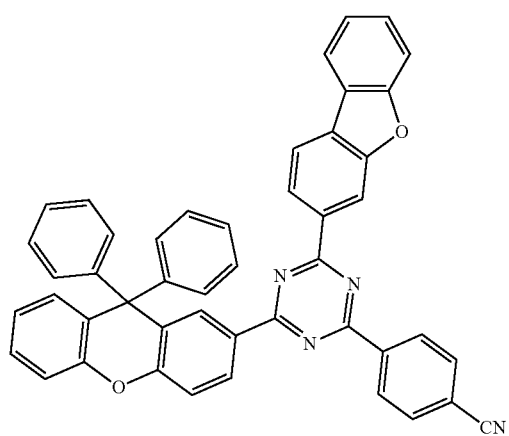
186
-continued
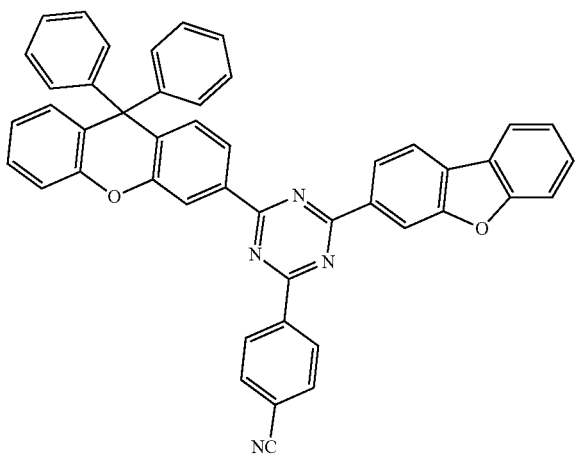
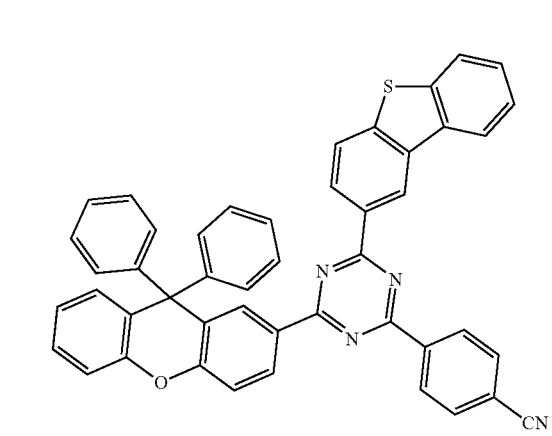

187
-continued
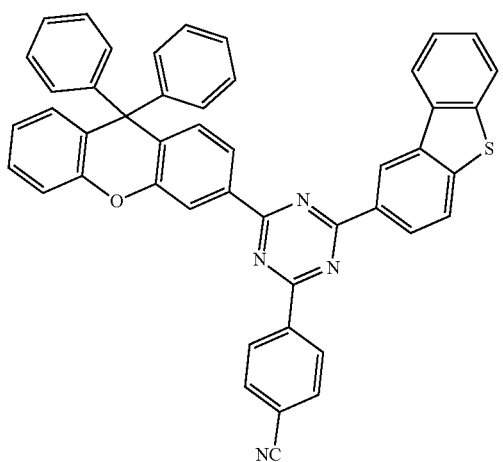
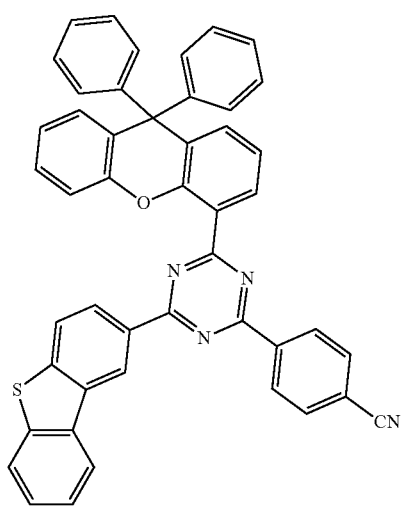
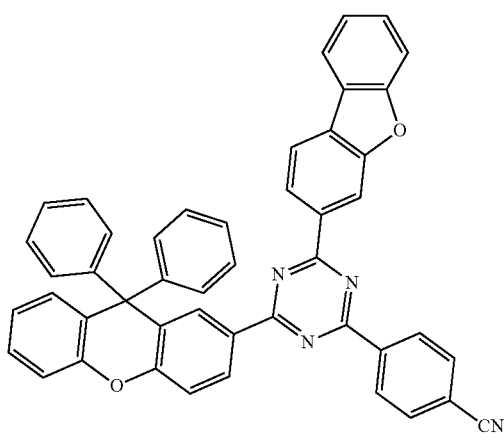
188
-continued
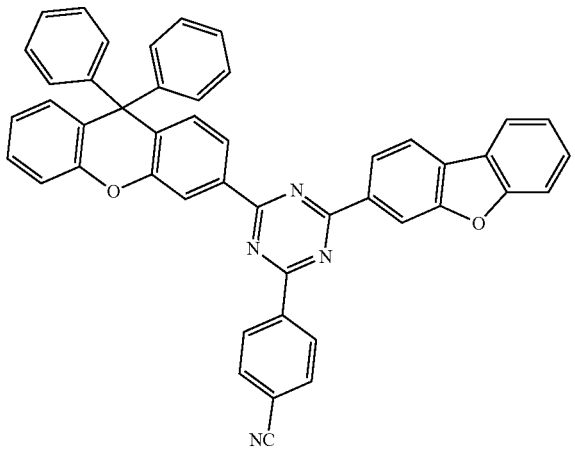
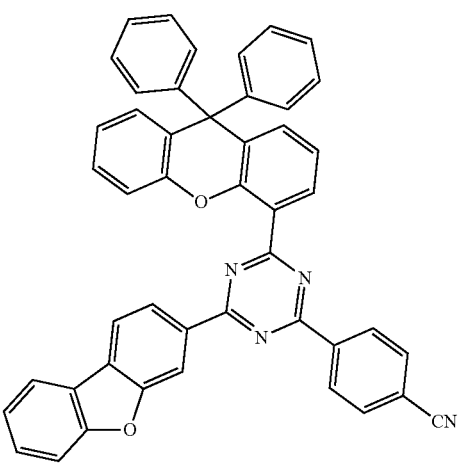
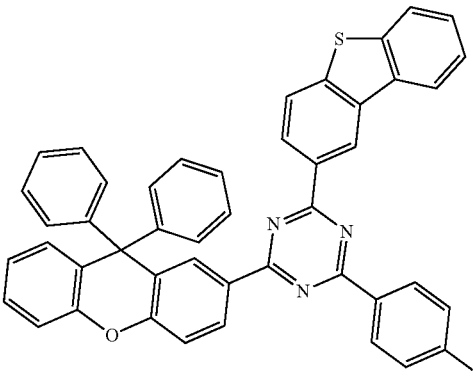

189
-continued
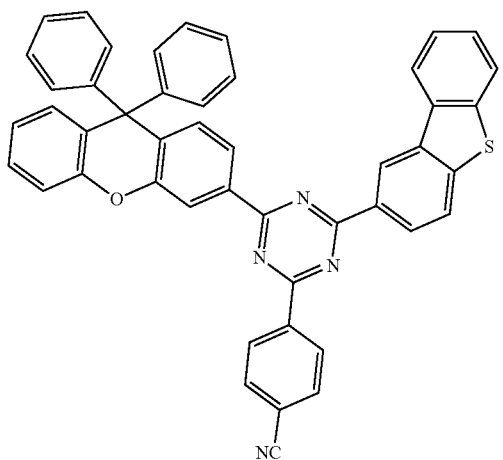
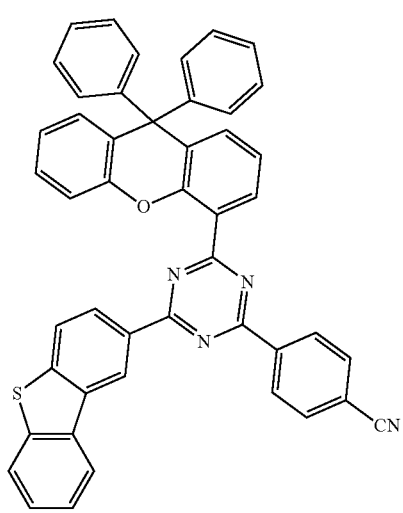
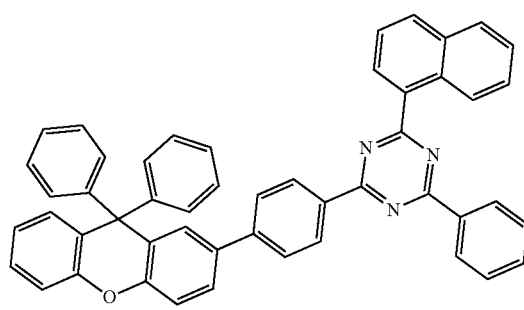
190
-continued
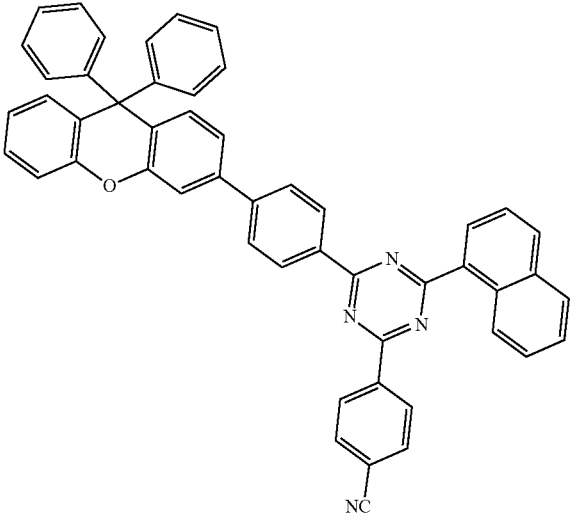
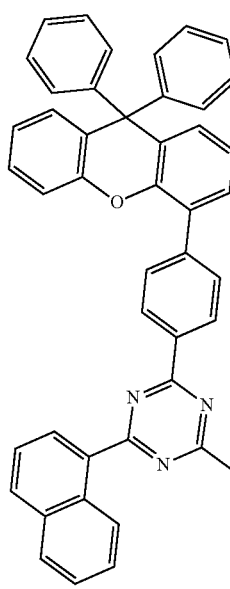
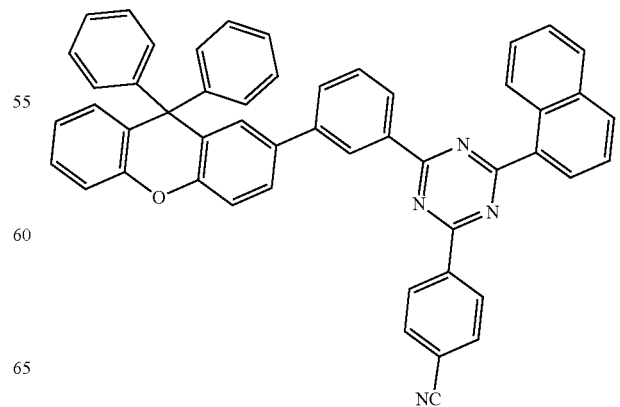

191
-continued
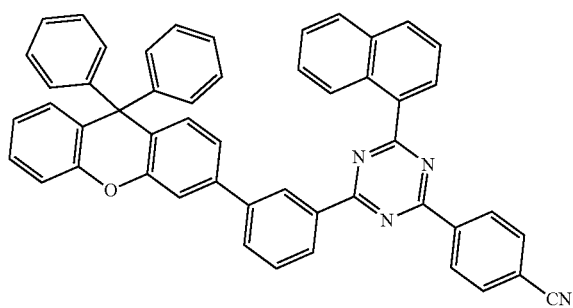
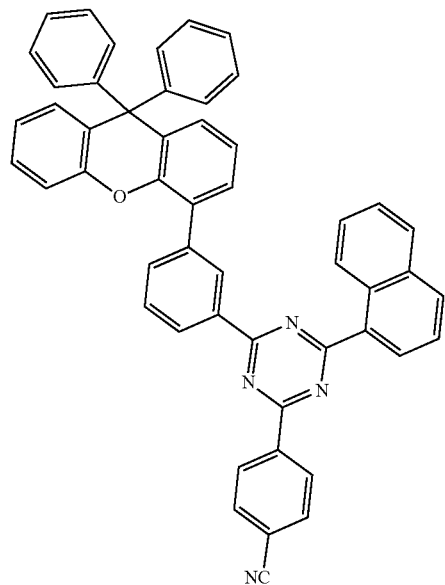
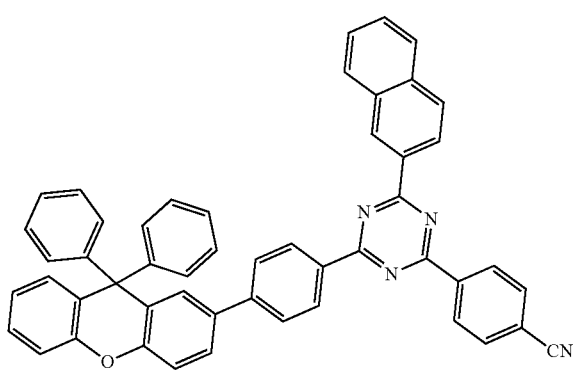
192
-continued
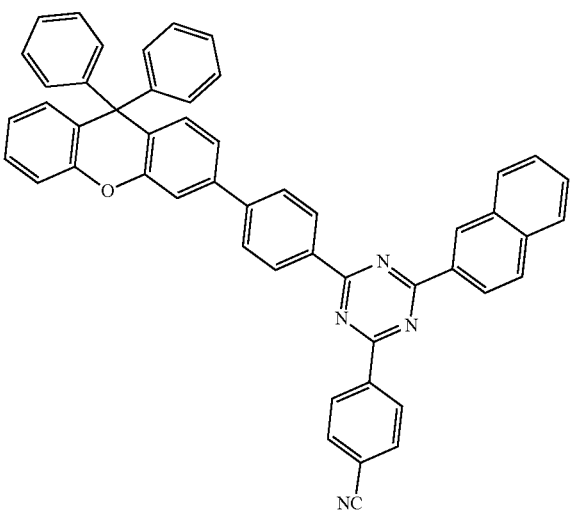
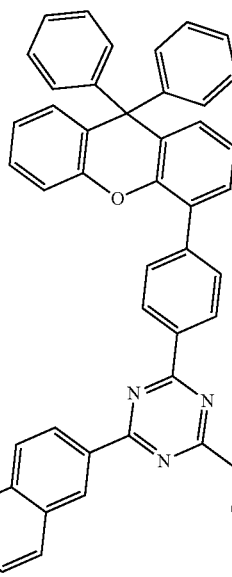
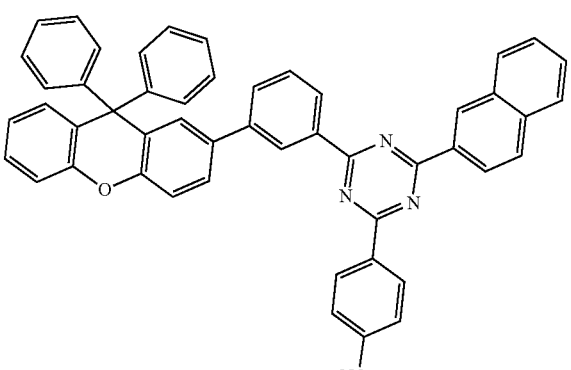

-continued
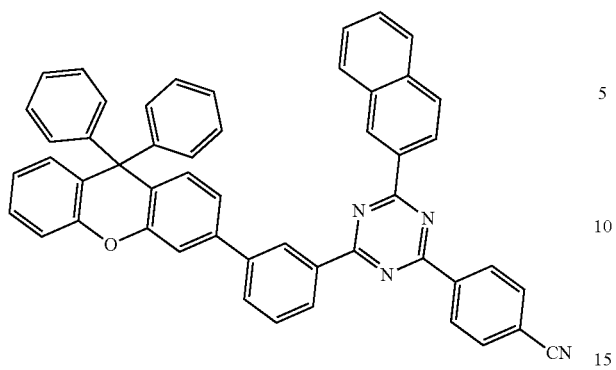
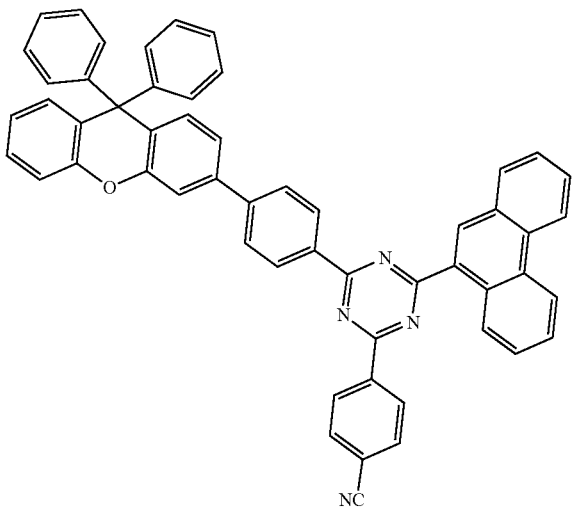
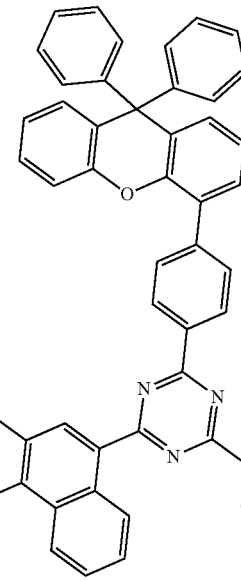
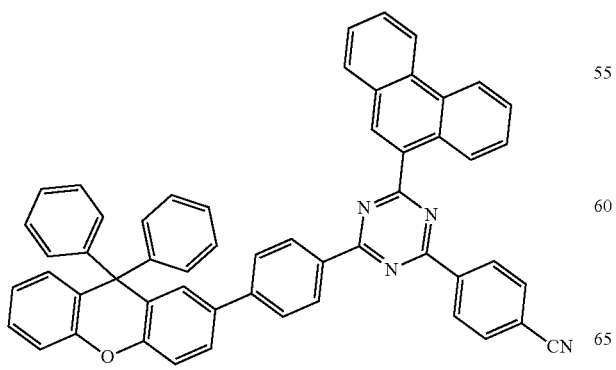
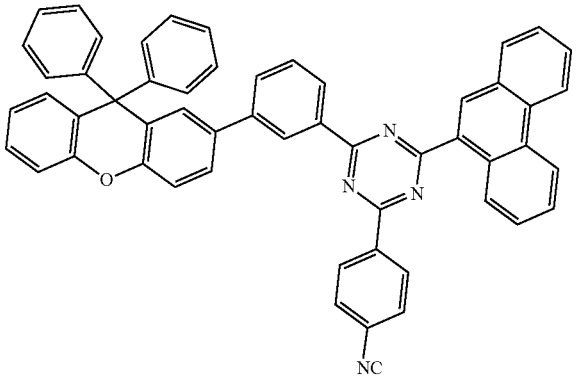

195
-continued
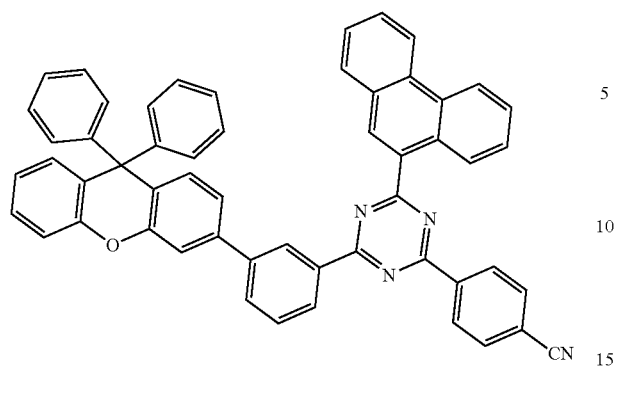
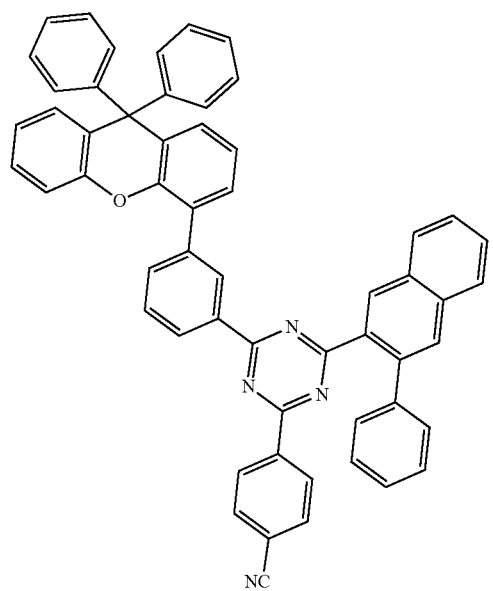
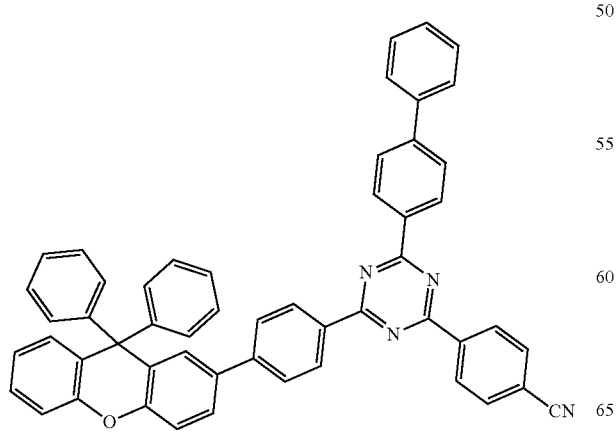
196
-continued
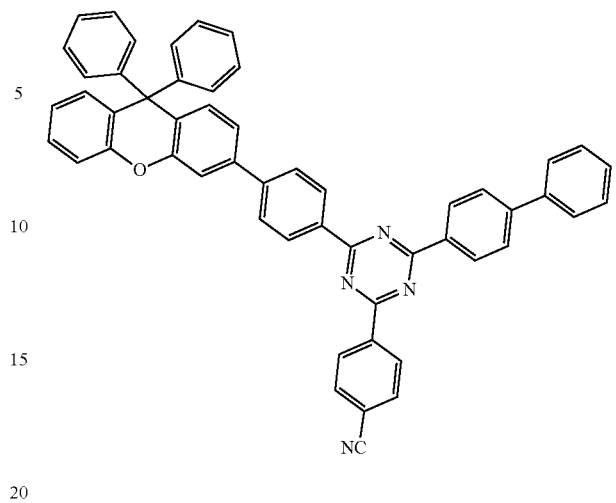
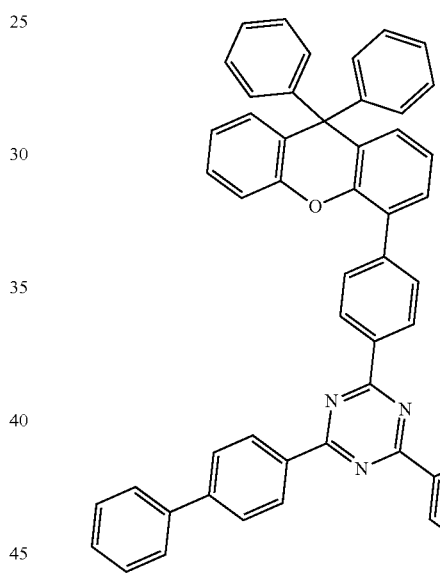
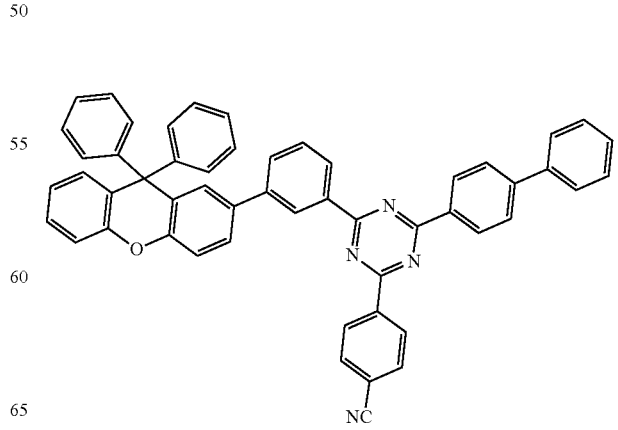

197
-continued
198
-continued
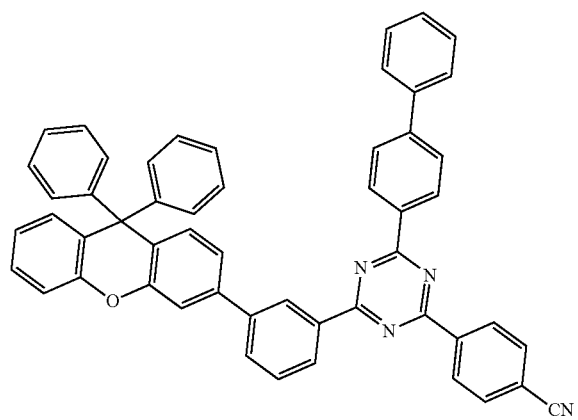
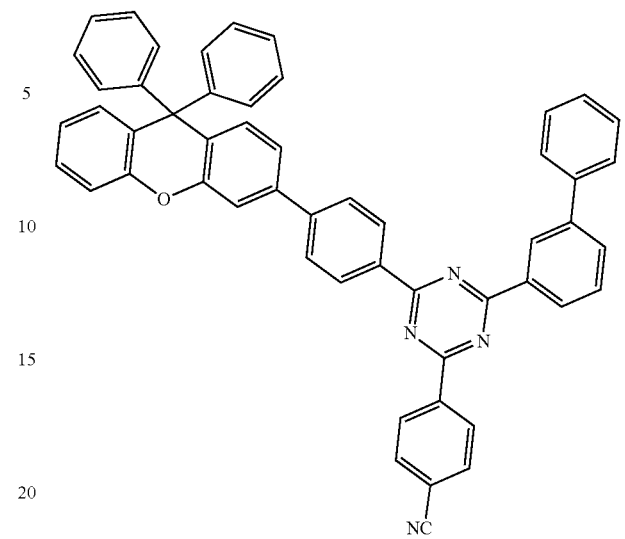
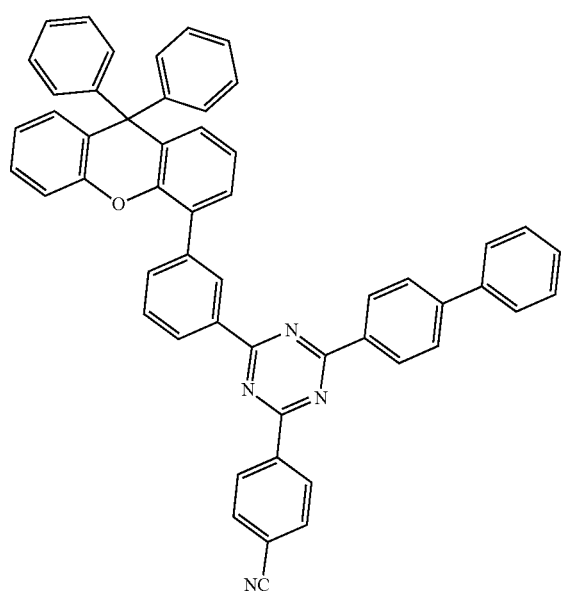
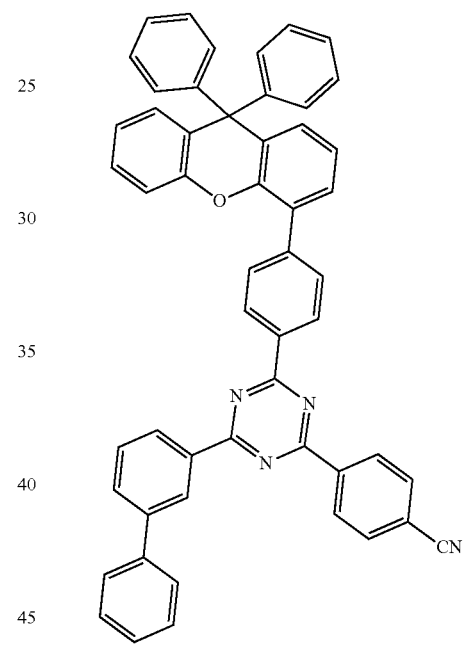
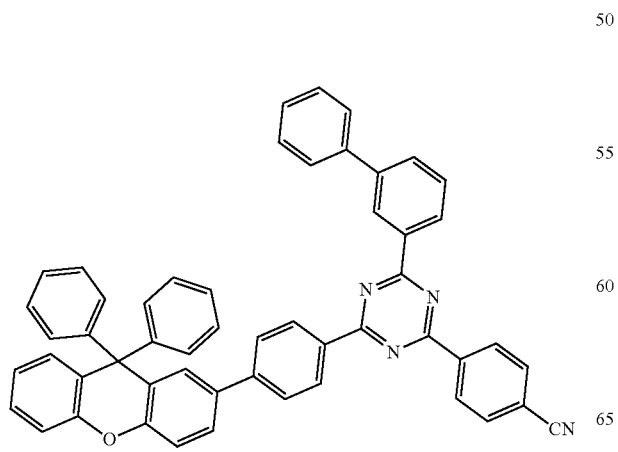
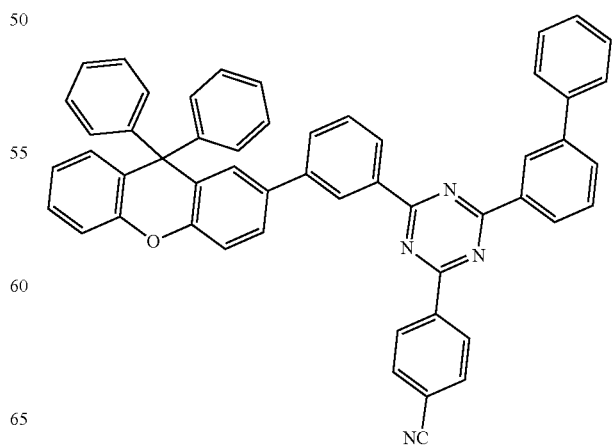

-continued
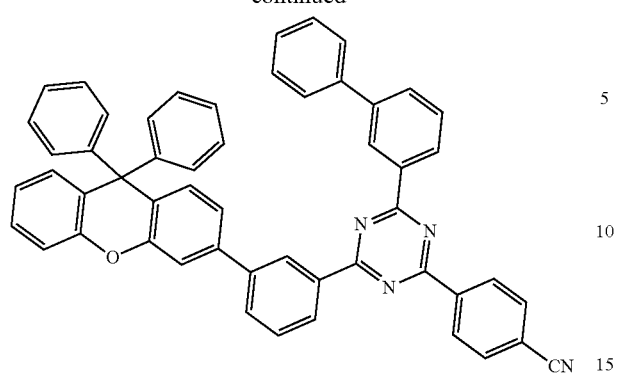
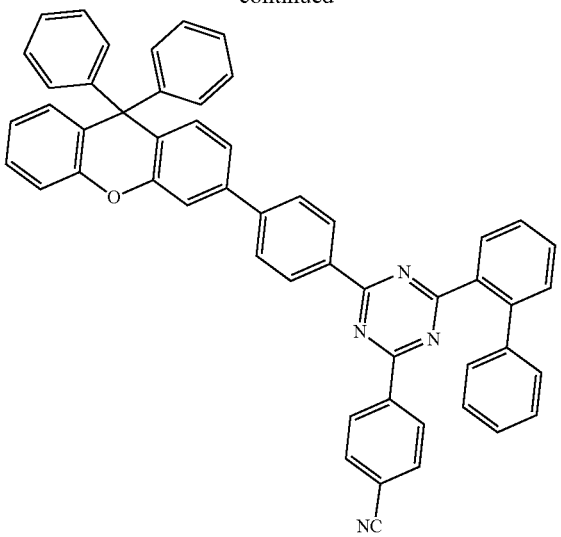
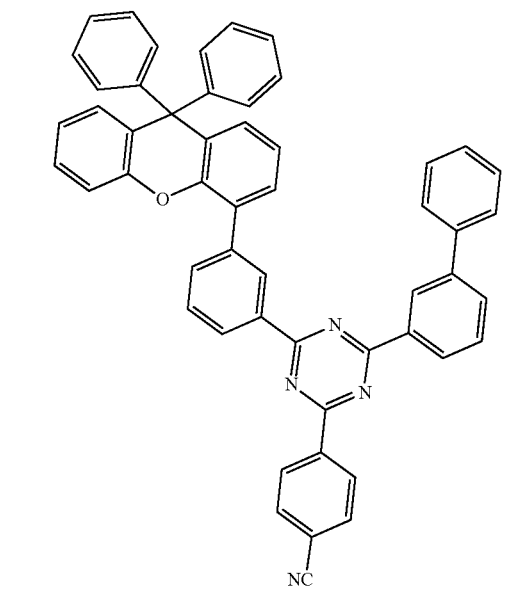
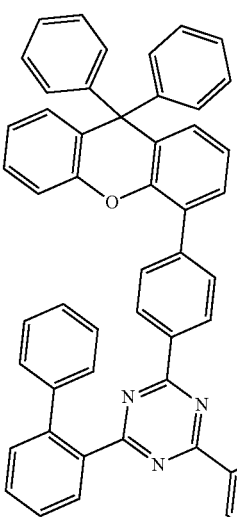
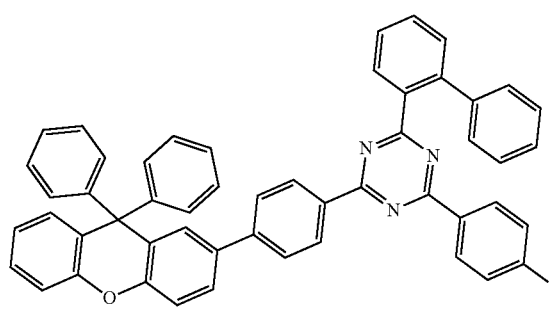
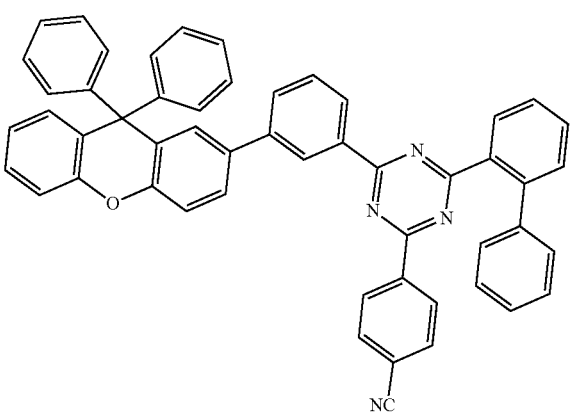

201
-continued
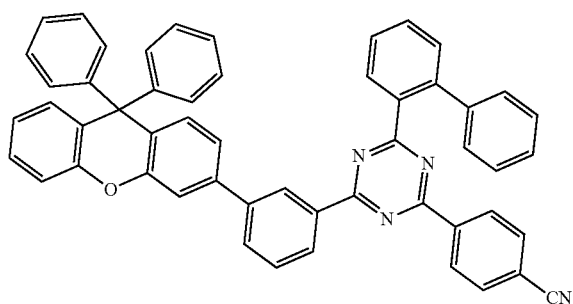
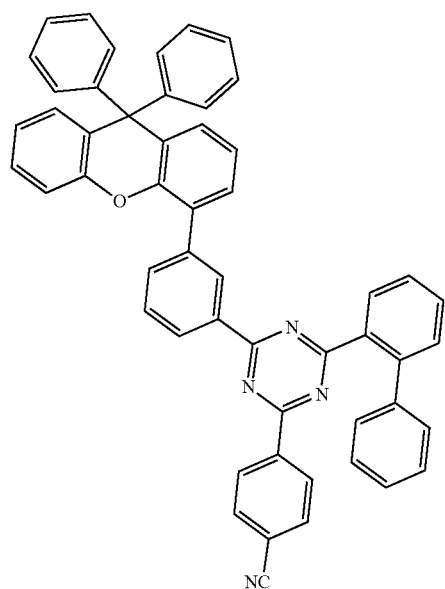
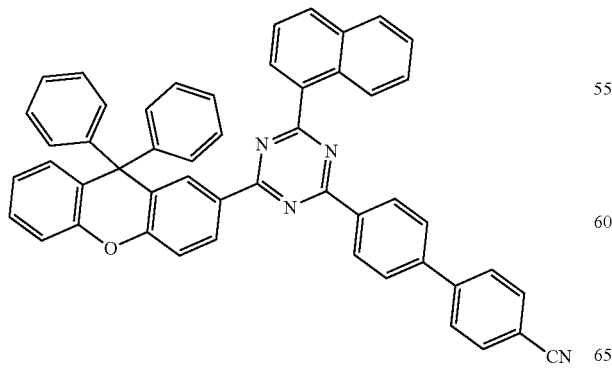
202
-continued
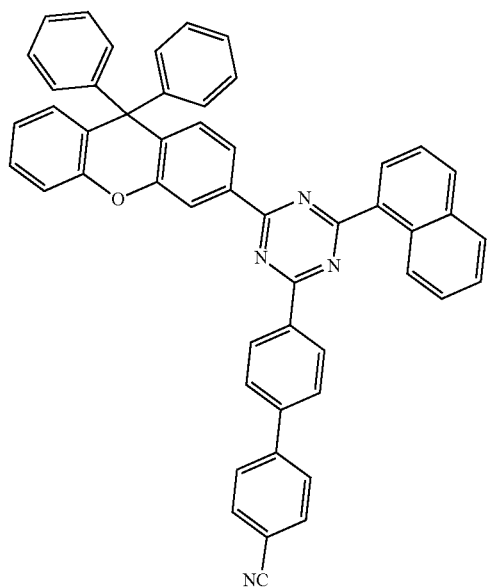
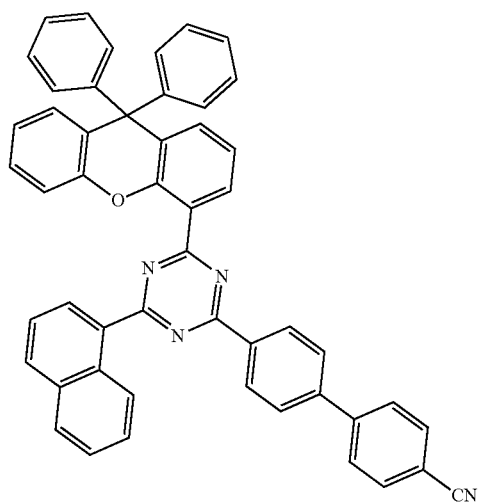
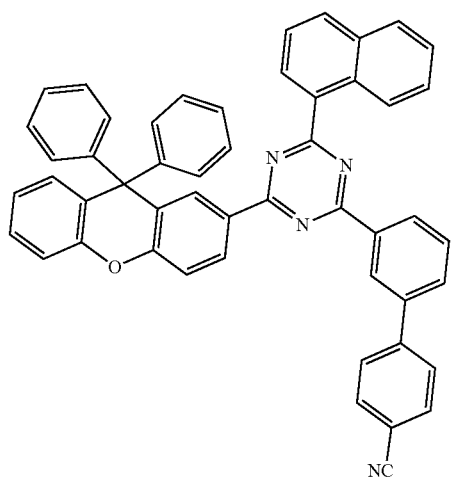

203
-continued
204
-continued
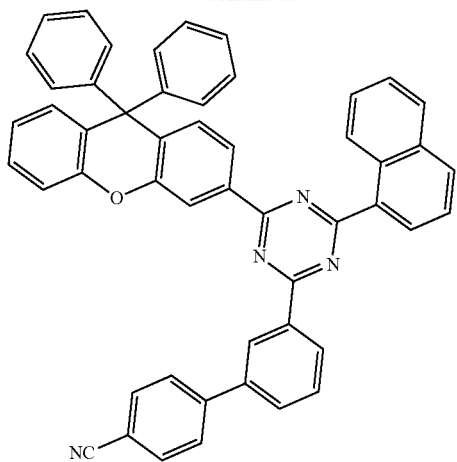
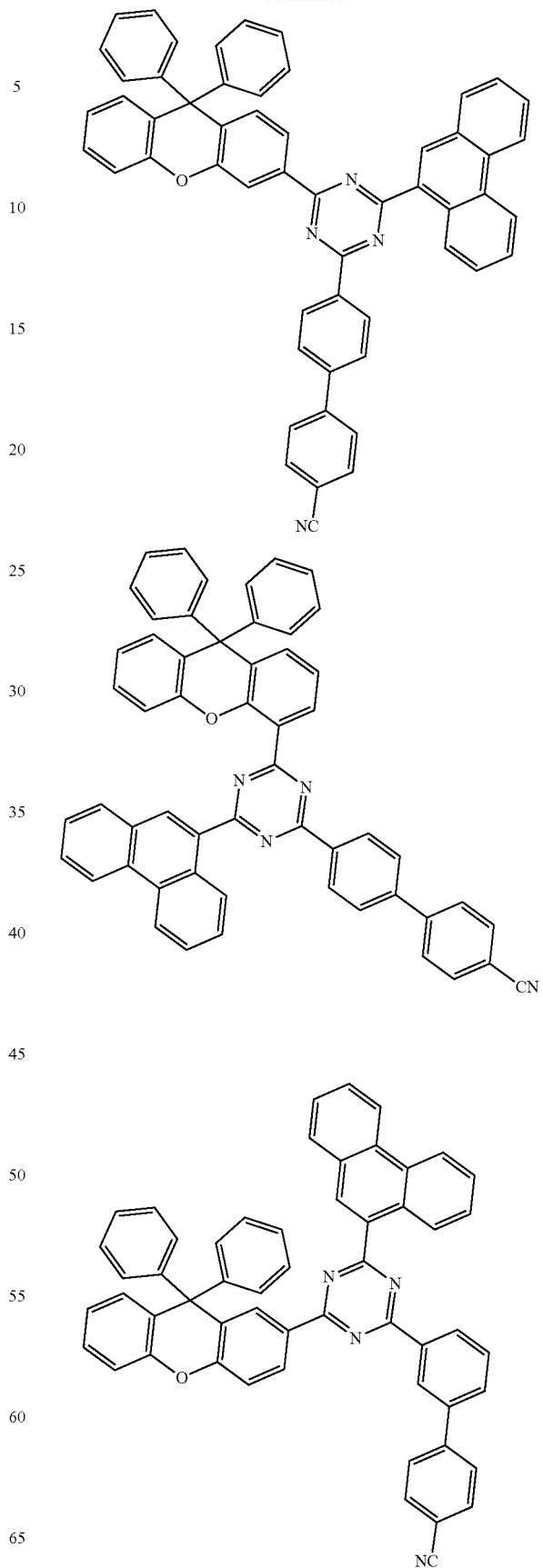

205
-continued
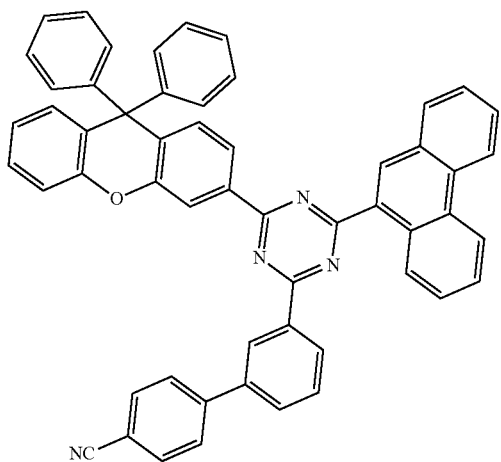
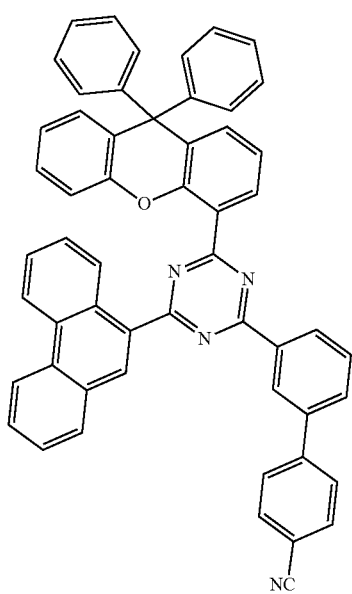
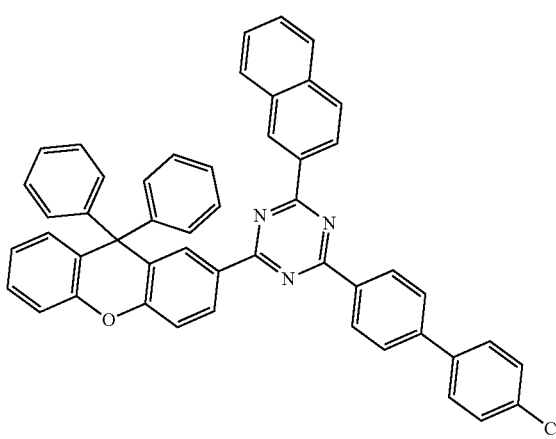
206
-continued
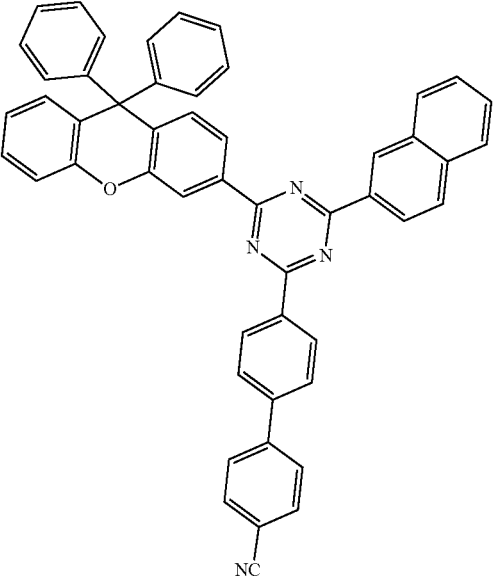
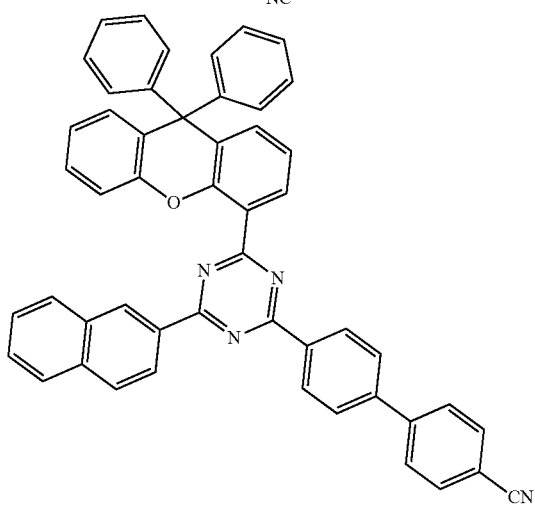
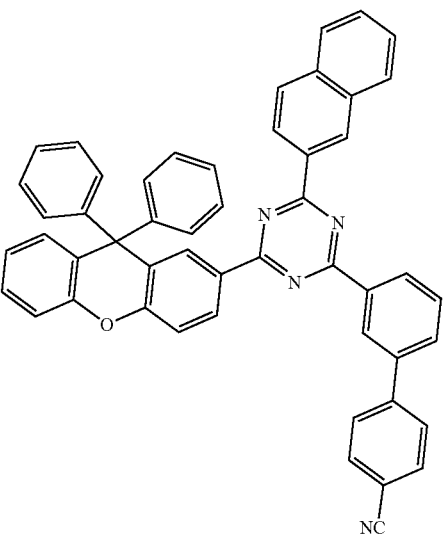

207
-continued
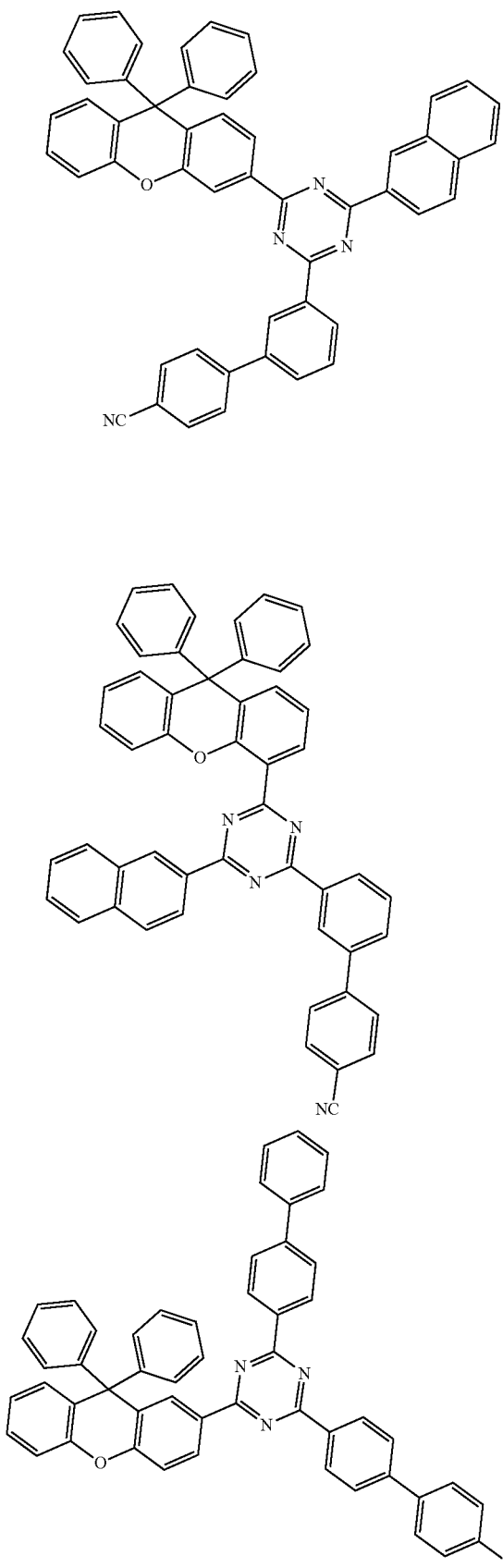
208
-continued
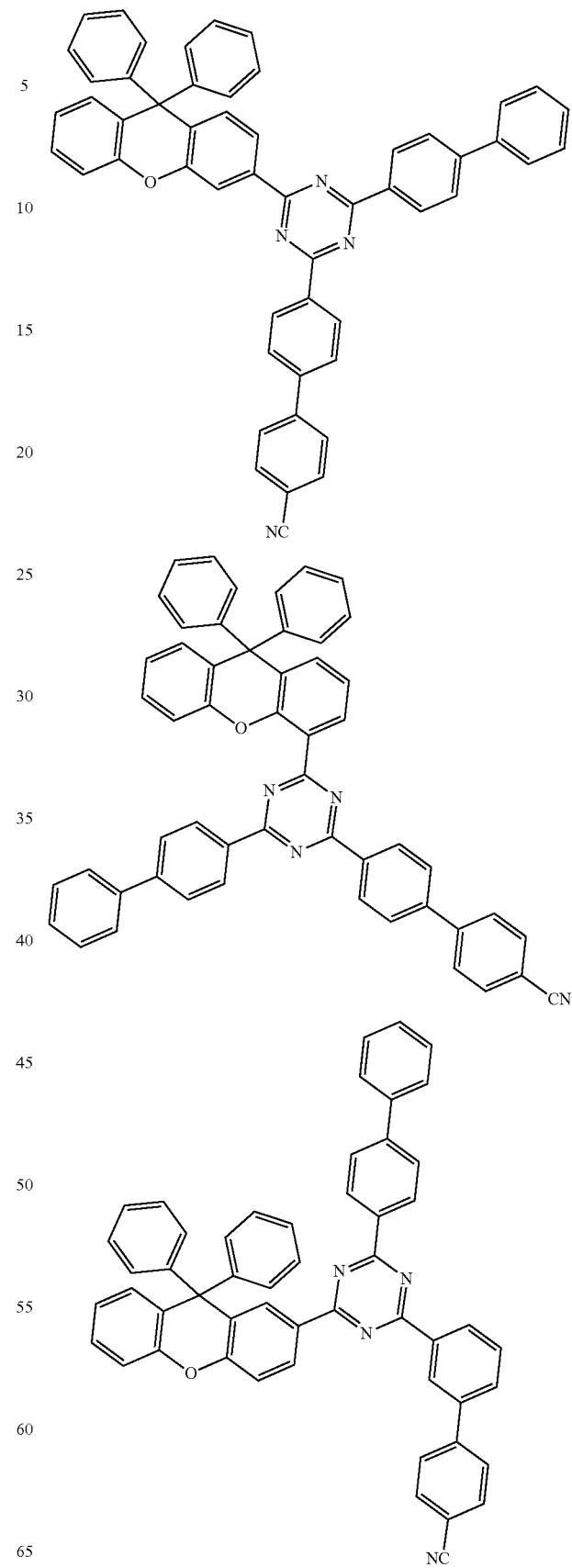

209
-continued
210
-continued
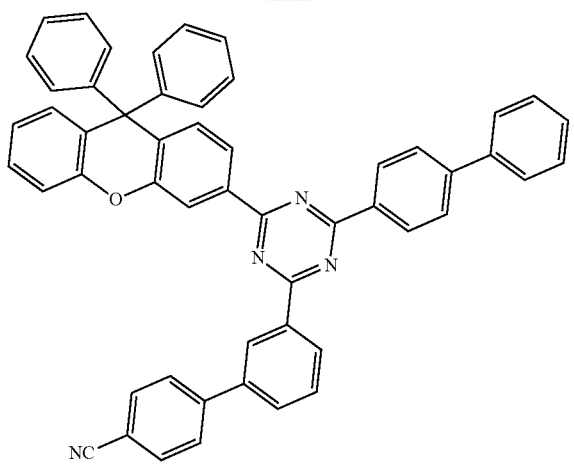
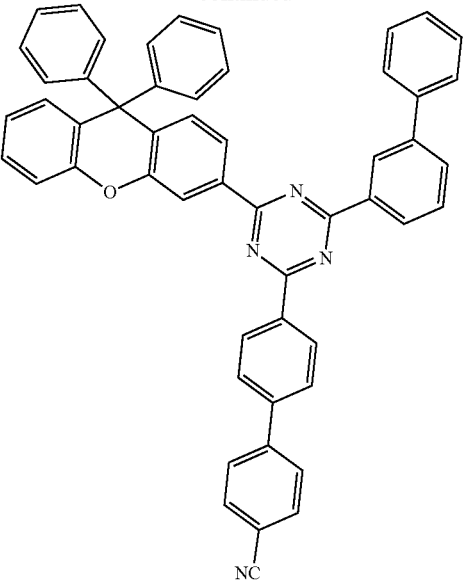
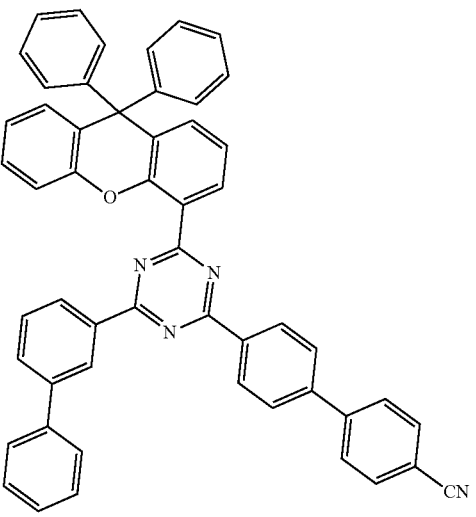
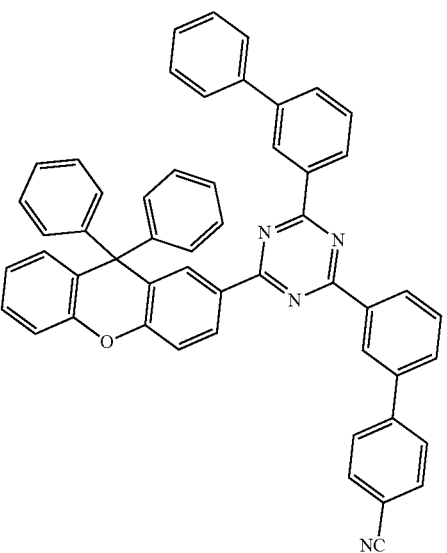

| 211 | 212 |
|---|---|
| -continued | -continued |
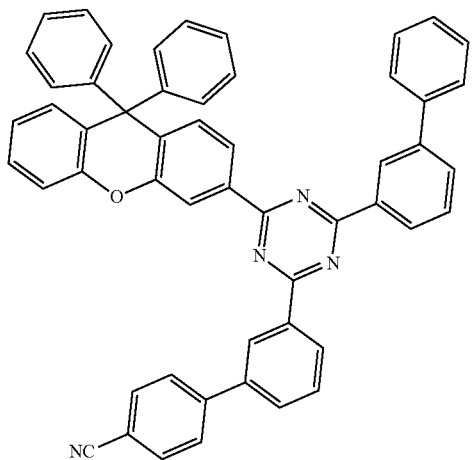
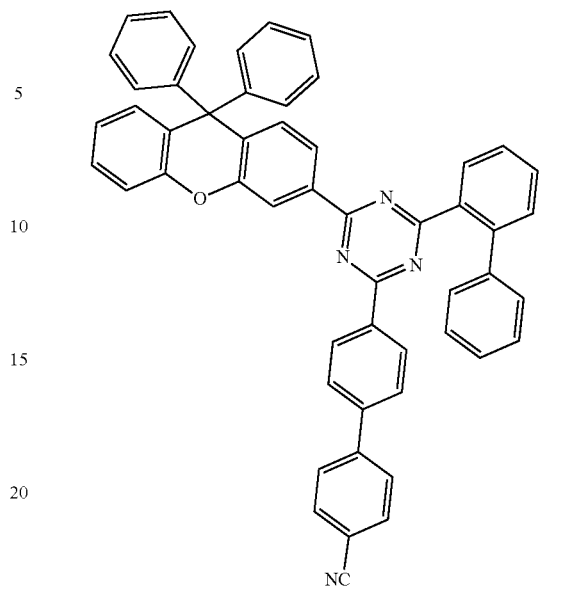
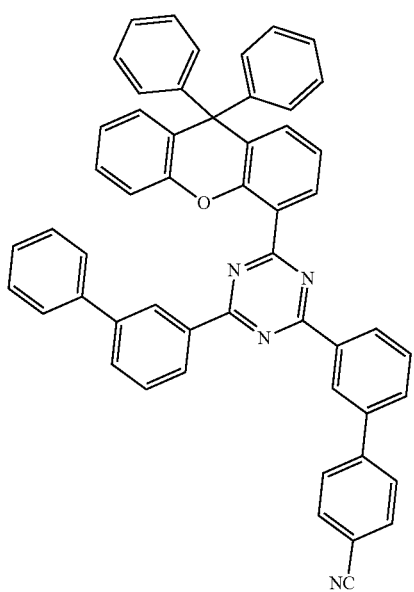
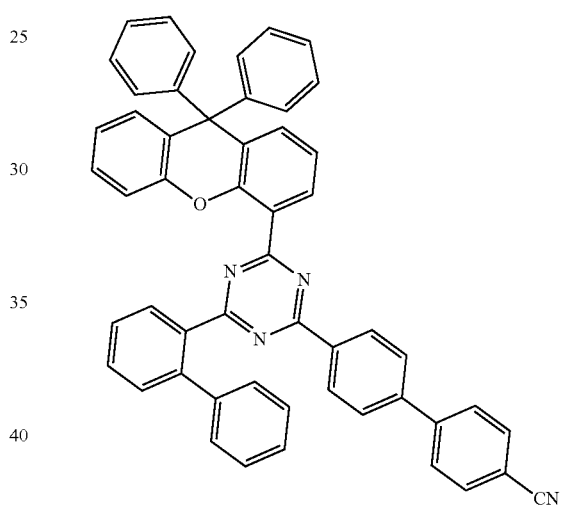
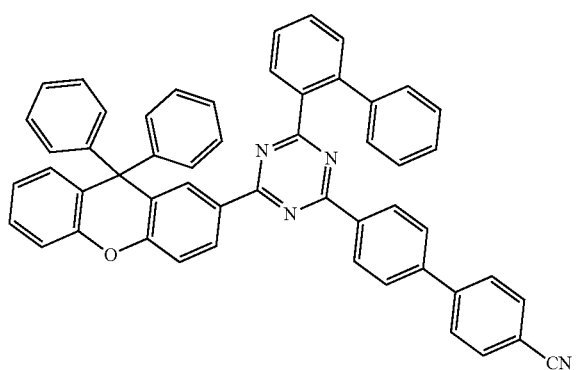
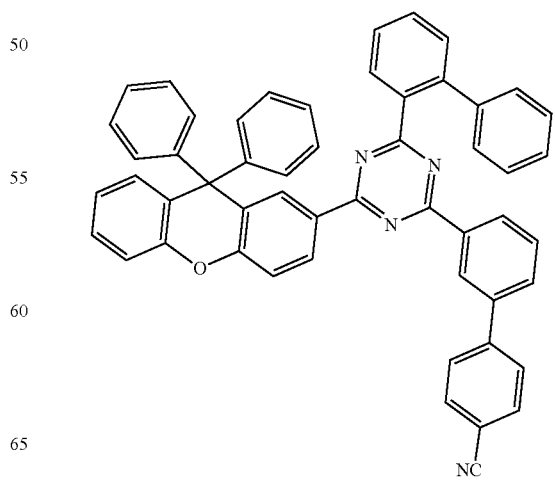

213
-continued
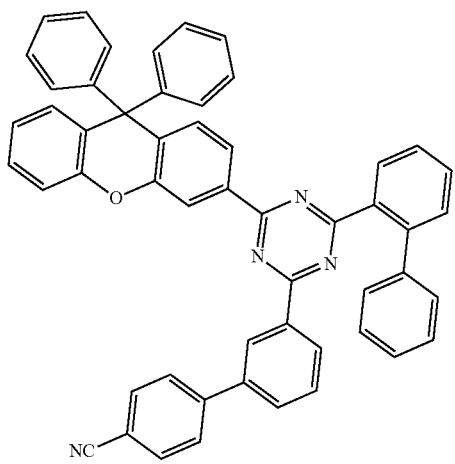
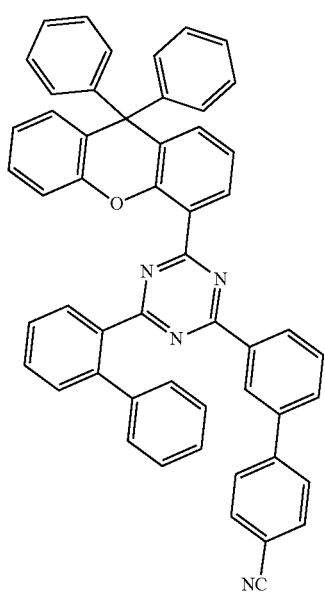 [SMILES: N#Cc1ccc(-c2cccc(-c3nc(-c4ccccc4-c4ccccc4)nc(-c4cccc5c4Oc4ccccc4C5(c4ccccc4)c4ccccc4)n3)c2)cc1]
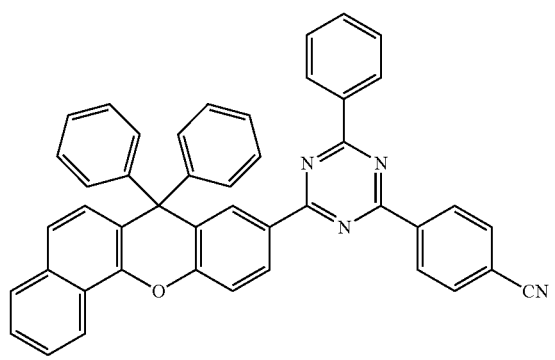
214
-continued
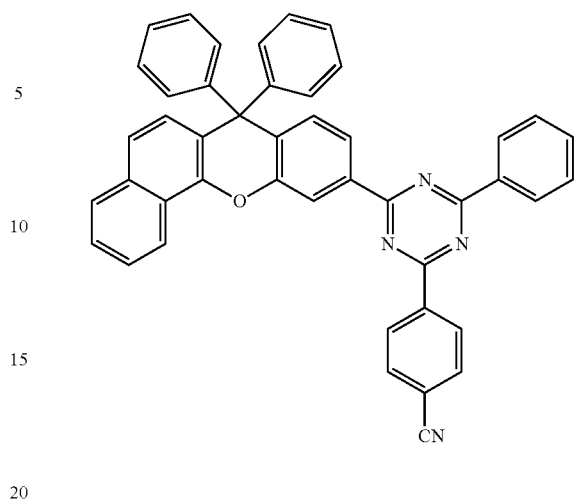
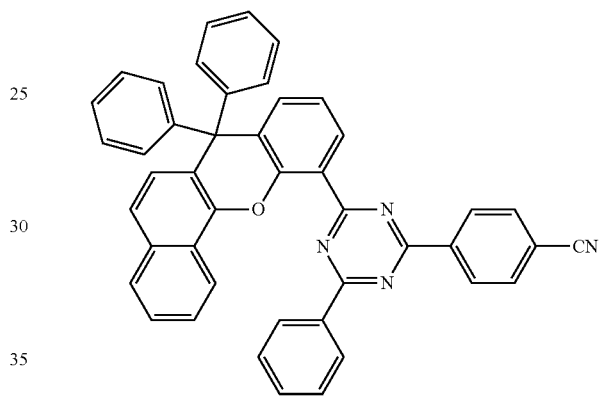
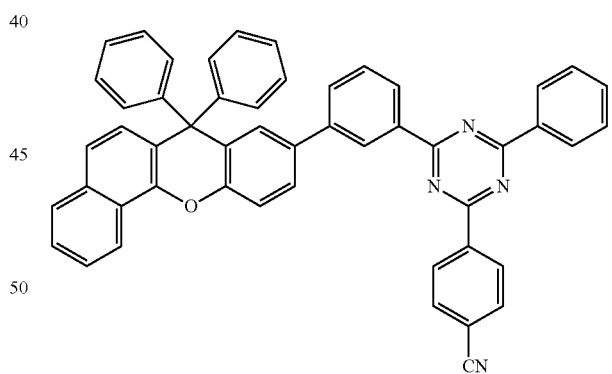

215
-continued
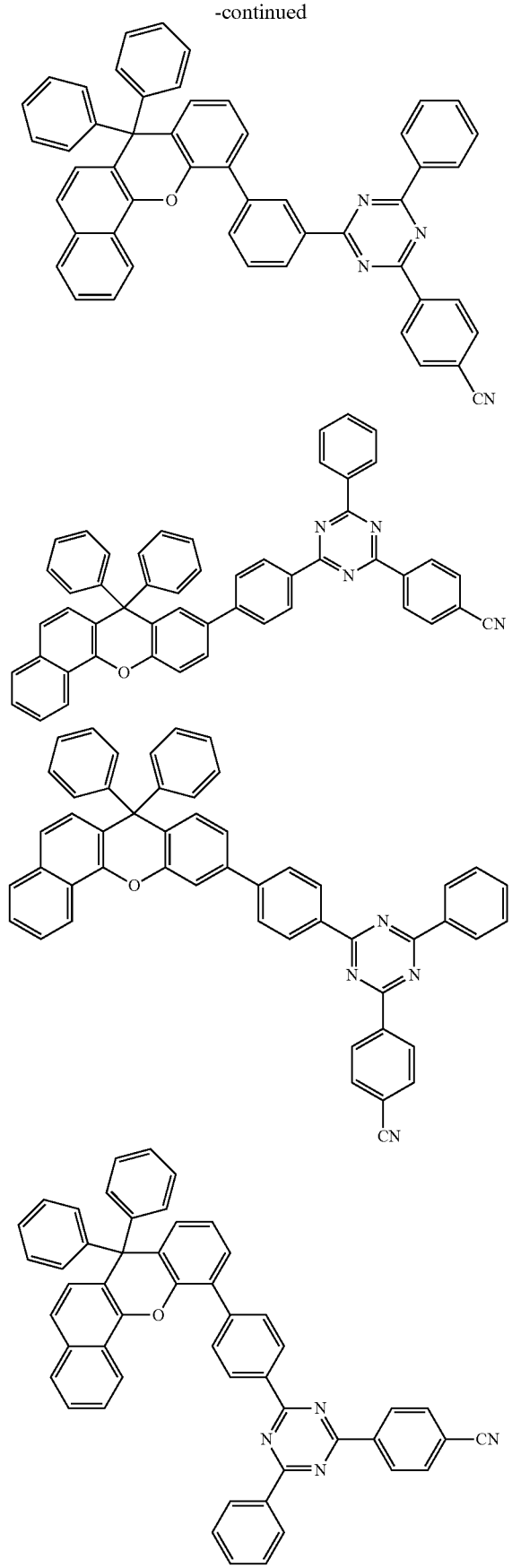
216
-continued
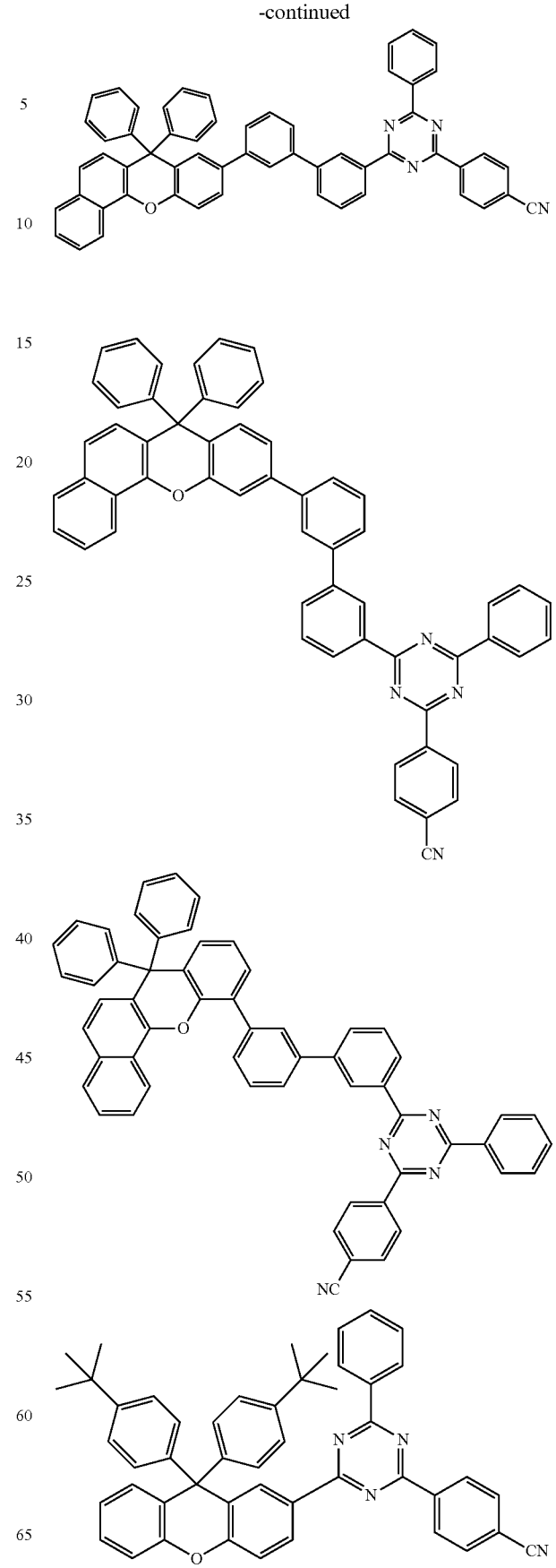

217
-continued
218
-continued
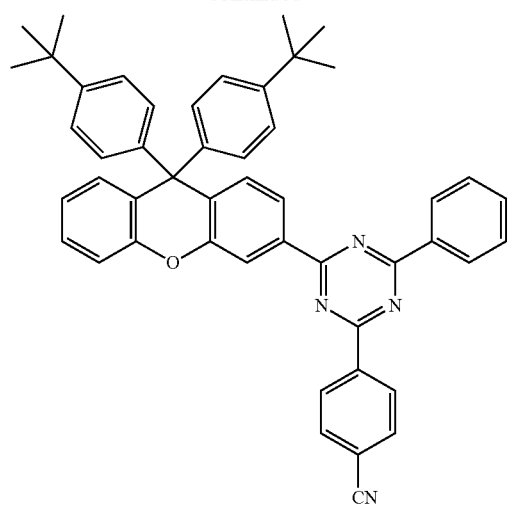
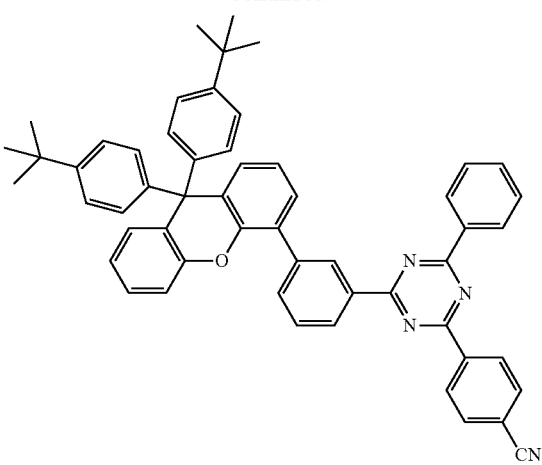
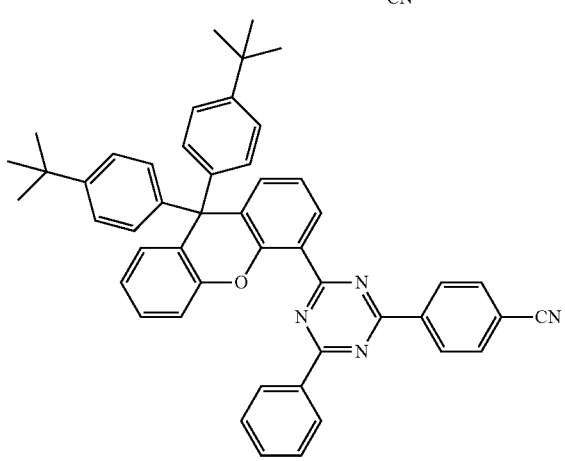
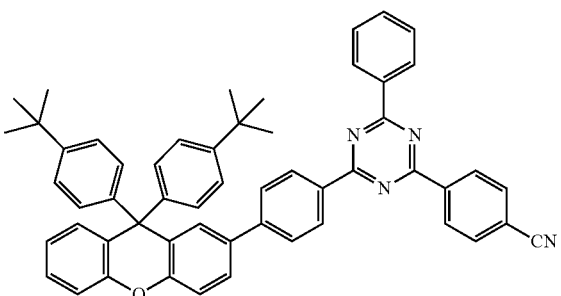
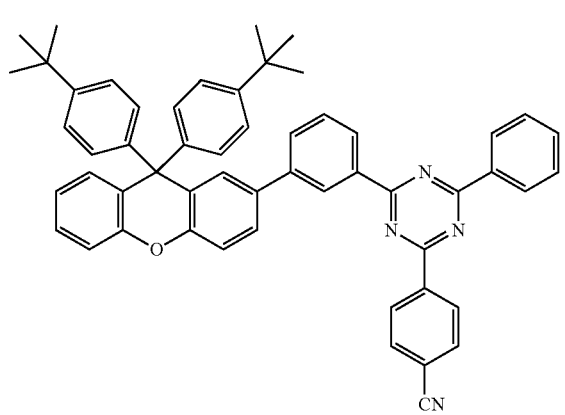
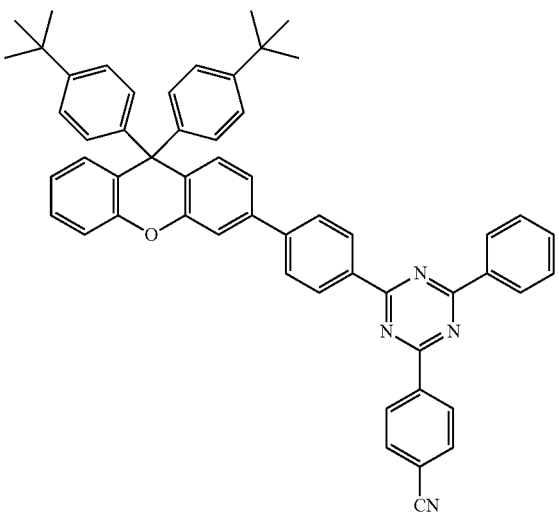
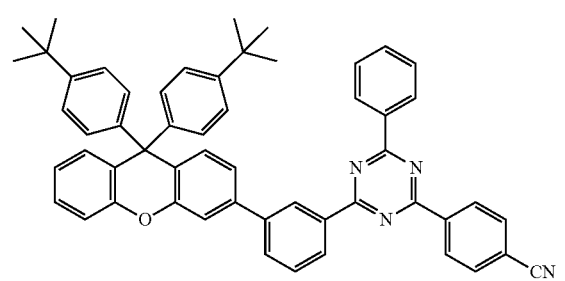

219
-continued
220
-continued
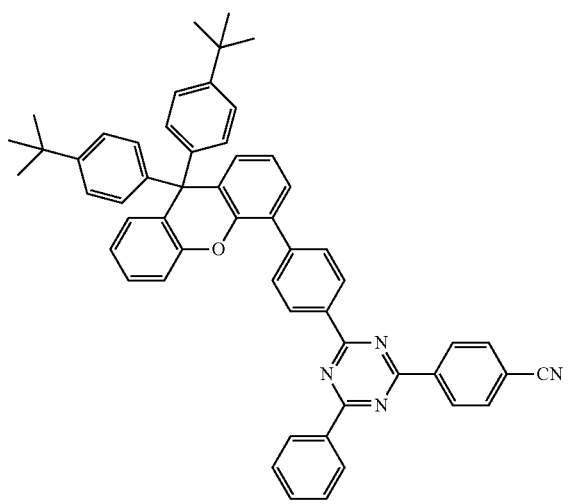
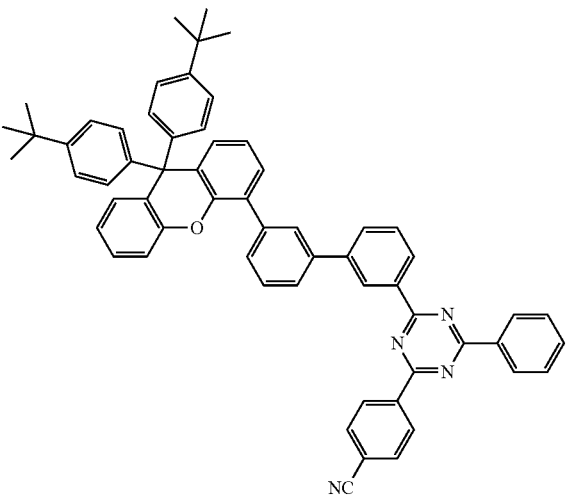
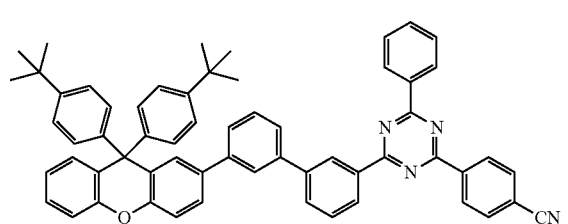
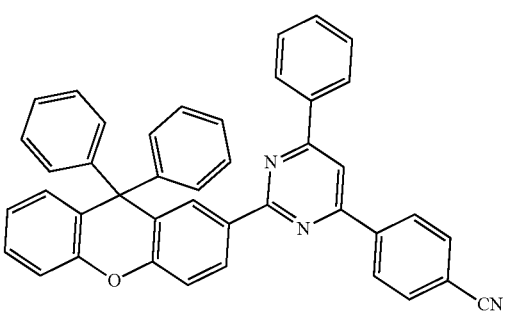
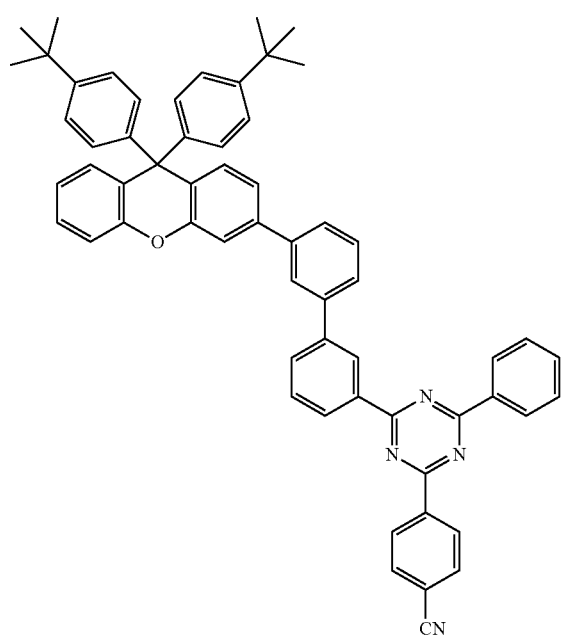
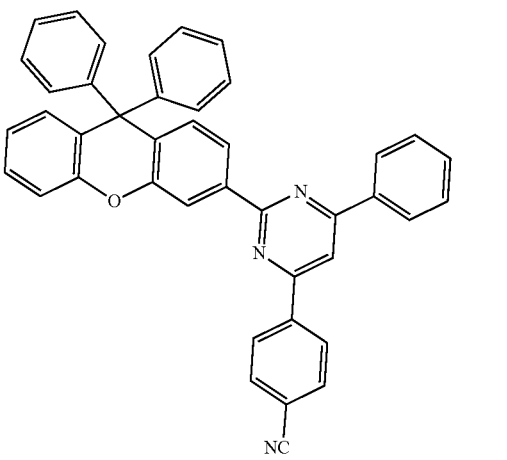
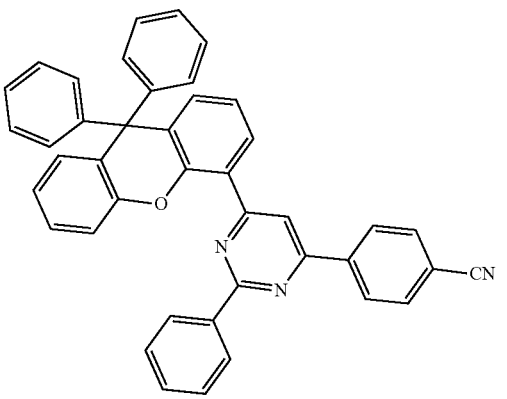

221
-continued
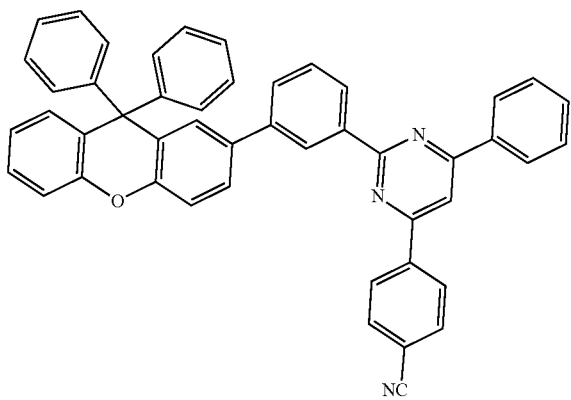
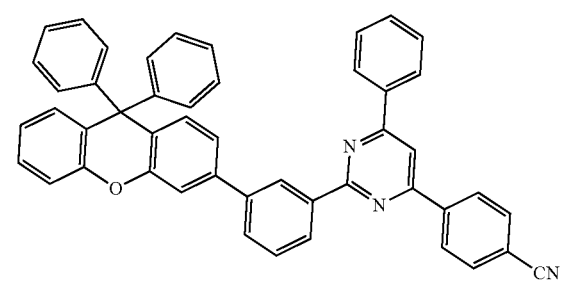
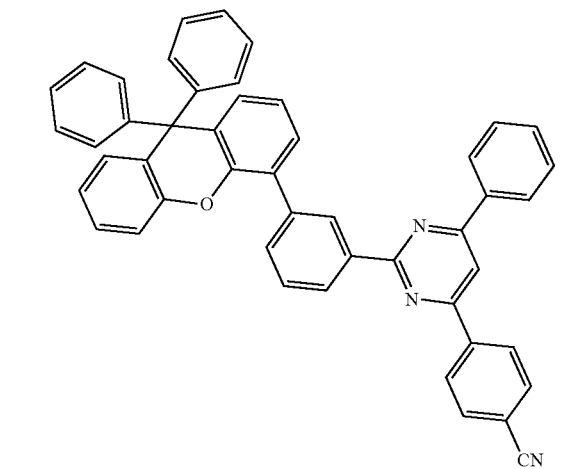
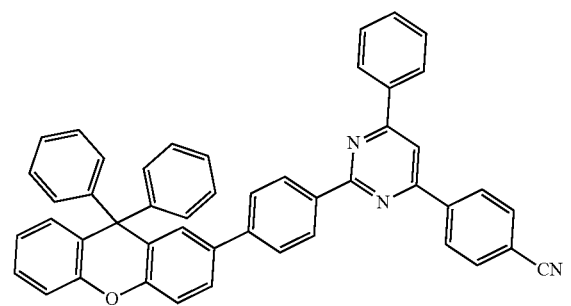
222
-continued
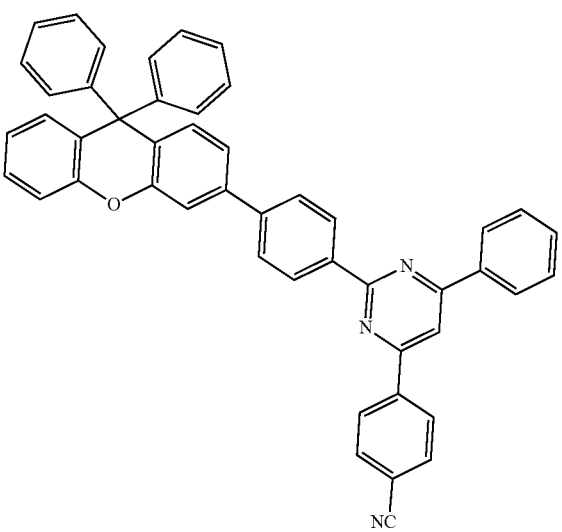
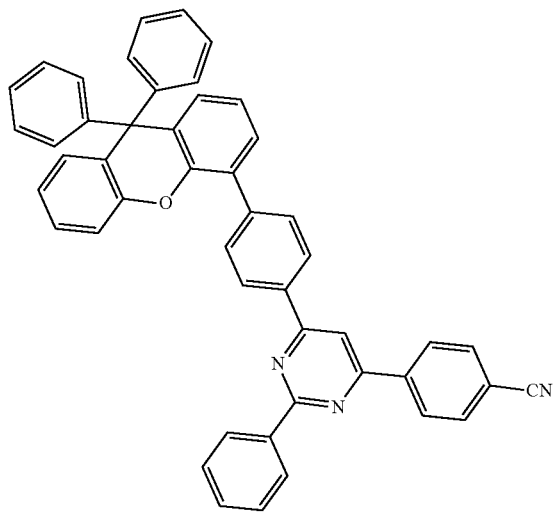
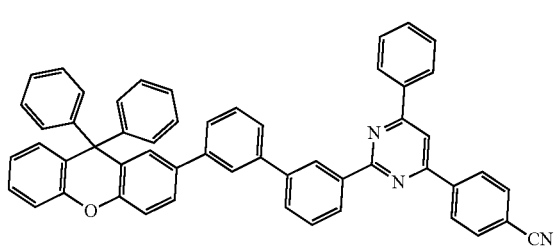

223
-continued
224
-continued
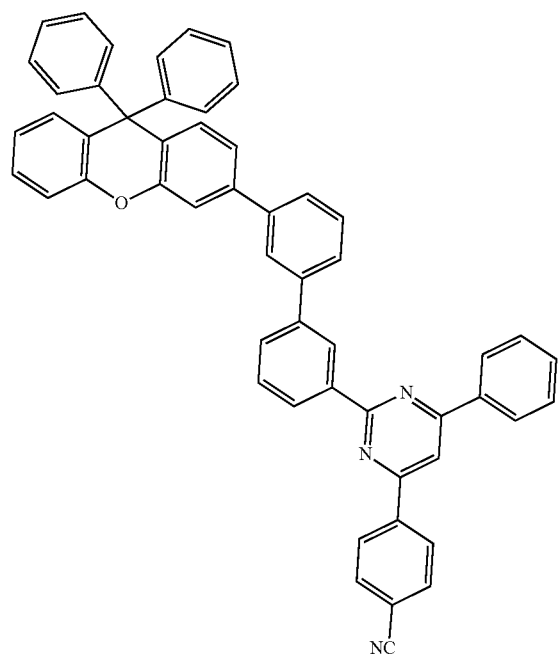 [SMILES: N#Cc1ccc(-c2cc(-c3ccccc3)nc(-c3cccc(-c4cccc(-c5ccc6c(c5)Oc5ccccc5C6(c5ccccc5)c5ccccc5)c4)c3)n2)cc1]
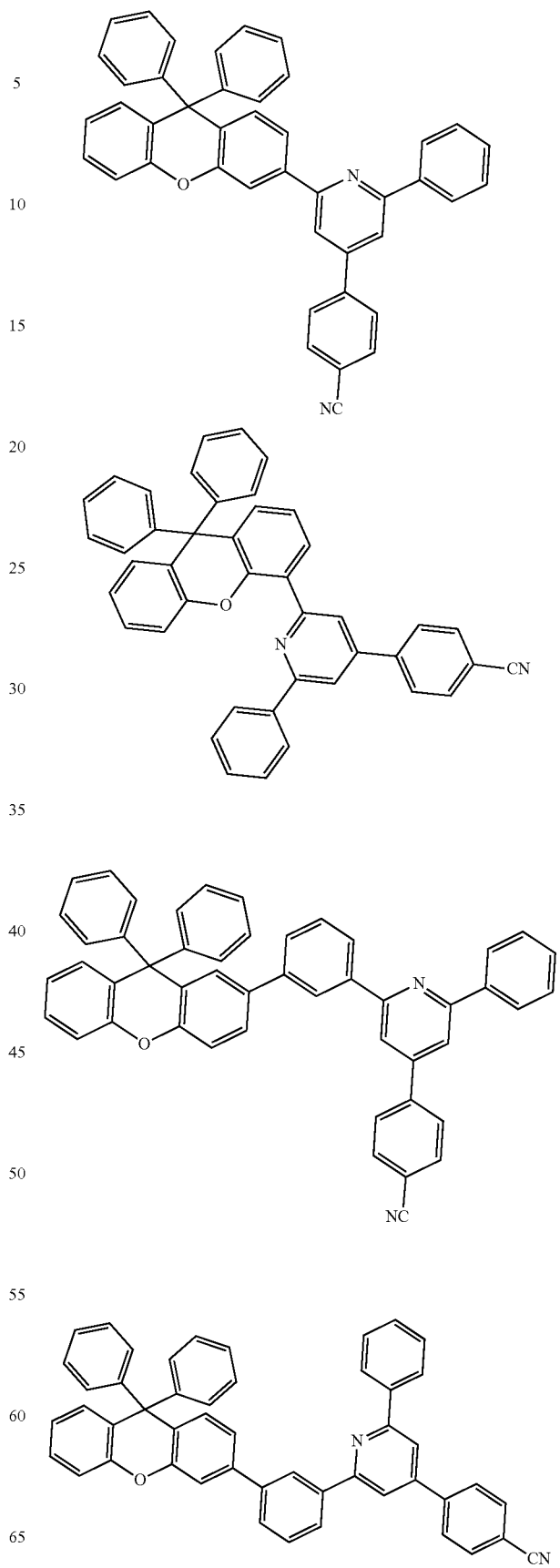

225
-continued
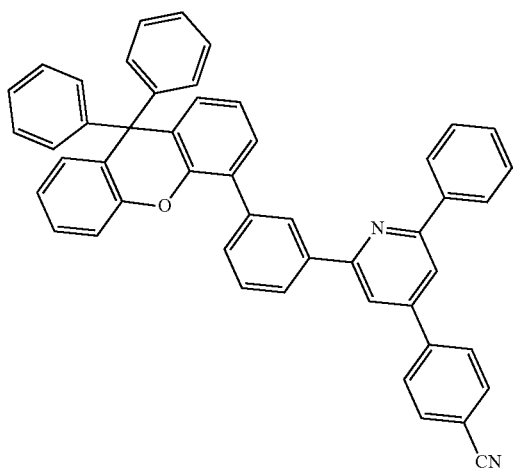
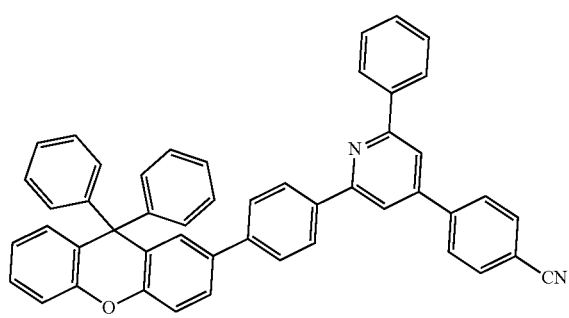
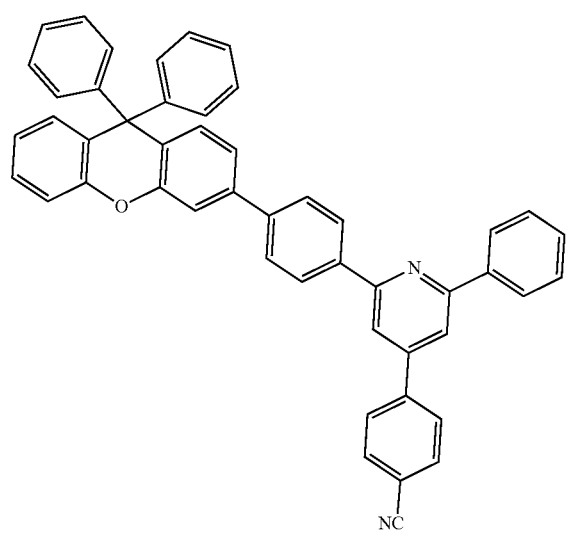
226
-continued
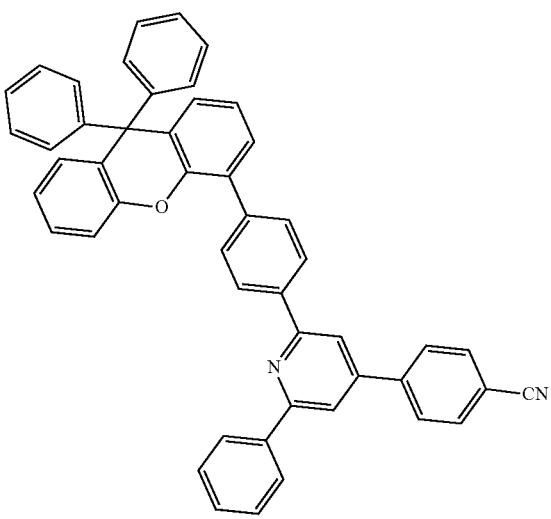
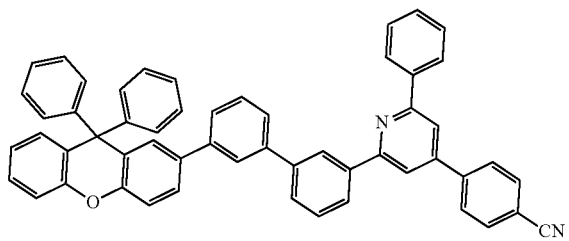
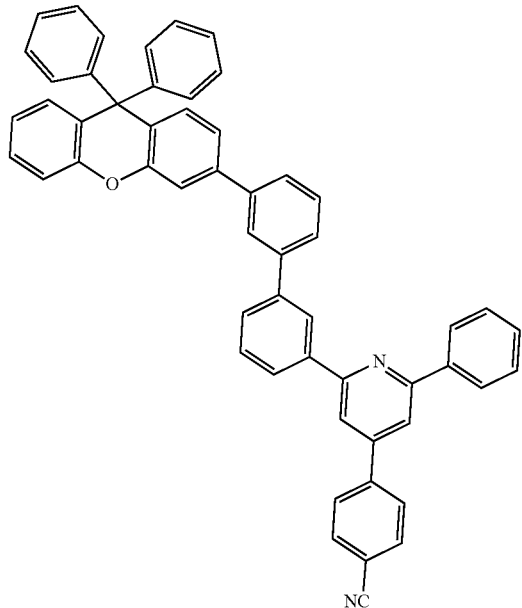

227
-continued
228
-continued
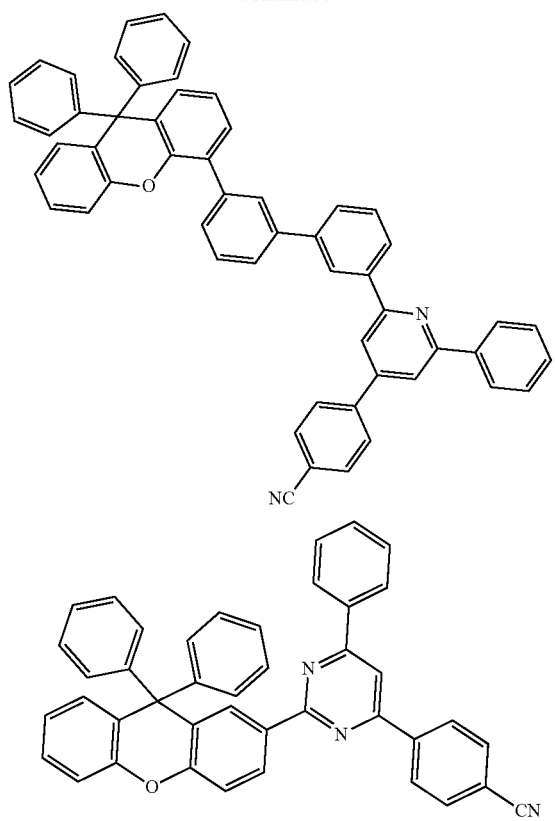
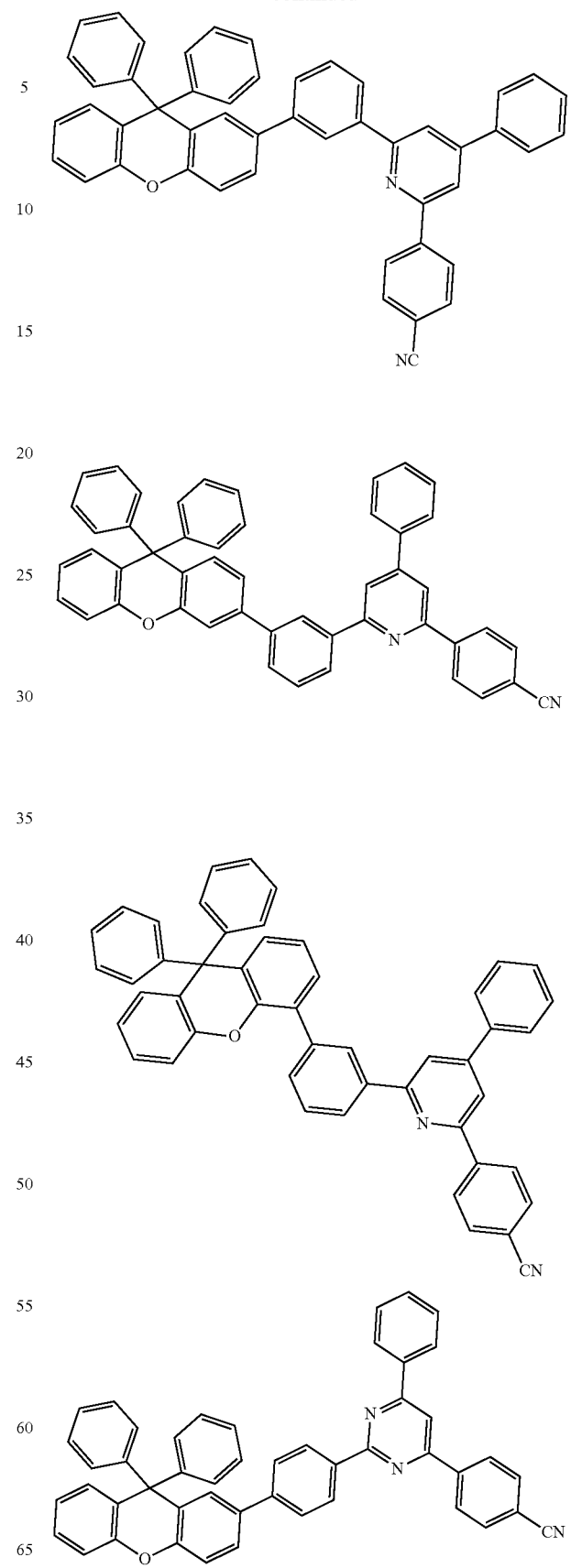

229
-continued
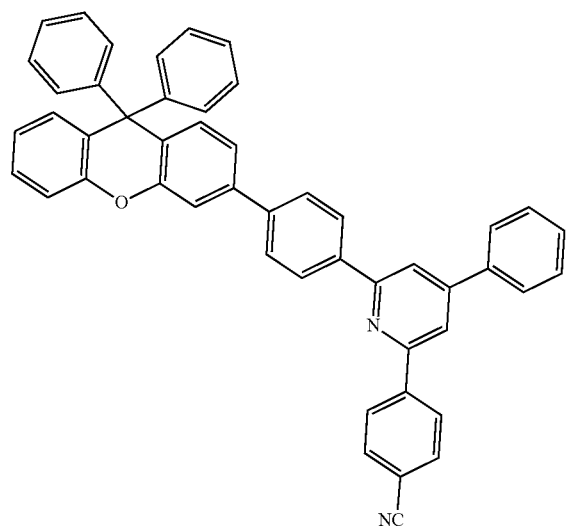
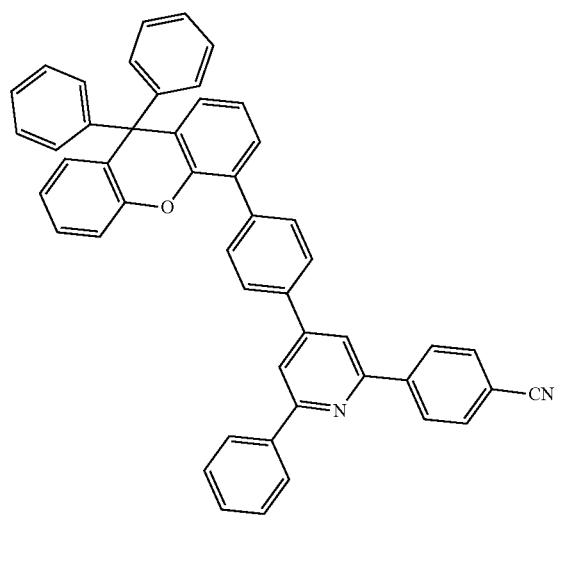
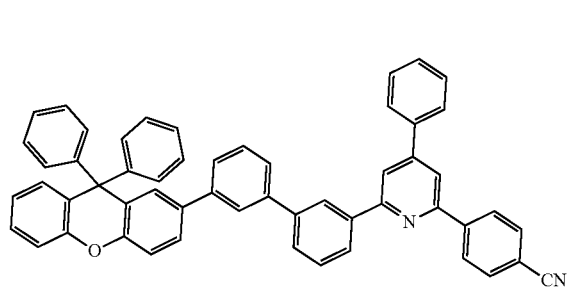
230
-continued
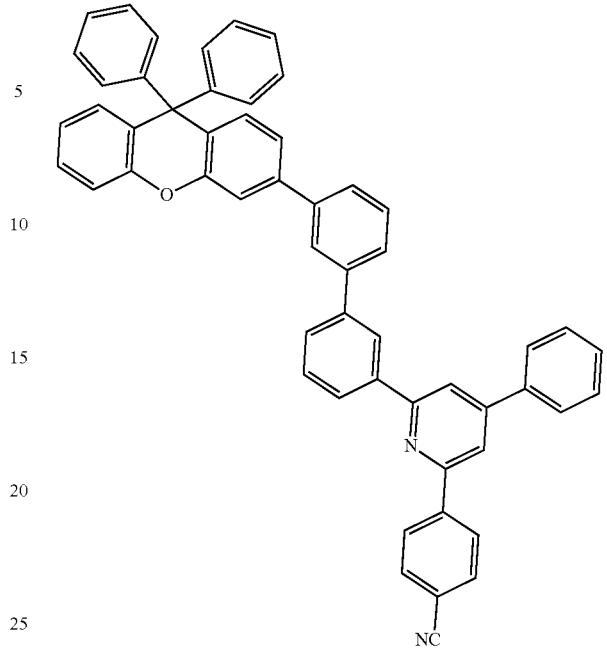
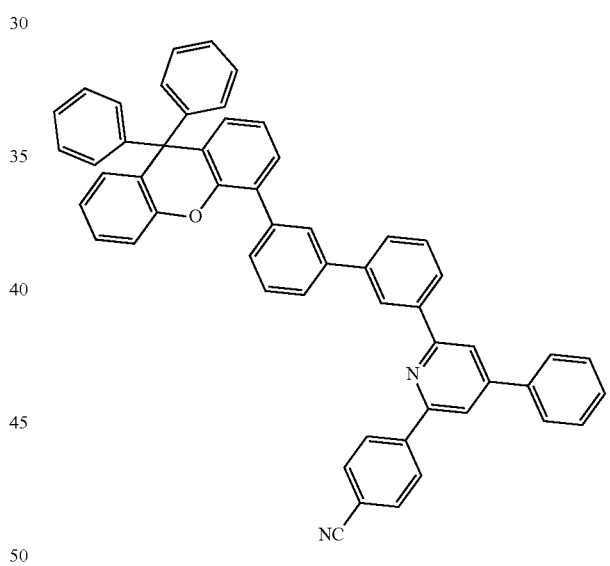
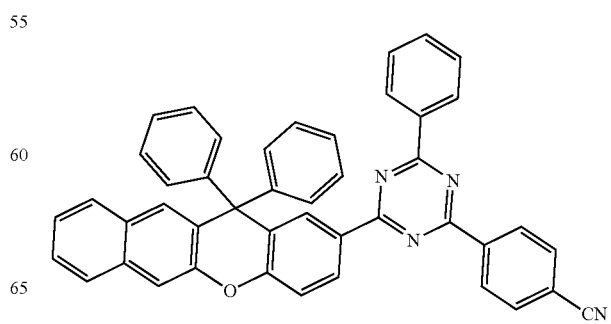

231
-continued
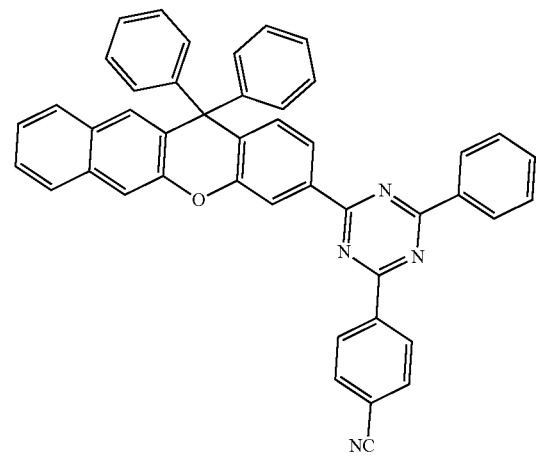
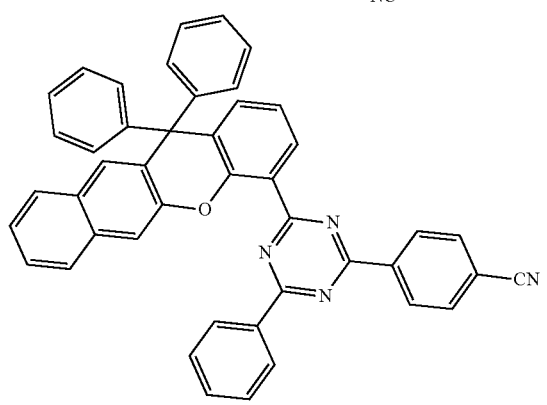
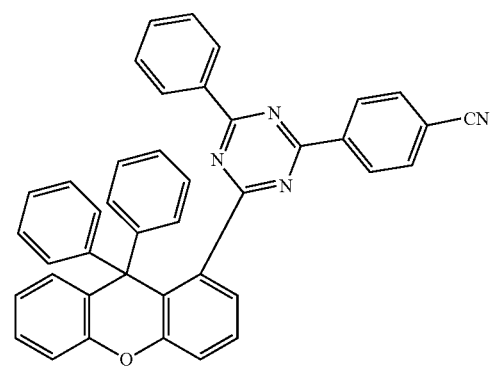
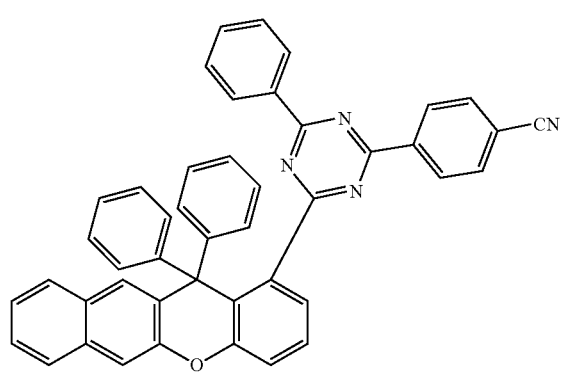
232
-continued
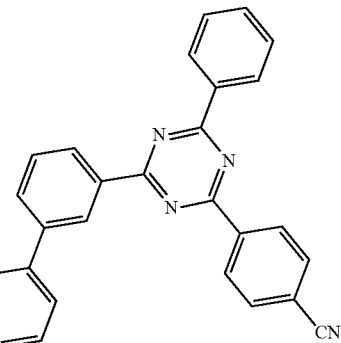
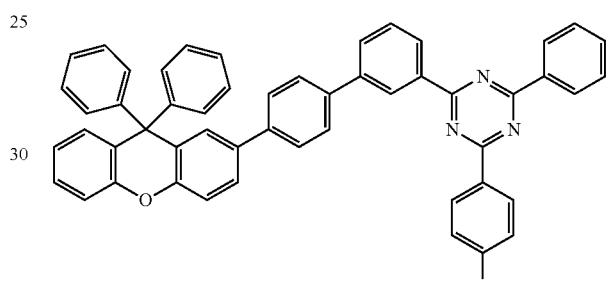
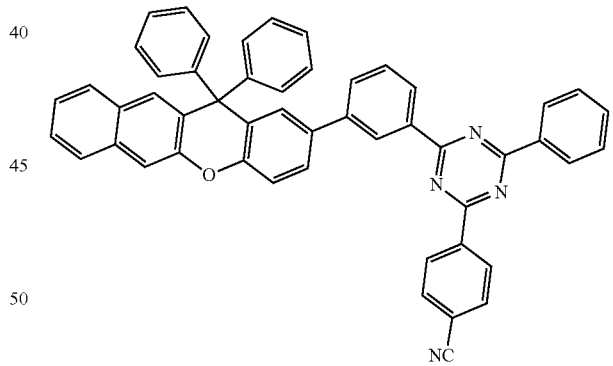
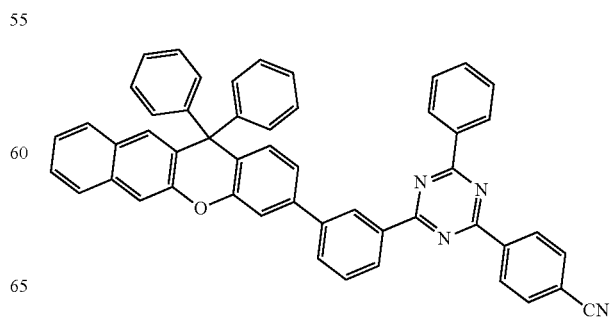

233
-continued
234
-continued
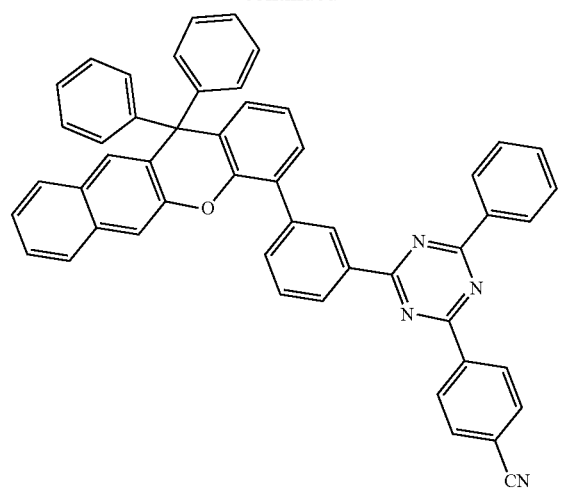
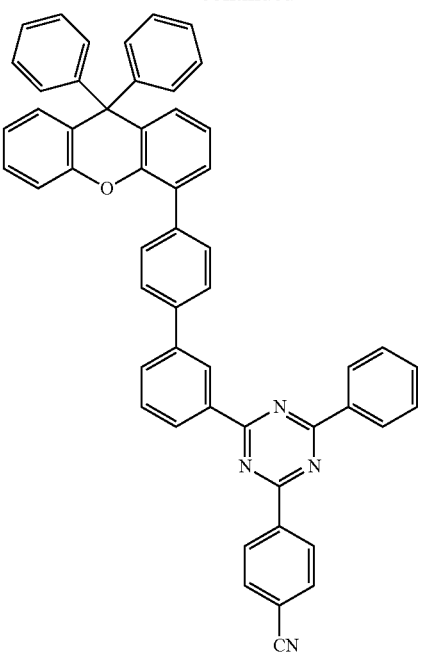
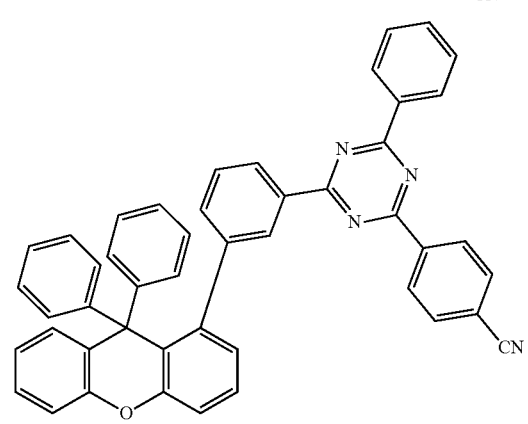 [SMILES: N#Cc1ccc(-c2nc(-c3ccccc3)nc(-c3cccc(-c4cccc5c4C(c4ccccc4)(c4ccccc4)c4ccccc4O5)c3)n2)cc1]
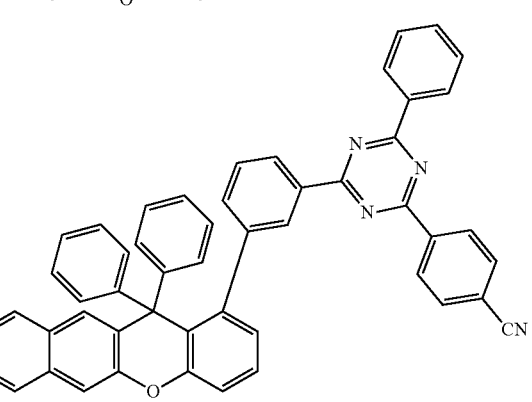

235
-continued
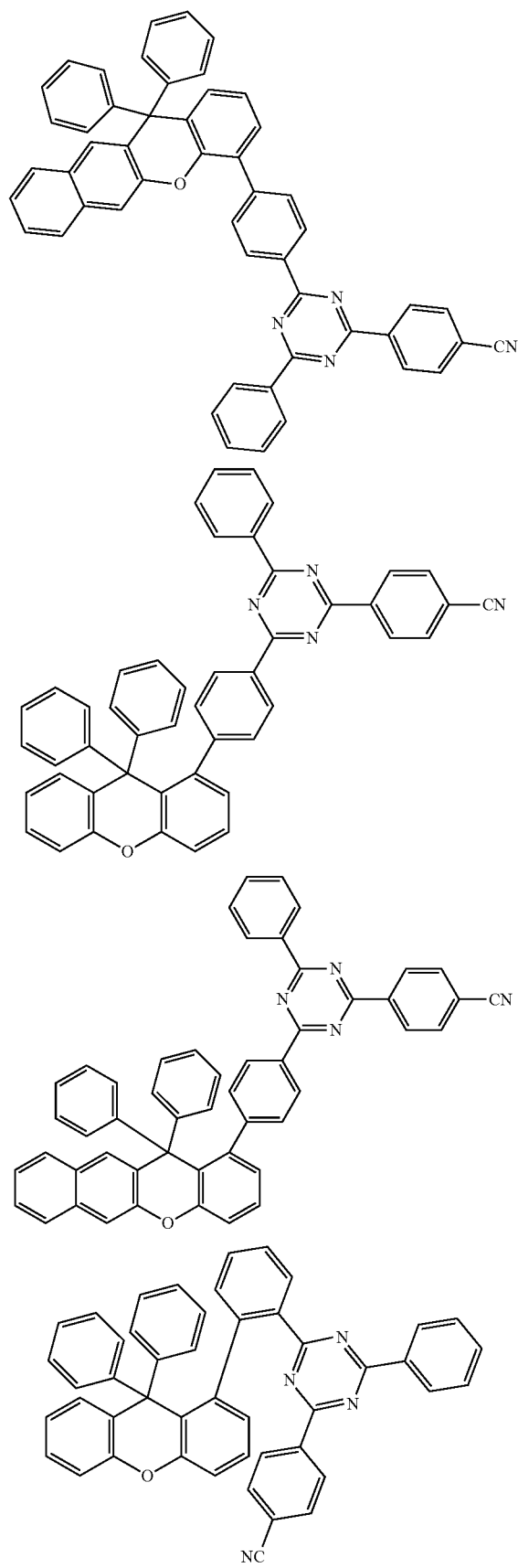
236
-continued
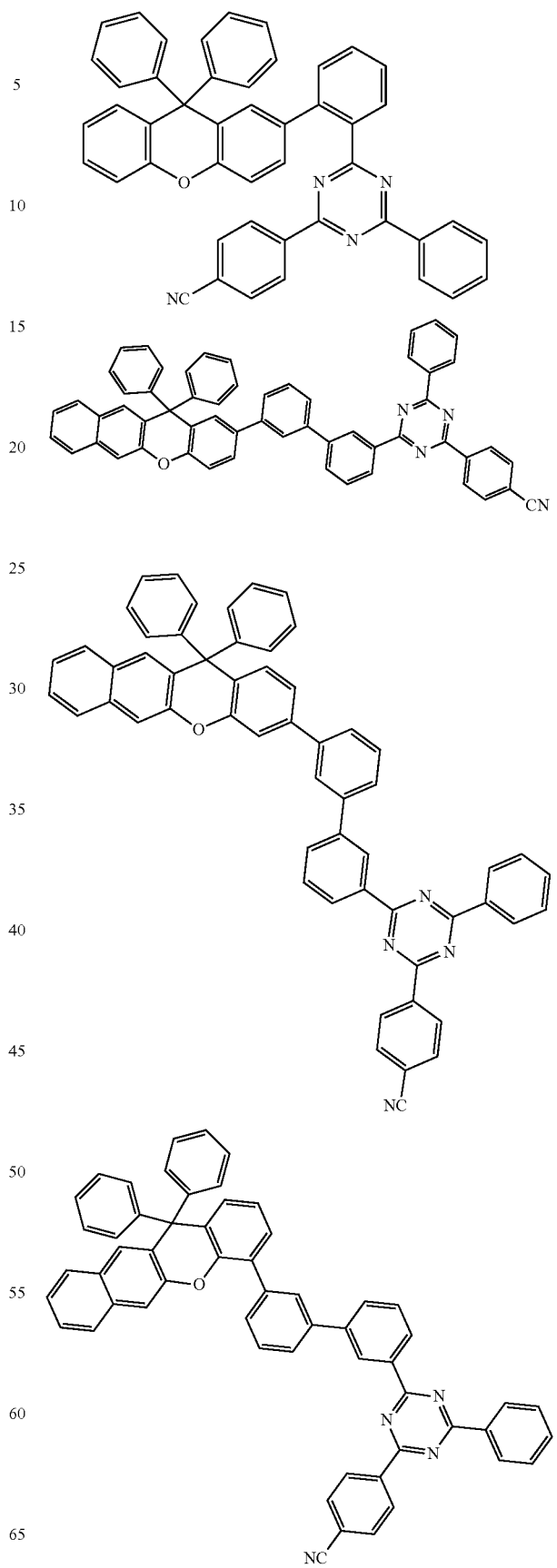

-continued
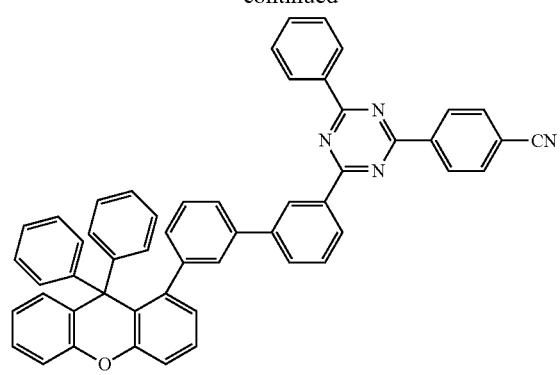
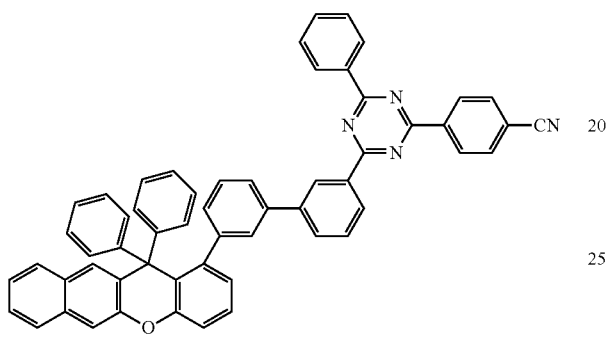
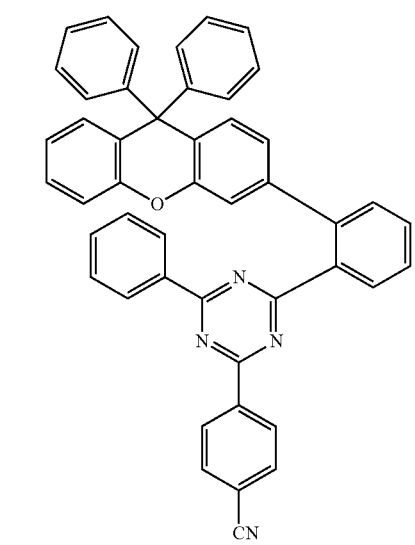
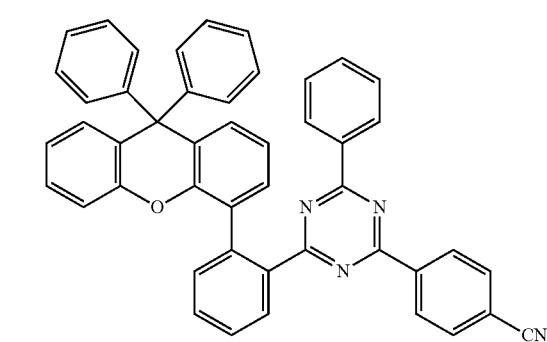
-continued
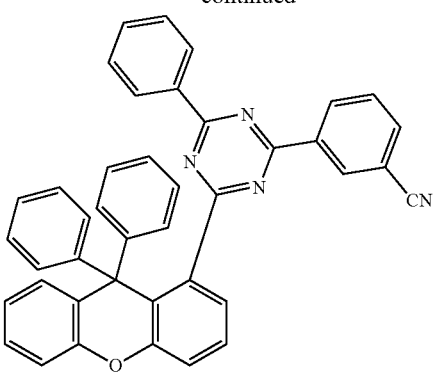
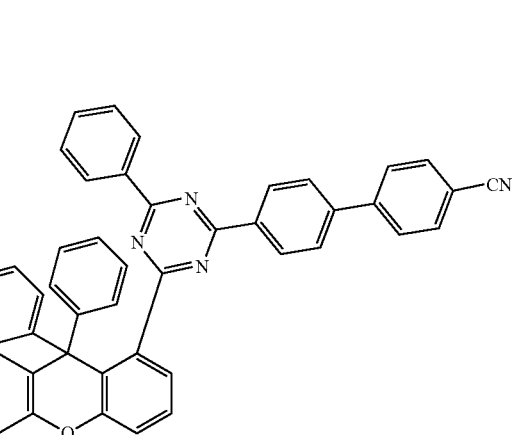
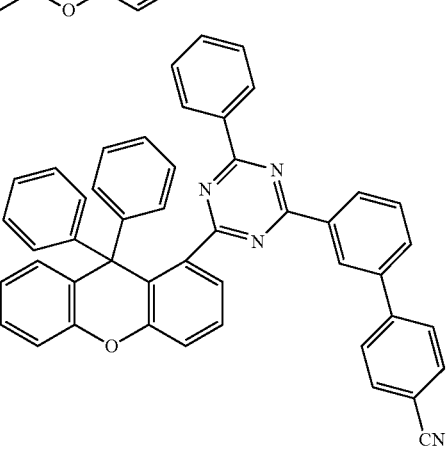
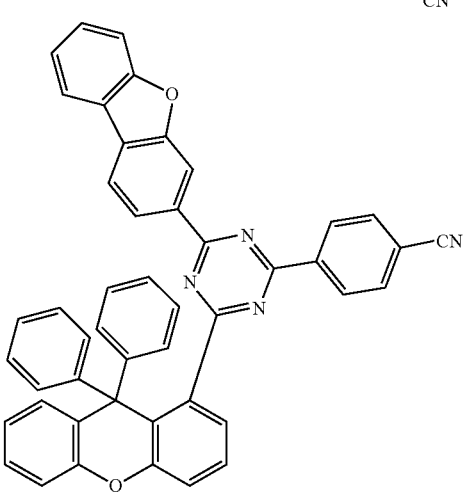

239
-continued
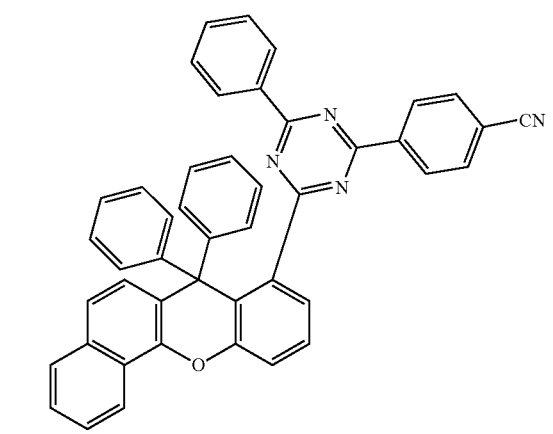
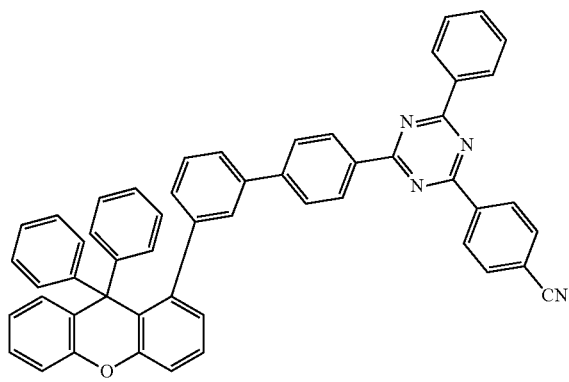
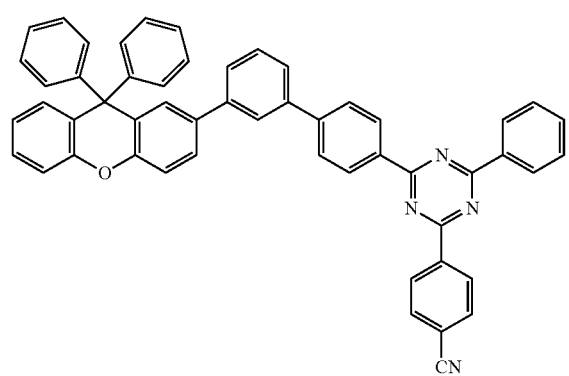
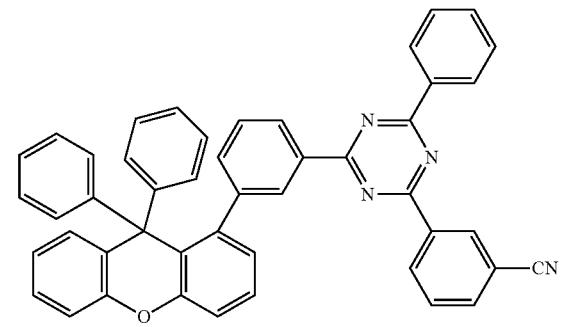
240
-continued
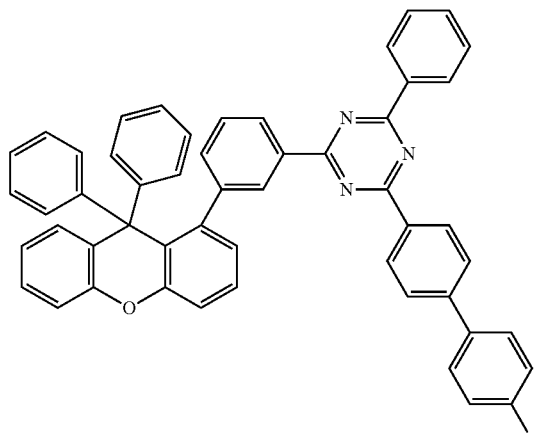

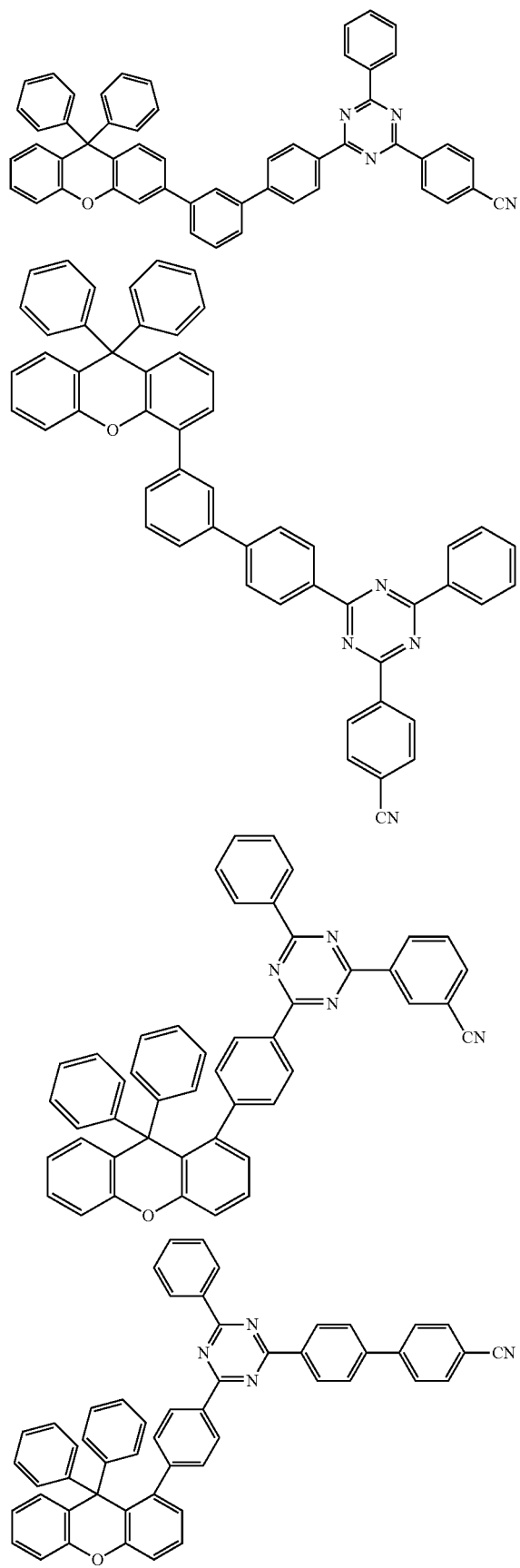
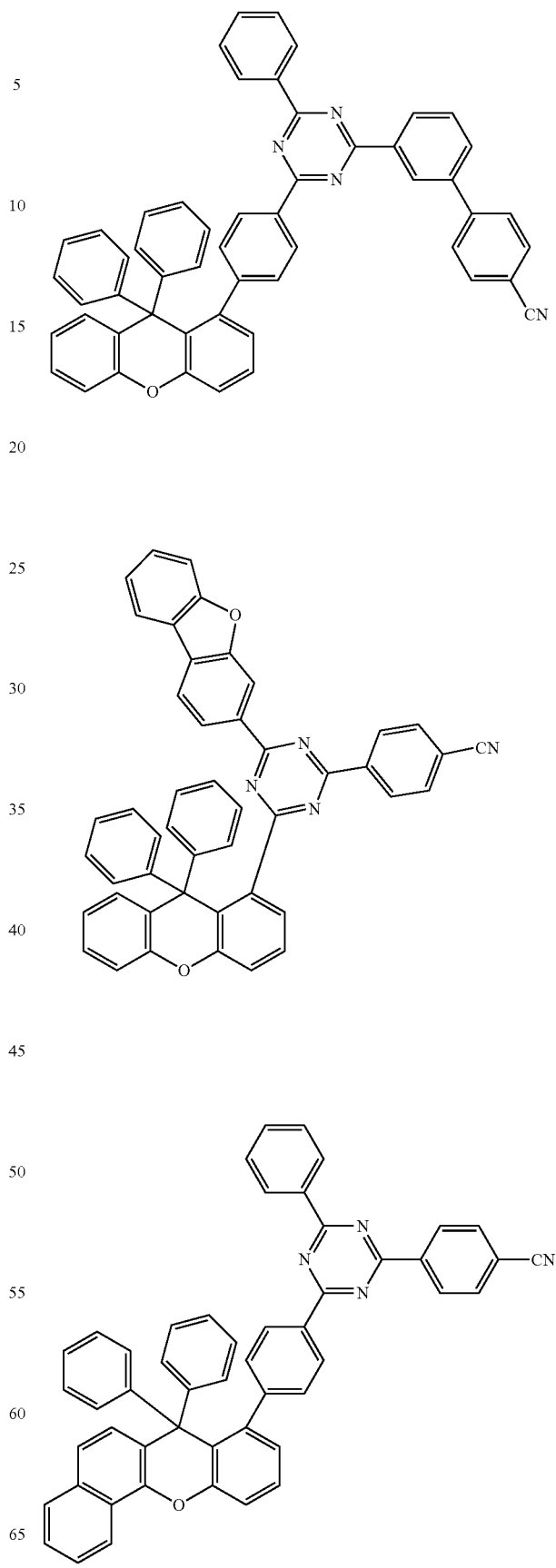

243
-continued
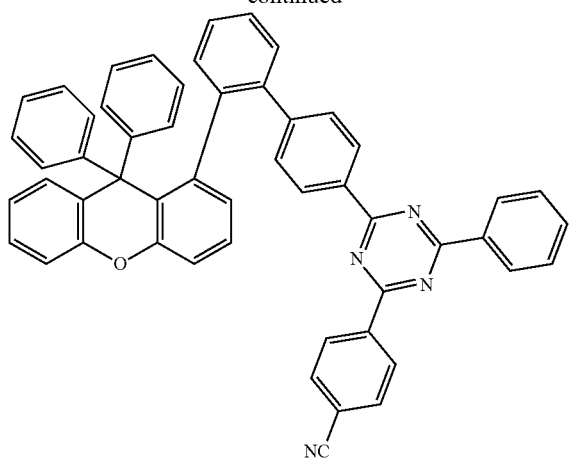
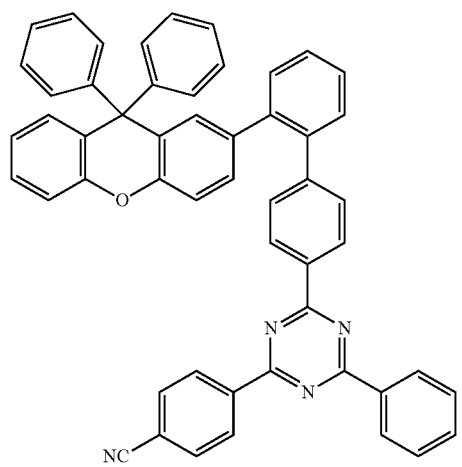 [SMILES: N#Cc1ccc(-c2nc(-c3ccccc3)nc(-c3ccc(-c4ccccc4-c4ccc5c(c4)C(c4ccccc4)(c4ccccc4)c4ccccc4O5)cc3)n2)cc1]
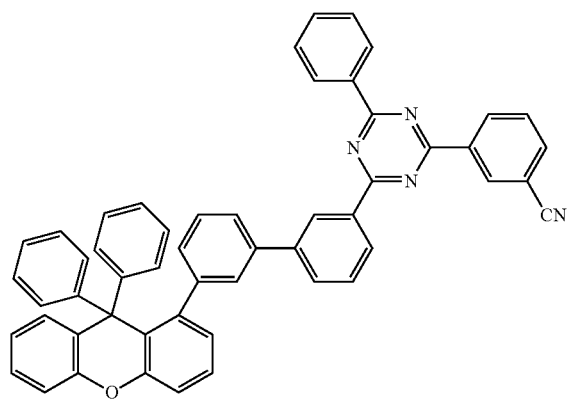
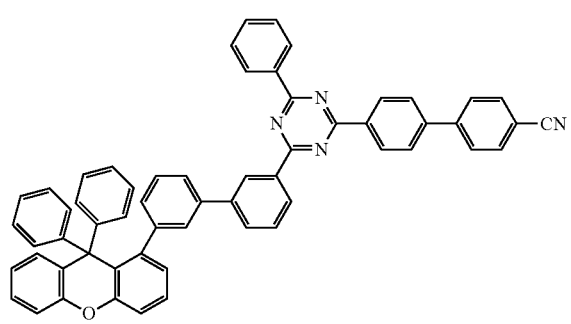
244
-continued
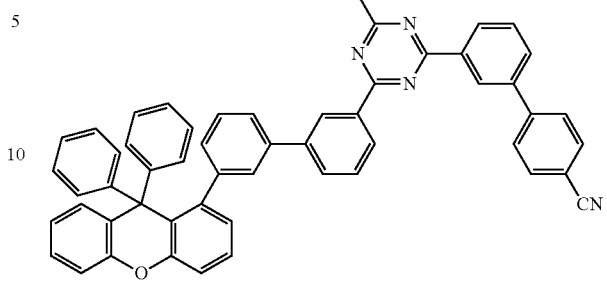
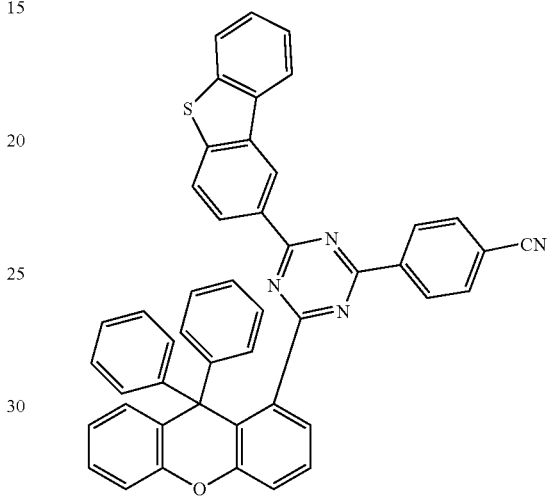
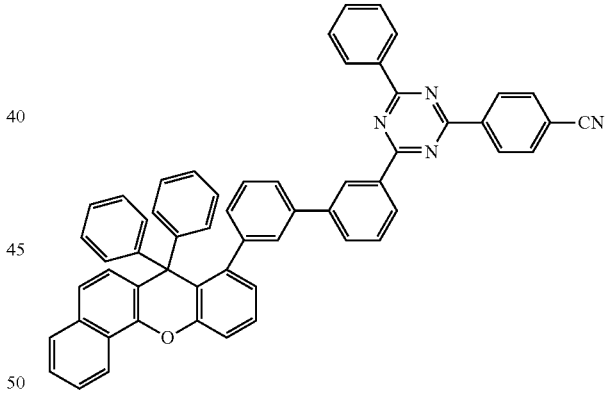
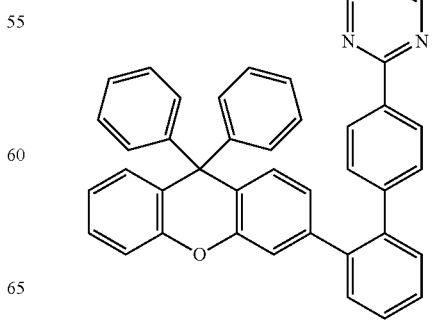

245
-continued
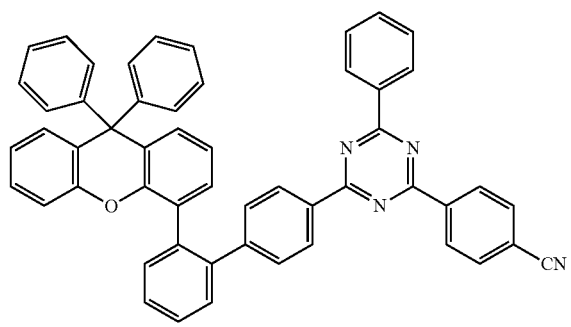
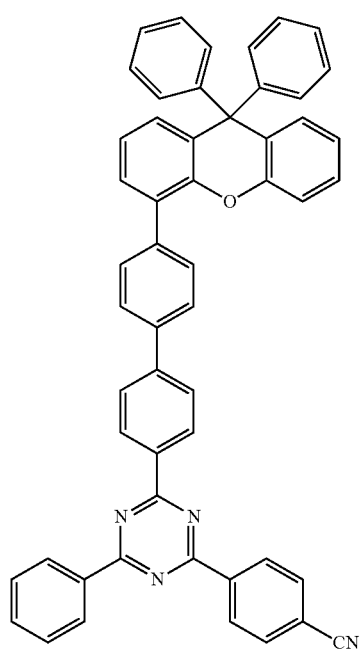
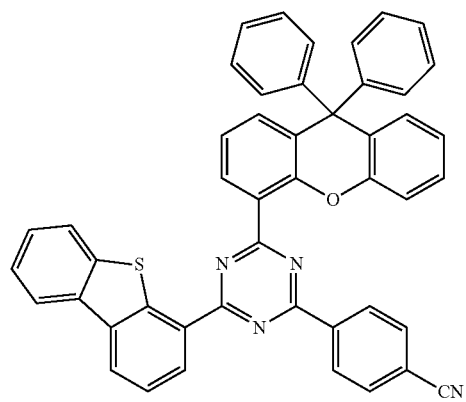
246
-continued
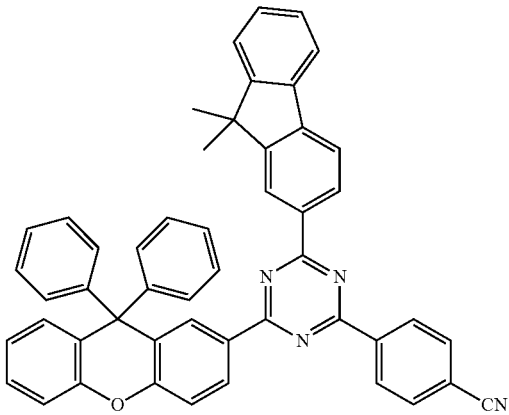
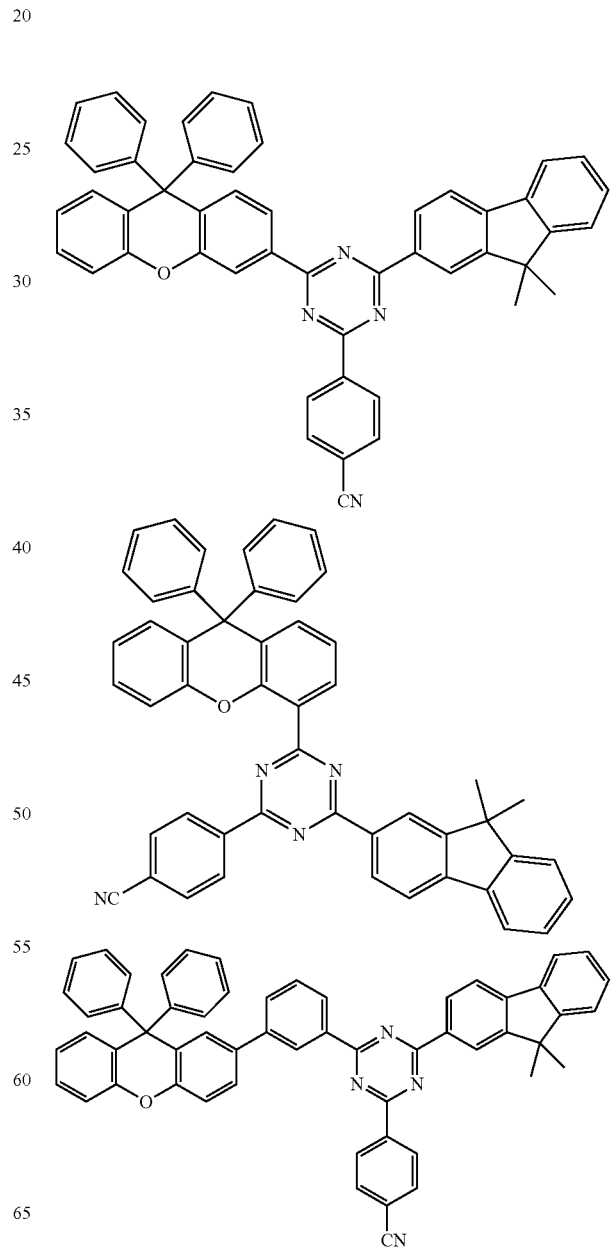

247
-continued
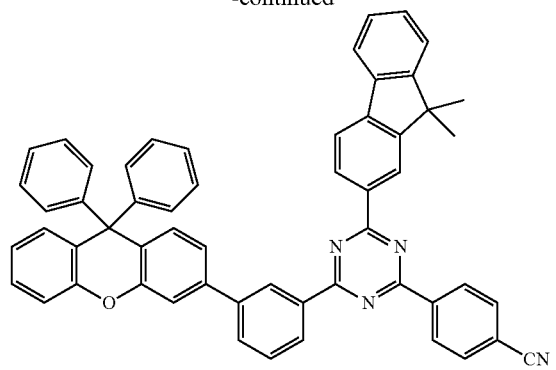
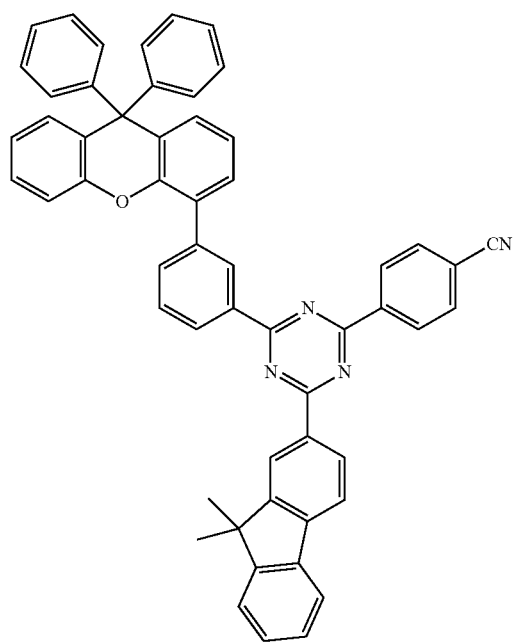
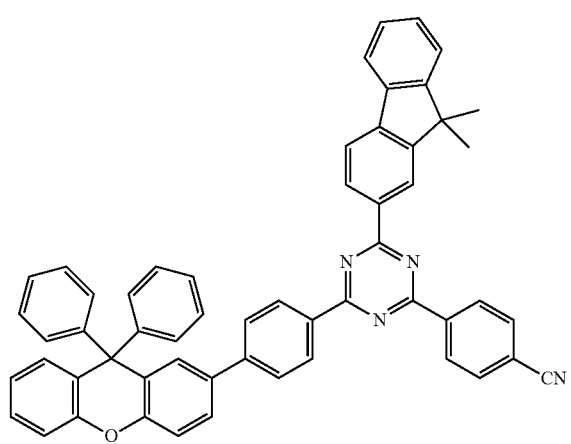
248
-continued
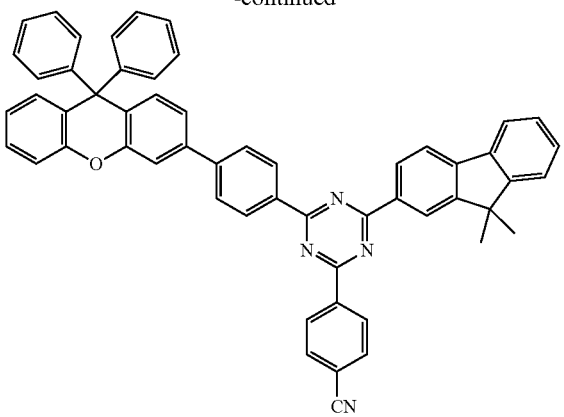
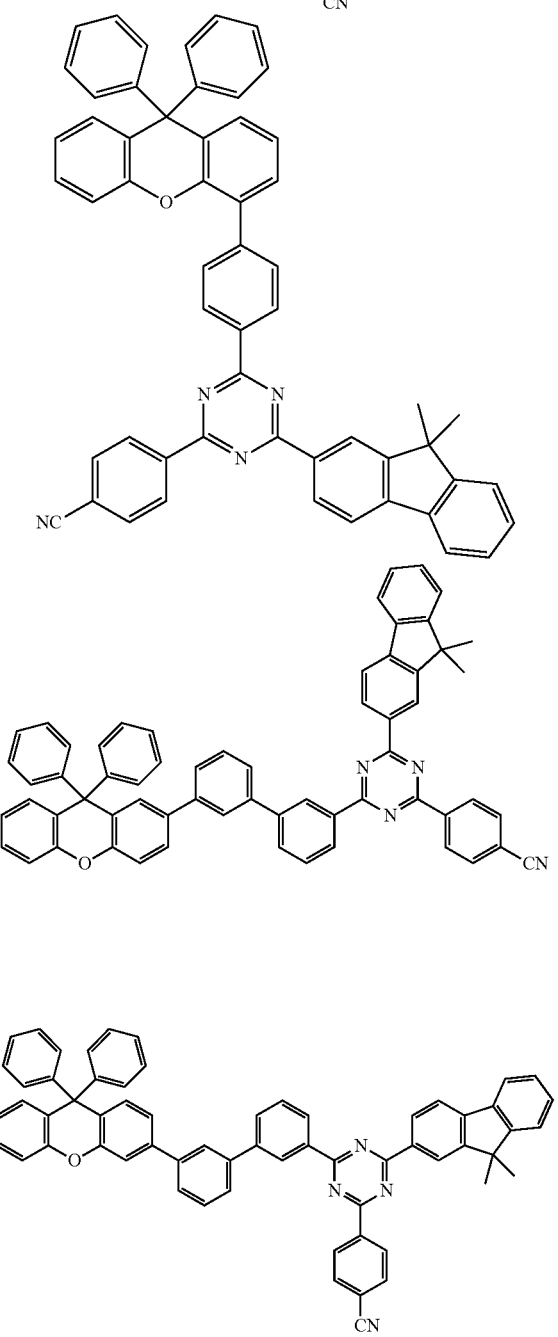

249
-continued
250
-continued
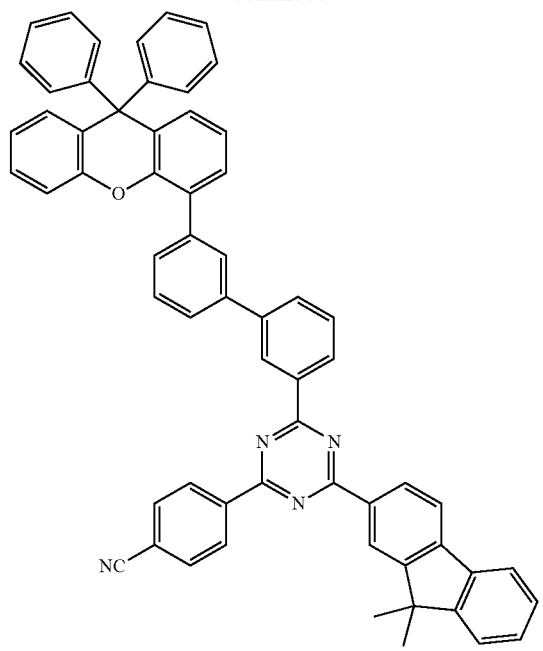
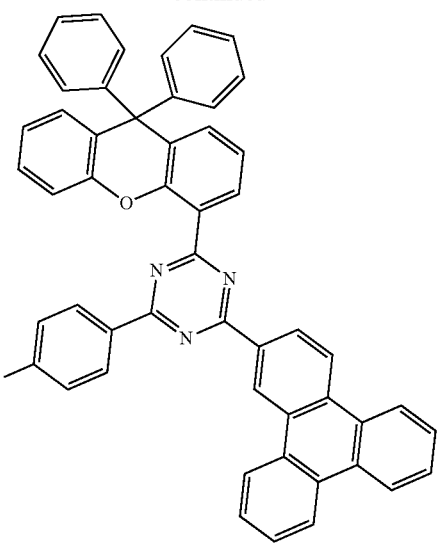
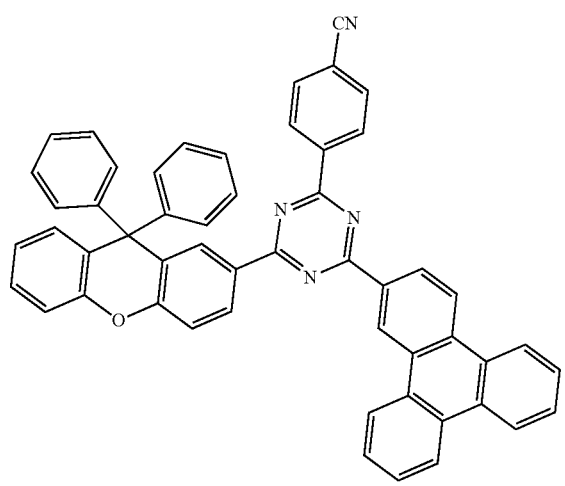
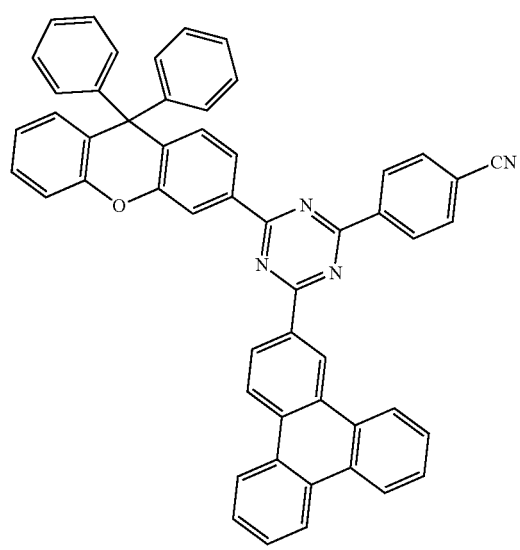
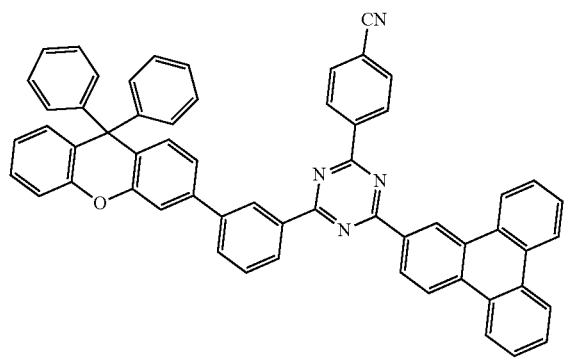

251
-continued
252
-continued
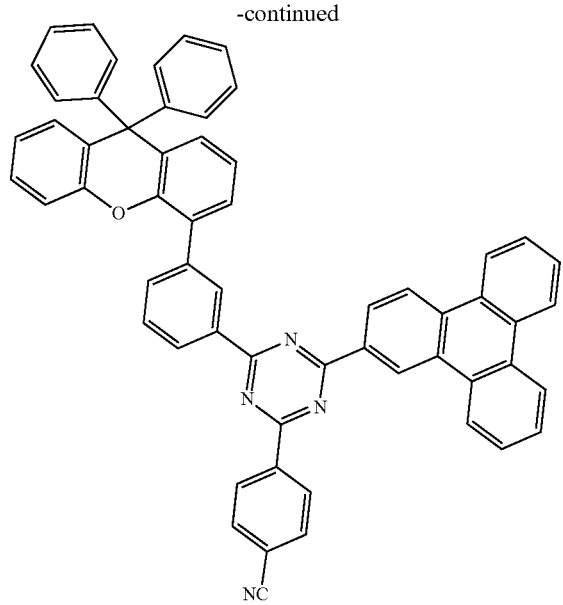
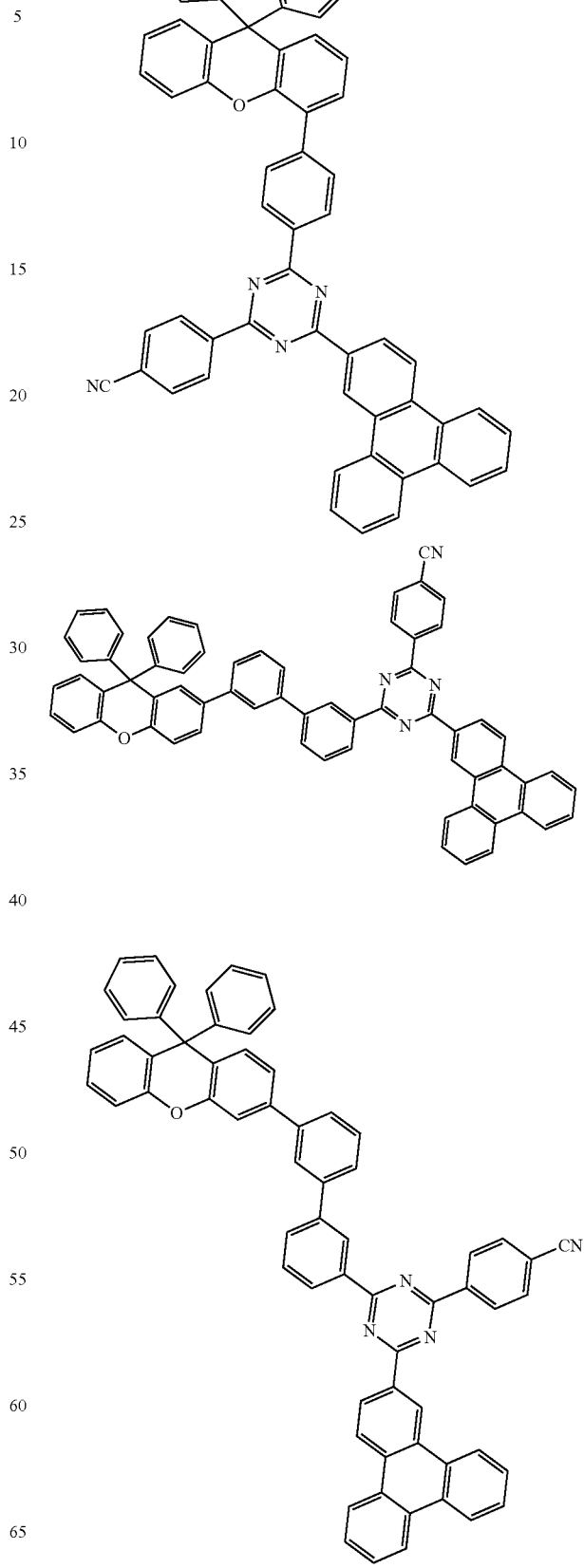

253
-continued
254
-continued
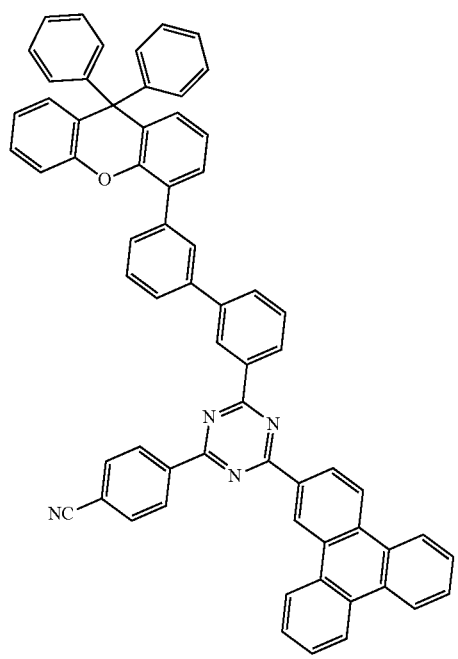
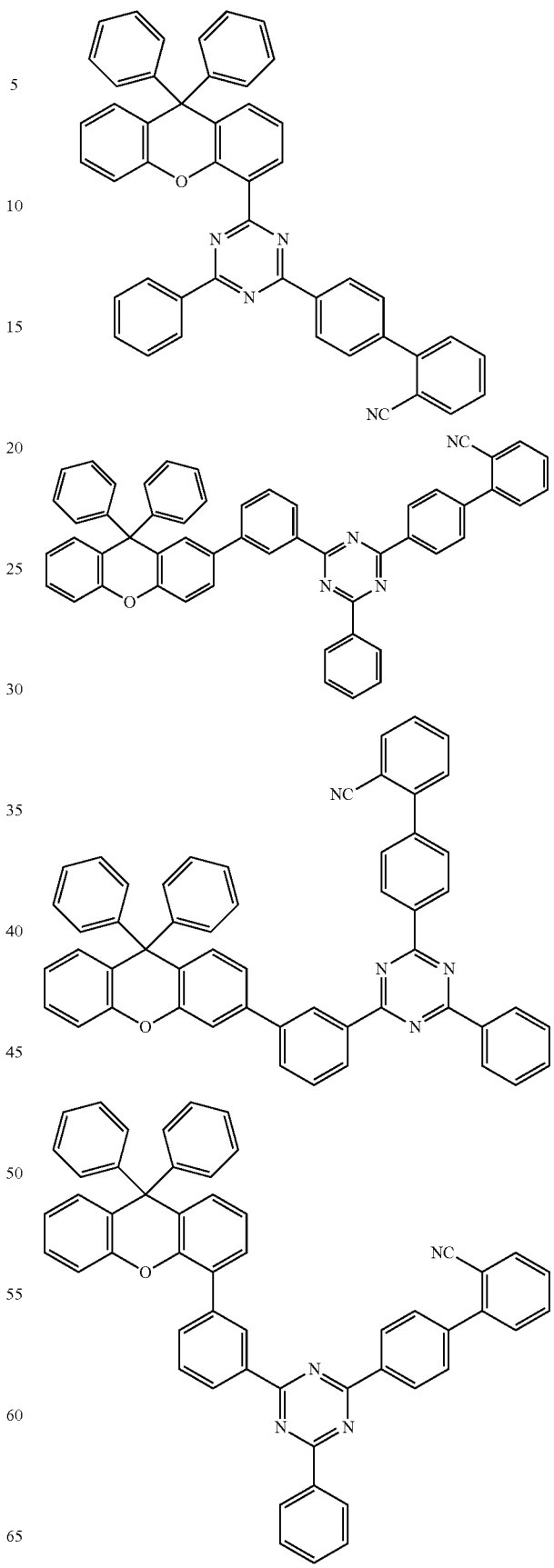

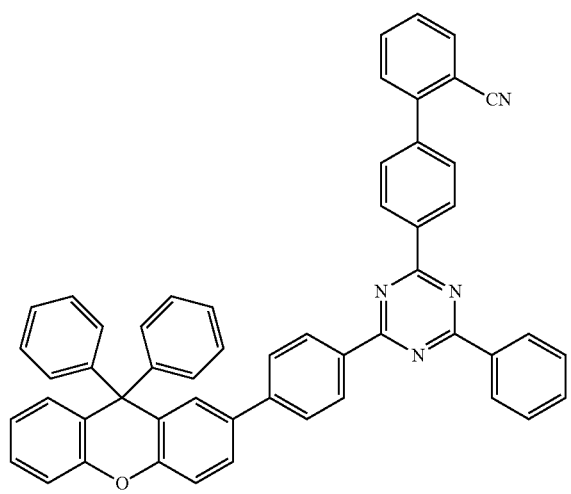
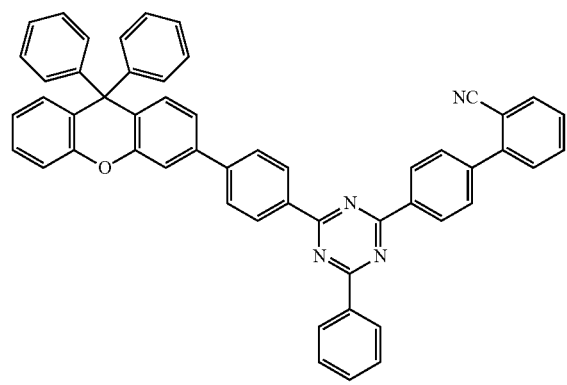
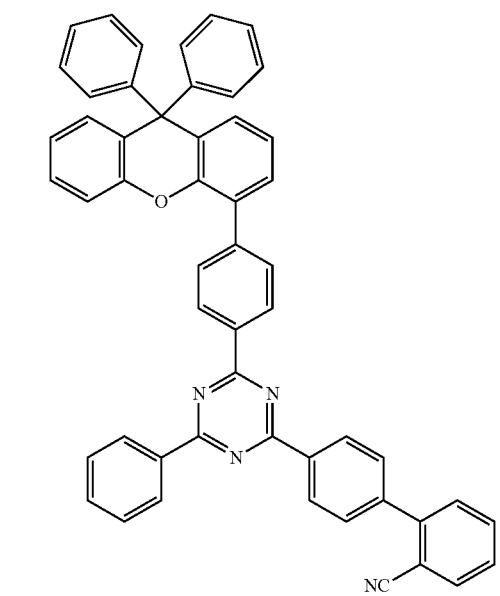
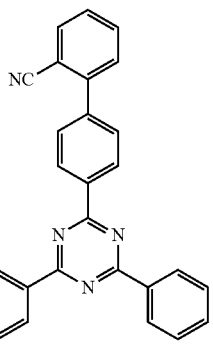
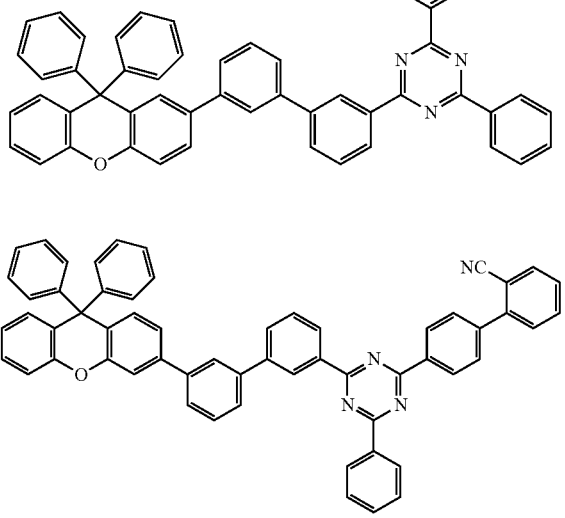
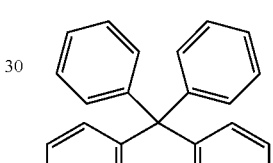
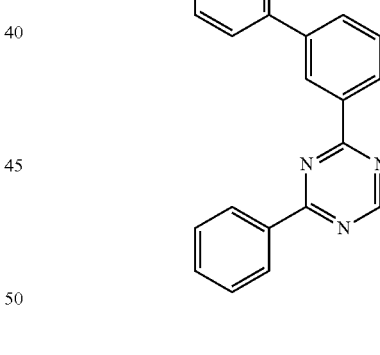
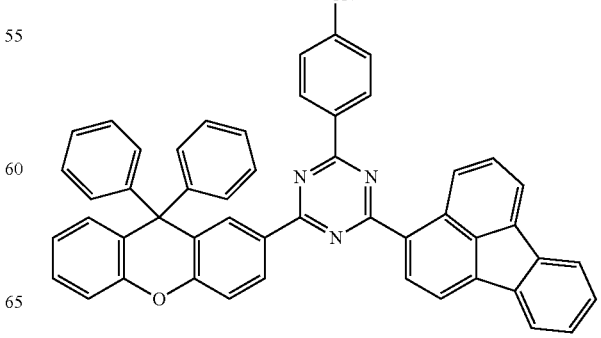

257
-continued
258
-continued
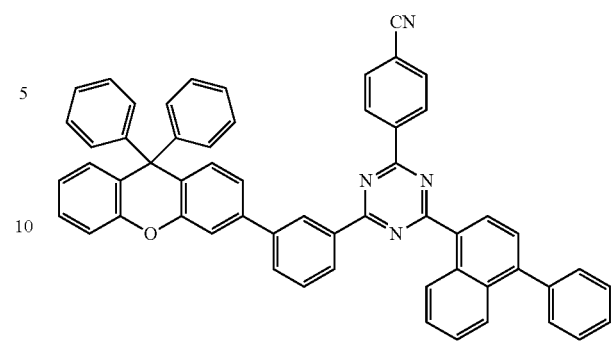
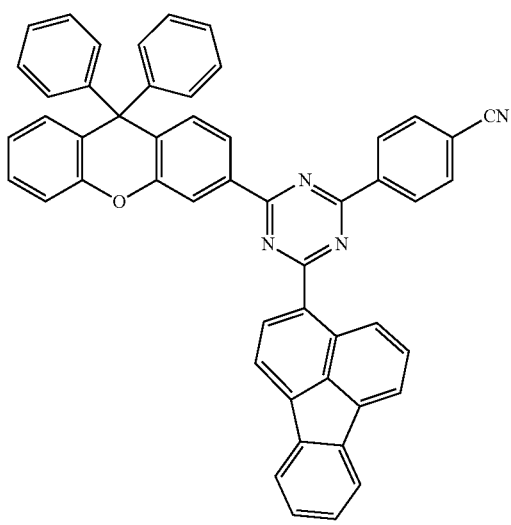
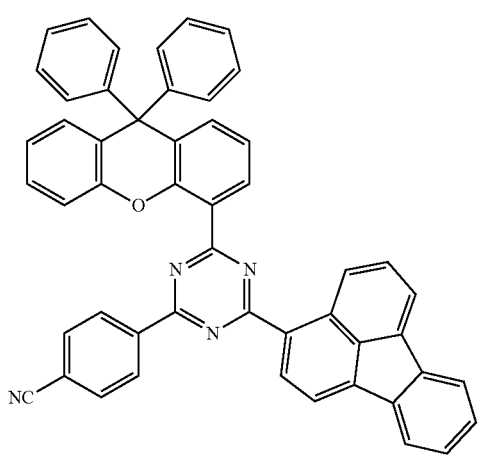
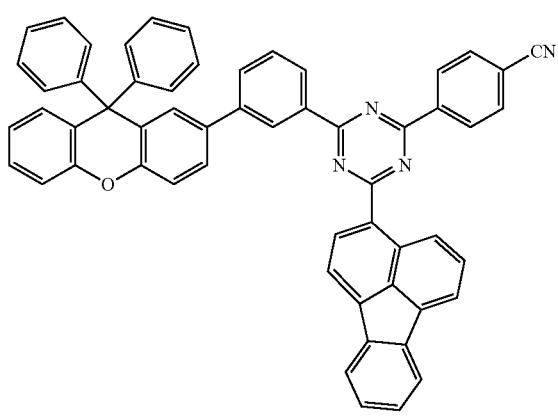
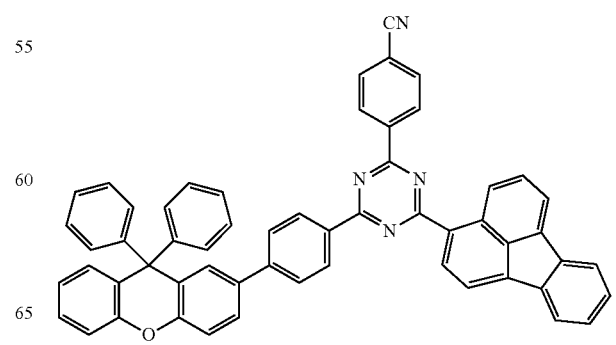

259
-continued

260
-continued

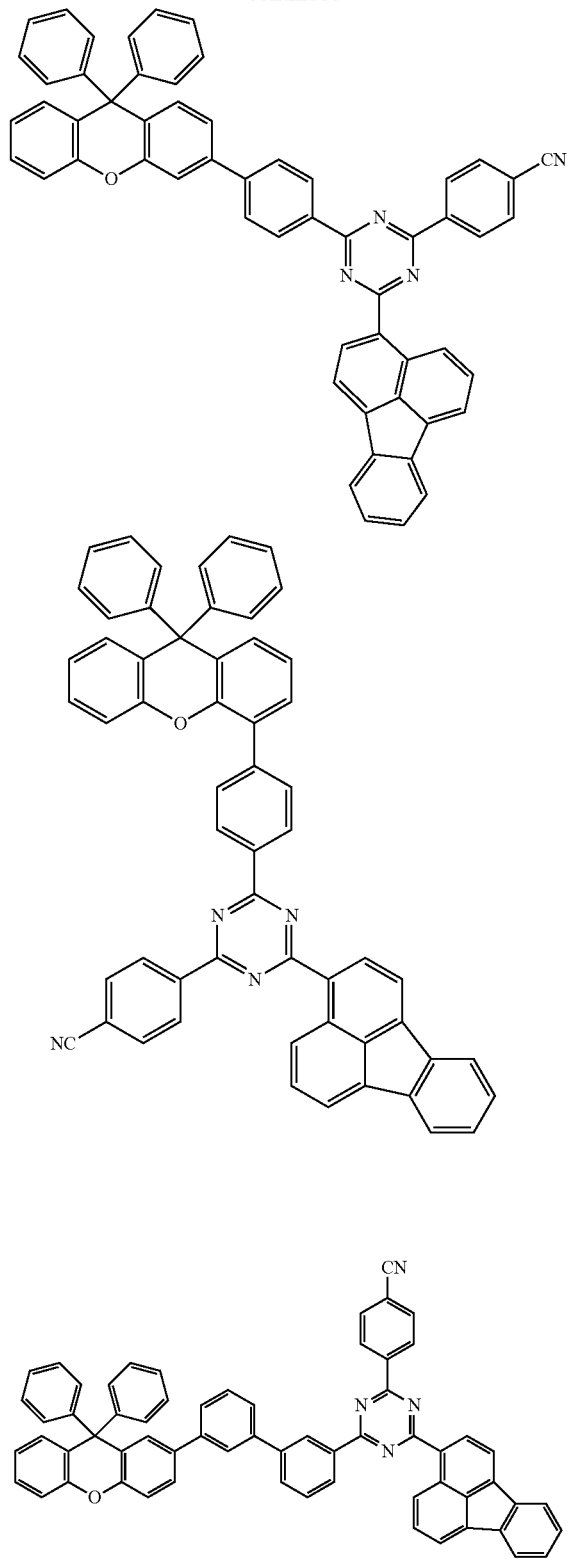

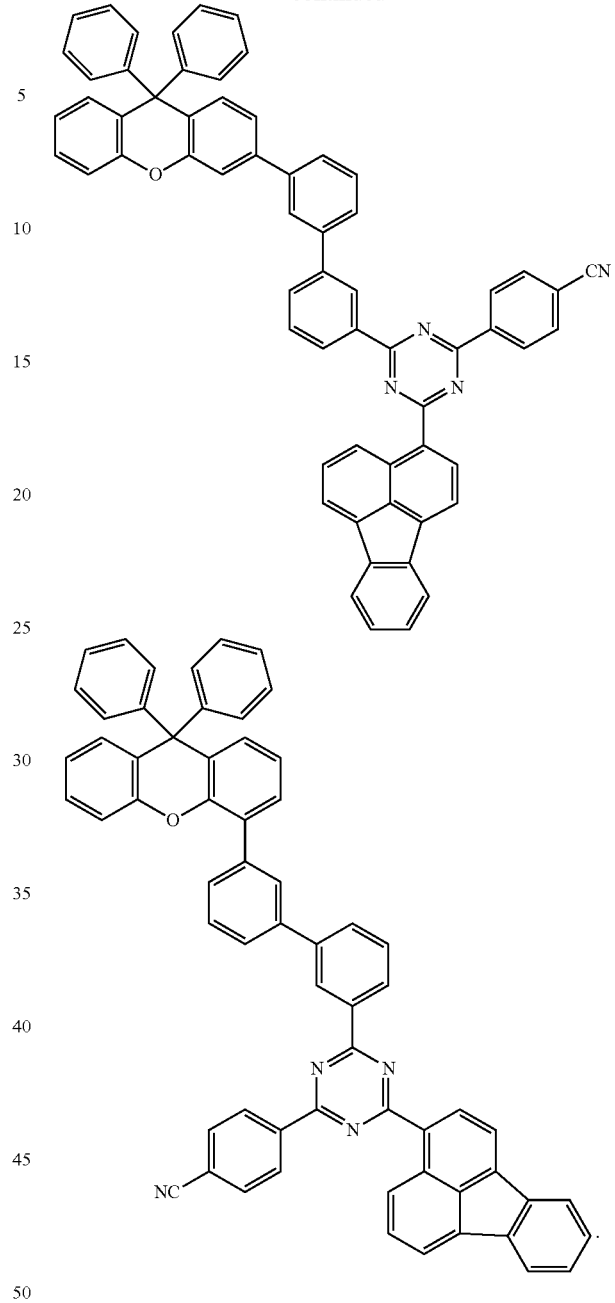

10. An organic light emitting device comprising:
a first electrode;
a second electrode that is provided to face the first electrode; and
an organic material layer including one or more layers that are provided between the first electrode and the second electrode,
wherein one or more layers of the organic material layer comprise the compound of claim 1.

* * * * *